US012253526B2

(12) United States Patent
Hara et al.

(10) Patent No.: US 12,253,526 B2
(45) Date of Patent: Mar. 18, 2025

(54) FLUORESCENT DYE AND USE THEREOF

(71) Applicants: Eisai R&D Management Co., Ltd., Tokyo (JP); SYSMEX CORPORATION, Kobe (JP)

(72) Inventors: Daiki Hara, Kobe (JP); Takafumi Motoki, Tsukuba (JP); Yuji Kazuta, Tsukuba (JP); Yoshihiko Norimine, Tsukuba (JP); Hiroyuki Amino, Tsukuba (JP); Masatoshi Suganuma, Kobe (JP); Shingo Fujiyama, Kobe (JP); Kazuto Yamashita, Kobe (JP); Masaya Okada, Kobe (JP); Yoichi Nishikawa, Kobe (JP); Shigeki Iwanaga, Kobe (JP)

(73) Assignees: Eisai R&D Management Co., Ltd., Tokyo (JP); SYSMEX CORPORATION, Kobe (JP)

( * ) Notice: Subject to any disclaimer, the term of this patent is extended or adjusted under 35 U.S.C. 154(b) by 613 days.

(21) Appl. No.: 17/163,993

(22) Filed: Feb. 1, 2021

(65) Prior Publication Data

US 2021/0255191 A1 Aug. 19, 2021

(30) Foreign Application Priority Data

Feb. 3, 2020 (JP) ................. 2020-016297

(51) Int. Cl.
| | | |
|---|---|---|
| C09B 57/00 | (2006.01) | |
| G01N 21/64 | (2006.01) | |
| G01N 33/58 | (2006.01) | |

(52) U.S. Cl.
CPC ........... *G01N 33/582* (2013.01); *C09B 57/00* (2013.01); *G01N 21/6428* (2013.01); *G01N 21/6458* (2013.01); *G01N 2021/6439* (2013.01)

(58) Field of Classification Search
CPC ............... C09B 57/00; G01N 33/582
See application file for complete search history.

(56) References Cited

U.S. PATENT DOCUMENTS

| 9,429,568 B2 | 8/2016 | Dyer et al. |
| 2014/0272990 A1 | 9/2014 | Zhou et al. |
| 2017/0045501 A1 | 2/2017 | Lavis et al. |

FOREIGN PATENT DOCUMENTS

| CN | 100361999 C | 1/2008 |
| CN | 104262378 A | 1/2015 |
| JP | 5526124 B2 | 6/2014 |
| JP | 2014-157150 A | 8/2014 |
| JP | 2016-512042 A | 4/2016 |
| JP | 2017-519844 A | 7/2017 |
| JP | 2017-149806 A | 8/2017 |
| WO | 2010/126077 A1 | 11/2010 |
| WO | 2014/144793 A1 | 9/2014 |
| WO | 2020/033681 A2 | 2/2020 |

OTHER PUBLICATIONS

No new references cited by the Examiner.*
Partial European Search Report, dated Jul. 7, 2021, issued by the European Patent Office in European Patent Application No. 21154523.1.
Extended European Search Report, dated Oct. 26, 2021, issued by the European Patent Office in European Patent Application No. 21154523.1.
Notice of Reasons for Refusal issued Dec. 5, 2023 in Japanese Application No. 2020-016297.
Chinese Office Action dated Mar. 16, 2024 in Application No. 202110040107.9.
Communication issued May 13, 2024 in European Application No. 21 154 523.1.
Office Action received in Chinese Application No. 202110040107.9 mailed Aug. 16, 2024.

* cited by examiner

*Primary Examiner* — Shawquia Jackson
(74) *Attorney, Agent, or Firm* — Sughrue Mion, PLLC

(57) ABSTRACT

Disclosed is: a fluorescent dye comprising a compound, a tautomer of the compound, or a salt of the compound or the tautomer; a labeled composite substance comprising the fluorescent dye and a composite substance which are bonded to each other; a composition containing the fluorescent dye or the labeled composite substance; and a method for acquiring information about a substance of interest by a super-resolution microscopy.

20 Claims, 6 Drawing Sheets

COMPOUND A       COMPOUND B

FIG. 5

| EXAMPLE NO. | DUTY CYCLE | EXAMPLE NO. | DUTY CYCLE |
|---|---|---|---|
| 1 | 0.11 | 19 | 0.15 |
| 2 | 0.04 | 20 | 0.12 |
| 3 | 0.03 | 21 | 0.24 |
| 4 | 0.05 | 22 | 0.12 |
| 5 | 0.06 | 23 | 0.15 |
| 6 | 0.06 | 24 | 0.09 |
| 7 | 0.04 | 25 | 0.22 |
| 8 | 0.04 | 26 | 0.18 |
| 9 | 0.10 | 27 | 0.19 |
| 10 | 0.09 | 28 | 0.11 |
| 11 | 0.08 | 29 | 0.20 |
| 12 | 0.06 | 30 | 0.17 |
| 13 | 0.14 | 31 | 0.17 |
| 14 | 0.11 | 32 | 0.17 |
| 15 | 0.09 | 33 | 0.13 |
| 16 | 0.13 | 34 | 0.27 |
| 17 | 0.04 | 35 | 0.31 |
| 18 | 0.05 | 36 | 0.03 |

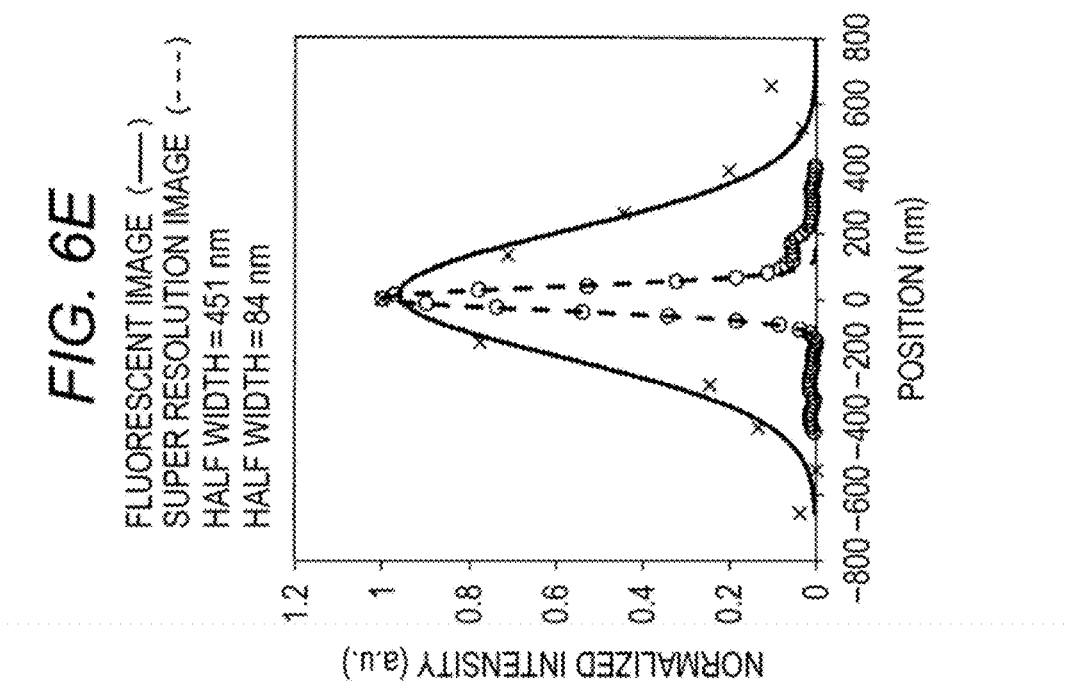
FIG. 6E
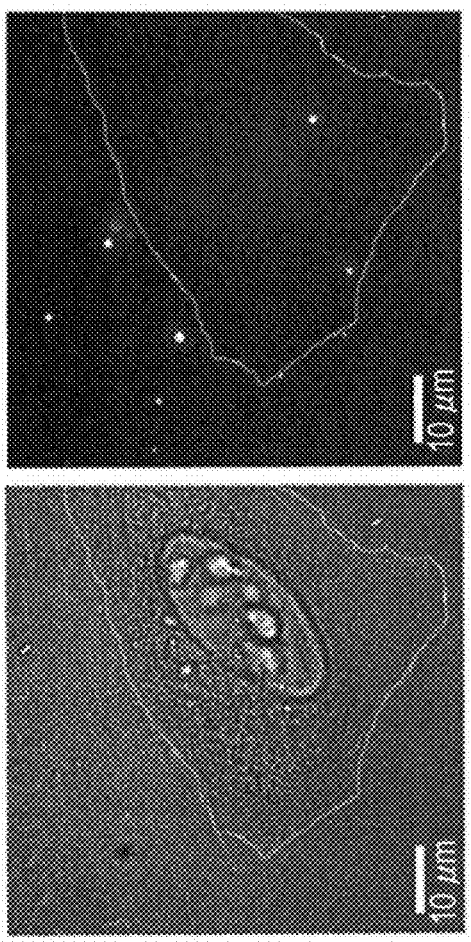
FIG. 6A
FIG. 6B
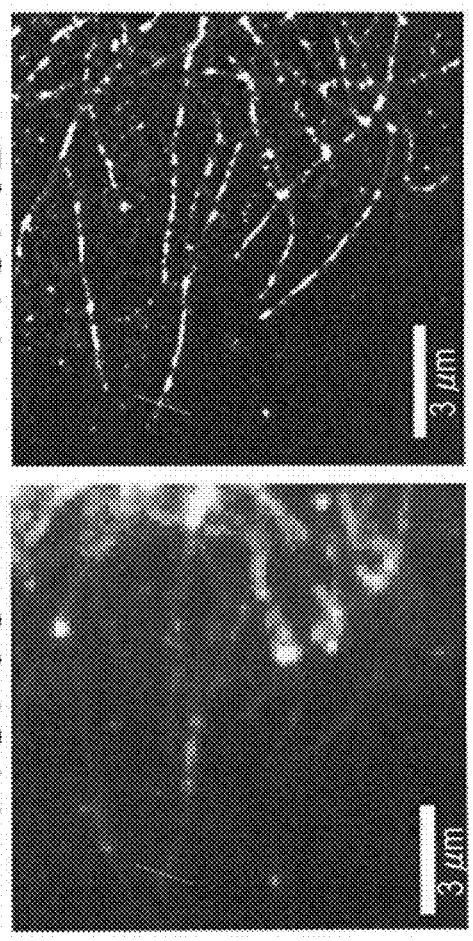
FIG. 6C
FIG. 6D

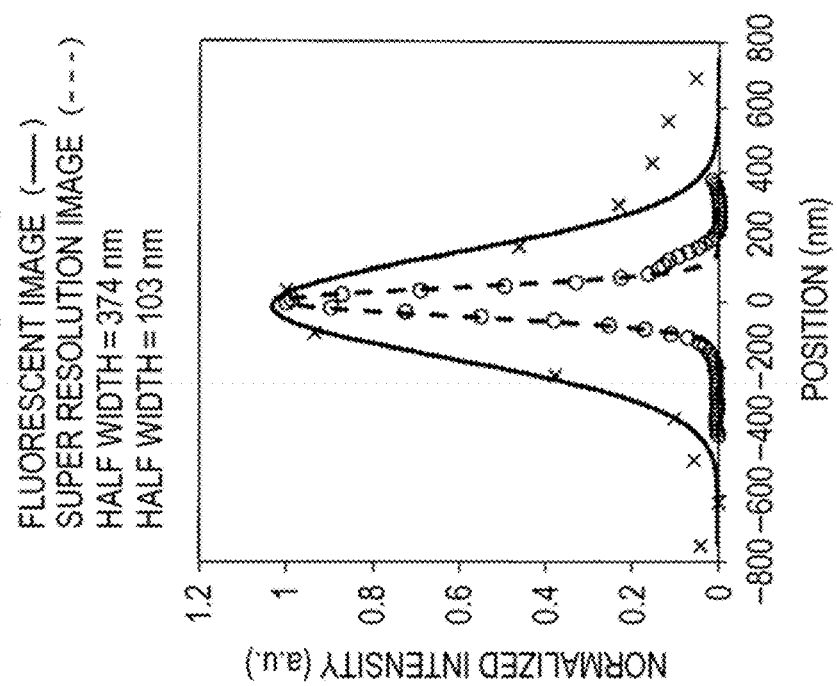
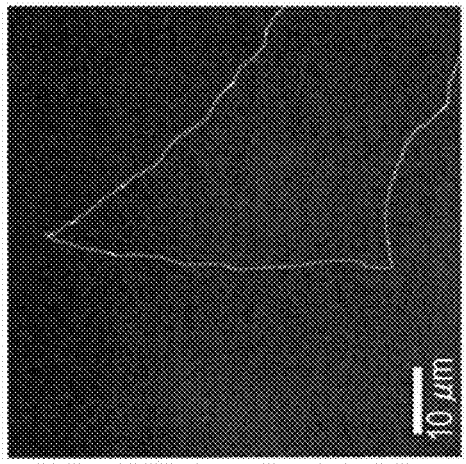
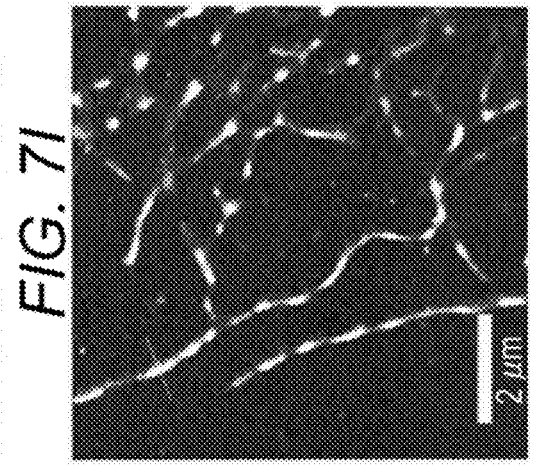
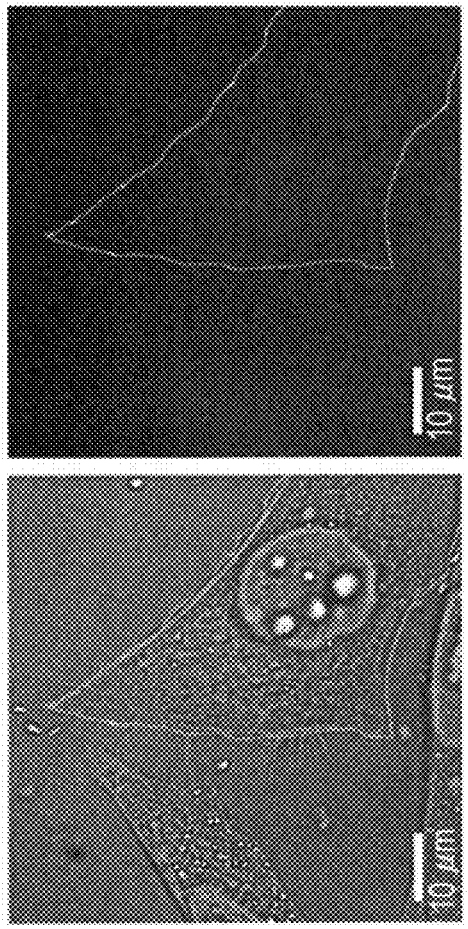
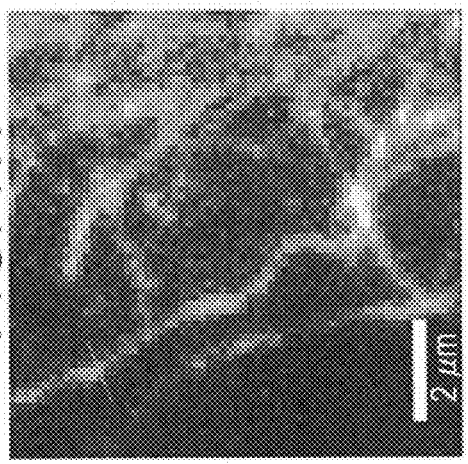

FLUORESCENT DYE AND USE THEREOF

CROSS REFERENCE TO RELATED APPLICATIONS

This application claims priority from prior Japanese Patent Application No. 2020-016297, filed on Feb. 3, 2020, entitled "FLUORESCENT DYE AND USE THEREOF", the entire contents of which are incorporated herein by reference.

FIELD OF THE INVENTION

The present invention relates to a fluorescent dye. The present invention also relates to a labeled composite substance comprising a fluorescent dye and a composite substance which are bonded to each other. The present invention also relates to a composition containing a fluorescent dye or a labeled composite substance. The present invention also relates to a method for acquiring information about a substance of interest by a super-resolution microscopy.

BACKGROUND

For the detection of a cell or a biological molecule with a fluorescence microscope or a flow cytometry, a fluorescent dye has been widely used. As one example of the fluorescent dye, a compound is known, which has such a backbone that an oxygen atom in a xanthene ring in a base backbone of a rhodamine compound is substituted by a silicon atom (wherein the backbone is also referred to as a ", Sirhodamine backbone", hereinafter) as disclosed in Chinese Patent Application Publication No. 100361999.

The purpose of the present invention is to provide a novel fluorescent dye, a novel labeled composite substance, a novel composition, and a novel method for acquiring information about a substance of interest.

SUMMARY OF THE INVENTION

The scope of the present invention is defined solely by the appended claims, and is not affected to any degree by the statements within this summary.

In rhodamine compounds, it is known that a state where an intramolecular spiro ring in which the spiro atom is a carbon atom located at position-9 in a xanthene ring moiety is formed (i.e., a ring-closed form) and a state where the spiro ring is cleaved (i.e., a ring-opened form) are in equilibrium with each other. A rhodamine compound in the ring-opened form exerts absorption and fluorescence, while a rhodamine compound in the ring-closed form is colorless and non-fluorescent. This is true for a fluorescent dye having an Si rhodamine backbone. The present inventors have focused on the reversible formation and a cleavage reaction of an intramolecular spiro ring in a fluorescent dye having an Si rhodamine backbone, and have attempted to produce a novel fluorescent dye. As a result, the present inventors have achieved the present invention by imparting a spiro-ring structure having an Si atom as a spiro atom to a fluorescent dye having an Si rhodamine backbone.

The present invention provides a fluorescent dye consisting of a compound represented by formula (I), a tautomer of the compound, or a salt of the compound or the tautomer:

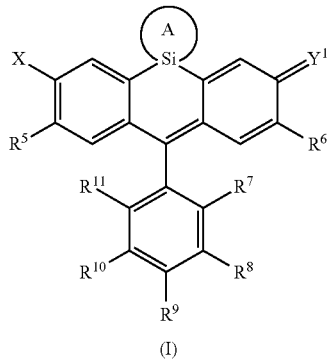

[Formula 1]

(I)

(wherein:

A represents an optionally substituted C4-C7 heterocyclic ring which contains an Si atom;

X represents a hydroxy group or $-N^+R^1R^2$;

$Y^1$ represents $=O$ or $=N^+R^3R^4$;

$R^1$, $R^2$, $R^3$, $R^4$, $R^5$ and $R^6$ independently represent an H atom, an optionally substituted C1-C6 alkyl group, or an optionally substituted C1-C6 heteroalkyl group;

at least one combination selected from a combination of $R^1$ and $R^2$, a combination of $R^3$ and $R^4$, a combination of $R^1$ and $R^5$, and a combination of $R^3$ and $R^6$ may together form an optionally substituted N-containing heterocyclic ring with an N atom to which they bind;

$R^7$, $R^8$, $R^9$, $R^{10}$ and $R^{11}$ are independently selected from the group consisting of an H atom, a halogen atom, an optionally substituted C1-C6 alkyl group, an optionally substituted C1-C6 alkoxy group, an optionally substituted C1-C6 alkylthio group, an optionally substituted amino group, an optionally substituted aryl group, an optionally substituted heteroaryl group, $-CO_2H$, $-CO_2^-$, $-SO_3H$, $-SO_3^-$, and -L-R;

L represents a bivalent linker which has 1 to 16 non-hydrogen atoms and has a linear structure, a branched structure, a cyclic structure or a structure that is an arbitrary combination of these structures, wherein, when there are one or more hetero atoms in the bivalent linker, the hetero atoms are contained as one or more groups independently selected from the group consisting of an ester group, an amine group, an amide group, an ether group, a thioether group and a carbonyl group;

R represents a reactive group; and at least one combination of adjacent two substituents among $R^7$, $R^8$, $R^9$, $R^{10}$ and $R^{11}$ may together form a ring;

provided that a compound in which at least one combination selected from a combination of $R^1$ and $R^5$ and a combination of $R^3$ and $R^6$ together form an optionally substituted N-containing heterocyclic ring with an N atom to which they bind and $R^2$ and $R^4$ independently represent an optionally substituted C1-C6 alkyl group, a tautomer of the compound and a salt of the compound or the tautomer are excluded).

The present invention provides a fluorescent dye consisting of a compound selected from following compounds, a tautomer of the compound, or a salt of the compound or the tautomer:

[Formula 5]
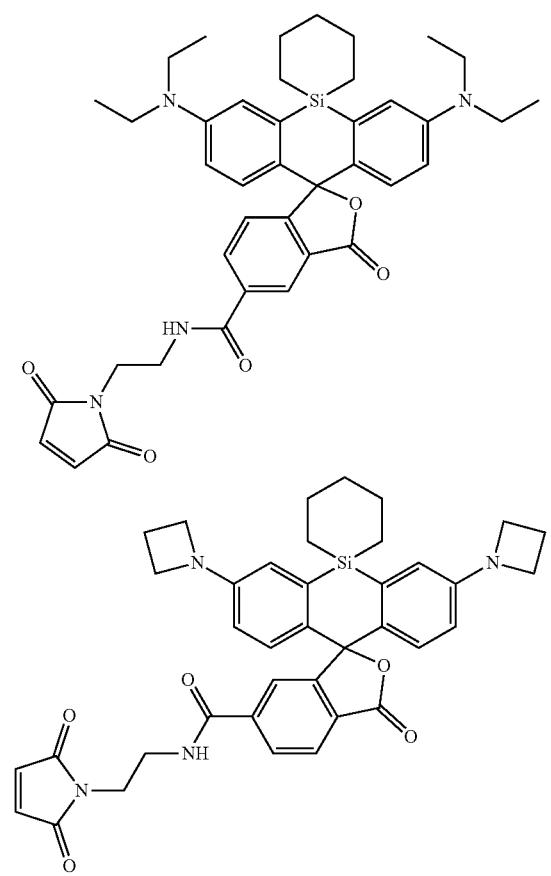
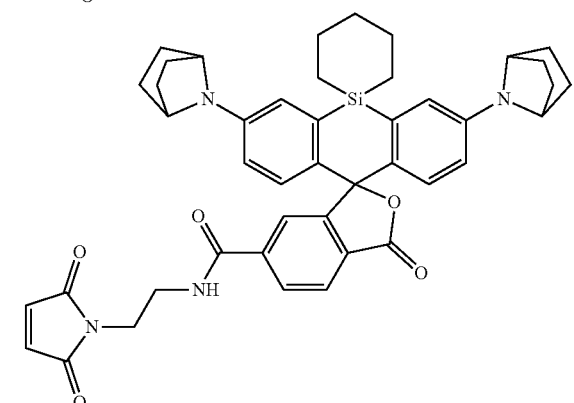
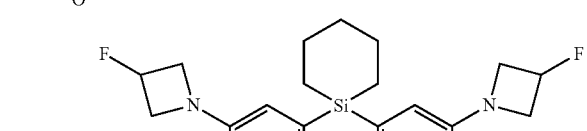
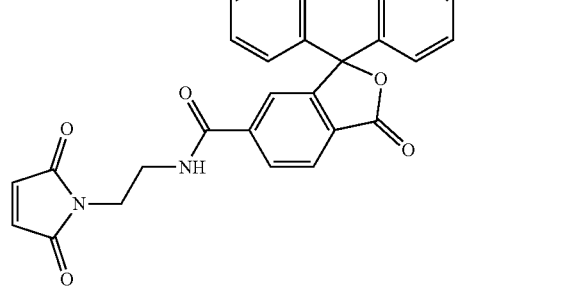
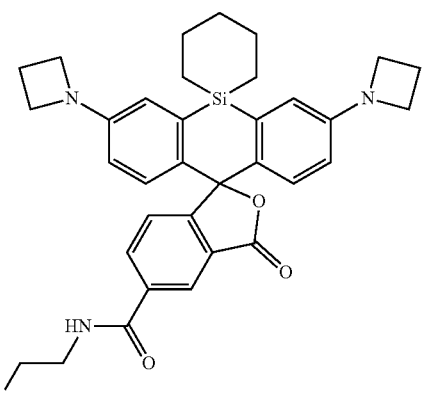
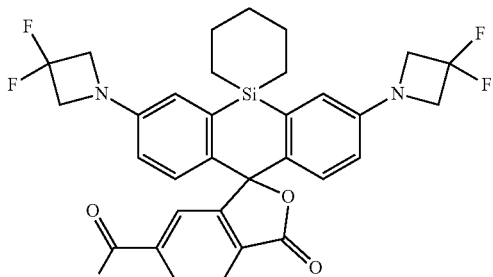
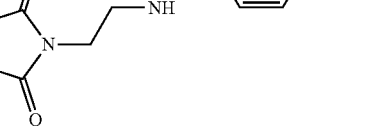
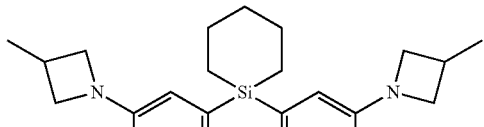
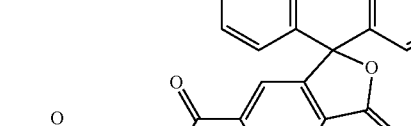
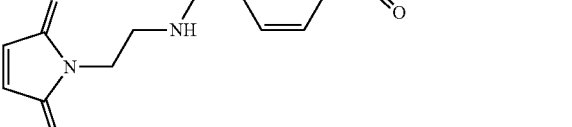
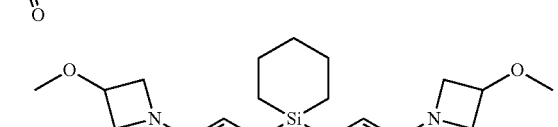
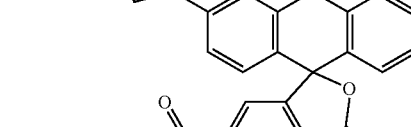
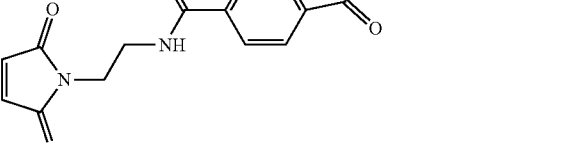

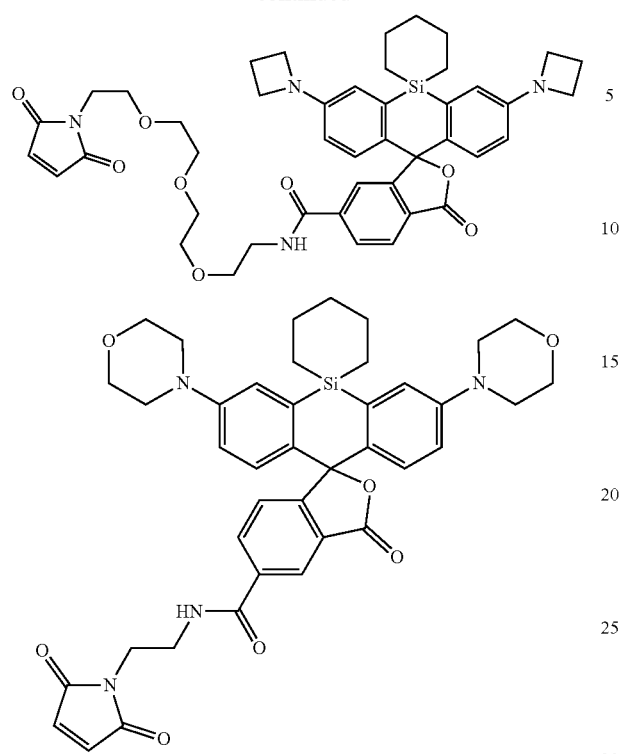
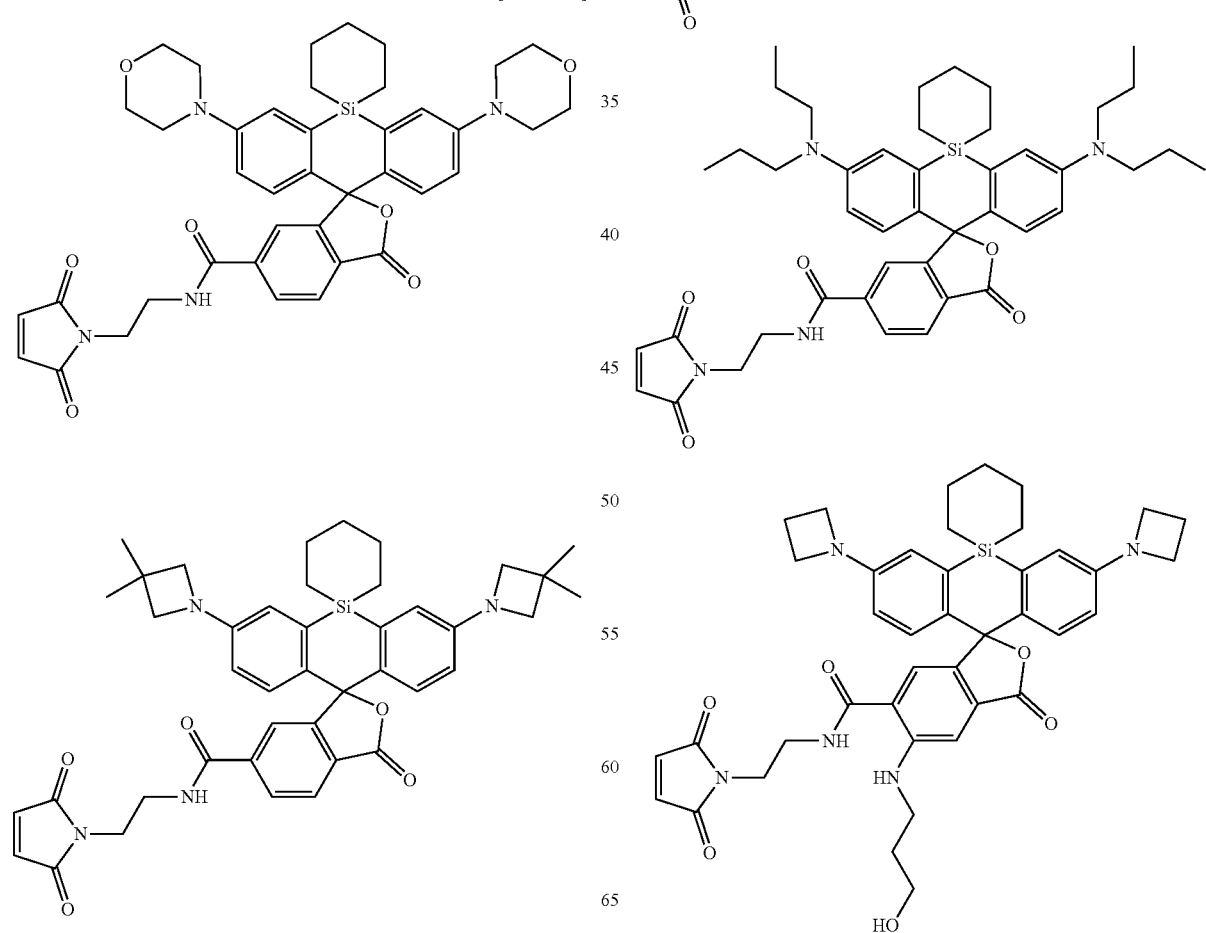

-continued

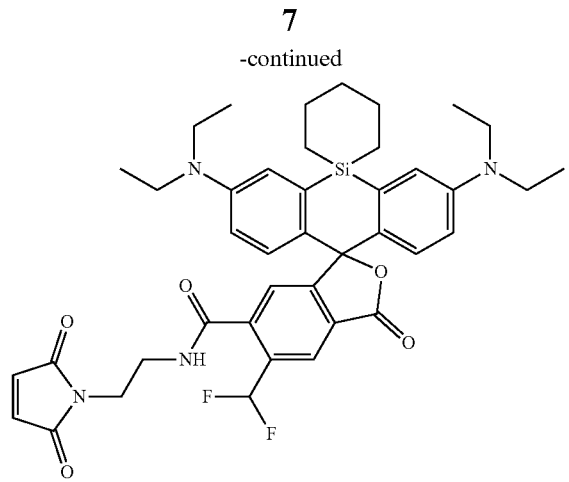

-continued

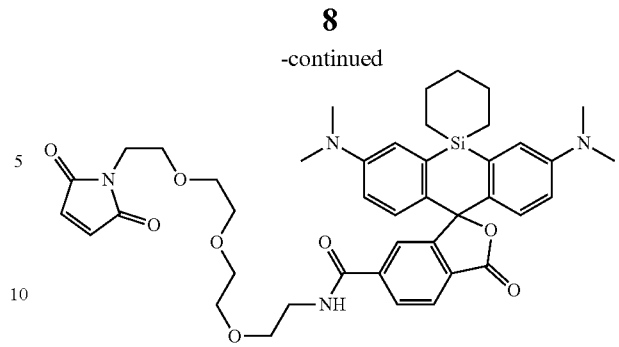

The present invention also provides a labeled composite substance comprising the fluorescent dye and a composite substance which are bonded to each other. The present invention also provides a composition containing the fluorescent dye or the labeled composite substance. The present invention provides a composition comprising the fluorescent dye or the labeled composite substance. The present invention also provides a method for acquiring information about a substance of interest, comprising: binding the fluorescent dye or the labeled composite substance to the substance of interest; and acquiring the information about the substance of interest by a super-resolution microscopy.

According to the present invention, a novel fluorescent dye, a novel labeled composite substance, a novel composition, and a novel method for acquiring information about a substance of interest are provided.

BRIEF DESCRIPTION OF THE DRAWINGS

FIG. 5 is a table showing the duty cycles of the fluorescent dye s of Examples 1 to 36.

FIG. 6A is a light transmission image of a cell that is immunostained using only an anti-mouse IgG antibody labeled with a fluorescent dye of Example 7 (a secondary antibody) without adding an anti-tubulin antibody (a primary antibody). FIG. 6B is a fluorescent image in the same field of view as that of FIG. 6A. In each of FIGS. 6A and 6B, the outline of the cell was shown by a dashed line. FIG. 6C is a fluorescent image of a cell immunostained with the primary antibody and the secondary antibody. FIG. 6D is a super-resolution image in the same field of view as that in FIG. 6C. In each of FIGS. 6C and 6D, a short line in an upper left part of the image is a part which was analyzed with respect to the line profile of the image of a stained microtube. FIG. 6E illustrates line profiles and half widths which were analyzed with respect to the images of FIGS. 6C and 6D.

FIG. 7F is a light transmission image of a cell that is immunostained using only an anti-mouse IgG antibody labeled with a fluorescent dye of Example 36 (a secondary antibody) without adding an anti-tubulin antibody (a primary antibody). FIG. 7G is a fluorescent image in the same field of view as that of FIG. 7F. In each of FIGS. 7F and 7G, the outline of the cell was shown by a dashed line. FIG. 7H is a fluorescent image of a cell immunostained with the primary antibody and the secondary antibody. FIG. 7I is a super-resolution image in the same field of view as that in FIG. 7H. In each of FIGS. 7H and 7I, a short line in an upper left part of the image is a part which was analyzed with respect to the line profile of the image of a stained microtube. FIG. 7J illustrates line profiles and half widths which were analyzed with respect to the images of FIGS. 7H and 7I.

DETAILED DESCRIPTION OF THE PREFERRED EMBODIMENTS

Abbreviations and Terms

Figure 1:
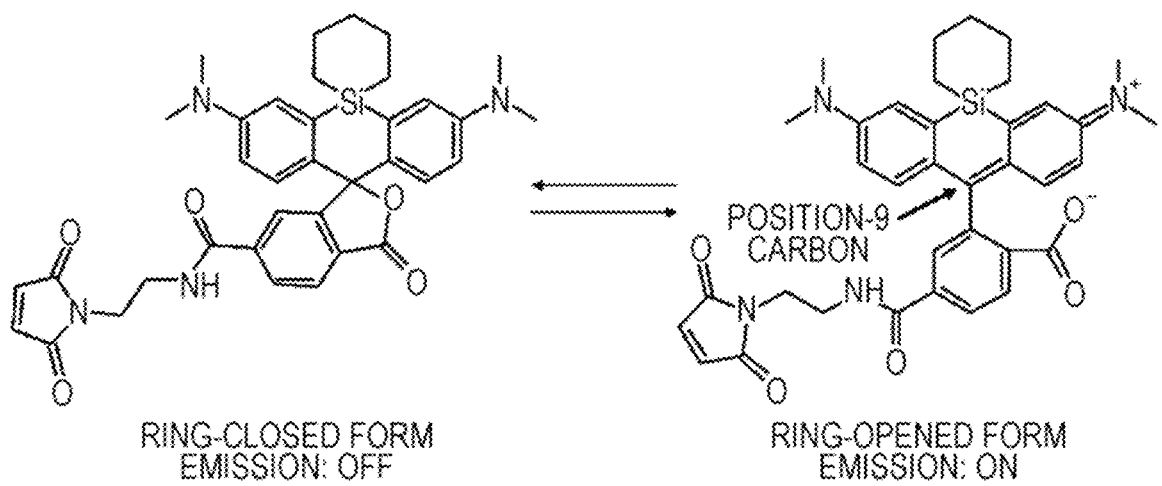
FIG. 1 illustrates structural formulae of a ring-opened form and a ring-closed form of the fluorescent dye of Example 19.

The abbreviations used in the description are conventional abbreviations which are publicly known to persons skilled in the art. In the description, the following abbreviations are used.

(A-taPhos)$_2$PdCl$_2$: bis[di-tert-butyl(4-dimethylaminophenyl)phosphine]dichloropalladium (II)
$^1$H-NMR: proton nuclear magnetic resonance spectroscopy
Bn: benzyl
Boc: tert-butoxycarbonyl
Bu: butyl
DAST: N,N-diethylaminosulfur trifluoride
DCM: dichloromethane
DDQ: 2,3-dichloro-5,6-dicyano-p-benzoquinone
DIPEA: N,N-diisopropylethylamine
DMAP: N,N-dimethyl-4-aminopyridine
DME: dimethoxyethane
DMF: N,N-dimethylformamide
DMSO: dimethylsulfoxide
HPLC: high performance liquid chromatography
LC-MS: liquid chromatography-mass spectrometry
MS: mass spectrometry
m-: meta
n-: normal
NBS: N-bromosuccinimide
NMP: N-methyl-2-pyrrolidone
o-: ortho
p-: para
PPTS: pyridinium para-toluenesulfonate
PyBOP: (benzotriazol-1-yloxy)tripyrrolidinophosphonium hexafluorophosphate
sec: secondary
t-: tertiary
tert: tertiary
TBAF: tetra-n-butylammonium fluoride
TBS: tertiary-butyldimethylsilyl
TEA: triethylamine
Tf: trifluoromethylsulfonyl
TFA: trifluoroacetic acid
THF: tetrahydrofuran
XPhos: 2-dicyclohexylphosphino-2',4',6'-triisopropylbiphenyl The term "alkyl group" refers to a monovalent group that is a linear or branched saturated hydrocarbon chain. In the fluorescent dye of the present embodiment, the alkyl group has 1 to 6 carbon atoms. In the description, an alkyl group having 1 to 6 carbon atoms refers to as a "C1-C6 alkyl group". Examples of the C1-C6 alkyl group include, but are not limited to, a methyl group, an ethyl group, a 1-propyl group, a 2-propyl group, a 1-butyl group, a 2-methyl-1-propyl group, a 2-butyl group, a 2-methyl-2-propyl (t-butyl) group, a 1-pentyl group, a 2-pentyl group, a 3-pentyl group, a 2-methyl-2-butyl group, a 3-methyl-2-butyl group, a 3-methyl-1-butyl group, a 2-methyl-1-butyl group, 1-hexyl group, a 2-hexyl group, a 3-hexyl group, a 2-methyl-2-pentyl group, a 3-methyl-2-pentyl group, a 4-methyl-2-pentyl group, a 3-methyl-3-pentyl group, a 2-methyl-3-pentyl group, a 2,3-dimethyl-2-butyl group, a 3,3-dimethyl-2-butyl group and a hexyl group.

The term "cycloalkyl group" refers to a saturated cyclic hydrocarbon group having 3 to 10 carbon atoms. Examples of the cycloalkyl group include: a monocyclic structure such as a cyclopropyl group, a cyclobutyl group, a cyclopentyl group and a cyclooctyl; and a polycyclic structure such as an adamantanyl group and a decahydronaphthyl group.

The term "heteroalkyl group" refers to a group having such a structure that at least one carbon atom other than a carbon atom located at a binding terminal in the above-mentioned alkyl group is substituted by a hetero atom selected from an oxygen atom, a nitrogen atom and a sulfur atom. The term "alkoxy group" refers to an alkyl-O— group. The term "alkylthio group" refers to an alkyl-S— group. The definition for the alkyl group is as mentioned above. The term "hydroxyalkyl group" refers to an alkyl group which is substituted by at least one, e.g., 1 to 3, hydroxy groups.

The term "aryl group" refers to an aromatic carbocyclic group which has one or more closed rings, wherein one or more of the closed rings may be independently condensed and/or crosslinked. Examples of the aryl group include, but are not limited to, a phenyl group, a naphthyl group, an anthracenyl group, a phenanthracenyl group, a biphenyl group and a pyrenyl group. The term "heteroaryl group" refers to a cyclic group having one or more closed rings in which at least one hetero atom selected from an oxygen atom, a nitrogen atom and a sulfur atom is contained in at least one of the rings, at least one of the rings is an aromatic ring, and one or more of the rings may be independently a condensed and/or crosslinked ring. Examples of the heteroaryl group include, but are not limited to, a quinolinyl group, an isoquinolinyl group, an indolyl group, a furyl group, a thienyl group, a pyrazolyl group, a quinoxalinyl group, a pyrrolyl group, an indazolyl group, a thieno[2,3-c]pyrazolyl group, a benzofuryl group, a pyrazolo[1,5-a]pyridyl group, a thiophenylpyrazolyl group, a benzothienyl group, a benzothiazolyl group, a thiazolyl group, a 2-phenylthiazolyl group and an isoxazolyl group.

The term "halogen atom" refers to a fluorine atom, a chlorine atom, a bromine atom or an iodine atom. The term "haloalkyl group" refers to an alkyl group as defined in the description which is substituted by one or more halogen atoms as defined in the description. In the haloalkyl group, the one or more halogen atoms may be the same as or different from each other.

The term "amino group" refers to a —NH$_2$ group.

The term "heterocyclic ring" refers to a saturated or partially unsaturated ring system containing one or more hetero atoms. The heterocyclic ring may be a monocyclic group, a dicyclic group, or a tricyclic group. The heterocyclic ring may contain an oxo group (=O) or a thioxo group (=S) which binds to a ring. In the description, when "A" is mentioned as a heterocyclic ring in formula (I), "A" is expressed as "heterocyclic ring A" or is simply expressed as "A".

The term "reactive group" refers to a functional group having reactivity with a specific substance which is to be labeled with the fluorescent dye of the present embodiment. Examples of the reactive group R in the fluorescent dye of the present embodiment include, but are not limited to, a hydroxy group, a carboxyl group, a sulfonate group, an unsaturated imide group, an unsaturated amide group, an unsaturated ester group, an activated carboxylic acid ester group, an amine group, an alcohol group, a nitrile group, a mercaptan group, a boronate group, a phosphoramidite group, a halogenated alkyl group, a halogenated sulfonyl group, an amide or ester group having a halogen atom at alpha-position, an isocyanate group, an isothiocyanate group, an azide group, an aldehyde group, an acylnitrile group and a photoactivatable group.

In the case where there are two or more substituents in a compound described in the description, the definitions for the substituents are independent of the definitions for other substituents. The combination of the types of the substituents or the combination of the numbers of the substituents is acceptable only when the combination can provide a chemically stable compound.

[1. Fluorescent Dye]

The present inventors have found that, when a spiro ring structure in which an Si atom acts as a spiro atom is imparted to a fluorescent dye having an Si rhodamine backbone, the duty cycle of the fluorescent dye is decreased. The term "duty cycle" as used herein refers to a ratio of the sum total of emission times of a fluorescent dye to the blinking duration time of the fluorescent dye, as mentioned in Experiment Example 2. When the duty cycle is smaller, the fluorescent dye emits light more sporadically. As a result, the single-molecule luminescence of the fluorescent dye can be detected more easily. Therefore, a fluorescent dye having a small duty cycle is suitable for a super-resolution microscopy. The present inventors can produce the fluorescent dye of the present embodiment which comprises a compound represented by formula (I) shown above, a tautomer of the compound, or a salt of the compound or the tautomer by employing a technique for decreasing the duty cycle of a fluorescent dye having an Si rhodamine backbone.

In another embodiment, in $R^1$, $R^2$, $R^3$, $R^4$, $R^5$, $R^6$, $R^7$, $R^8$, $R^9$, $R^{10}$ and $R^{11}$, the substituents for the optionally substituted C1-C6 alkyl group, the optionally substituted C1-C6 heteroalkyl, the optionally substituted C1-C6 alkoxy group and the optionally substituted C1-C6 alkylthio group may be independently selected from a halogen atom, a C1-C6 alkoxy group, a C1-C6 alkylthio group, an amino group, an aryl group, a heteroaryl group, —$CO_2H$ and —$SO_3H$. In $R^1$, $R^2$, $R^3$, $R^4$, $R^5$, $R^6$, $R^7$, $R^8$, $R^9$, $R^{10}$ and $R^{11}$, the substituents for the optionally substituted amino group, the optionally substituted N-containing heterocyclic ring, the optionally substituted aryl group and the optionally substituted heteroaryl group may be independently selected from a halogen atom, a C1-C6 alkyl group, a C1-C6 hydroxyalkyl group, a C1-C6 alkoxy group, a C1-C6 alkylthio group, an amino group, an aryl group, a heteroaryl group, —$CO_2H$ and —$SO_3H$.

In still another embodiment, in formula (I), X represents —$NR^1R^2$ and $Y^1$ represents =$N^+R^3R^4$. In this case, in formula (I), it is preferred that $R^1$, $R^2$, $R^3$ and $R^4$ independently represent an optionally substituted C1-C6 alkyl group or an optionally substituted O-containing C1-C6 heteroalkyl group. In formula (I), each of the combination of $R^1$ and $R^2$ and the combination of $R^3$ and $R^4$ may together form an optionally substituted N-containing heterocyclic ring with an N atom to which they bind. Examples of the N-containing heterocyclic ring include an azetidine ring, a pyrrolidine ring, a piperidine ring, a morpholine ring and an oxazepane ring. Each of "$R^1$ and $R^2$" and "$R^3$ and $R^4$" may be linked to each other at two sites or more. In this case, the N-containing heterocyclic ring forms a bridged ring. An example of the bridged ring is a 7-azabicyclo[2.2.1]heptane ring. In a specific embodiment, each of the substituents in $R^1$, $R^2$, $R^3$ and $R^4$ is unsubstituted or is substituted by a halogen atom or a C1-C6 alkoxy group.

In still another embodiment, in formula (I), X represents a hydroxy group and $Y^1$ represents =O.

In the present embodiment, the heterocyclic ring A is an optionally substituted heterocyclic ring which contains an Si atom as a hetero atom, and has 4 to 7 carbon atoms. In the description, a heterocyclic ring having 4 to 7 carbon atoms is referred to as a "C4-C7 heterocyclic ring". The heterocyclic ring A may also contain a hetero atom other than the Si atom (e.g., an oxygen atom, a nitrogen atom, a sulfur atom) in a ring. For example, the heterocyclic ring A may be substituted by one or more substituents independently selected from a halogen atom, a C1-C6 alkyl group, a C1-C6 haloalkyl group, a C1-C6 alkoxy group, a C1-C6 alkylthio group, an amino group, an aryl group, a heteroaryl group, —$CO_2H$ and —$SO_3H$. The heterocyclic ring A is preferably monocyclic, and examples of the heterocyclic ring A include, but are not limited to, the rings shown below. Each of the rings shown below may be substituted.

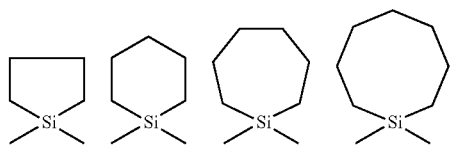

[Formula 2]

In a specific embodiment, the heterocyclic ring A is a C4 or C5 heterocyclic ring shown below. Each of the rings shown below may be substituted.

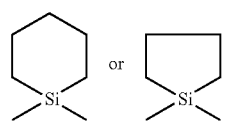

[Formula 3]

In still another embodiment, the heterocyclic ring A is unsubstituted.

In still another embodiment, in formula (I), each of $R^8$ and $R^{11}$ represents an H atom.

In still another embodiment, in formula (I), $R^7$ represents —$CO_2^-$. In this case, a tautomer of the compound of formula (I) is a compound represented by formula (II). In formula (II), $Y^2$ represents a hydroxy group or —$NR^3R^4$, and the definitions for A, X, $R^5$, $R^6$ and $R^8$ to $R^{11}$ are the same as those defined in formula (I).

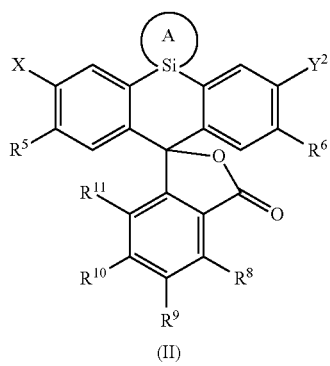

(II)

In the present embodiment, L may be saturated or partially unsaturated. In still another embodiment, -L-R represents —CONH-L'-R. L' is a bivalent linker which has 1 to 13 non-hydrogen atoms and has a linear structure, a branched structure, a cyclic structure or a structure that is an arbitrary combination of these structures. In the case where there are one or more hetero atoms in the bivalent linker, the hetero atoms are contained as one or more groups independently selected from the group consisting of an ester group, an amine group, an amide group, an ether group, a thioether group and a carbonyl group. The amine group in L and L' is a secondary or tertiary amine. In a specific embodiment, L-R represents —CONH—$(CH_2)_n$—R (wherein n represents an integer of 1 to 13). In another embodiment, n represents an integer of 1 to 6. In still another embodiment, n represents an integer of 1, 2 or 3. In a specific embodiment, L represents —CONH—$C_2H_4$—$(C_2H_4O)_m$—R (wherein m represents 1, 2 or 3). In a specific embodiment, R represents 1-male imide.

In a specific embodiment, either one of $R^9$ or $R^{10}$ represents any one of the groups shown below.

[Formula 5]

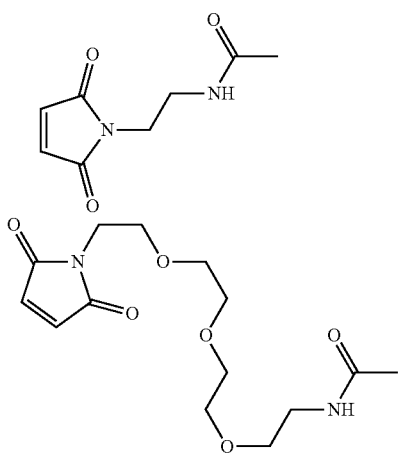

In this case, the remainder of $R^9$ and $R^{10}$ represents a group that is different from -L-R. In a specific embodiment, the remainder group is a hydrogen atom; a halogen atom; a C1-C6 alkyl group which may be substituted by one or more substituents independently selected from the group consisting of a halogen atom, a C1-C6 alkoxy group and a C1-C6 alkylthio group; or an amino group which may be substituted by one or more substituents independently selected from the group consisting of a C1-C6 alkyl group and a C1-C6 hydroxyalkyl group.

Preferred examples of the compound of formula (I) or the tautomer of the compound include compounds represented by the structural formulae shown below. However, the fluorescent dye of the present embodiment is not limited to these compounds.

[Formula 6]

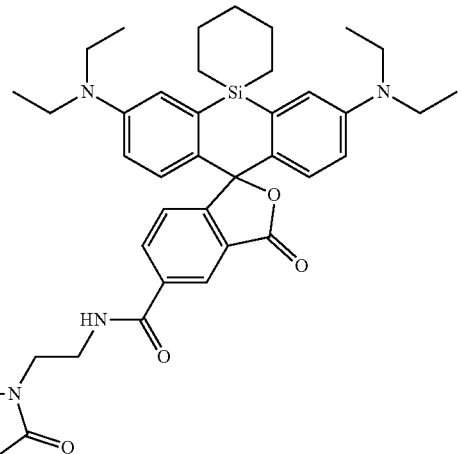

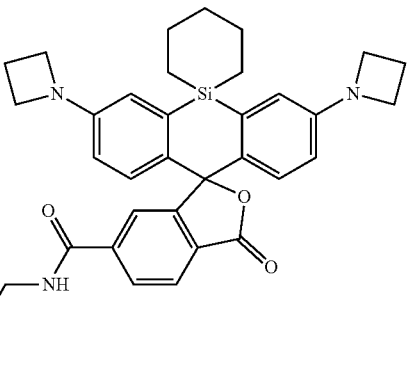

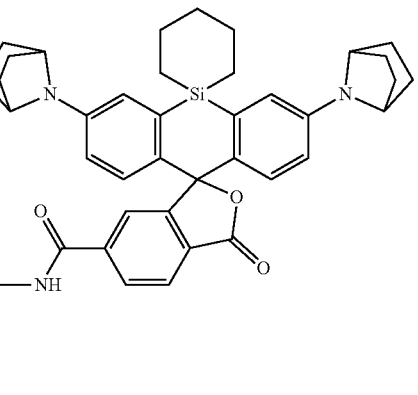

-continued
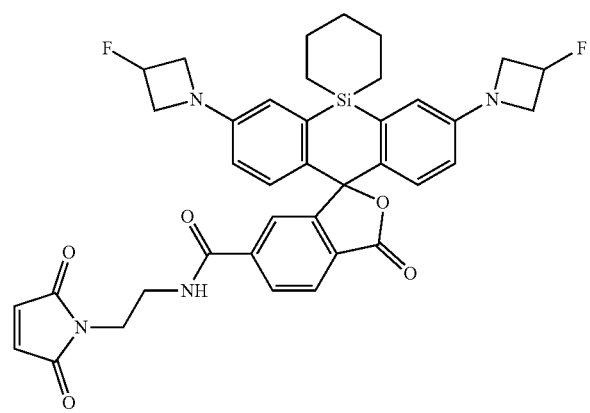
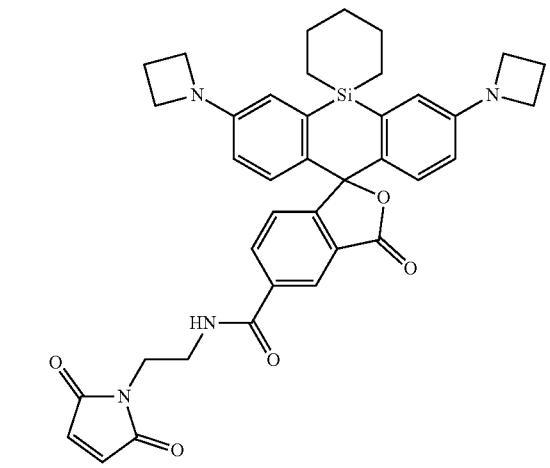
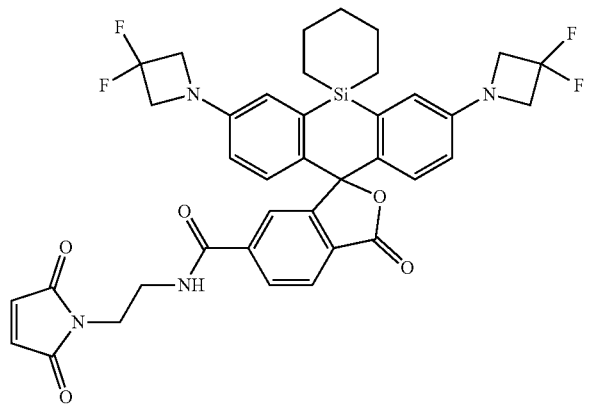
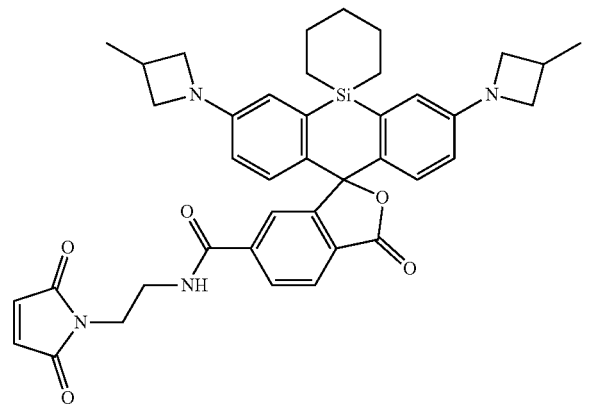
-continued
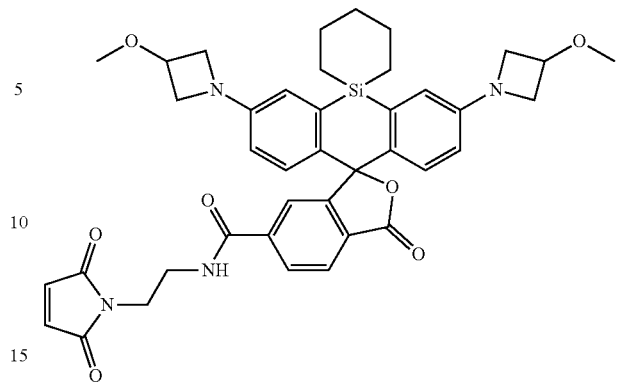
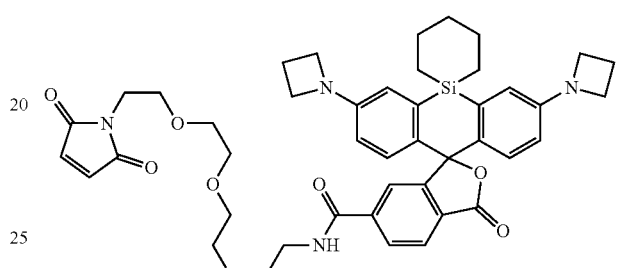
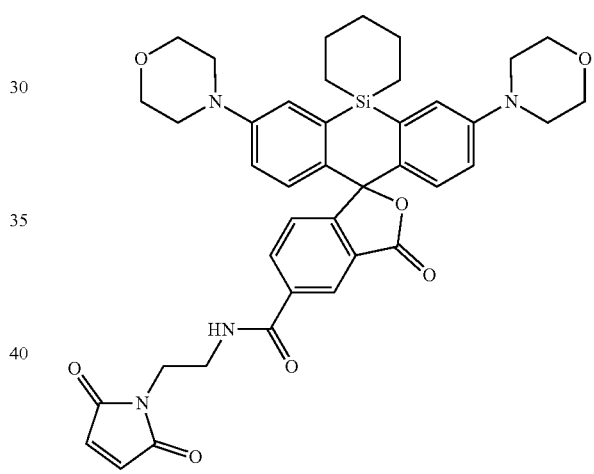
[Formula 7]
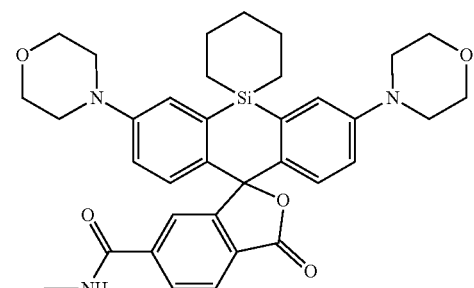
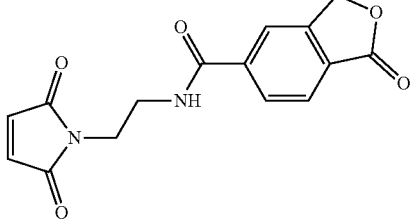

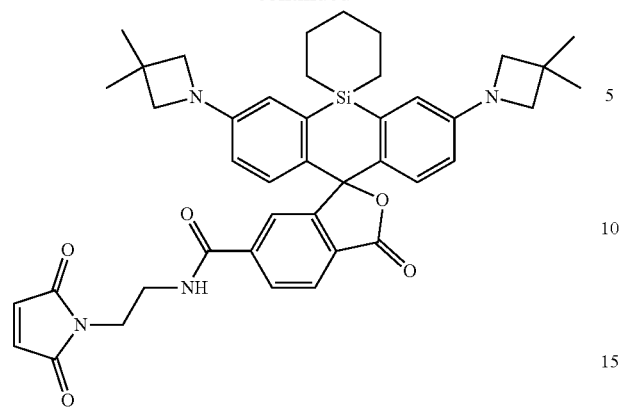
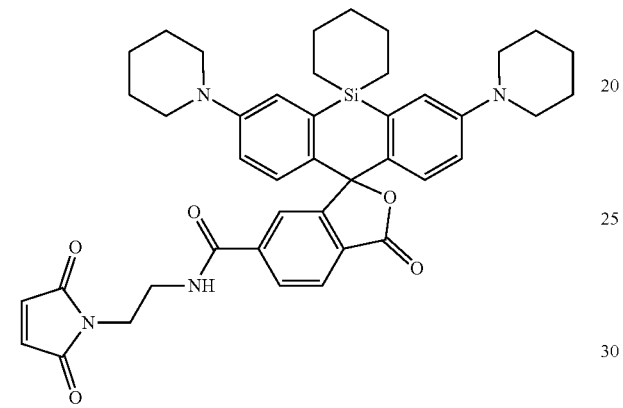
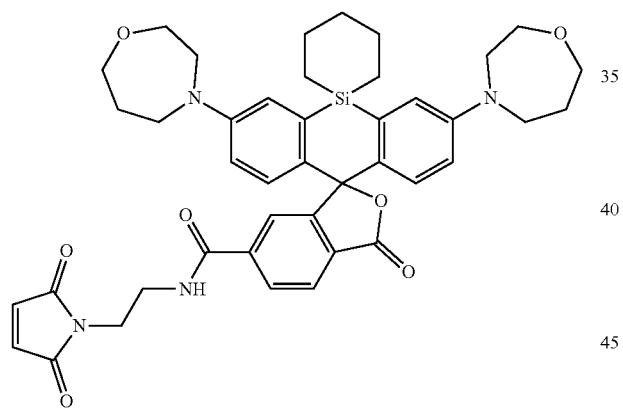
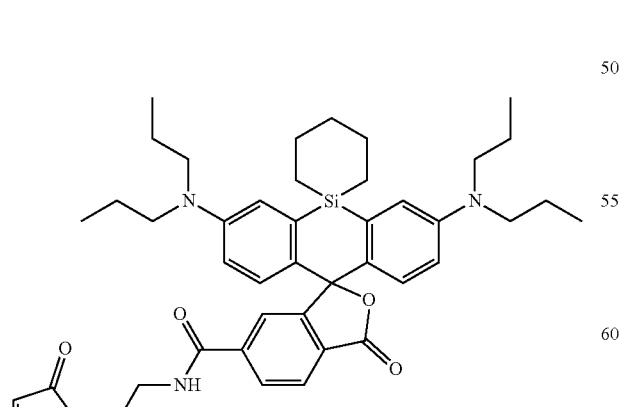
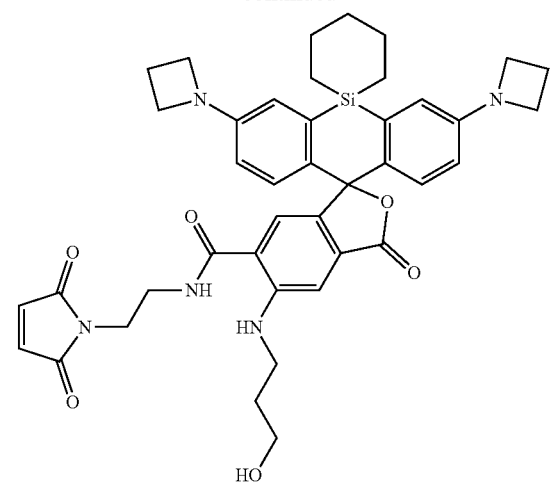
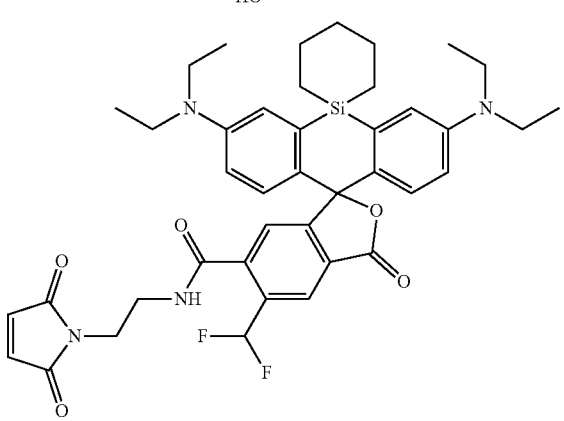
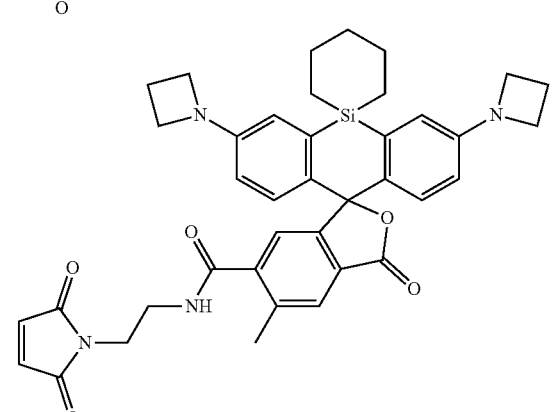
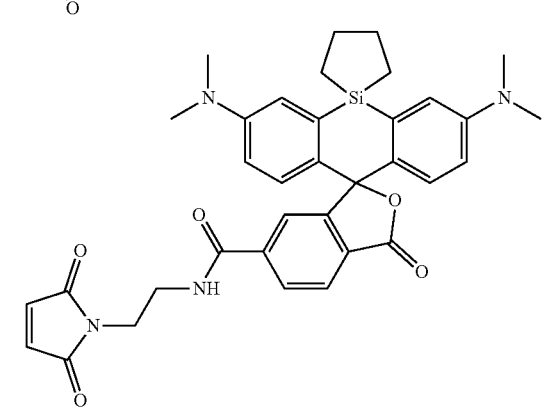

-continued

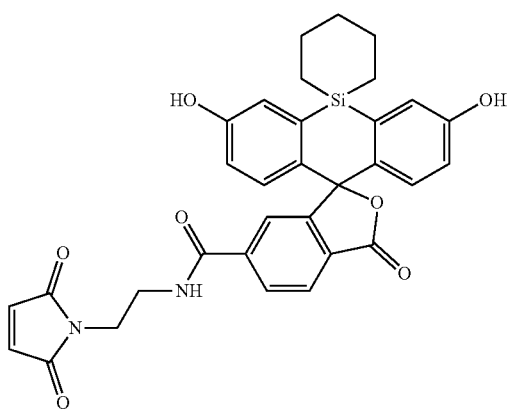

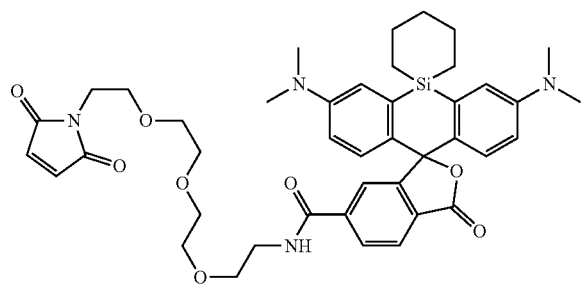

<General Production Method>

Next, the method for synthesizing the compound of formula (I) or a salt thereof is described.

The compound of formula (I-2) can be synthesized from a compound of formula (I-1) which has such a structure that $R^7$ is COO— and either one of $R^9$ or $R^{10}$ is COOH in formula (I) by the method shown in scheme 1-1.

Scheme 1-1

[Formula 8]

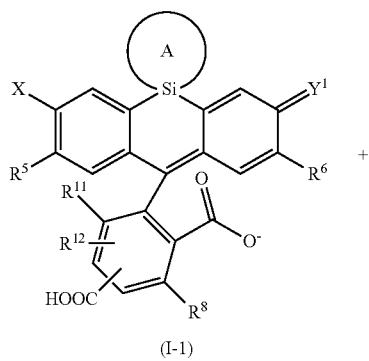

(I-1)

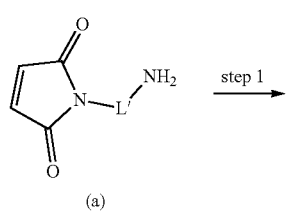

(a)

-continued

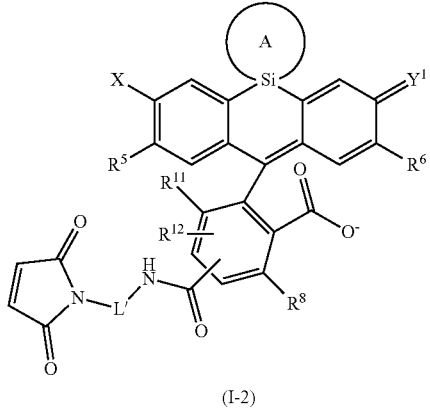

(I-2)

In the formulae, A, X, $Y^1$ and $R^5$ to $R^{11}$ are as defined in formula (I); L' represents a bivalent linker having 1 to 13 non-hydrogen atoms and having a linear structure, a branched structure, a cyclic structure or a structure that is an arbitrary combination of these structures, wherein, when there are one or more hetero atoms in the bivalent linker, the hetero atoms are contained as one or more groups independently selected from the group consisting of an ester group, an amine group, an amide group, an ether group, a thioether group and a carbonyl group; and $R^{12}$ represents a group selected from the group consisting of an H atom, a halogen atom, an optionally substituted C1-C6 alkyl group, an optionally substituted C1-C6 alkoxy group, an optionally substituted C1-C6 alkylthio group, an optionally substituted amino group, an optionally substituted aryl group, an optionally substituted heteroaryl group, $SO_3H$ and $SO_3$. Each of formulae (I-1), (a) and (1-2) may be provided as a salt thereof. The type of the salt is not particularly limited, and a TFA salt or the like can be used. The compound of formula (a) may be synthesized by a known method, or a commercially available product may be used. As an example of the commercially available product, a N-(2-aminoethyl) maleimide TFA salt can be used. The reaction shown in step 1 is a common amidation reaction, and a condensing agent may be used if necessary. As an example of the condensing agent, PyBOP may be used. The solvent to be used in the reaction is not particularly limited, as long as the solvent is inert. For example, THF, DME, DMF, NMP, DMSO, a mixture thereof or the like may be used as the solvent. In order to accelerate the reaction, a base may be added. The base is not particularly limited, and TEA, DIPEA, pyridine or the like may be used.

As an alternative method, a maleimide moiety may be constructed in the final stage, as shown in scheme 1-2.

Scheme 1-2

[Formula 9]

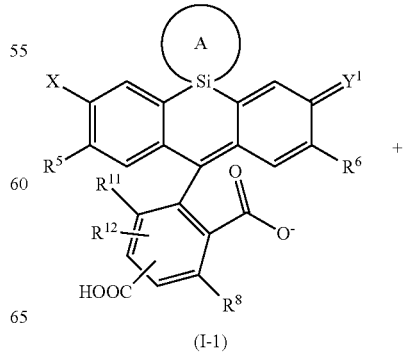

(I-1)

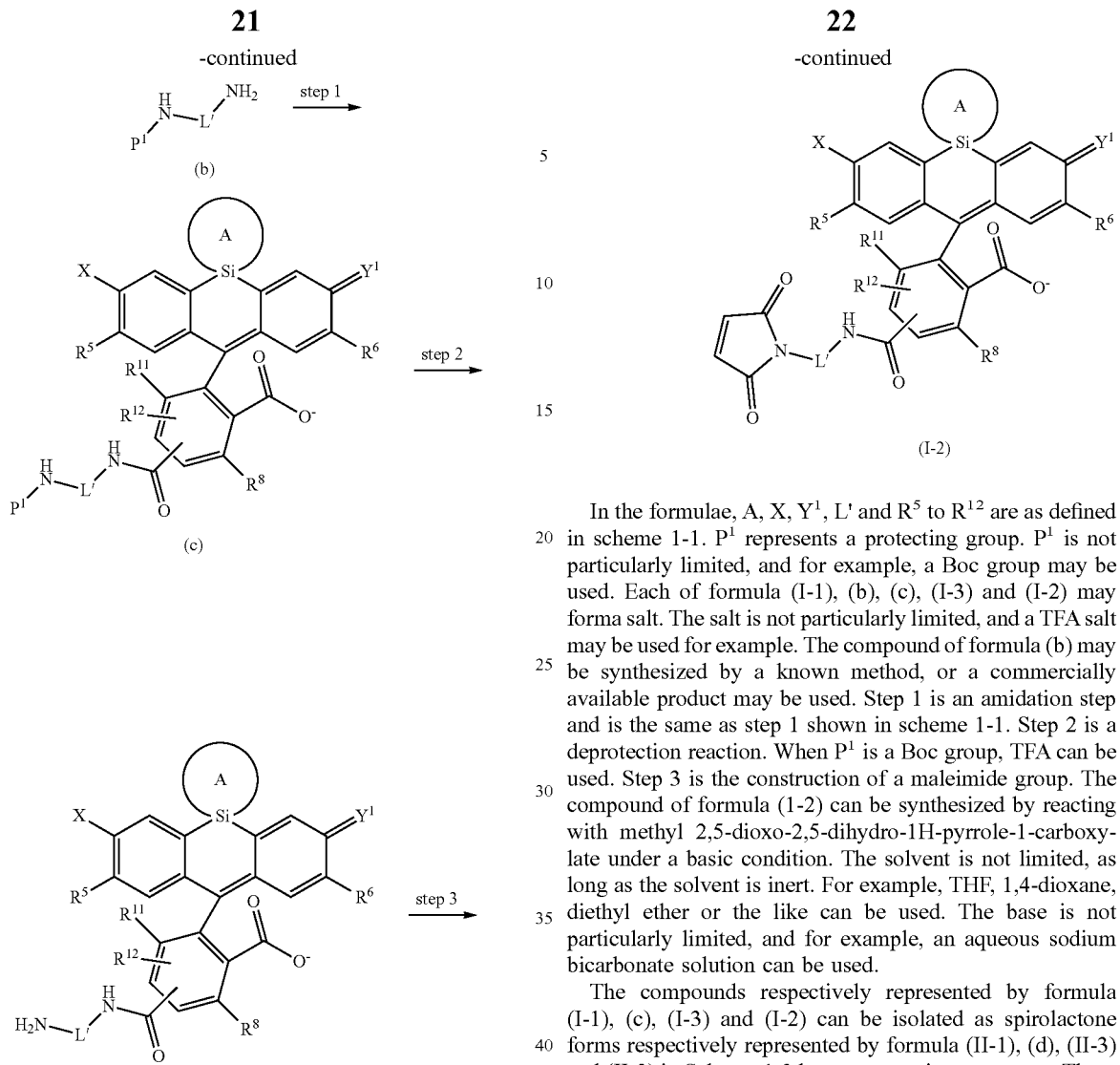

In the formulae, A, X, $Y^1$, L' and $R^5$ to $R^{12}$ are as defined in scheme 1-1. $P^1$ represents a protecting group. $P^1$ is not particularly limited, and for example, a Boc group may be used. Each of formula (I-1), (b), (c), (I-3) and (I-2) may form a salt. The salt is not particularly limited, and a TFA salt may be used for example. The compound of formula (b) may be synthesized by a known method, or a commercially available product may be used. Step 1 is an amidation step and is the same as step 1 shown in scheme 1-1. Step 2 is a deprotection reaction. When $P^1$ is a Boc group, TFA can be used. Step 3 is the construction of a maleimide group. The compound of formula (1-2) can be synthesized by reacting with methyl 2,5-dioxo-2,5-dihydro-1H-pyrrole-1-carboxylate under a basic condition. The solvent is not limited, as long as the solvent is inert. For example, THF, 1,4-dioxane, diethyl ether or the like can be used. The base is not particularly limited, and for example, an aqueous sodium bicarbonate solution can be used.

The compounds respectively represented by formula (I-1), (c), (I-3) and (I-2) can be isolated as spirolactone forms respectively represented by formula (II-1), (d), (II-3) and (II-2) in Scheme 1-3 by an appropriate treatment. These compounds can exist in the equilibrium states shown in scheme 1-3 with each other when dissolved in a proper buffering solution.

Scheme 1-3

[Formula 10]

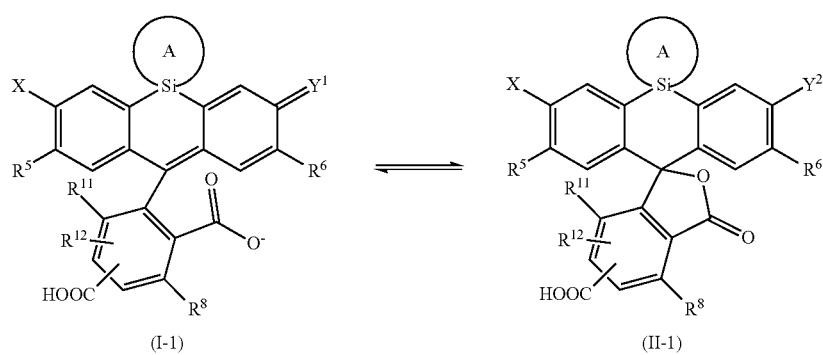

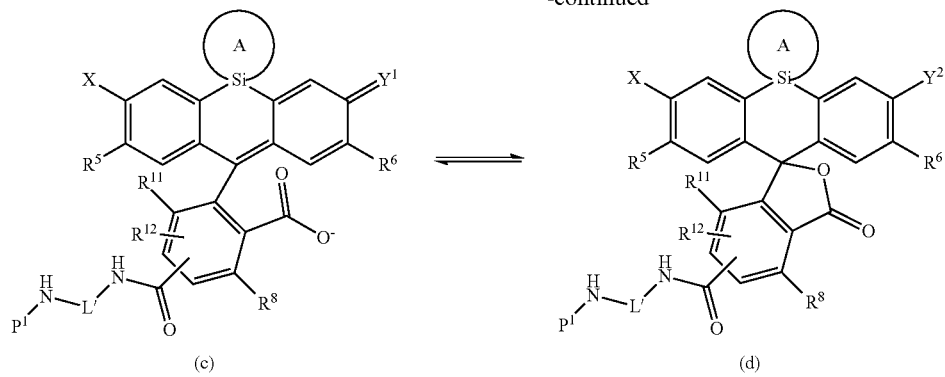
(c) ⇌ (d)
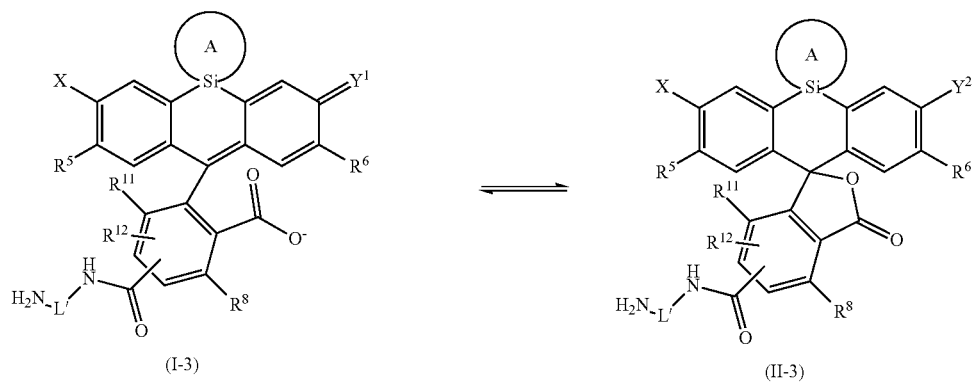
(I-3) ⇌ (II-3)
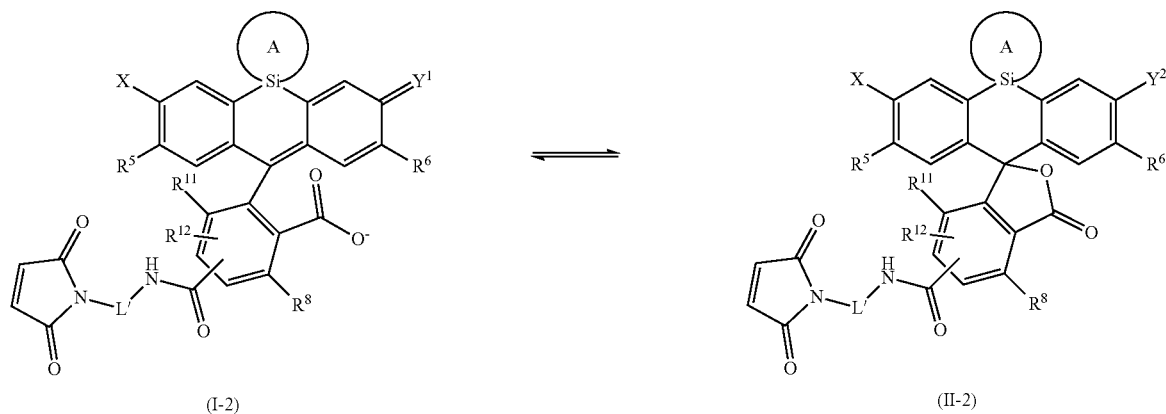
(I-2) ⇌ (II-2)
Formulae (I-1), (c), (I-3) and (I-2) are as defined in scheme 1-2. Formulae (II-1), (d), (II-3) and (II-2), A, X, $Y^2$, $R^5$ to $R^{11}$ are as defined in formula (II), and L' and $R^{12}$ are as defined in scheme 1-2.
The compound of formula (I-1) can be synthesized by the method shown in scheme 2-1 from a compound of formula (e) and a compound of formula (f).
Scheme 2-1
[Formula 11]
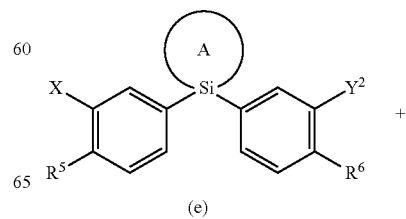
(e)

-continued

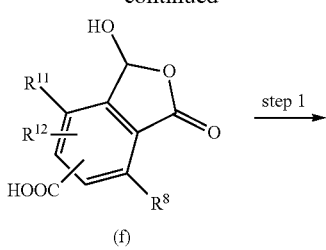

(f)

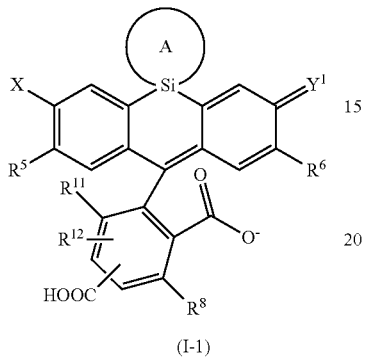

(I-1)

A, X, Y$^1$ and R$^5$ to R$^{11}$ in the compounds of formulae (e) and (f) are as defined in formula (II), and formula (I-1) is as defined in scheme 1-1. In formula (e), X and Y$^2$ are preferably NR$^1$R$^2$ and NR$^3$R$^4$, respectively, and R$^1$ to R$^4$ are as defined in formula (II). In formula (I-1), X and Y$^1$ are preferably NR$^1$R$^2$ and N$^+$R$^3$R$^4$, respectively, and R$^1$ to R$^4$ are as defined in formula (I). Step 1 is an oxidation reaction subsequent to the condensation reaction, in which xylene or acetic acid can be used as a solvent, and copper (II) bromide can be used as an oxidizing agent. The reaction can be accelerated by heating. The heating is generally carried out at 80° C. to 140° C. If necessary, heating with microwaves may be employed.

A compound of formula (I-4) which has such a structure that X is NR$^1$H and Y$^1$ is N$^+$R$^3$H in formula (I-1) can be produced by the method shown in scheme 2-2 from a compound of formula (g) and a compound of formula (f).

Scheme 2-2

[Formula 12]

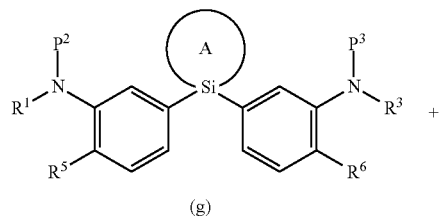

(g)

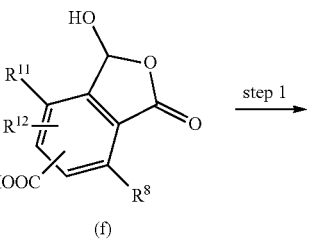

(f)

-continued

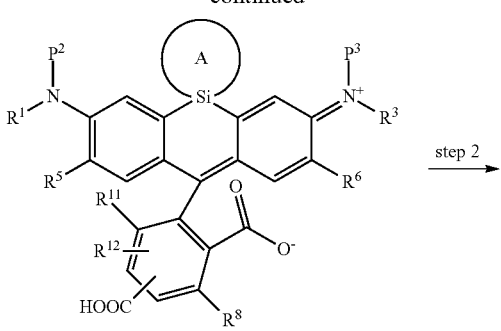

(h)

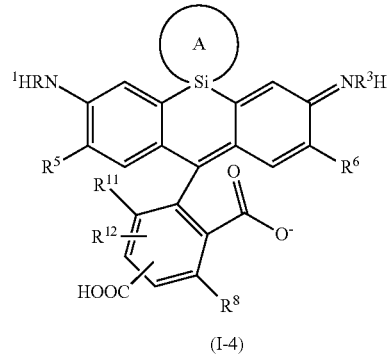

(I-4)

In the compounds respectively represented by formulae (f), formula (h) and formula (I-4), R$^1$ to R$^{12}$ and A are as defined in scheme 1-1. In formula (g), R$^1$ to R$^5$ are as defined in formula (II), and P$^2$ and P$^3$ represent protecting groups which are the same as or different from each other. The protecting group is not particularly limited, and for example, an allyl group can be used. Step 1 is the same reaction as that mentioned in scheme 2-1, and step 2 is a deprotection reaction. In the deprotection reaction, when each of P$^2$ and P$^3$ is an allyl group for example, 1,3-dimethylbarbituric acid can be used in the presence of tetrakis(triphenylphosphine) palladium (0). The solvent is not particularly limited, as long as the solvent is inert. For example, DCM can be used.

The compound of formula (e) to be used in scheme 2-1 can be synthesized by the following method.

Scheme 2-3

[Formula 13]

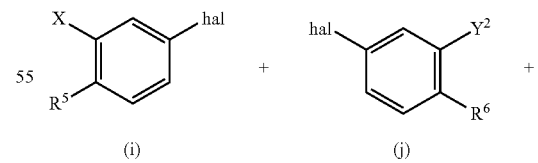

(i) (j)

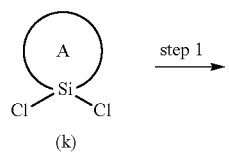

(k)

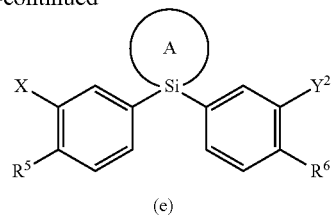

(e)

In the formulae, ring A, X, $Y^2$, $R^5$ and $R^6$ are as defined in scheme 2-1, and hal represents a halogen atom. The compound of formula (e) can be synthesized by acting an alkyl metal reagent on a compound of formula (i) and a compound of formula (j) and then reacting the resultant compound with a cyclic dichlorosilane reagent represented by formula (k). As the compound of formula (i) and the compound of formula (j), commercially available products may be used. Alternatively, these compounds may be synthesized by known methods. As the halogen atom, a bromine atom or the like can be used. As the alkyl metal reagent, n-butyllithium or the like can be used. The solvent is not particularly limited, as long as the solvent is inert. For example, THF, diethyl ether or the like may be used. The reaction temperature is generally room temperature or lower, and is preferably 0° C.

The compound of formula (g) to be used in scheme 2-2 can be synthesized by the following method.

Scheme 2-4

[Formula 14]

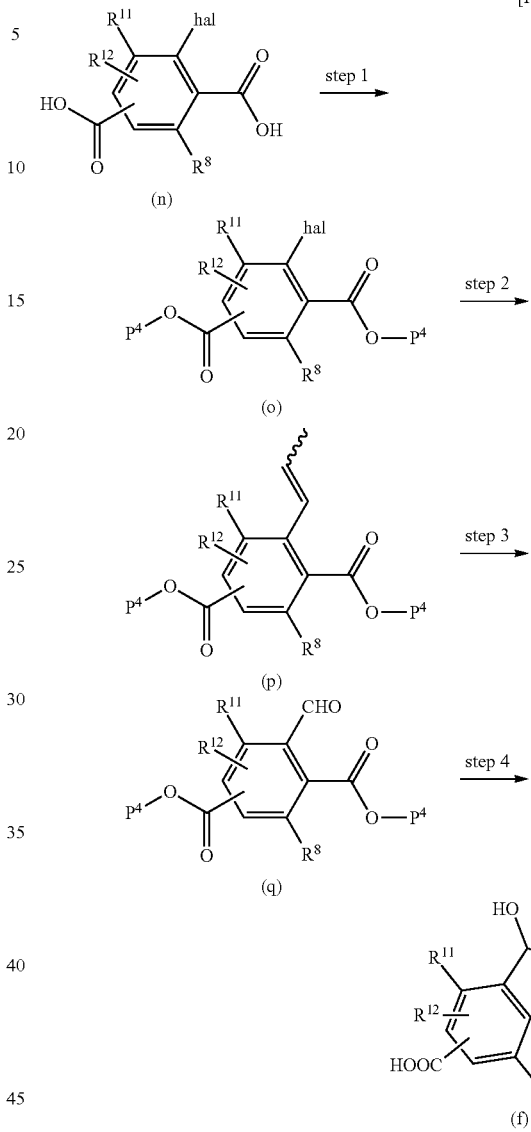

In the formulae, ring A, $R^1$, $R^3$, $R^5$, $R^6$, $P^2$ and $P^3$ are as defined in scheme 2-2, and hal represents a halogen atom. Step 1 is the same method as that shown in scheme 2-3. As the compound of formula (l) and the compound of formula (m), commercially available products may be used. Alternatively, these compounds may be synthesized by known methods or the methods mentioned in Production Examples.

The method for producing the compound of formula (f) to be used in scheme 2-1 and scheme 2-2 is not limited to one method. For example, the compound can be synthesized by the following method.

Scheme 2-5

[Formula 15]

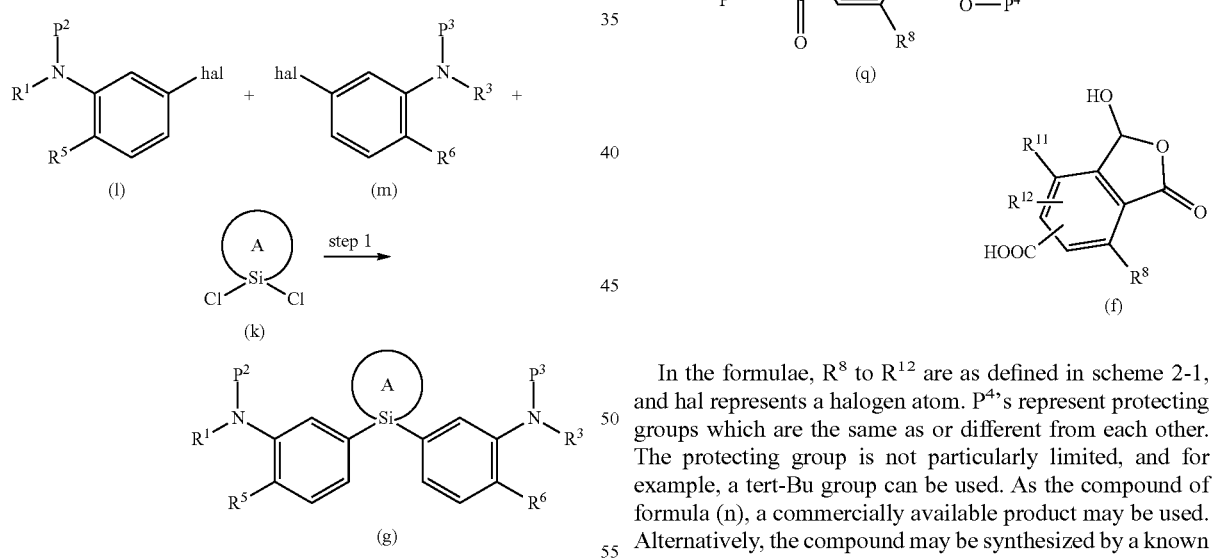

In the formulae, $R^8$ to $R^{12}$ are as defined in scheme 2-1, and hal represents a halogen atom. $P^4$'s represent protecting groups which are the same as or different from each other. The protecting group is not particularly limited, and for example, a tert-Bu group can be used. As the compound of formula (n), a commercially available product may be used. Alternatively, the compound may be synthesized by a known method or the method mentioned in Production Examples. In the case where the protecting group $P^4$ is a tert-Bu group, the compound of formula (o) can be produced by converting a carboxyl group in the compound of formula (n) to an acid chloride and then reacting the resultant product with potassium tert-butoxide. The solvent is not particularly limited, as long as the solvent is inert. For example, dichloromethane, THF or a mixed solvent thereof can be used as the solvent. With respect to the reaction temperature, the reaction can be generally carried out at 0° C. to room temperature. Alternatively, the compound of formula (o) may be produced by reacting the compound of formula (n) with di-tert-butyl dicarbonate in the presence of DMAP. The solvent is not particularly limited, as long as the solvent is inert. For example, THF, diethyl ether, DMF, dichloromethane, toluene, 1,4-dioxane or a mixed solvent thereof may be used as the solvent. With respect to the reaction temperature, the reaction can be generally accelerated by heating, and can be carried out at room temperature to the boiling point of the solvent. The compound of formula (p) can be produced from the compound of formula (o) and tri-n-butyl(1-propenyl)tin by a Migita-Kosugi-Stille cross coupling reaction. The halogen atom is not particularly limited, and for example, a bromine atom can be used. As the catalyst, tetrakis(triphenylphosphine)palladium (0) can be used. As the solvent, NMP can be used. With respect to the reaction temperature, the reaction can be generally accelerated by heating, and the reaction can be preferably carried out at 120° C. The compound of formula (p) can be generally produced as a mixture of geometrical isomers thereof, in which the abundance ratio of the isomers is not particularly limited. The compound of formula (q) can be produced by the oxidative cleavage of a 1-propenyl group in the compound of formula (p). The oxidizing agent is not particularly limited, and for example, the compound can be produced by dissolving the compound of formula (p) in a water-containing solvent and then adding a base, a catalytic amount of osmium tetroxide and an excess amount of sodium periodate. The solvent is not particularly limited, as long as the solvent is inert. For example, 1,4-dioxane can be used. As the base, 2,6-lutidine can be used as the solvent. The compound of formula (f) can be produced by deprotecting the compound of formula (q). The reaction condition is not particularly limited, and for example, when the protecting group $P^4$ is a tert-Bu group, TFA can be used.

In formula (n), formula (o) and formula (p) in scheme 2-5, when $R^{12}$ is hal, the compound synthesized in step 3 is expressed as "formula (r)" in scheme 2-6. The compound of formula (q) can also be synthesized by the method of scheme 2-6 from the compound of formula (r).

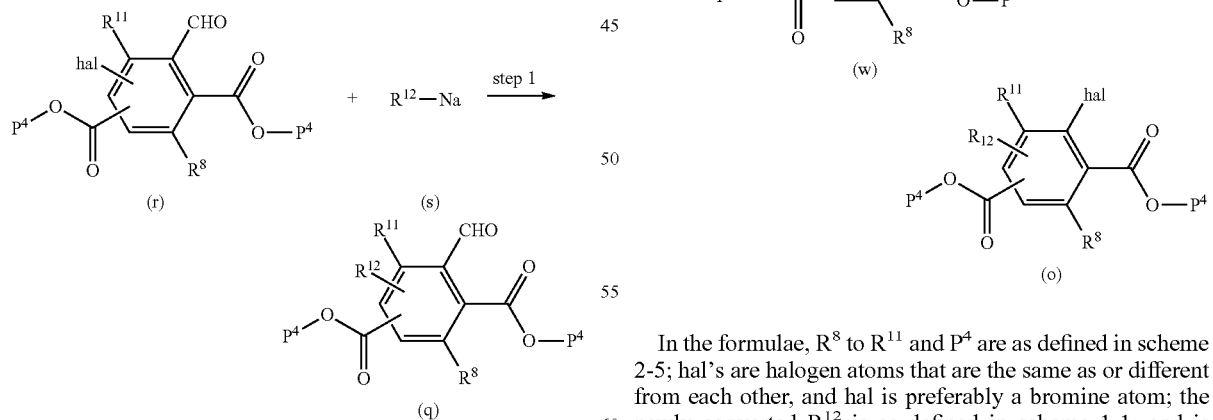

Scheme 2-6

[Formula 16]

In the formulae, $R^8$ to $R^{11}$, hal and $P^4$ are as defined in scheme 2-5. The newly introduced $R^{12}$ is as defined in scheme 1-1, and is preferably an optionally substituted C1-C6 alkoxy group or an optionally substituted C1-C6 alkylthio group. The halogen atom is not particularly limited, and for example, a fluorine atom can be used. Step 1 is an aromatic nucleophilic substitution reaction, in which, as the compound represented by formula(s), sodium methoxide, sodium methanethiolate or the like can be used. The solvent is not particularly limited, as long as the solvent is inert. For example, THF, diethyl ether, methanol or a mixture thereof can be used as the solvent.

In the case where $R^{12}$ in formula (n) in scheme 2-5 represents hal, formula (n) can be expressed as "formula (t)" in scheme 2-7. The compound of formula (o) can be produced from the compound of formula (t) from the method shown in scheme 2-7.

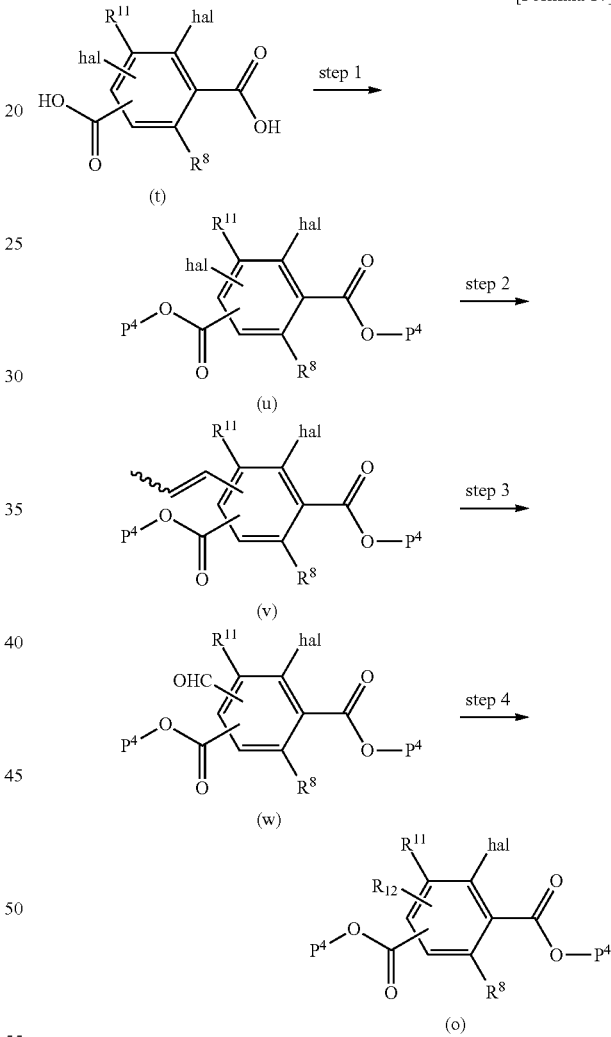

Scheme 2-7

[Formula 17]

In the formulae, $R^8$ to $R^{11}$ and $P^4$ are as defined in scheme 2-5; hal's are halogen atoms that are the same as or different from each other, and hal is preferably a bromine atom; the newly converted $R^{12}$ is as defined in scheme 1-1; and is preferably an optionally substituted C1-C6 alkyl group. As the compound of formula (t), a commercially available product may be used. Alternatively, the compound may be synthesized by a known method. The compound of formula (u) can be produced by the same method as step 1 in scheme 2-5. The compound of formula (v) can be synthesized by introducing a propenyl group into one of two hal's in formula (u) selectively. More specifically, the compound of formula (v) can be synthesized from the compound of formula (u) and tri-n-butyl(1-propenyl)tin by a Migitacompounds are dissolved in a proper buffering solution, these compounds can exist in the equilibrium state shown in scheme 2-9.

Scheme 2-9

[Formula 19]

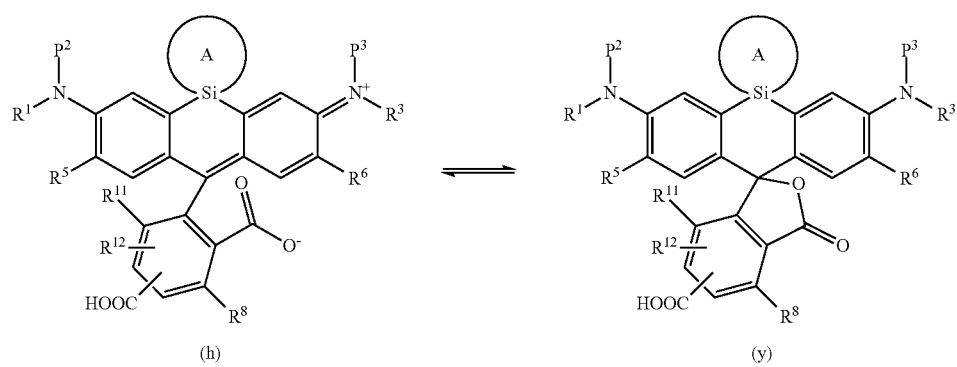

(h)　　　　　　　　　　　　　　(y)

Kosugi-Stille cross coupling reaction. As the catalyst, tetrakis(triphenylphosphine)palladium (0) can be used. As the solvent, NMP can be used. With respect to the reaction temperature, the reaction can be generally accelerated by heating, and the reaction can be preferably carried out at 120° C. The compound of formula (v) is generally produced as a mixture of geometrical isomers thereof, in which the abundance ratio of the isomers is not particularly limited. The compound of formula (w) can be synthesized by the same method as step 3 in scheme 2-5. The aldehyde group in the compound of formula (w) can be converted to $R^{12}$ via step 4 by various methods. Step 4 may be composed of a single stage or a plurality of stages. In an example of the single stage, the compound of formula (w) is reacted with DAST to induce into a difluoromethyl group. In an example of the plurality of stages, the compound of formula (w) is reacted with sodium borohydride and the resultant alcohol is converted to bromine by Appel reaction and is then substituted by sodium methoxide to convert into a methoxymethyl group.

The compound of formula (f) can have the structure represented by formula (x) due to tautomerism. In general, the compound is produced as a mixture of these compounds, in which the abundance ratio of the compounds is not particularly limited.

In the formula, A, $R^1$ to $R^{12}$, $P^2$ and $P^3$ are as defined in scheme 2-2.

The compound of formula (I-1) can also be synthesized by the method shown in scheme 3-1.

Scheme 3-1

[Formula 20]

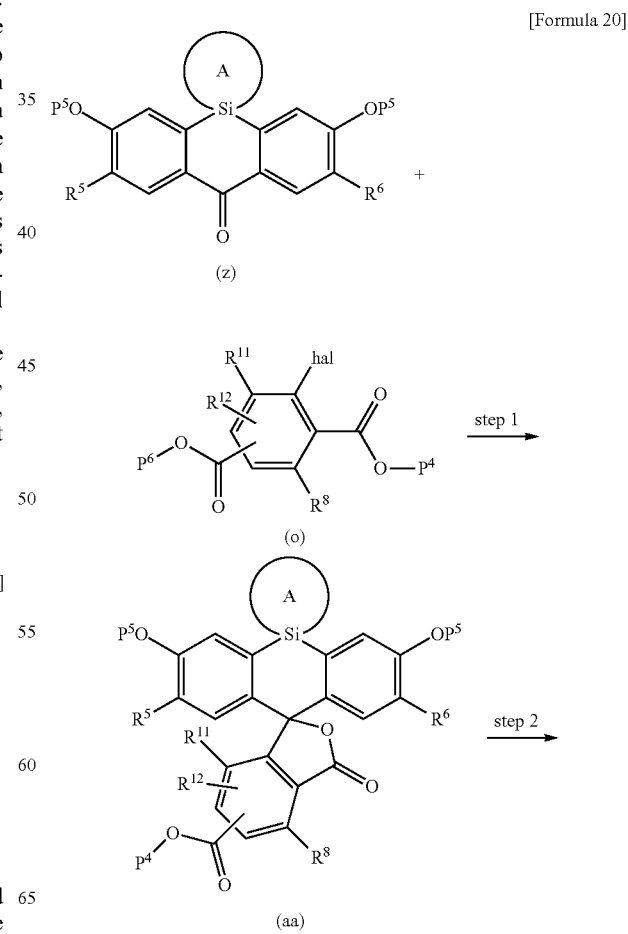

Scheme 2-8

[Formula 18]

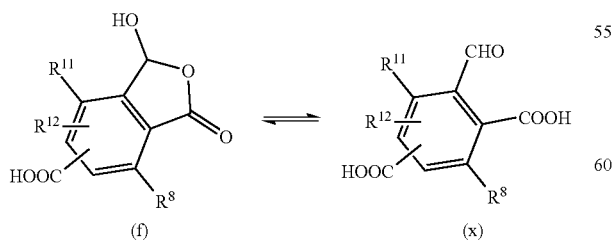

(f)　　　　　　　　　　　　(x)

The compound represented by formula (h) can be isolated as a spirolactone form represented by formula (y) in scheme 2-9 when subjected to an appropriate treatment. When these

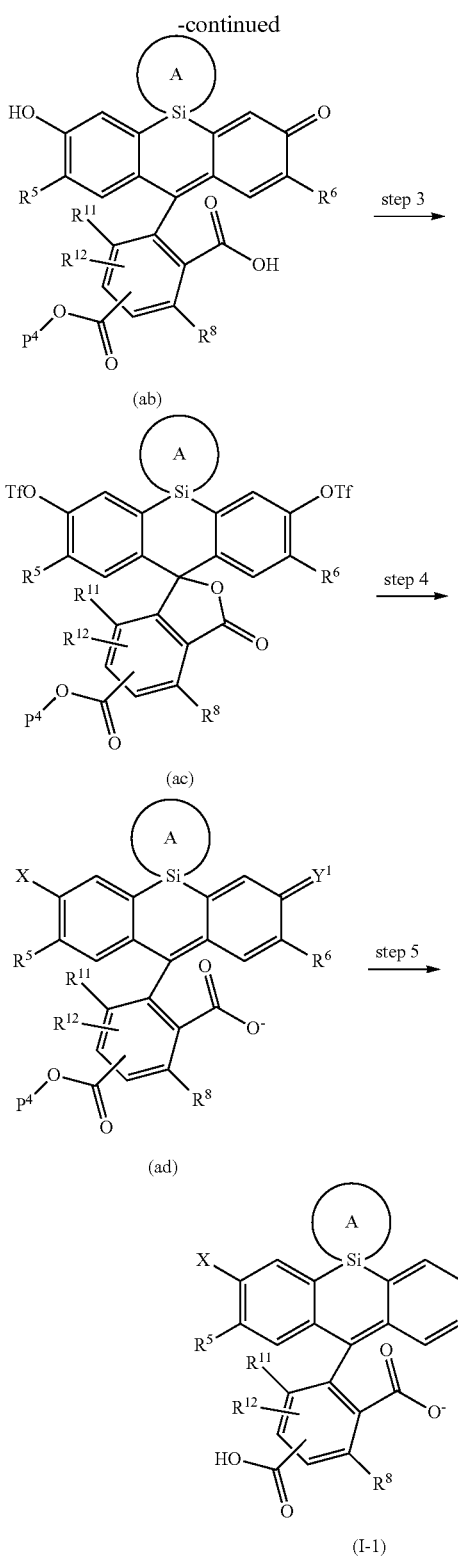

(ab)

(ac)

(ad)

(I-1)

In the formulae, ring A, X, $Y^1$ and $R^1$ to $R^{12}$ are as defined in scheme 1-1, and hal and $P^4$ are as defined in scheme 2-5; and $P^5$'s represent protecting groups that are the same as or different each other. The protecting group $P^4$ is not particularly limited, and for example, a tert-Bu group can be used. The protecting group $P^5$ is not particularly limited, and for example, a TBS group can be used. As the halogen atom, a bromine atom can be used. The compound of formula (I-1) may form a salt. The salt is not particularly limited, and for example, a TFA salt can be used. The compound of formula (aa) can be synthesized by reacting the compound of formula (o) with an alkyl metal reagent and then adding the compound of formula (z). As the alkyl metal reagent, n-butyllithium can be used. With respect to the reaction temperature, the reaction is generally carried out at room temperature or lower, and the reaction can be carried out at −100° C. to room temperature. The solvent is not particularly limited, as long as the solvent is inert. For example, THF, n-hexane and a mixture thereof can be used as the solvent. It is possible to add a Lewis acid as a catalyst. As the Lewis acid, a boron trifluoride diethyl ether complex can be used. The compound of formula (ab) can be synthesized by deprotecting the protecting group $P^5$ in the compound of formula (aa). In the case where the protecting group $P^5$ is a TBS group, the deprotection can be carried out with, for example, TBAF. The solvent is not particularly limited, as long as the solvent is inert. For example, THF can be used as the solvent. The compound of formula (ac) can be synthesized by reacting the compound of formula (ab) with trifluoromethanesulfonic anhydride. The base is not particularly limited, and for example, pyridine can be used. The solvent is not particularly limited, and for example, dichloromethane can be used. In the case where X is $NR^1R^2$ and $Y^1$ is $N^+R^3R^4$, the compound of formula (ad) can be synthesized from the compound of formula (ac) by a Buchwald-Hartwig reaction. As the palladium catalyst to be used in the reaction, tetrakis(triphenylphosphine)palladium (0), palladium (II) acetate, tris(benzylideneacetone)dipalladium (0), $(A-taPhos)_2PdCl_2$ or the like can be used, and a phosphorus ligand such as XPhos may be added thereto as required. As the base, cesium carbonate, sodium tert-butoxide, potassium tert-butoxide and the like can be used. As the solvent, 1,4-dioxane, toluene, THF and the like can be used. The reaction can be generally accelerated by heating, and the reaction can be generally carried out in a sealed tube at 100° C. to at 120° C. If necessary, heating with microwaves may also be employed. The compound of formula (I-1) can be synthesized by deprotecting the protecting group $P^4$ in formula (ad). In the case where $P^4$ is a tert-Bu group, TFA can be used.

In the case where $R^{12}$ in formula (o) represents hal, formula (o) can be expressed as "formula (u)" in scheme 3-2. The compound of formula (aa) can be synthesized from the compound of formula (u) by the method shown in scheme 3-2.

Scheme 3-2

[Formula 21]

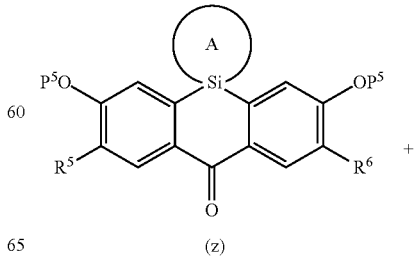

(z)

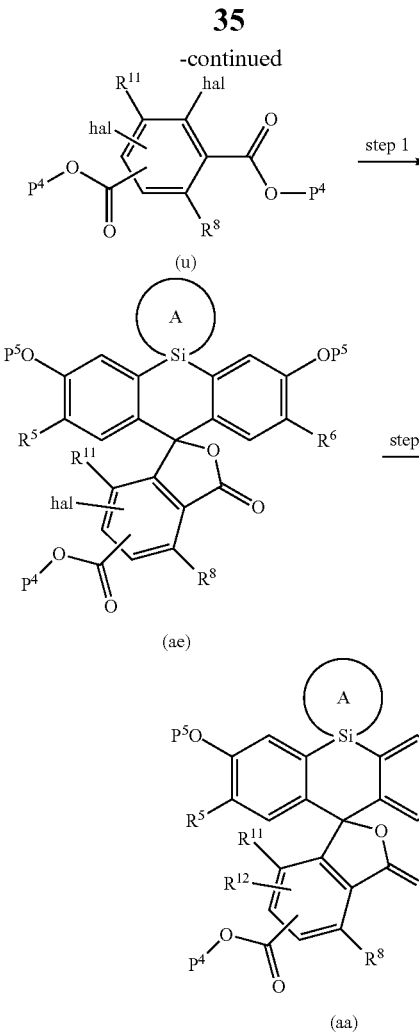

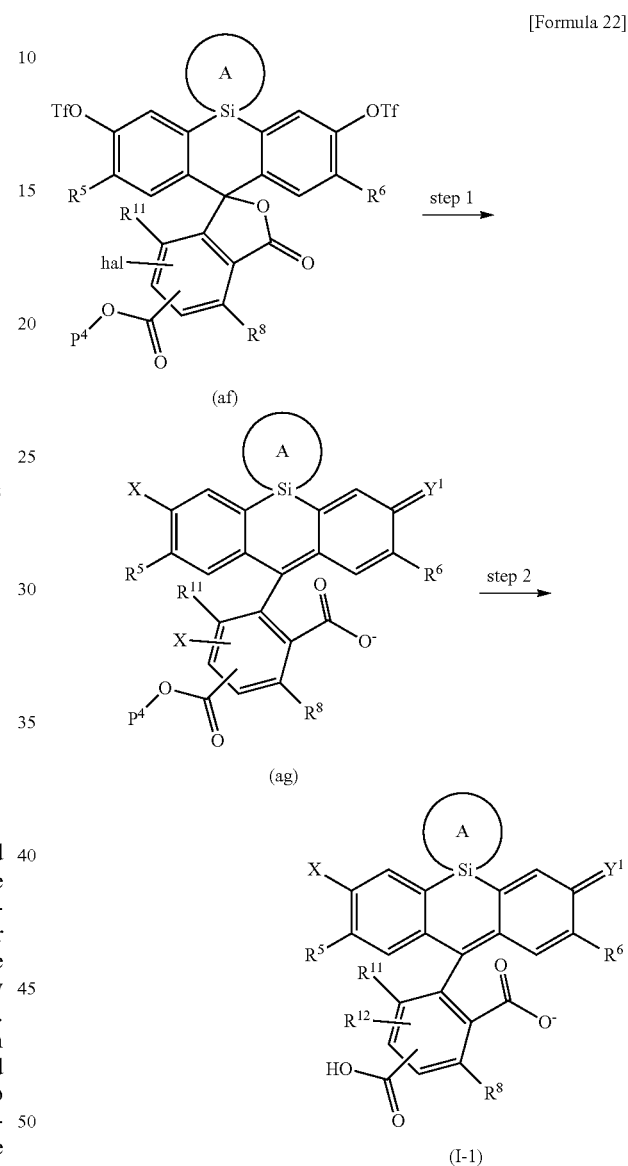

(ac) can be expressed as "formula (af)" in scheme 3-3. The compound of formula (I-1) can be synthesized from the compound of formula (af) by the method shown in scheme 3-3.

In the formulae, ring A, $P^4$, $P^5$ and $R^5$ to $R^{12}$ are as defined in scheme 3-1; and hal's are halogen atoms which are the same as or different from each other. The hal in the compound of formula (ae) is not particularly limited, and for example, a chlorine atom can be used. Step 1 is the same reaction as step 1 in scheme 3-1, and can be achieved by transmetalating only one of two halogen atoms in formula u. $R^{12}$ which is newly introduced in step 2 is as defined in scheme 1-1, and is preferably an optionally substituted C1-C6 alkyl group. The method for introducing $R^{12}$ in step 2 is not particularly limited, and for example, a Suzuki-Miyaura cross coupling reaction or a Migita-Kosugi-Stille cross coupling reaction can be employed. As the palladium catalyst, tetrakis(triphenylphosphine)palladium (0), tris(benzylideneacetone)dipalladium (0), (A-taPhos)$_2$PdCl$_2$ or the like can be used, and a phosphorus ligand such as XPhos may be added thereto as required. In the case where Suzuki-Miyaura cross coupling is employed, the reaction can be accelerated by adding an aqueous inorganic base solution. As the base, potassium carbonate can be used. As the solvent, 1,4-dioxane, DMF or the like can be used. The source for $R^{12}$ is not particularly limited, and for example, trimethylboroxine or tetramethyltin can be used. The reaction can be accelerated by heating, and the reaction is generally carried out at 100° C. to 180° C. If necessary, heating with microwaves may also be employed.

In the case where $R^{12}$ in formula (o), formula (aa), formula (ab) and formula (ac) in scheme 3-1 is hal, formula (ac) can be expressed as "formula (af)" in scheme 3-3. The compound of formula (I-1) can be synthesized from the compound of formula (af) by the method shown in scheme 3-3.

In the formulae, ring A, X, $Y^1$, hal, $P^4$ and $R^1$ to $R^{11}$ are as defined in scheme 3-1. The hal is not particularly limited, and for example, a chlorine atom can be used. $R^{12}$ is as defined in scheme 1-1, and is preferably an optionally substituted amino group. The compound of formula (I-1) may be used as a salt thereof. The type of the salt is not particularly limited, and for example, a TFA salt can be used. Step 1 is the same reaction as step 4 in scheme 3-1. In the reaction, OTf as well as hal can be substituted simultaneously. Step 2 is the same reaction as step 5 in scheme 3-1. In the reaction, the deprotection of the protecting group $P^4$ as well as the conversion of X to $R^{12}$ can be achieved. X is not particularly limited, as long as the above-mentioned step can be achieved. For example, an azetidin-1-yl group can be used as X. In this case, as $R^{12}$ that is to be produced by the conversion, a 3-hydroxypropylamino group can be used.

Scheme 3-4

The compound of formula (z) to be used in scheme 3-1 and scheme 3-2 can be synthesized by the following method.

[Formula 23]

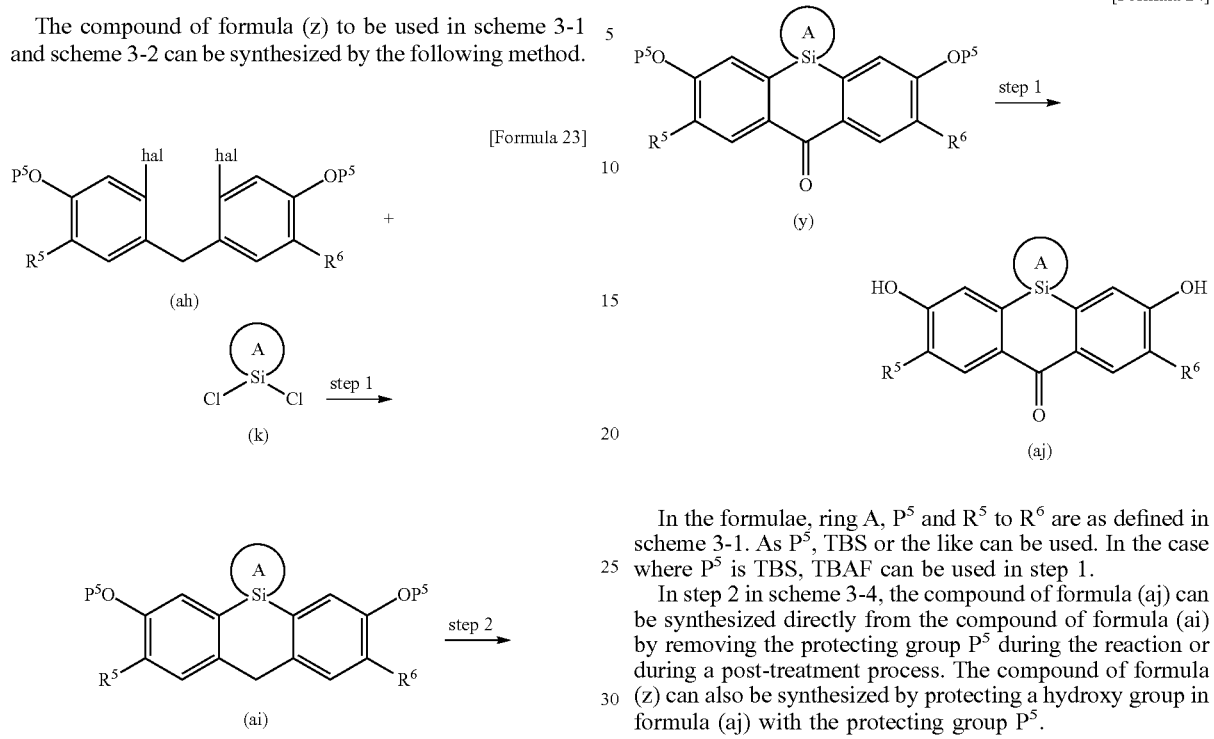

In the formulae, ring A, hal, $P^5$ and $R^5$ to $R^6$ are as defined in scheme 3-1. As the halogen atom, a bromine atom or the like can be used. The protecting group $P^5$ is not particularly limited, and for example, a TBS group can be used. The compound of formula (ai) can be synthesized by reacting a compound of formula (ah) which can be synthesized by a known method with an alkyl metal reagent and then reacting the resultant product with a cyclic dichlorosilane reagent represented by formula (k). As the alkyl metal reagent, sec-butyllithium can be used. The solvent is not particularly limited, as long as the solvent is inert. For example, THF can be used as the solvent. With respect to the reaction temperature, the reaction can be carried out at −78° C. to room temperature. The compound of formula (z) can be synthesized by reacting the compound of formula (ai) with an oxidizing agent. As the oxidizing agent, potassium permanganate, DDQ, chloranil or the like can be used. The solvent is not particularly limited, as long as the solvent is inert. For example, dichloromethane, methanol, 1,4-dioxane, acetone, water and a mixed solvent thereof can be used as the solvent.

The compound of formula (aj) can be synthesized by deprotecting the protecting group $P^5$ in formula (z).

Scheme 3-5

[Formula 24]

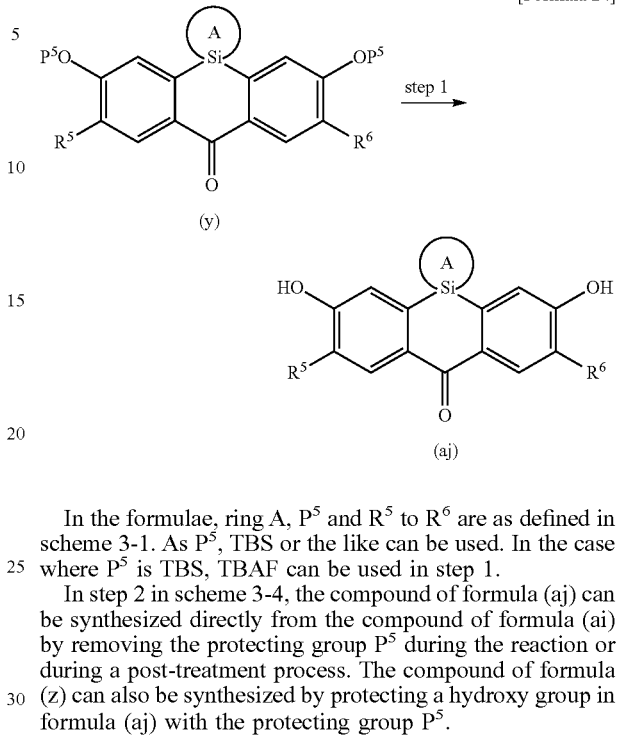

In the formulae, ring A, $P^5$ and $R^5$ to $R^6$ are as defined in scheme 3-1. As $P^5$, TBS or the like can be used. In the case where $P^5$ is TBS, TBAF can be used in step 1.

In step 2 in scheme 3-4, the compound of formula (aj) can be synthesized directly from the compound of formula (ai) by removing the protecting group $P^5$ during the reaction or during a post-treatment process. The compound of formula (z) can also be synthesized by protecting a hydroxy group in formula (aj) with the protecting group $P^5$.

Scheme 3-6

[Formula 25]

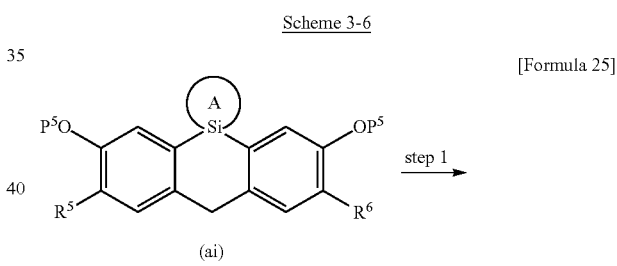

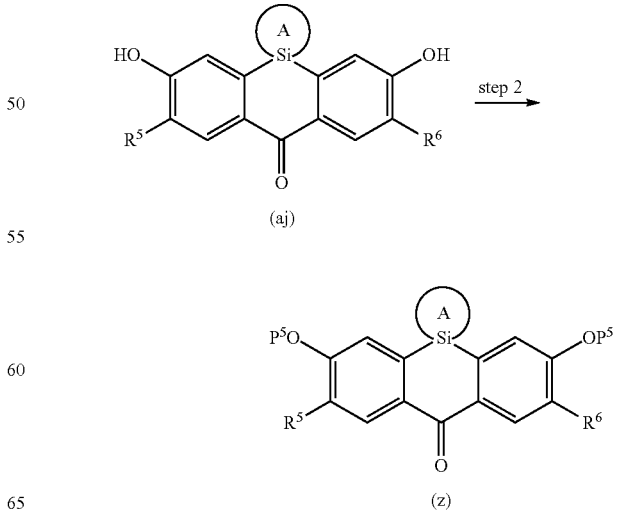

In the formulae, ring A and $R^5$ to $R^6$ are as defined in scheme 3-1; and $P^5$'s represent protecting groups which are the same as or different from each other. $P^5$ in formula (ai) is not particularly limited, as long as $P^5$ can be deprotected easily. For example, a TBS group can be used as $P^5$. Step 1 is the same as step 2 in scheme 3-4. In the case where the deprotection reactions which occur simultaneously are insufficient, it is possible to subject a crude product to a deprotection reaction as required. For example, when the protecting group $P^5$ is a TBS group, the crude product is reacted with TBAF to produce the compound of formula (aj). The protecting group $P^5$ to be introduced in step 2 is not particularly limited, and for example, a TBS group can be used. In the case where $P^5$ in formula (z) is TBS, TBSCl can be used in step 2. The solvent is not particularly limited, as long as the solvent is inert. For example, DMF, dichloromethane or a mixture thereof can be used as the solvent. As the base, imidazole can be used.

The compounds respectively represented by formulae (ad) and (ag) can be isolated as spirolactone forms respectively represented by formulae (ak) and (al) in scheme 3-7 by a proper treatment. These compounds can exist in an equilibrium state shown in scheme 3-7 with each other when dissolved in a proper buffering solution. Formula (ad) is as defined in scheme 3-1, and formula (ag) is as defined in scheme 3-3. In formulae (ak) and (al), A, X, $Y^1$ and $R^5$ to $R^{11}$ are as defined in formula (II), and $P^4$ and $R^{12}$ are as defined in scheme 3-1.

The compound of formula (I-5) which has such a structure that X is OH and $Y^1$ is O in formula (I-1) can be synthesized by the method shown in scheme 3-8.

Scheme 3-8

[Formula 27]

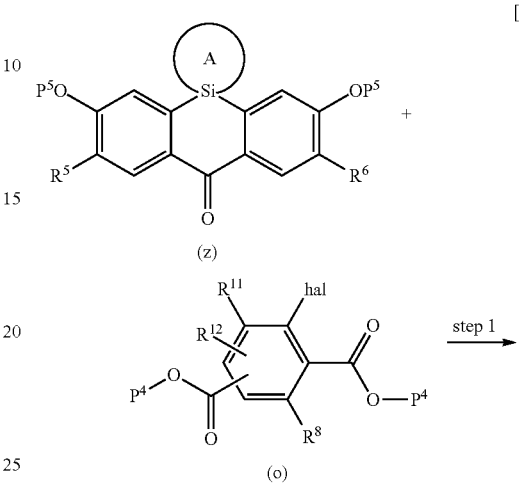

Scheme 3-7

[Formula 26]

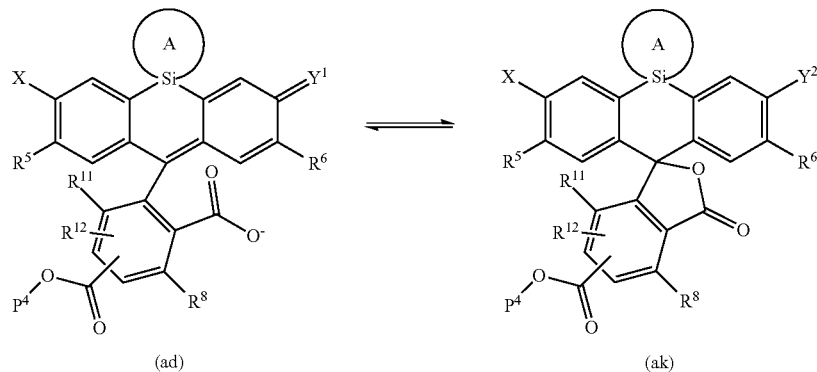

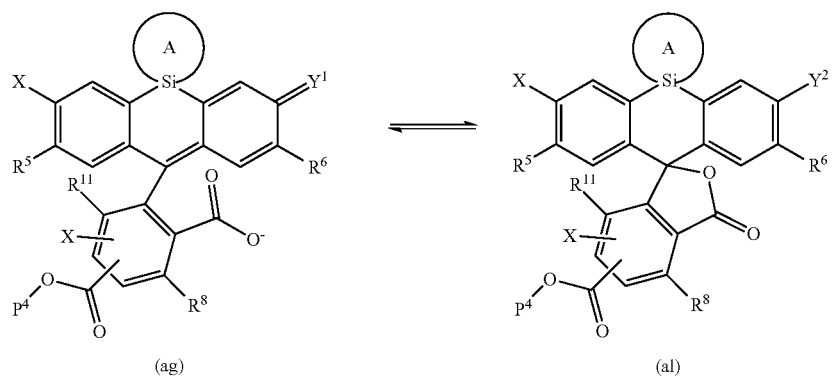

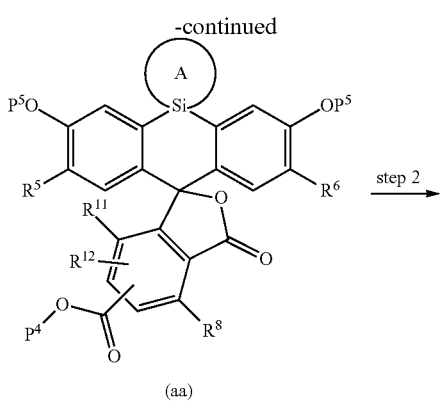

(aa)

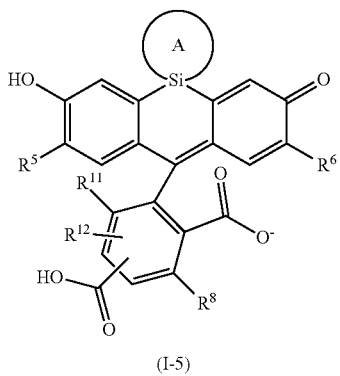

(ab)

(I-5)

In the formulae, ring A and $R^1$ to $R^{12}$ are as defined in scheme 1-1; hal and $P^4$ are as defined in scheme 2-5; and $P^5$'s represent protecting groups that are the same as or different each other. The protecting group $P^4$ is not particularly limited, and for example, a tert-Bu group can be used. The protecting group $P^5$ is not particularly limited, and for example, a TBS group can be used. The halogen atom is not particularly limited, and for example, a bromine atom can be used. The compound of formula (I-5) may be used as a salt thereof. The type of the salt is not particularly limited, and for r example, a TFA salt can be used. The compound of formula (aa) can be synthesized by reacting the compound of formula (o) with an alkyl metal reagent and then adding the compound of formula (z). As the alkyl metal reagent, n-butyllithium can be used for example. With respect to the reaction temperature, the reaction is generally carried out at room temperature or lower, and the reaction can be carried out at −100° C. to room temperature. The solvent is not particularly limited, as long as the solvent is inert. For example, THF, n-hexane and a mixture thereof can be used as the solvent. It is possible to add a Lewis acid as a catalyst. As the Lewis acid, a boron trifluoride diethyl ether complex can be used. The compound of formula (ab) can be synthesized by deprotecting the protecting group $P^5$ in the compound of formula (aa). In the case where the protecting group $P^5$ is a TBS group, the deprotection can be carried out with, for example, TBAF. The solvent is not particularly limited, as long as the solvent is inert. For example, THF can be used as the solvent. The compound of formula (1-5) can be synthesized by deprotecting the protecting group $P^4$ in formula (ab). In the case where $P^4$ is a tert-Bu group, TFA can be used.

The compound of formula (I-6) which has such a structure that X is $NR^1R^2$ and $Y^1$ is $N^+R^3R^4$ in formula (I-1) can be synthesized by the method shown in scheme 4-1.

Scheme 4-1

[Formula 28]

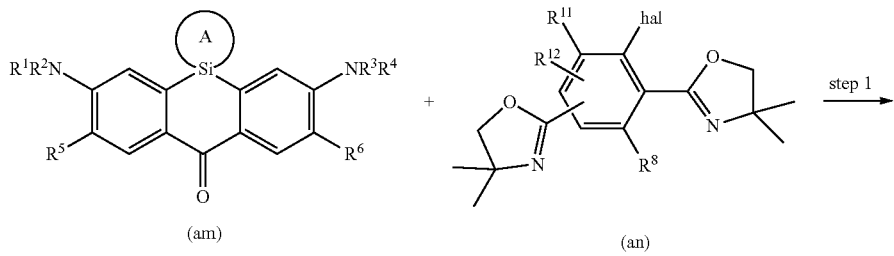

(am) + (an) → step 1

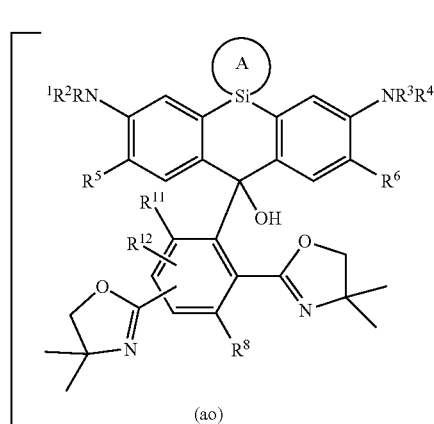

(ao)

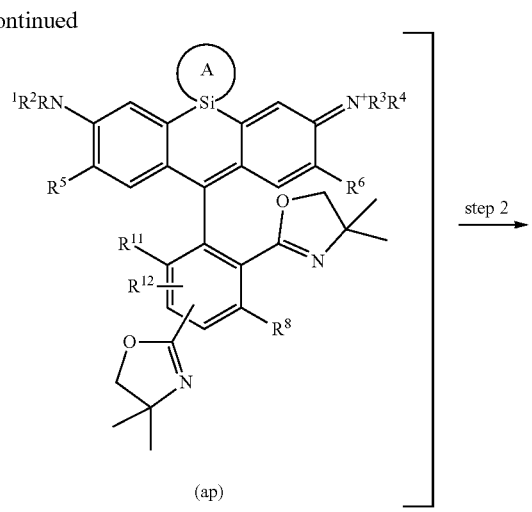

(ap)

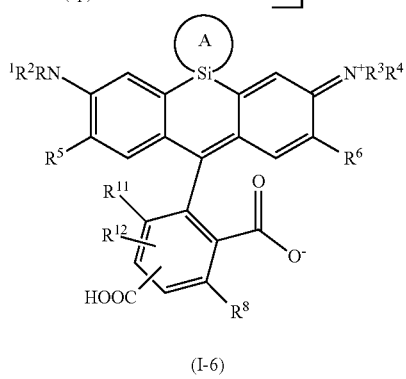

(I-6)

In the formulae, X and $Y^1$ respectively represent $NR^1R^2$ and $N^+R^3R^4$; A and $R^1$ to $R^{12}$ are as defined in scheme 1-1; and hal represents a halogen atom, preferably a bromine atom. The compound of formula (ao) can exist in an equilibrium state with the compound of formula (ap) or can be produced as a mixture thereof. The compounds respectively represented by formula (an) and formula (ao) can be produced as salts thereof. The compound of formula (ao) can be produced by reacting the compound of formula (an) with an alkyl metal reagent and then adding the compound of formula (am). As the alkyl metal reagent, a tert-butyllithium can be used. The solvent is not particularly limited, as long as the solvent is inert. For example, THF or the like can be used as the solvent. With respect to the reaction temperature, the reaction can be carried out at −78° C. to room temperature. In general, the compound of formula (ao) can proceed to the subsequent step without the need to isolate. The compound of formula (I-6) can be synthesized by converting the 4,4-dimethyl-4,5-dihydrooxazole group in the compound of formula (ao) to a carboxyl group. The reaction condition is not particularly limited. In general, an acid-catalyzed hydrolysis reaction can be employed. The acid is not particularly limited, and for example, 5N hydrochloric acid can be used. In general, the reaction can be accelerated by heating. Therefore, the reaction can be carried out at 80° C. to the boiling point of the solvent.

The compound of formula (am) to be used in scheme 4-1 can be synthesized by the following method.

Scheme 4-2

[Formula 29]

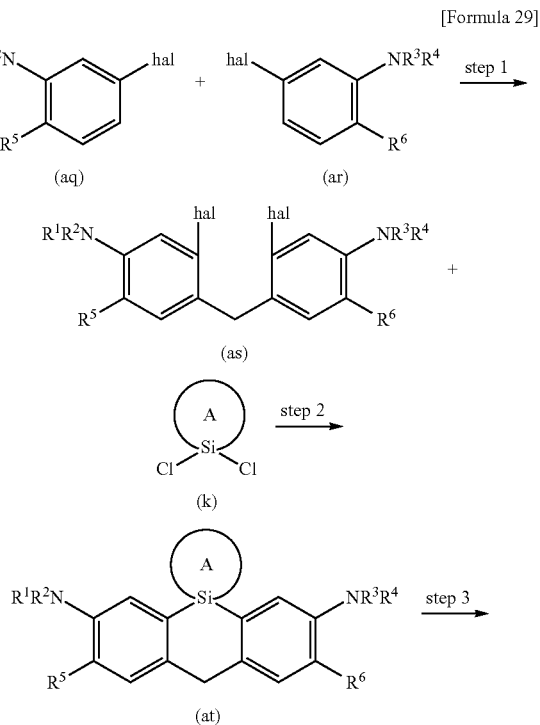

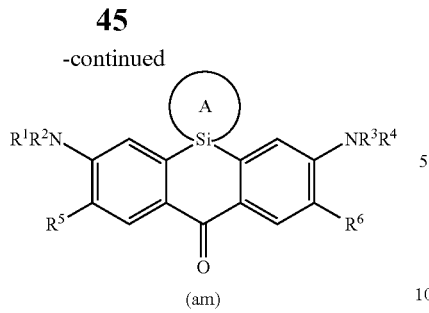

(am)

In the formulae, ring A and $R^1$ to $R^6$ are as defined in scheme 4-1; and hal represents a halogen atom. As the compounds of formula (aq) and formula (ar), commercially available products may be used. Alternatively, these compounds may be synthesized by a known method or the method mentioned in Production Examples. The halogen atom is not particularly limited, and for example, a bromine atom can be used. The compound of formula (as) can be synthesized by reacting a mixture of the compounds of formula (aq) and formula (ar) with formaldehyde under acidic conditions. As the solvent, acetic acid can be used. With respect to the reaction temperature, the reaction can be generally accelerated by heating, and the reaction can be carried out at 50° C. to 120° C. The compound of formula (at) can be synthesized by reacting the compound of formula (as) with an alkyl metal reagent and then reacting the resultant product with a cyclic dichlorosilane reagent represented by formula (k). As the alkyl metal reagent, sec-butyllithium can be used. The solvent is not particularly limited, as long as the solvent is inert. For example, THF can be used as the solvent. With respect to the reaction temperature, the reaction can be carried out at −78° C. to room temperature. The compound of formula (am) can be synthesized by reacting the compound of formula (at) with an oxidizing agent. As the oxidizing agent, potassium permanganate, DDQ, chloranil or the like can be used. The solvent is not particularly limited, as long as the solvent is inert. For example, dichloromethane, methanol, 1,4-dioxane, acetone, water and a mixed solvent thereof can be used as the solvent.

The compound of formula (am) can also be synthesized by the method shown in scheme 4-3.

Scheme 4-3

[Formula 30]

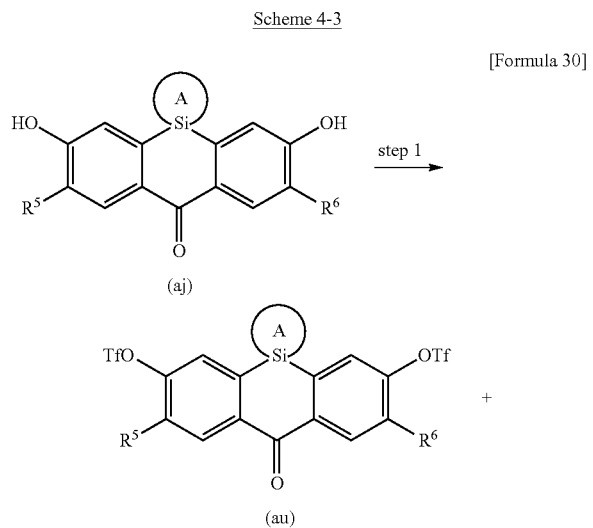

In the formulae, ring A and $R^1$ to $R^6$ are as defined in scheme 4-1. The compound of formula (au) can be synthesized by reacting the compound of formula (aj) with trifluoromethanesulfonic anhydride. As the base, pyridine can be used. The solvent is not particularly limited, as long as the solvent is inert. For example, dichloromethane or the like can be used as the solvent. The compound of formula (am) can be synthesized from the compound of formula (au) by a Buchwald-Hartwig reaction. As the palladium catalyst to be used in the reaction, tetrakis(triphenylphosphine)palladium (0), palladium (II) acetate, tris(benzylideneacetone)dipalladium (0), (A-taPhos)$_2$PdCl$_2$ or the like can be used, and a phosphorus ligand such as XPhos may be added thereto as required. As the base, cesium carbonate, sodium tert-butoxide, potassium tert-butoxide and the like can be used. As the solvent, 1,4-dioxane, toluene, THF and the like can be used. The reaction can be accelerated by heating. In general, the reaction can be carried out in a sealed tube at 100° C. to 120° C. If necessary, heating with microwaves may also be employed. As the compounds of formulae (av) and (aw), commercially available products may be used. Alternatively, these compounds may be synthesized by a known method or the method mentioned in Production Examples.

[2. Labeled Composite Substance]

Within the scope of the present disclosure, a labeled composite substance is also included, which comprises the fluorescent dye of the present embodiment and a composite substance bonded to the fluorescent dye. The term "composite substance" refers to a substance which can covalently bind to the fluorescent dye of the present embodiment. Examples of the composite substance include a surface (e.g., a bead, a solid support, a resin, a particle, or an assay plate), a biological molecule or a biomolecule (e.g., a protein, a nucleotide, a polynucleotide, a nucleic acid including DNA and RNA, a substrate for an enzyme, an antibody, a nanobody, a polypeptide, a polypeptide-based toxin, an amino acid, a lipid, a hydrocarbon, a hapten, an ionic complexing agent such as a metal chelating agent, a micro-particle, a synthetic or natural polymer, a cell, a virus, other fluorescent molecule or a surface), a small molecule (e.g., a drug, a drug compound), or other moiety of interest such as a cycloalkane or a cyanobenzothiazole. Other preferred examples of the composite substance include, but are not limited to: a lanthanide-complexed group; a nickel-complexed group; a cobalt-complexed group; ethylenediaminetetraacetic acid; nitrilotriacetic acid; a nucleotide; a substrate for an enzyme; an enzyme inhibitor, preferably an irreversible enzyme inhibitor capable of forming a covalent bond to an enzyme; a receptor agonist; a ligand capable of binding to a nucleic acid at a KD of 10 UM or more; a substrate for a SNAP-tag; a ligand capable of binding to a protein at a KD of 10 UM or more; a substrate for a SNAP-tag; a substrate for a CLIP-tag; a substrate for a Halo-tag; a ligand capable of binding to a dihydrofolate reductase; methotrexate; trimethoprim; a substrate for a biotin ligase; a substrate for a phosphopeptidyl transferase; a substrate for a lipoic acid ligase; biotin; a ligand capable of binding to streptavidin, avidin or neutravidin; an enzyme cofactor; a hormone; a toxin; a fluorophore; a nucleic acid polymer; a hapten; an antigen; a drug; a lipid; a lipid assembly; a non-biological organic polymer; a polymer microparticle; an animal cell; a plant cell; a bacterium; yeast; a virus; and a protest. In a preferred embodiment, the composite substance is a protein or a nucleic acid.

The composite substance-binding site in the fluorescent dye of the present embodiment is not particularly limited. The binding site is preferably at least one of $R^7$, $R^8$, $R^9$, $R^{10}$ or $R^{11}$, more preferably at least one of $R^8$, $R^9$ or $R^{10}$. Particularly preferably, the composite substance-binding site in the fluorescent dye of the present embodiment is a reactive group R in $R^8$, $R^9$ or $R^{10}$ that is represented by -L-R.

[3. Composition]

Within the scope of the present disclosure, a composition is also included, which contains the fluorescent dye or the labeled composite substance of the present embodiment (wherein the composition is also simply referred to as "composition", hereinafter). The composition of the present embodiment may be a reagent composition which can be used in a super-resolution microscopy. The term "super-resolution microscopy" refers to an imaging technique using a super-resolution microscope that is a microscope having a resolution beyond the light diffraction limit, and is known in the art.

The fluorescent dye of the present embodiment has tautomerism, in which a state where an intramolecular spiro ring is formed (i.e., a ring-closed form) and a state where the spiro ring is cleaved (i.e., a ring-opened form) are in equilibrium with each other. Therefore, the fluorescent dye of the present embodiment is capable of blinking spontaneously. Therefore, the composition of the present embodiment is preferably a reagent composition for use in a localization microscopy that is one type of super-resolution microscopy. The term "localization microscopy" refers to a super-resolution microscopy which relies on the detection of the single-molecule luminescence of a fluorescent substance and is typified by a photoactivated localization microscopy (PALM), a blinking assisted localization microscopy (BALM) and a points accumulation for imaging in nanoscale topography (PAINT) method. In the localization microscopy, firstly, a substance of interest is bound to a fluorescent substance which can switch between a light-emitting state and a light-quenched state, then the fluorescent substance bonded to the substance of interest is caused to emit light, and then images of the fluorescent substance are captured while shifting the time so that the images cannot be spatially superposed. The molecules of the light-emitting fluorescent substance are detected one by one, and the position of the detected single molecule of the fluorescent substance is determined with the precision of the order of several tens nm. The image capturing and the detection are repeated several thousand times to several tens of thousands of times to superpose multiple pieces of information relating to the position of a single molecule of the fluorescent substance. In this manner, a super-resolution image of the substance of interest is constructed. Furthermore, the possibility that the fluorescent dye can also be used in a stimulated emission depletion microscopy (STED), a structured illumination microscopy (SIM), a super-resolution optical fluctuation imaging (SOFI) method, a minimal emission fluxes (MINFLUX) method which are known as super-resolution microscopies other than the localization microscopy cannot be denied.

If necessary, the composition of the present embodiment may contain an additive that has been commonly used in the preparation of reagents. Examples of the additive include a dissolution aid, a pH modifier, a buffering agent and an isotonizing agent. The amount of the additive to be blended can be determined properly by a person skilled in the art. The form of the composition of the present embodiment is not particularly limited, and the form may be a solid form (e.g., a powder, crystals, granules, tablets, a freeze-dried product) or a liquid form (e.g., a solution, a suspension, an emulsion).

[4. Method for Acquiring Information about Substance of Interest]

Within the scope of the present disclosure, a method for acquiring information about a substance of information (wherein the method is also referred to as an "information acquisition method", hereinafter) is also included, which comprises binding the fluorescent dye or the labeled composite substance of the present embodiment to the substance of interest and then acquiring the information about the substance of interest by a super-resolution microscopy. In the method, a known super-resolution microscope can be used. An example of the microscope is HM-1000 (Sysmex Corporation). As mentioned above, since the fluorescent dye of the present embodiment is capable of blinking spontaneously, the information acquisition method of the present embodiment is suitable for a localization microscopy among super-resolution microscopies.

The mode of the binding between the fluorescent dye or the labeled composite substance of the present embodiment to the substance of interest is not particularly limited. The mode of the binding may be determined appropriately depending on the types of the substance of interest. In the case where the substance of interest is a tissue, a cell, an organelle or a biological molecule (e.g., a protein, a nucleic acid), the fluorescent dye or the labeled composite substance of the present embodiment can be bonded to the substance of interest by a staining method that is known in the field of biology. Examples of the staining method include, an immunohistochemical method and a fluorescent labeled antibody method.

In the information acquisition method of the present embodiment, information about the substance of interest can be acquired from an image of the substance of interest which is obtained by the super-resolution microscopy. The information about the substance of interest may be information about the structure of the substance of interest or information about the amount of the substance of interest. Examples of the information about the structure of the substance of interest include the size of the substance of interest, the form of the substance of interest, and the degree of aggregation of the substance of interest. Examples of the information about the amount of the substance of interest include the presence or absence of the substance of interest, and the concentration of the substance of interest and the content (weight) of the substance of interest and a measurement value indicating the concentration or the content (weight). In scope of the information about the amount of the substance of interest, information indicating the amount of the substance of interest by stages (e.g., "small", "intermediate", "large") is also included. In a preferred embodiment, the information about the substance of interest is information about the structure of the substance of interest.

Hereinbelow, the present disclosure is described in more detail with reference to examples. However, the present disclosure is not limited to these examples.

EXAMPLES

In Examples, Reference Examples and Production Examples mentioned below, the term "room temperature" generally refers to a temperature falling within the range from about 10° C. to about 35° C. All "percents (%)" are by weight, unless otherwise specified.

The chemical shift of a proton nuclear magnetic resonance spectrum was recorded in a δ unit (ppm) with respect to tetramethylsilane, and a coupling constant was recorded in hertz (Hz). The abbreviations for splitting patterns are as follows.

s: singlet, d: doublet, t: triplet, q: quartet, quin: quintet, m: multiplet, br.s.: broad singlet In Production Examples and Examples, a reaction using a microwave reaction device was carried out using "Initiator (trademark)" (manufactured by Biotage).

With respect to silica gel column chromatography, the silica gel used was "Silica Gel60" (70-230 mesh) (manufactured by Merck), "PSQ60B" (manufactured by Fuji Silysia Chemical Ltd.) or a commercially available pre-packed column. As the pre-packed column, any one of S-size (16×60 mm), M-size (20×75 mm), L-size (26×100 mm), 2L-size (26×150 mm) and 3L-size (46×130 mm) of "Hi-Flash (trademark) Column (Silicagel)" (manufactured by YAMAZEN) or any one of 10 g-size, 25 g-size and 50 g-size of "Biotage (trademark) SNAP Ultra Silica Cartridge" (manufactured by Biotage) was used.

With respect to reverse-phase chromatography, "YMC*GEL ODS-A 12 nm S-50 μm" (manufactured by YMC) or a commercially available pre-packed column was used. As the pre-packed column, "YMC-DispoPack AT ODS-25" (40 g or 120 g) (manufactured by YMC) or "Biotage (trademark) SNAP Ultra C18" (12 g) (manufactured by Biotage) was used.

With respect to thin-layer chromatography: when there was an expression "silica gel", TLC Silica gel 60 $F_{254}$ (manufactured by Merck) was used; and when there was an expression "NH silica gel", CHROMATOREX TLC Plates NH (manufactured by Fuji Silysia Chemical Ltd.) or $NH_2$ silica gel $60F_{254}$ Plate-Wako (thickness: 0.75 mm) (manufactured by Wako Pure Chemical Industries, Ltd.) was used.

With respect to a phase separator, ISOLUTE (registered trademark) Phase Separator (manufactured by Biotage) was used.

The chemical names of the compounds shown below, except commonly used reagents, were those chemical names listed in "E-Notebook" ver. 12 and ver. 13 (PerkinElmer) or "ChemDraw Professional" ver. 17.1 (PerkinElmer).

As the physical amounts of the compounds shown below, those physical amounts shown in "E-Notebook", ver. 12 and ver. 13 (PerkinElmer) or "ACD/ChemSketch 2017.2" (ACD) were employed.

Production Example 1

Synthesis of di-tert-butyl 2-bromo-5-chloroterephthalate

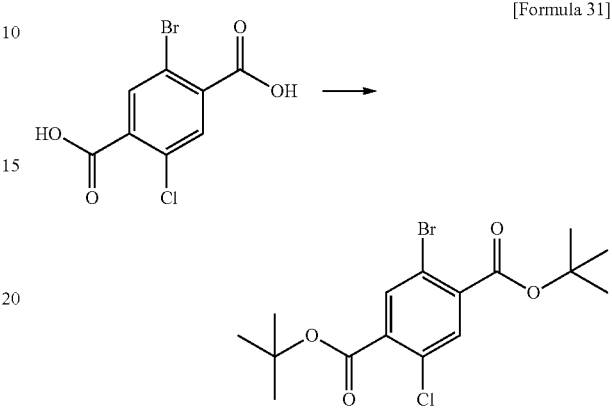

[Formula 31]

To a mixture of 2-bromo-5-chloroterephthalic acid (500 mg, 1.79 mmol, CAS No. 500550-60-7), DCM (10.0 mL), THF (5.00 mL) and DMF (1 drop) was added dropwise oxalyl chloride (626 μL, 7.16 mmol). The resultant solution was stirred at room temperature for 1 hour. The solvent was distilled away under a reduced pressure to produce the corresponding acid chloride. Potassium tert-butoxide (803 mg, 7.16 mmol) was added slowly to a solution of the acid chloride in THF (5.00 mL) under an ice bath, and the resultant solution was stirred at room temperature overnight. Ice and a saturated aqueous ammonium chloride solution were added to the solution to terminate the reaction, and the aqueous layer was extracted with ethyl acetate. The organic layer was washed with water and saturated saline, and the resultant product was dried over anhydrous magnesium sulfate. The solvent was distilled away under a reduced pressure, and the resultant residue was purified by silica gel column chromatography (n-heptane/ethyl acetate) to yield the title compound (408 mg, 1.04 mmol).

$^1$H-NMR (400 MHZ, $CDCl_3$) δ (ppm): 1.61 (s, 9H), 1.61 (s, 9H), 7.70 (s, 1H), 7.94 (s, 1H).

Production Example 2

Synthesis of di-tert-butyl 2-bromo-5-(trifluoromethyl)terephthalate

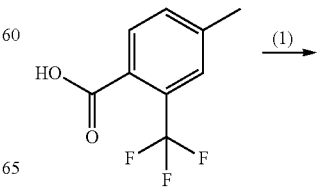

[Formula 32]

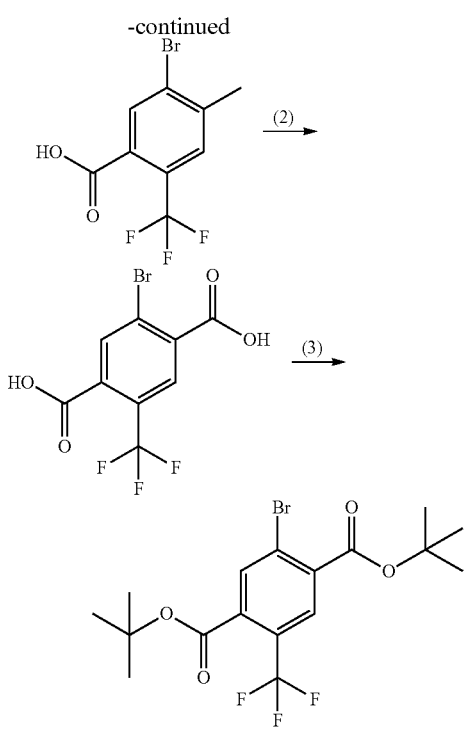

(1) Synthesis of 5-bromo-4-methyl-2-(trifluoromethyl)benzoic acid

To a solution of 4-methyl-2-(trifluoromethyl)benzoic acid (1.36 g, 6.66 mmol, CAS No. 120985-64-0) in sulfuric acid (7.10 mL, 133 mmol) was added NBS (1.19 g, 6.66 mmol).

The resultant solution was stirred at room temperature overnight. Ice was added to the reaction mixture under an ice bath to terminate the reaction. The generated solid material was collected to yield a crude product (2.49 g) of the title compound.

$^1$H-NMR (400 MHZ, DMSO-d$_6$) δ (ppm): 2.47 (s, 3H), 7.86 (s, 1H), 8.02 (s, 1H).

(2) Synthesis of 2-bromo-5-(trifluoromethyl)terephthalic acid

To a mixture of the compound produced in Production Example 2-(1) (2.29 g), pyridine (13.7 mL, 170 mmol) and water (45.8 mL) was added potassium permanganate (3.84 g, 24.3 mmol). The resultant solution was stirred at 50° C. for 2.3 hours. Water (100 mL) was further added to the solution, and the resultant solution was stirred at 50° C. for 4.2 hours. Potassium permanganate (10.8 g, 68.4 mmol) was further added to the solution, and the resultant solution was stirred at 50° C. for 4.5 hours. The solution was cooled to room temperature, and then insoluble matters were filtrated out. The insoluble matters were washed with a dilute aqueous pyridine solution, and dimethyl sulfide was added to the eluate. Newly generated insoluble matters were filtrated out, and the eluate was concentrated at 50° C. under a reduced pressure. The resultant residue was dissolved in water (10.0 mL), and concentrated hydrochloric acid was added to the resultant solution under an ice bath. The generated solid material was collected to yield a crude product (2.74 g) of the title compound.

$^1$H-NMR (400 MHZ, DMSO-d$_6$) δ (ppm): 8.12 (s, 1H), 8.15 (s, 1H).

(3) Synthesis of di-tert-butyl 2-bromo-5-(trifluoromethyl)terephthalate

A mixture of the compound produced in Production Example 2-(2) (2.74 g), di-tert-butyl dicarbonate (7.64 g, 35.0 mmol), DMAP (214 mg, 1.75 mmol), toluene (28.0 mL) and DMF (2.80 mL) was stirred at 80° C. for 2 hours. Subsequently, DMAP (214 mg, 1.75 mmol) and di-tert-butyl dicarbonate (7.64 g, 35.0 mmol) were further added to the solution, and the resultant solution was stirred at 80° C. for 3.5 hours. Subsequently, di-tert-butyl dicarbonate (3.00 g, 13.8 mmol) was further added to the solution, and the resultant solution was stirred at 80° C. for 1.5 hours. The solution was cooled to room temperature, and then the solvent was distilled away under a reduced pressure. The resultant residue was purified by silica gel column chromatography (n-heptane/ethyl acetate) to yield the title compound (1.66 g, 3.90 mmol). $^1$H-NMR (400 MHZ, CDCl$_3$) δ (ppm): 1.58 (s, 9H), 1.62 (s, 9H), 7.95 (s, 1H), 7.98 (s, 1H).

Production Example 3

Synthesis of di-tert-butyl 2-bromo-5-fluoroterephthalate

[Formula 33]

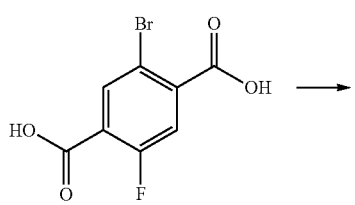

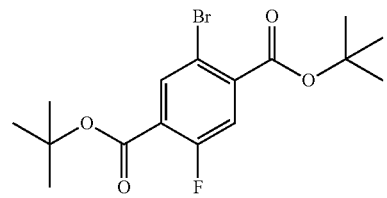

A mixture of 2-bromo-5-fluoroterephthalic acid (200 mg, 760 µmol, CAS No. 1245807-64-0), di-tert-butyl dicarbonate (664 mg, 3.04 mmol), DMAP (18.6 mg, 152 µmol), toluene (5.00 mL) and DMF (500 µL) was stirred at 80° C. for 5 hours. The solution was cooled to room temperature and was then diluted with ethyl acetate. The organic layer was washed with water twice, and the solvent was distilled away under a reduced pressure. The residue was purified by silica gel column chromatography (n-heptane/ethyl acetate) to yield the title compound (70.0 mg, 187 µmol).

$^1$H-NMR (400 MHZ, CDCl$_3$) δ (ppm): 1.59 (s, 9H), 1.61 (s, 9H), 7.42 (d, J=10.54 Hz, 1H), 8.07 (d, J=6.64 Hz, 1H).

Production Example 4

Synthesis of 3,7-bis((tert-butyldimethylsily)oxy)-10H-spiro[dibenzo[b,e]siline-5,1'-silinan]-10-one

[Formula 34]

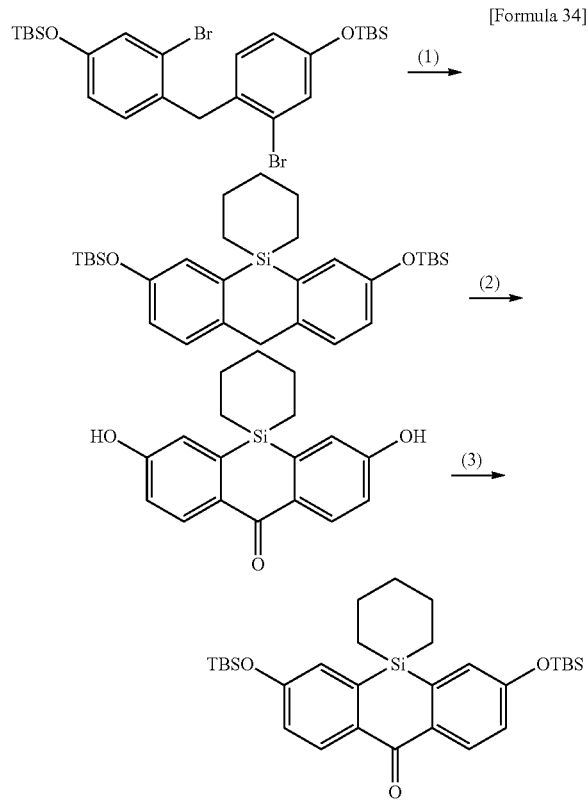

(1) Synthesis of 3,7-bis((tert-butyldimethylsily)oxy)-10H-spiro[dibenzo[b,e]siline-5,1'-silinane]

To a solution of bis(2-bromo-4-((tert-butyldimethylsilyl)oxy)phenyl)methane (4.95 g, 8.44 mmol, CAS No. 1383118-97-5) in THF (49.8 mL, 608 mmol) was added dropwise sec-butyllithium (a 1.05M cyclohexane-hexane solution, 22.9 mL, 24.1 mmol) at −78° C. over 20 minutes. The solution was stirred at the same temperature for 1 hour, and then a solution of cyclopentamethylenedichlorosilane (2.71 g, 16.0 mmol, CAS No. 2406-34-0) in THF (19.5 mL) was added dropwise to the solution over 10 minutes. The resultant solution was stirred at room temperature for 1 hour and 30 minutes, and then ice and a saturated aqueous ammonium chloride solution were added to the solution to terminate the reaction. The aqueous layer was extracted with ethyl acetate, and then the organic layer was washed with water and saturated saline. The mixture was dried over anhydrous magnesium sulfate, and then the solvent was distilled away under a reduced pressure. The resultant residue was purified by silica gel column chromatography (n-heptane/ethyl acetate) to yield the title compound (3.68 g, 7.01 mmol).

$^1$H-NMR (400 MHZ, CDCl$_3$) δ (ppm): 0.22 (s, 12H), 1.01 (s, 18H), 1.02-1.06 (m, 4H), 1.66 (br.s., 2H), 1.92-2.03 (m, 4H), 3.95 (s, 2H), 6.79 (dd, J=8.40, 2.54 Hz, 2H), 7.15-7.20 (m, 4H).

(2) Synthesis of 3,7-dihydroxy-10H-spiro[dibenzo[b,e]siline-5,1'-silinan]-10-one A solution of the compound produced by the method of Production Example 4-(1) (10.1 g, 19.2 mmol) in acetone (505 mL) was dispensed into 101 13-mm test tubes. Potassium permanganate (81.3 mg, 514 μmol; 8.21 g, 51.9 mmol in total) was added to each of the test tubes under an ice bath. The resultant solution was stirred at room temperature overnight, and then DCM was added to each of the test tubes. Generated insoluble matters were filtrated out, and the eluates were collected in a single eggplant-shaped flask. The solvent was distilled away under a reduced pressure, and the residue was purified by silica gel column chromatography (n-heptane/ethyl acetate) to yield the title compound (1.97 g, 6.35 mmol).

ESI-MS m/z 311 [M+H]$^+$

(3) Synthesis of 3,7-bis((tert-butyldimethylsily)oxy)-10H-spiro[dibenzo[b,e]siline-5,1'-silinan]-10-one To a solution of the compound produced in Production Example 4-(2) (590 mg, 1.90 mmol) in DMF (10.0 mL) were added imidazole (776 mg, 11.4 mmol) and tert-butyldimethylsilyl chloride (859 mg, 5.70 mmol). The resultant solution was stirred at room temperature overnight, and then ice was added to the solution to terminate the reaction. The aqueous layer was extracted with ethyl acetate, and then the organic layer was washed with water three times. The solvent was distilled away under a reduced pressure, and the residue was purified by silica gel column chromatography (n-heptane/ethyl acetate) to yield the title compound (954 mg, 1.77 mmol).

$^1$H-NMR (400 MHZ, CDCl$_3$) δ (ppm): 0.27 (s, 12H), 1.02 (s, 18H), 0.99-1.05 (m, 4H), 1.71 (br.s., 2H), 1.96-2.07 (m, 4H), 6.99 (dd, J=8.59, 2.73 Hz, 2H), 7.22 (d, J=2.73 Hz, 2H), 8.36 (d, J=8.59 Hz, 2H).

Production Example 5

Synthesis of tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate and 10-oxo-10H-spiro[dibenzo[b,e]siline-5,1'-silinane]-3,7-diylbis(trifluoromethanesulfonate)

[Formula 35]

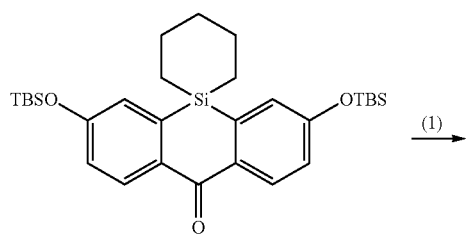

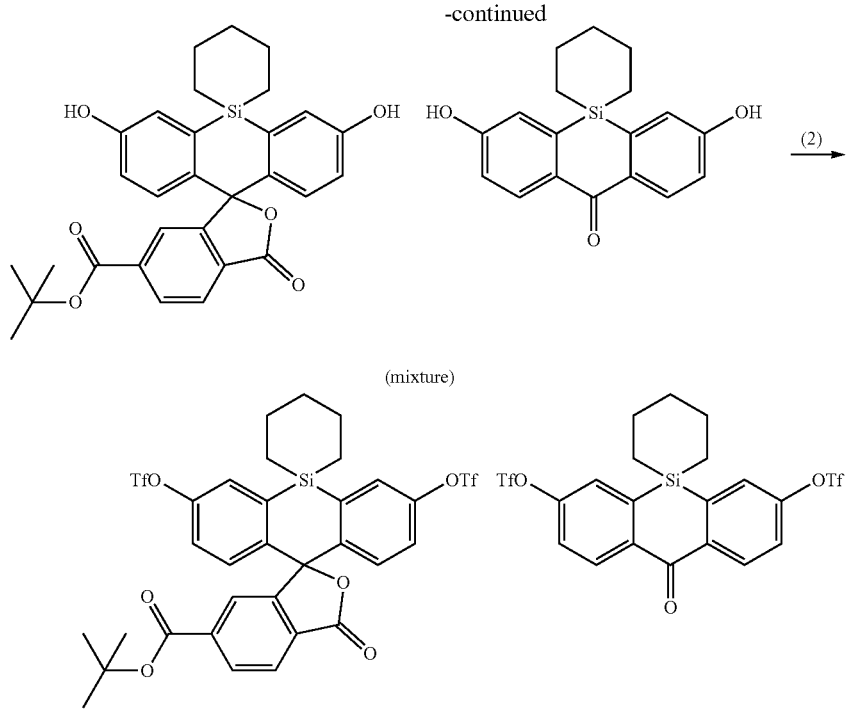

(1) Synthesis of tert-butyl 3',7'-dihydroxy-3-oxo-3H-dispiro[isobenzofuran-1,10'-dibenzo[b,e]siline-5',1''-silinane]-6-carboxylate To a mixed solution of a di-tert-butyl 2-bromoterephthalate (1.54 g, 4.31 mmol, CAS No. 1456885-46-3) in THF (20.0 mL)/n-hexane (10.0 mL) was added dropwise n-butyllithium (a 2.65-M hexane solution, 1.62 mL, 4.31 mmol) under a nitrogen atmosphere at an inside temperature of −95° C. or lower. The solution was stirred at the same temperature for 10 minutes, and then a solution of 3,7-bis((tert-butyldimethylsily)oxy)-10H-spiro[dibenzo[b,e]siline-5,1'-silinan]-10-one (580 mg, 1.08 mmol) produced in Production Example 4-(3) in THF (10.0 mL) was added dropwise to the solution at an inside temperature of −95° C. or lower. The solution was stirred at the same temperature for 5 minutes, and then a boron trifluoride diethyl ether complex (273 μL, 2.15 mmol) was added dropwise to the solution. The reaction mixture was heated to room temperature slowly and was then stirred at room temperature 6 hours. A saturated aqueous ammonium chloride solution was added to the solution under an ice bath to terminate the reaction. The aqueous layer was extracted with ethyl acetate, and then the organic layer was washed with water and saturated saline. The mixture was dried over anhydrous magnesium sulfate, and the solvent was distilled away to yield a mixture containing an adduct. THF (10.0 mL) and tetrabutylammonium fluoride (a 1.00-M THF solution, 5.38 mL, 5.38 mmol) were added to the resultant mixture, and the resultant solution was stirred at room temperature for 7 hours. A saturated aqueous ammonium chloride solution was added to the solution under an ice bath to terminate the reaction. The aqueous layer was extracted with ethyl acetate, and the organic layer was concentrated under a reduced pressure. The resultant residue was purified by silica gel column chromatography (n-heptane/ethyl acetate) to yield the title compound as a mixture (670 mg) with 3,7-dihydroxy-10H-spiro[dibenzo[b,e]siline-5,1'-silinan]-10-one.

ESI-MS m/z 515 [M+H]$^+$ (Retention time: 1.48 minutes)
ESI-MS m/z 311 [M+H]$^+$ (Retention time: 1.18 minutes)

(2) Synthesis of tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate and 10-oxo-10H-spiro[dibenzo[b,e]siline-5,1'-silinane]-3,7-diylbis(trifluoromethanesulfonate)

To a solution of the mixture produced in Production Example 5-(1) (670 mg) in DCM (10.0 mL) were added pyridine (1.05 mL, 13.0 mmol) and trifluoromethanesulfonic anhydride (1.09 mL, 6.51 mmol) under an ice bath. The resultant solution was stirred at room temperature overnight, and then ice-cooled water was added to the solution to terminate the reaction. The aqueous layer was extracted with DCM, and the organic layer was washed with 1N hydrochloric acid and water. The solvent was distilled away under a reduced pressure, and the residue was purified by silica gel column chromatography (n-heptane/ethyl acetate) to yield tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (472 mg, 606 μmol) and 10-oxo-10H-spiro[dibenzo[b,e]siline-5,1'-silinane]-3,7-diylbis(trifluoromethanesulfonate) (197 mg, 343 μmol).

tert-Butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate $^1$H-NMR (400 MHZ, CDCl$_3$) δ (ppm): 1.27-1.31 (m, 2H), 1.32-1.39 (m, 2H), 1.58 (s, 9H).1.79 (br.s., 2H), 2.05-2.18 (m, 4H), 7.19-7.24 (m, 2H), 7.28-7.35 (m, 2H), 7.73 (d, J=2.73 Hz, 2H), 7.92 (s, 1H), 8.03 (d, J=7.42 Hz, 1H), 8.21 (dd, J=8.20, 1.17 Hz, 1H).

10-Oxo-10H-spiro[dibenzo[b,e]siline-5,1'-silinane]-3,7-diylbis(trifluoromethane sulfonate)

$^1$H-NMR (400 MHZ, CDCl$_3$) δ (ppm): 1.06-1.17 (m, 4H), 1.76 (br.s., 2H), 2.04 (br.s., 4H), 7.48 (dd, J=8.79, 2.54 Hz, 2H), 7.70 (d, J=2.73 Hz, 2H), 8.53 (d, J=8.59 Hz, 2H).

Production Example 6

Synthesis of tert-butyl 3-oxo-3',7'-bis(((trifluoromethyl)sulfonyl)oxy)-3H-dispiro[isobenzofuran-1,10'-dibenzo[b,e]siline-5',1''-silinane]-5-carboxylate

[Formula 36]

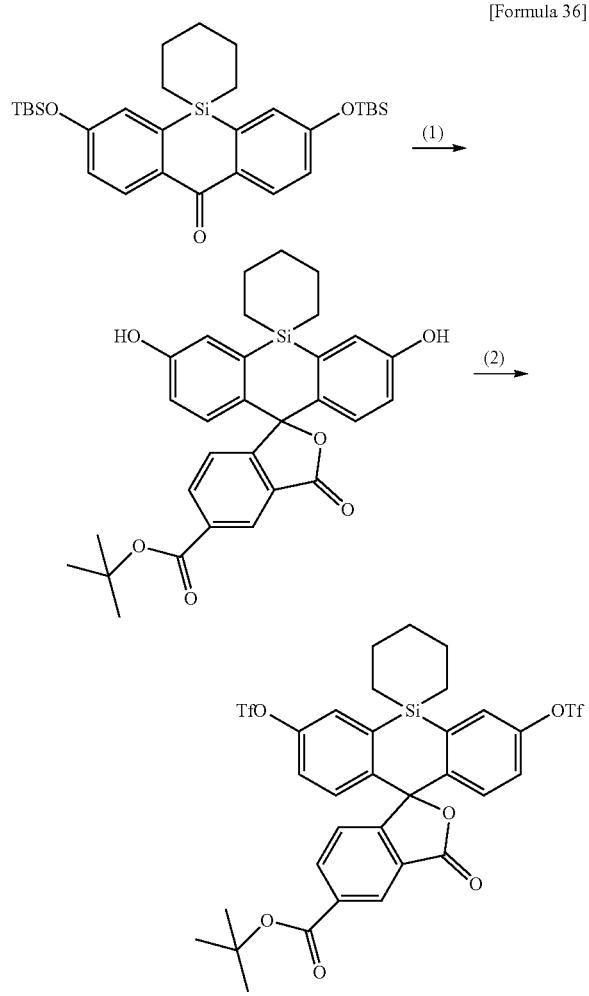

(1) Synthesis of tert-butyl 3',7'-dihydroxy-3-oxo-3H-dispiro[isobenzofuran-1,10'-dibenzo[b,e]siline-5',1''-silinane]-5-carboxylate To a mixed solution of di-tert-butyl 4-bromoisophthalate (374 mg, 1.05 mmol, CAS No. 1431377-56-8) in THF (10.0 mL)/n-hexane (5.00 mL) was added dropwise n-butyllithium (a 2.65-M hexane solution, 395 μL, 1.05 mmol) under a nitrogen atmosphere at an inside temperature of −95° C. or lower. The solution was stirred at the same temperature for 10 minutes, and then a solution of 3,7-bis((tert-butyldimethylsily)oxy)-10H-spiro[dibenzo[b,e]siline-5,1'-silinan]-10-one produced in Production Example 4-(3) (94.0 mg, 174 μmol) in THF (5.00 mL) was added dropwise to the solution at an inside temperature of −95° C. or lower. The solution was stirred at the same temperature for 10 minutes, and then a boron trifluoride diethyl ether complex (44.0 μL, 349 μmol) was added dropwise to the solution. The reaction mixture was heated to −78° C., and was then stirred at the same temperature for 2 hours. The reaction mixture was heated to −45° C., and was then stirred at the same temperature for 1 hour and 20 minutes. The reaction mixture was heated to −20° C. and was then stirred at the same temperature for 30 minutes. The reaction mixture was heated to 0° C., and was then stirred at the same temperature for 30 minutes. After the disappearance of the raw materials was confirmed, ice-cooled water and a saturated aqueous ammonium chloride solution were added to the solution to terminate the reaction. The aqueous layer was extracted with ethyl acetate, and then the organic layer was washed with water. The solvent was distilled away to yield a mixture containing the adduct. The resultant mixture was dissolved in THF (5.00 mL), then tetrabutylammonium fluoride (a 1.00-M THF solution, 872 μL, 872 μmol) was added to the solution under an ice bath. The reaction mixture was stirred at room temperature 4 hours. A saturated aqueous ammonium chloride solution was added to the solution under an ice bath to terminate the reaction. The aqueous layer was extracted with ethyl acetate, and then the organic layer was washed with a saturated aqueous ammonium chloride solution, water and saturated saline. The mixture was dried over anhydrous magnesium sulfate, and then the solvent was distilled away under a reduced pressure. The resultant residue was purified by silica gel column chromatography (n-heptane/ethyl acetate) to yield the title compound (62.0 mg, 120 μmol).
ESI-MS m/z 515 [M+H]+

(2) Synthesis of tert-butyl 3-oxo-3',7'-bis(((trifluoromethyl)sulfonyl)oxy)-3H-dispiro[isobenzofuran-1,10'-dibenzo[b,e]siline-5',1''-silinane]-5-carboxylate The title compound (31.0 mg, 40.0 μmol) was produced in the same manner as in Production Example 5-(2) from the compound produced in Production Example 6-(1) (62.0 mg, 120 μmol).

$^1$H-NMR (400 MHZ, CDCl$_3$) δ (ppm): 1.26-1.33 (m, 4H), 1.63 (s, 9H), 1.78 (br.s., 2H), 2.02 (br.s., 2H), 2.16 (br.s., 2H), 7.16-7.20 (m, 4H), 7.42-7.47 (m, 1H), 7.73 (d, J=2.34 Hz, 2H), 8.40 (dd, J=8.20, 1.56 Hz, 1H), 8.59-8.64 (m, 1H).

Production Example 7

Synthesis of tert-butyl 5-chloro-3-oxo-3',7'-bis(((trifluoromethyl)sulfonyl)oxy)-3H-dispiro[isobenzofuran-1,10'-dibenzo[b,e]siline-5',1''-silinane]-6-carboxylate

[Formula 37]

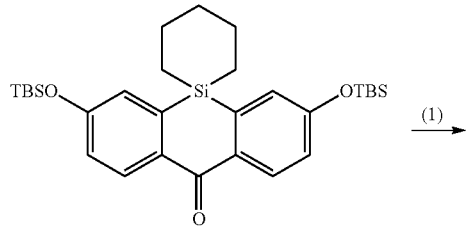

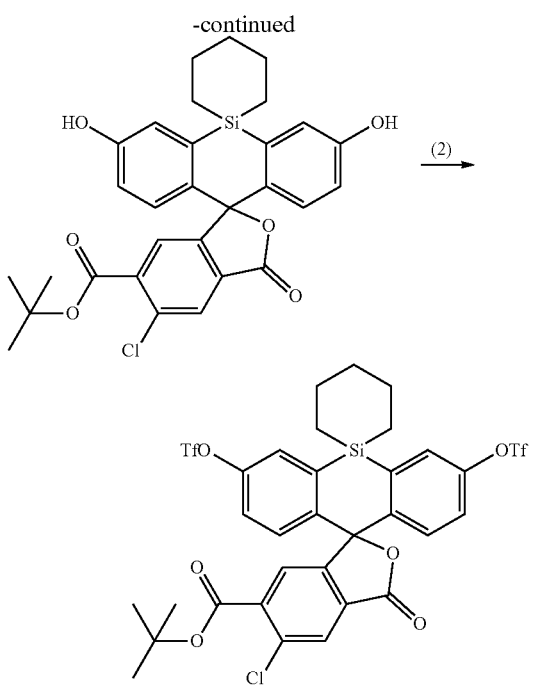

(1) Synthesis of tert-butyl 5-chloro-3',7'-dihydroxy-3-oxo-3H-dispiro[isobenzofuran-1,10'-dibenzo[b,e]siline-5',1"-silinane]-6-carboxylate To a mixed solution of di-tert-butyl 2-bromo-5-chloroterephthalate (945 mg, 2.41 mmol) produced in Production Example 1 in THF (20.0 mL)/n-hexane (10.0 mL) was added dropwise n-butyllithium (a 2.65-M hexane solution, 910 µL, 2.41 mmol) at an inside temperature of −95° C. or lower under a nitrogen atmosphere. The solution was stirred at the same temperature for 10 minutes, and then a solution of 3,7-bis((tert-butyldimethylsily)oxy)-10H-spiro[dibenzo[b,e]siline-5,1'-silinan]-10-one (130 mg, 241 µmol) produced in Production Example 4-(3) in THF (10.0 mL) was added dropwise to the solution at an inside temperature of −95° C. or lower. The solution was stirred at the same temperature for 5 minutes, and then a boron trifluoride diethyl ether complex (61.0 µL, 482 µmol) was added dropwise to the solution. The reaction mixture was heated to room temperature slowly, and was then stirred at room temperature overnight. Ice was added to the solution to terminate the reaction, and the aqueous layer was extracted with ethyl acetate. The organic layer was washed with saturated saline, and the resultant product was dried over anhydrous magnesium sulfate. The solvent was distilled away to yield a mixture containing the adduct. THF (10.0 mL) and tetrabutylammonium fluoride (a 1.00-M THF solution, 1.21 mL, 1.21 mmol) were added to the resultant mixture, and the resultant solution was stirred at room temperature overnight. Subsequently, ice and a saturated aqueous ammonium chloride solution were added to the solution to terminate the reaction. The aqueous layer was extracted with ethyl acetate, and then the organic layer was washed with water. The solvent was distilled away under a reduced pressure, and the resultant residue was purified by silica gel column chromatography (n-heptane/ethyl acetate) to yield the title compound (119 mg, 217 µmol).
ESI-MS m/z 549 [M+H]$^+$ (2) Synthesis of tert-butyl 5-chloro-3-oxo-3',7'-bis(((trifluoromethyl)sulfonyl)oxy)-3H-dispiro[isobenzofuran-1,10'-dibenzo[b,e]siline-5',1"-silinane]-6-carboxylate To a mixture of the compound produced in Production Example 7-(1) (119 mg, 217 µmol), DCM (5.00 mL) and pyridine (140 µL, 1.73 mmol) was added dropwise trifluoromethanesulfonic anhydride (142 µL, 867 µmol) under an ice bath. The solution was heated to room temperature, was then stirred for 2.5 hours. Subsequently, ice was added to the solution to terminate the reaction, and the aqueous layer was extracted with DCM. The organic layer was washed with dilute hydrochloric acid and water, and then the solvent was distilled away under a reduced pressure. The resultant residue was purified by silica gel column chromatography (n-heptane/ethyl acetate) to yield the title compound (128 mg, 157 µmol).
$^1$H-NMR (400 MHZ, CDCl$_3$) δ (ppm): 1.22-1.33 (m, 4H), 1.60 (s, 9H), 1.78 (br.s., 2H), 2.03 (br.s., 2H), 2.08-2.19 (m, 2H), 7.22-7.25 (m, 4H), 7.64 (s, 1H), 7.73 (d, J=2.34 Hz, 2H), 8.04 (s, 1H).

Production Example 8

Synthesis of tert-butyl 5-methyl-3-oxo-3',7'-bis(((trifluoromethyl)sulfonyl)oxy)-3H-dispiro[isobenzofuran-1,10'-dibenzo[b,e]siline-5',1"-silinane]-6-carboxylate

[Formula 38]

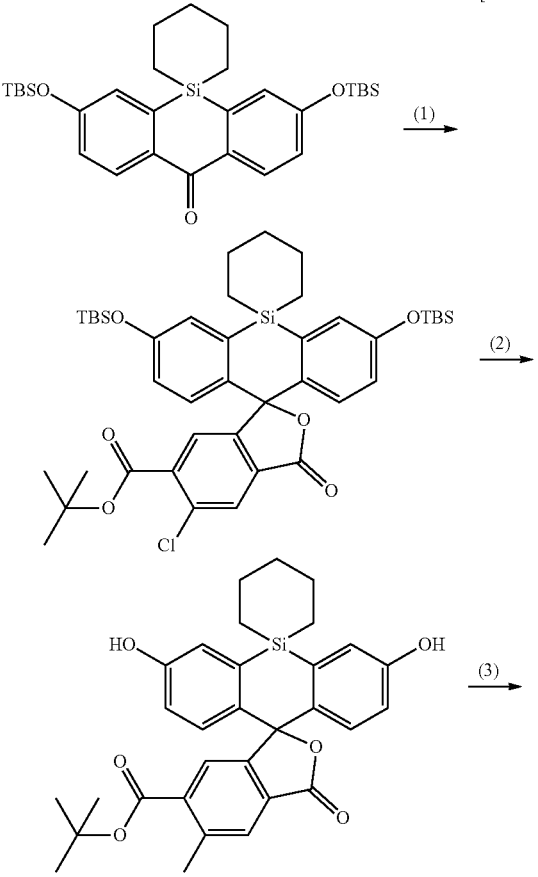

-continued

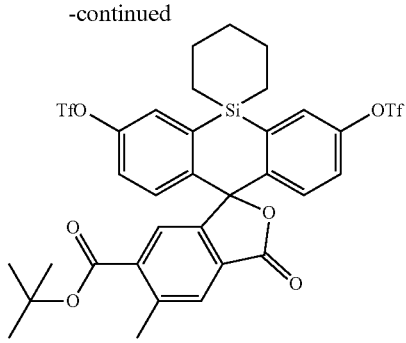

(1) Synthesis of tert-butyl 3',7'-bis((tert-butyldimethylsily)oxy)-5-chloro-3-oxo-3H-dispiro[isobenzofuran-1,10'-dibenzo[b,e]siline-5',1"-silinane]-6-carboxylate To a mixed solution of di-tert-butyl 2-bromo-5-chloro-terephthalate (4.27 g, 10.9 mmol) produced by the method of Production Example 1 in THF (50.0 mL)/n-hexane (25.0 mL) was added dropwise n-butyllithium (a 2.65-M hexane solution, 4.11 mL, 10.9 mmol) under a nitrogen atmosphere at an inside temperature of −95° C. or lower. The solution was stirred at the same temperature for 10 minutes, and then a solution of 3,7-bis((tert-butyldimethylsily)oxy)-10H-spiro[dibenzo[b,e]siline-5,1'-silinan]-10-one (587 mg, 1.09 mmol) produced in Production Example 4-(3) in THF (25.0 mL) was added dropwise to the solution at an inside temperature of −95° C. or lower. The solution was stirred at the same temperature for 5 minutes, and then a boron trifluoride diethyl ether complex (276 μL, 2.18 mmol) was added dropwise to the solution. The reaction mixture was heated to room temperature slowly, and was then stirred at room temperature for 5.5 hours. Subsequently, ice and a saturated aqueous ammonium chloride solution were added to the solution to terminate the reaction. The aqueous layer was extracted with ethyl acetate, and then the organic layer was washed with water. The solvent was distilled away, and the resultant residue was purified by silica gel column chromatography (n-heptane/ethyl acetate) to yield the title compound (purity: 53%, 1.58 g, 1.08 mmol).
$^1$H-NMR (400 MHZ, CDCl$_3$) δ (ppm): 0.21 (s, 12H), 0.98 (s, 18H), 1.16-1.23 (m, 4H), 1.61 (s, 9H), 1.73 (br.s., 2H), 2.00 (br.s., 2H), 2.07-2.18 (m, 2H), 6.72 (dd, J=8.59, 2.73 Hz, 2H), 6.90 (d, J=8.59 Hz, 2H), 7.29 (d, J=2.73 Hz, 2H), 7.57 (s, 1H), 7.98 (s, 1H).

(2) Synthesis of tert-butyl 3',7'-dihydroxy-5-methyl-3-oxo-3H-dispiro[isobenzofuran-1,10'-dibenzo[b,e]siline-5',1"-silinane]-6-carboxylate A mixture of the compound produced in Production Example 8-(1) (purity: 53%, 100 mg, 68.0 μmol), trimethylboroxine (48.0 μL, 341 μmol), (A-taPhos)$_2$PdCl$_2$ (19.3 mg, 27.0 μmol), a 1-N aqueous potassium carbonate solution (341 μL, 341 μmol) and 1,4-dioxane (3.00 mL) was stirred with a microwave irradiation device under a nitrogen atmosphere at 180° C. for 10 minutes. The solution was cooled to room temperature, and was then diluted with ethyl acetate. The organic layer was washed with water and saturated saline, and the resultant product was dried over anhydrous magnesium sulfate. The solvent was distilled away under a reduced pressure to produce an intermediate.

The intermediate was dissolved in THF (5.00 mL), and then tetrabutylammonium fluoride (a 1-M THF solution, 341 μL, 341 μmol) was added to the solution. The reaction mixture was stirred at room temperature for 1.5 hours, and then a saturated aqueous ammonium chloride solution was added to the solution to terminate the reaction. The aqueous layer was extracted with ethyl acetate, and the organic layer was washed with water twice. The solvent was distilled away under a reduced pressure, and the residue was purified by silica gel column chromatography (n-heptane/ethyl acetate) to yield the title compound (19.0 mg, 36.0 μmol).
ESI-MS m/z 529 [M+H]$^+$ (3) Synthesis of tert-butyl 5-methyl-3-oxo-3',7'-bis(((trifluoromethyl)sulfonyl)oxy)-3H-dispiro[isobenzofuran-1,10'-dibenzo[b,e]siline-5',1"-silinane]-6-carboxylate The title compound (80.0 mg, 101 μmol) was produced in the same manner as in Production Example 5-(2) from the compound produced by the method of Production Example 8-(2) (97.0 mg, 183 μmol).
$^1$H-NMR (400 MHZ, CDCl$_3$) δ (ppm): 1.28-1.34 (m, 4H), 1.58 (s, 9H), 1.78 (br.s., 2H), 2.04 (br.s., 2H), 2.13 (br.s., 2H), 2.67 (s, 3H), 7.18-7.23 (m, 2H), 7.27-7.31 (m, 2H), 7.72 (d, J=2.73 Hz, 2H), 7.73 (s, 1H), 7.85 (s, 1H).

Production Example 9

Synthesis of 3,7-dimorpholino-10H-spiro[dibenzo[b,e]siline-5,1'-silinan]-10-one

[Formula 39]

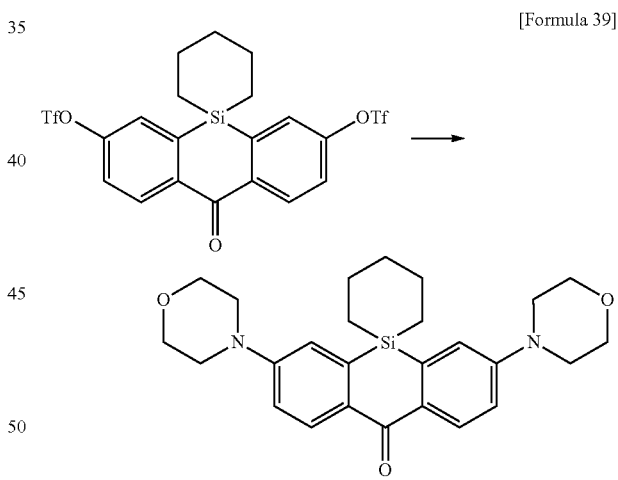

A mixture of 10-oxo-10H-spiro[dibenzo[b,e]siline-5,1'-silinane]-3,7-diylbis(trifluoromethanesulfonate) (122 mg, 212 μmol) produced in Production Example 5-(2), morpholine (51.8 mg, 595 μmol), tris(dibenzylideneacetone)dipalladium (0) (19.4 mg, 21.0 μmol), XPhos (30.4 mg, 64.0 μmol), cesium carbonate (194 mg, 595 μmol) and 1,4-dioxane (2.00 mL) was stirred in a sealed tube under a nitrogen atmosphere at 110° C. for 4 hours. The resultant solution was cooled to room temperature, and was then diluted with DCM. Insoluble matters were filtrated out, and the filtrate was concentrated. The residue was purified by silica gel column chromatography (n-heptane/ethyl acetate) to yield a crude product (103 mg) of the title compound.
ESI-MS m/z 449 [M+H]$^+$

Production Example 10

Synthesis of 3,7-bis(dimethylamino)-10H-spiro[dibenzo[b,e]siline-5,1'-silinan]-10-one

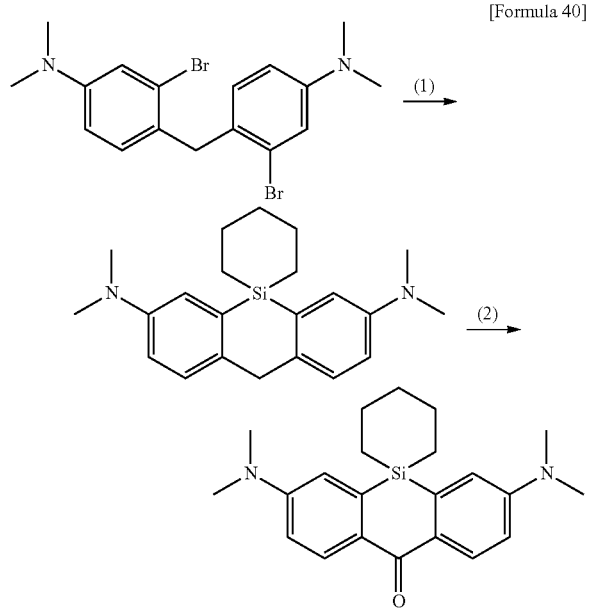

[Formula 40]

(1) Synthesis of N3,N3,N7,N7-tetramethyl-10H-spiro[dibenzo[b,e]siline-5,1'-silinane]-3,7-diamine To a solution of 4,4'-methylenebis(3-bromo-N,N-dimethylaniline) (500 mg, 1.21 mmol, CAS No. 63594-70-7) in THF (15.0 mL) was added dropwise sec-butyllithium (a 1.00-M cyclohexane-hexane solution, 3.46 mL, 3.46 mmol) at −78° C. over 20 minutes. The resultant solution was stirred at the same temperature for 30 minutes, and then a solution of cyclopentamethylenedichlorosilane (390 mg, 2.31 mmol) in THF was added dropwise to the solution. The solution was stirred at room temperature for 3.5 hours, and then ice and a saturated aqueous ammonium chloride solution were added to the solution to terminate the reaction. The aqueous layer was extracted with DCM, and the organic layer was dried over magnesium sulfate. The solvent was distilled away under a reduced pressure, and the resultant residue was purified by silica gel column chromatography (n-heptane/ethyl acetate) to yield the title compound (292 mg, 833 μmol).

ESI-MS m/z 351 [M+H]$^+$

(2) Synthesis of 3,7-bis(dimethylamino)-10H-spiro[dibenzo[b,e]siline-5,1'-silinan]-10-one To a solution of the compound produced in Production Example 10-(1) (232 mg, 662 μmol) in acetone (20.0 mL) was added potassium permanganate (282 mg, 1.79 mmol) under an ice bath over 30 minutes. The solution was stirred at the same temperature for 1 hour, and was then diluted with DCM. The generated insoluble matters were removed by the filtration through Celite. The eluate was concentrated under a reduced pressure at room temperature or lower, and the resultant residue was purified by silica gel column chromatography (n-heptane/ethyl acetate) to yield the title compound (82.0 mg, 225 μmol).

$^1$H-NMR (400 MHZ, CDCl$_3$) δ (ppm): 0.98-1.10 (m, 4H), 1.72 (br.s., 2H), 2.00-2.10 (m, 4H), 3.11 (s, 12H), 6.85 (dd, J=9.18, 2.93 Hz, 2H), 6.98 (d, J=2.73 Hz, 2H), 8.40 (d, J=9.37 Hz, 2H).

ESI-MS m/z 365 [M+H]$^+$

Production Example 11

Synthesis of 3,7-bis(dimethylamino)-10H-spiro[dibenzo[b,e]siline-5,1'-silolan]-10-one

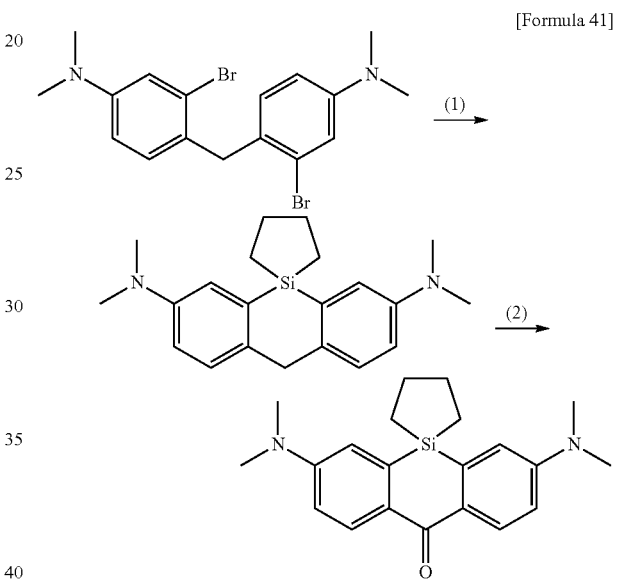

[Formula 41]

(1) Synthesis of N3,N3,N7,N7-tetramethyl-10H-spiro[dibenzo[b,e]siline-5,1'-silolane]-3,7-diamine The title compound (286 mg, 850 μmol) was produced in the same manner as in Production Example 10-(1) from 4,4'-methylenebis(3-bromo-N,N-dimethylaniline) (500 mg, 1.21 mmol) and cyclotetramethylenedichlorosilane (357 mg, 2.31 mmol, CAS No. 2406-33-9).

ESI-MS m/z 337 [M+H]$^+$

(2) Synthesis of 3,7-bis(dimethylamino)-10H-spiro[dibenzo[b,e]siline-5,1'-silolan]-10-one The title compound (115 mg, 328 μmol) was produced in the same manner as in Production Example 10-(2) from the compound produced in Production Example 11-(1) (276 mg, 820 μmol).

$^1$H-NMR (400 MHZ, CDCl$_3$) δ (ppm): 1.04-1.11 (m, 4H), 1.91-2.00 (m, 4H), 3.09 (s, 12H), 6.75 (d, J=3.12 Hz, 2H), 6.85 (dd, J=8.98, 2.73 Hz, 2H), 8.40 (d, J=8.98 Hz, 2H).

ESI-MS m/z 351 [M+H]$^+$

Production Example 12

Synthesis of 3,3'-(silinane-1,1-diyl)bis(N,N-diethylaniline)

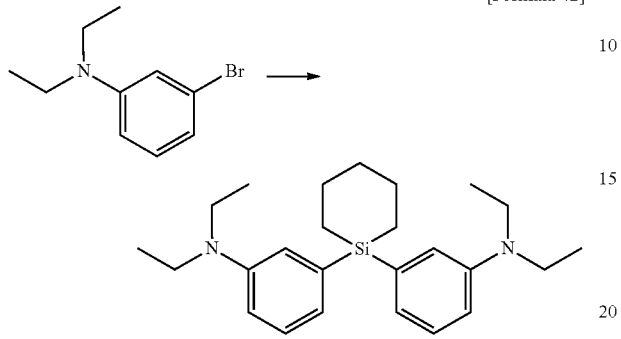

[Formula 42]

To a solution of 3-bromo-N,N-diethylaniline (6.16 g, 27.0 mmol, CAS No. 53142-19-1) in diethyl ether (70.0 mL) was added dropwise n-butyllithium (a 2.67-M n-hexane solution, 10.6 mL, 28.4 mmol) slowly under a nitrogen atmosphere and under an ice bath. The resultant solution was stirred at the same temperature for 3 hours, and then a solution of cyclopentamethylenedichlorosilane (2.74 g, 16.2 mmol) in diethyl ether (10.0 mL) was added dropwise to the solution. The solution was heated to room temperature and was then stirred for 18 hours. Water was added to the solution to terminate the reaction, and the aqueous layer was extracted with ethyl acetate. The organic layer was washed with saturated saline, and the resultant product was dried over anhydrous magnesium sulfate. The solvent was distilled away under a reduced pressure, and the residue was purified by silica gel column chromatography (n-heptane/ethyl acetate) to yield the title compound (3.52 g, 8.92 mmol).

$^1$H-NMR (400 MHZ, CDCl$_3$) δ (ppm): 1.06-1.21 (m, 16H), 1.46-1.58 (m, 2H), 1.74-1.85 (m, 4H), 3.32 (q, J=7.03 Hz, 8H), 6.69 (ddd, J=8.30, 2.83, 0.98 Hz, 2H), 6.81-6.91 (m, 4H), 7.20 (dd, J=8.40, 7.22 Hz, 2H).

ESI-MS m/z 395 [M+H]$^+$

Production Example 13

Synthesis of 1,1'-(silinane-1,1-diylbis(3,1-phenylene))dipyrrolidine

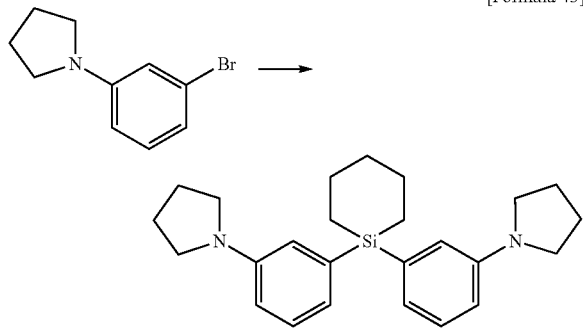

[Formula 43]

The title compound (365 mg, 934 μmol) was produced in the same manner as in Production Example 12 from 1-(3-bromophenyl) pyrrolidine (882 mg, 3.90 mmol, CAS No. 219928-13-9).

$^1$H-NMR (400 MHZ, CDCl$_3$) δ (ppm): 1.13-1.23 (m, 4H), 1.46-1.56 (m, 2H), 1.74-1.85 (m, 4H), 1.94-2.04 (m, 8H), 3.22-3.32 (m, 8H), 6.54-6.62 (m, 2H), 6.78 (d, J=2.34 Hz, 2H), 6.85 (d, J=7.03 Hz, 2H), 7.21 (dd, J=8.20, 7.03 Hz, 2H).

Production Example 14

Synthesis of 7,7'-(silinane-1,1-diyl)bis(1-allyl-1,2,3,4-tetrahydroquinoline)

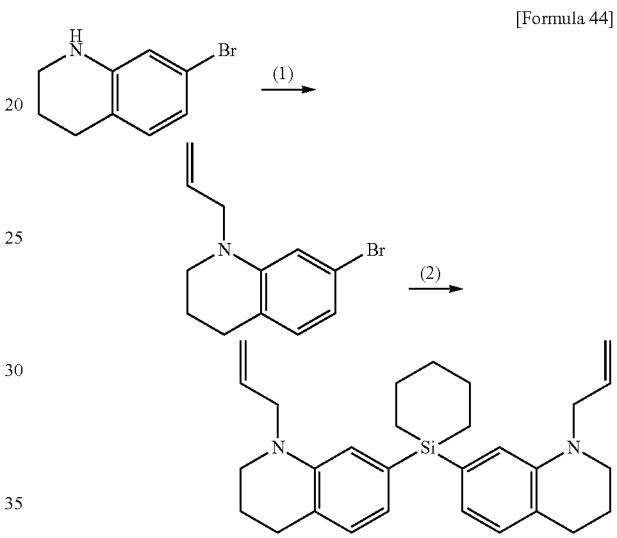

[Formula 44]

(1) Synthesis of 1-allyl-7-bromo-1,2,3,4-tetrahydroquinoline

A mixture of 7-bromo-1,2,3,4-tetrahydroquinoline (10.6 g, 50.0 mmol, CAS No. 114744-51-3), potassium carbonate (27.6 g, 200 mmol), allyl bromide (12.1 g, 100 mmol) and DMF (20.0 mL) was stirred at room temperature for 24 hours. Water was added to the reaction mixture to terminate the reaction, and then ethyl acetate and saturated saline were added to the resultant solution. Separately collected organic layers were combined, and the resultant solution was washed with water and saturated saline. The mixture was dried over anhydrous magnesium sulfate, and the solvent was distilled away under a reduced pressure. The residue was purified by silica gel column chromatography (n-heptane/ethyl acetate) to yield the title compound (12.4 g, 49.2 mmol).

$^1$H-NMR (400 MHZ, CDCl$_3$) δ (ppm): 1.89-1.98 (m, 2H), 2.69 (t, J=6.25 Hz, 2H), 3.24-3.29 (m, 2H), 3.83 (dt, J=4.88, 1.66 Hz, 2H), 5.15 (t, J=1.56 Hz, 1H), 5.17-5.21 (m, 1H), 5.74-5.89 (m, 1H), 6.60-6.68 (m, 2H), 6.77 (d, J=7.81 Hz, 1H).

(2) Synthesis of 7,7'-(silinane-1,1-diyl)bis(1-allyl-1,2,3,4-tetrahydroquinoline)

The title compound (2.30 g, 5.20 mmol) was produced in the same manner as in Production Example 12 from the compound produced in Production Example 14-(1) (5.04 g, 20.0 mmol).

$^1$H-NMR (400 MHZ, CDCl$_3$) δ (ppm): 1.03-1.14 (m, 4H), 1.43-1.53 (m, 2H), 1.67-1.84 (m, 4H), 1.88-2.01 (m, 4H), 2.75 (t, J=6.44 Hz, 4H), 3.19-3.31 (m, 4H), 3.84 (dt, J=5.47, 1.56 Hz, 4H), 5.06-5.21 (m, 4H), 5.81 (ddt, J=17.13, 10.30, 5.22 Hz, 2H), 6.70-6.81 (m, 4H), 6.92 (d, J=7.42 Hz, 2H).

Production Example 15

Synthesis of 3-hydroxy-1-oxo-1,3-dihydroisobenzofuran-5-carboxylic acid

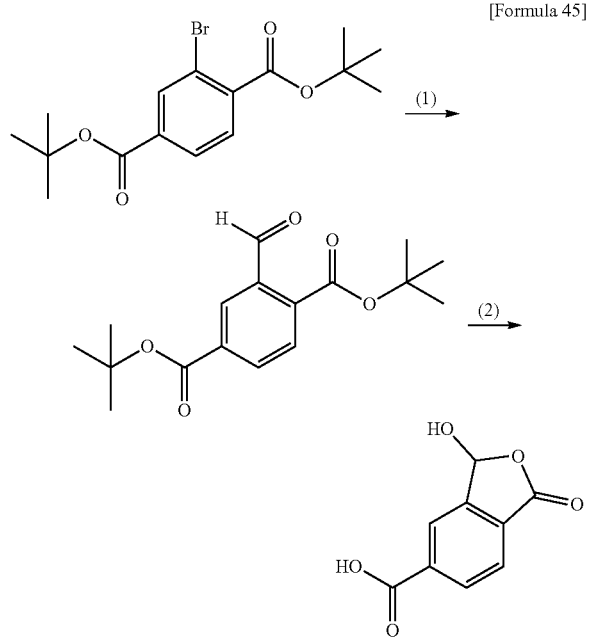

(1) Synthesis of di-tert-butyl 2-formylterephthalate

A mixture of di-tert-butyl 2-bromoterephthalate (3.57 g, 10.0 mmol), tetrakis(triphenylphosphine)palladium (0) (1.16 g, 1.00 mmol), tri-n-butyl(1-propenyl)tin (4.30 g, 13.0 mmol) and NMP (10.0 mL) was stirred at 120° C. for 4 hours. The solution was cooled to room temperature, and then the reaction mixture was purified directly by silica gel column chromatography (n-heptane/ethyl acetate) to yield di-tert-butyl 2-(prop-1-en-1-yl)terephthalate (2.90 g, 9.11 mmol) as a mixture of geometrical isomers thereof.

Sodium periodate (5.78 g, 27.0 mmol) was added to a mixture of di-tert-butyl 2-(prop-1-en-1-yl)terephthalate (2.87 g, 9.00 mmol), 1,4-dioxane (80.0 mL), water (20.0 mL), 2,6-lutidine (2.09 mL, 18.0 mmol) and osmium tetroxide (a 4% aqueous solution, 1.43 mL, 225 μmol), and the resultant solution was stirred at room temperature for 18 hours. Water and DCM were added to the reaction mixture, and the resultant solution was stirred at room temperature for 5 minutes. The organic layer was separated with a phase separator, and the solvent was distilled away under a reduced pressure. The resultant residue was purified by silica gel column chromatography (n-heptane/ethyl acetate) to yield the title compound (1.45 g, 4.73 mmol).

$^1$H-NMR (400 MHZ, CDCl$_3$) δ (ppm): 1.62 (s, 9H), 1.62 (s, 9H), 7.91 (d, J=8.59 Hz, 1H), 8.17-8.25 (m, 1H), 8.43 (d, J=1.17 Hz, 1H), 10.56 (s, 1H).

(2) Synthesis of 3-hydroxy-1-oxo-1,3-dihydroisobenzofuran-5-carboxylic acid

To a solution of the compound produced in Production Example 15-(1) (1.38 g, 4.50 mmol) in DCM (20.0 mL) was added TFA (3.47 mL). The resultant solution was stirred at room temperature for 18 hours. The solvent was distilled away under a reduced pressure to yield the title compound (874 mg, 4.50 mmol).

$^1$H-NMR (400 MHZ, DMSO-d$_6$) δ (ppm): 6.67 (s, 1H), 7.96 (d, J=8.20 Hz, 1H), 8.12-8.16 (m, 1H), 8.19 (dd, J=8.01, 1.37 Hz, 1H).

ESI-MS m/z 193 [M−H]$^-$

Production Example 16

Synthesis of 1-hydroxy-3-oxo-1,3-dihydroisobenzofuran-5-carboxylic acid

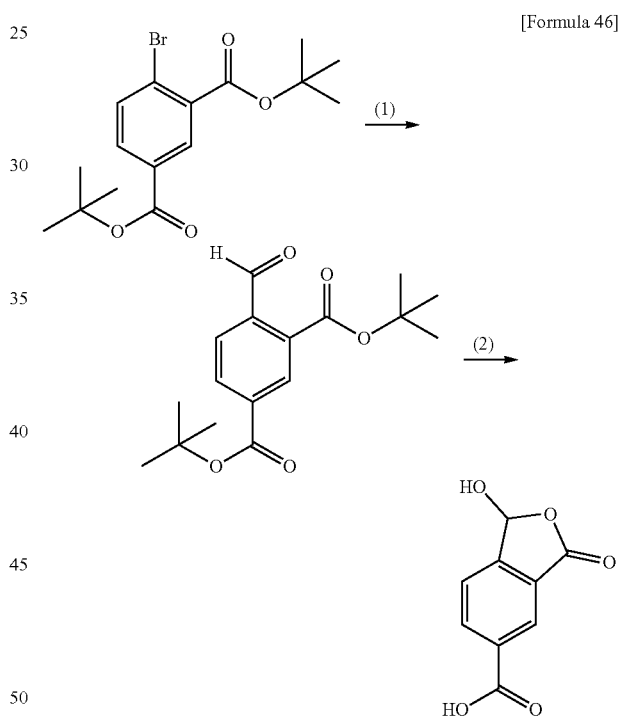

(1) Synthesis of di-tert-butyl 4-formylisophthalate

Di-tert-butyl 4-(prop-1-en-1-yl) isophthalate (1.05 g, 3.30 mmol) was produced as a mixture of geometrical isomers thereof in the same manner as in Production Example 15-(1) from di-tert-butyl 4-bromoisophthalate (1.18 g, 3.30 mmol). The title compound (610 mg, 1.99 mmol) was produced in the same manner as in Production Example 15-(1) from di-tert-butyl 4-(prop-1-en-1-yl) isophthalate (955 mg, 3.00 mmol).

$^1$H-NMR (400 MHZ, CDCl$_3$) δ (ppm): 1.62 (s, 9H), 1.64 (s, 9H), 7.90 (d, J=8.20 Hz, 1H), 8.16-8.21 (m, 1H), 8.49 (d, J=1.17 Hz, 1H), 10.63 (d, J=0.78 Hz, 1H).

(2) Synthesis of 1-hydroxy-3-oxo-1,3-dihydroisobenzofuran-5-carboxylic acid

The title compound (369 mg, 1.90 mmol) was produced in the same manner as in Production Example 15-(2) from the compound produced in Production Example 16-(1) (582 mg, 1.90 mmol).

$^1$H-NMR (400 MHZ, DMSO-d$_6$) δ (ppm): 6.68-6.77 (m, 1H), 7.76-7.86 (m, 1H), 8.20-8.27 (m, 1H), 8.29-8.37 (m, 2H), 13.53 (br.s., 1H).

ESI-MS m/z 193 [M−H]$^−$

Production Example 17

Synthesis of 6-fluoro-3-hydroxy-1-oxo-1,3-dihydroisobenzofuran-5-carboxylic acid

[Formula 47]

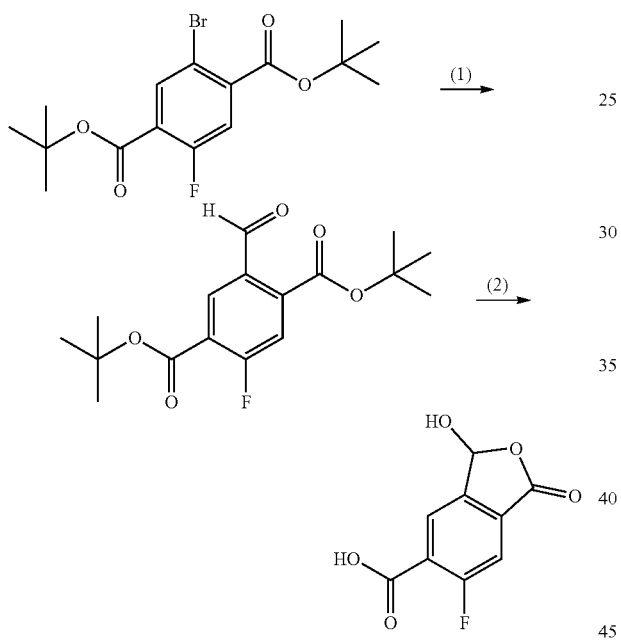

(1) Synthesis of di-tert-butyl 2-fluoro-5-formylterephthalate

The title compound (935 mg, 2.88 mmol) was produced in the same manner as in Production Example 15-(1) from di-tert-butyl 2-bromo-5-fluoroterephthalate (2.26 g, 6.02 mmol) produced by the method of Production Example 3.

$^1$H-NMR (400 MHZ, CDCl$_3$) δ (ppm): 1.63 (s, 9H), 1.65 (s, 9H), 7.60 (d, J=10.54 Hz, 1H), 8.40 (d, J=7.03 Hz, 1H), 10.53 (s, 1H).

(2) Synthesis of 6-fluoro-3-hydroxy-1-oxo-1,3-dihydroisobenzofuran-5-carboxylic acid A crude product (119 mg) of the title compound was produced in the same manner as in Production Example 15-(2) from the compound (163 mg, 503 μmol) produced by the method of Production Example 17-(1).

ESI-MS m/z 211 [M−H]$^−$

Production Example 18

Synthesis of 6-chloro-3-hydroxy-1-oxo-1,3-dihydroisobenzofuran-5-carboxylic acid

[Formula 48]

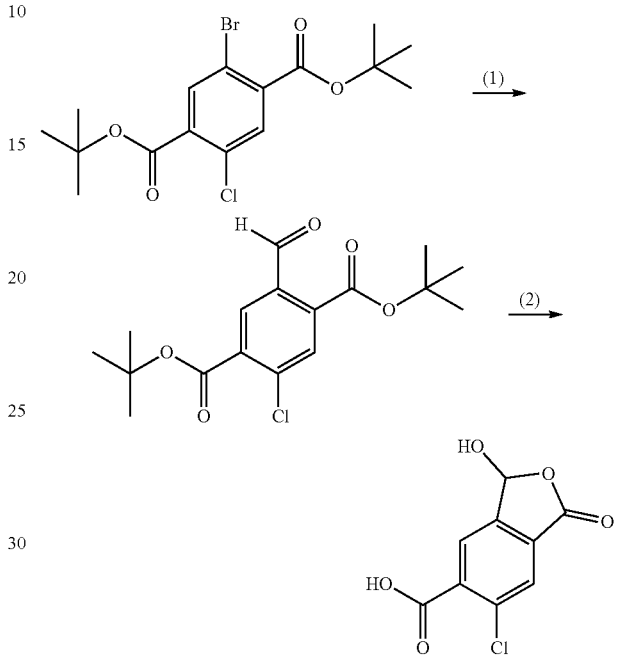

(1) Synthesis of di-tert-butyl 2-chloro-5-formylterephthalate

Di-tert-butyl 2-chloro-5-(prop-1-en-1-yl)terephthalate (405 mg, 1.15 mmol) was produced as a mixture of geometrical isomers thereof in the same manner as in Production Example 15-(1) from di-tert-butyl 2-bromo-5-chloroterephthalate (568 mg, 1.45 mmol) produced by the method of Production Example 1.

The title compound (330 mg, 968 μmol) was produced in the same manner as in Production Example 15-(1) from 2-chloro-5-(prop-1-en-1-yl)terephthalate (388 mg, 1.10 mmol).

$^1$H-NMR (400 MHz, CDCl$_3$) δ (ppm): 1.61 (s, 9H), 1.63 (s, 9H), 7.91 (s, 1H), 8.18 (s, 1H), 10.54 (s, 1H).

(2) Synthesis of 6-chloro-3-hydroxy-1-oxo-1,3-dihydroisobenzofuran-5-carboxylic acid The title compound (217 mg, 949 μmol) was produced in the same manner as in Production Example 15-(2) from the compound produced in Production Example 18-(1) (324 mg, 950 μmol).

$^1$H-NMR (400 MHz, DMSO-d$_6$) δ (ppm): 6.66 (br.s., 1H), 7.94 (s, 1H), 8.31 (br.s., 1H).

ESI-MS m/z 227 [M−H]$^−$

Production Example 19

Synthesis of 6-bromo-3-hydroxy-1-oxo-1,3-dihydroisobenzofuran-5-carboxylic acid

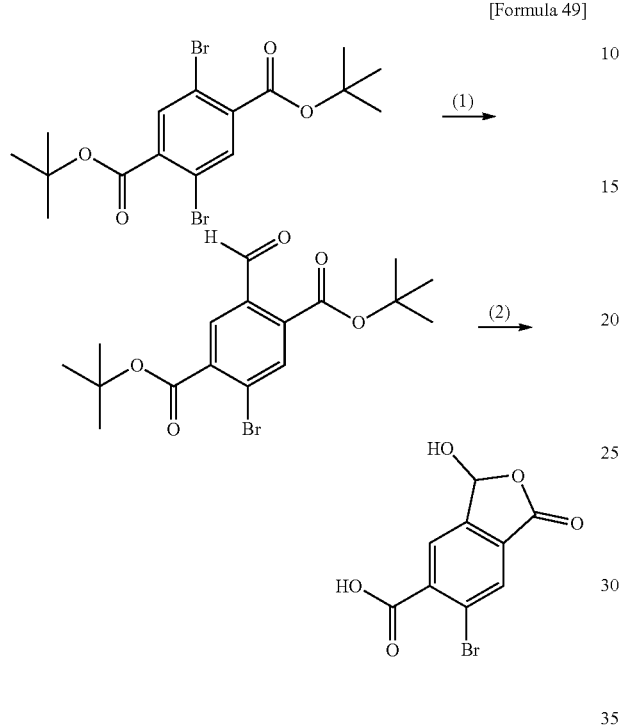

[Formula 49]

(1) Synthesis of di-tert-butyl 2-bromo-5-formylterephthalate

A mixture of di-tert-butyl 2,5-dibromoterephthalate (872 mg, 2.00 mmol, CAS #868158-34-3), tri-n-butyl(1-propenyl)tin (728 mg, 2.20 mmol), tetrakis(triphenylphosphine)palladium (0) (231 mg, 200 µmol) and NMP (4.00 mL) was stirred at 120° C. for 3 hours. The resultant solution was cooled to room temperature, and then the reaction mixture was purified directly by silica gel column chromatography (n-heptane/ethyl acetate) to yield di-tert-butyl 2-bromo-5-(prop-1-en-1-yl)terephthalate (710 mg, 1.79 mmol) as a mixture of geometrical isomers thereof.

The title compound (220 mg, 571 µmol) was produced in the same manner as in Production Example 15-(1) from di-tert-butyl 2-bromo-5-(prop-1-en-1-yl)terephthalate (695 mg, 1.75 mmol).

$^1$H-NMR (400 MHz, CDCl$_3$) δ (ppm): 1.62 (s, 9H), 1.63 (s, 9H), 8.12 (s, 2H), 10.54 (s, 1H).

(2) Synthesis of 6-bromo-3-hydroxy-1-oxo-1,3-dihydroisobenzofuran-5-carboxylic acid The title compound (150 mg, 549 µmol) was produced in the same manner as in Production Example 15-(2) from the compound produced in Production Example 19-(1) (212 mg, 550 µmol).

$^1$H-NMR (400 MHZ, DMSO-d$_6$) δ (ppm): 6.68 (br.s, 1H), 7.92 (br.s., 1H), 8.13 (s, 1H), 8.35 (br.s., 1H).

ESI-MS m/z 271 [M−H]$^-$

Production Example 20

Synthesis of 6-(difluoromethyl)-3-hydroxy-1-oxo-1,3-dihydroisobenzofuran-5-carboxylic acid

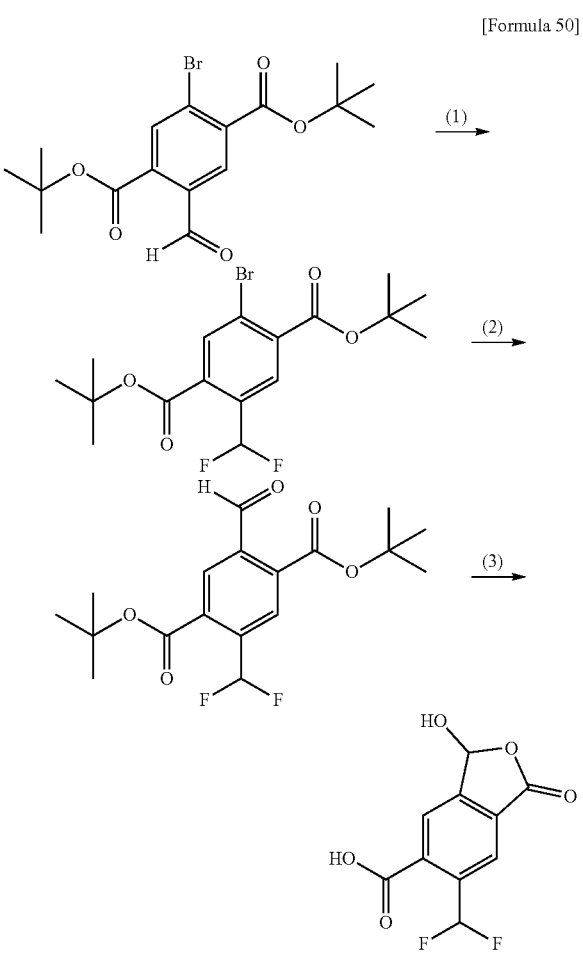

[Formula 50]

(1) Synthesis of di-tert-butyl 2-bromo-5-(difluoromethyl)terephthalate

To a solution of di-tert-butyl 2-bromo-5-formylterephthalate (308 mg, 800 µmol) produced in Production Example 19-(1) in DCM (3.00 mL) was added dropwise DAST (262 µL, 2.00 mmol) under an ice bath. The reaction mixture was stirred at room temperature for 12 hours, and then a saturated aqueous sodium bicarbonate solution was added to the solution under an ice bath to terminate the reaction. Dichloromethane and a saturated aqueous sodium bicarbonate solution were added to the mixture, and the resultant solution was stirred at room temperature for 5 minutes. The organic layer was separated with a phase separator, and the eluate was concentrated under a reduced pressure. The residue was purified by silica gel column chromatography (n-heptane/ethyl acetate) to yield the title compound (301 mg, 739 µmol).

$^1$H-NMR (400 MHZ, CDCl$_3$) δ (ppm): 1.61 (s, 9H), 1.62 (s, 9H), 7.39 (t, J=55.45 Hz, 1H), 8.00 (s, 1H), 8.15 (s, 1H).

(2) Synthesis of di-tert-butyl 2-(difluoromethyl)-5-formylterephthalate

The title compound (132 mg, 370 μmol) was produced in the same manner as in Production Example 15-(1) from a compound produced by the method of Production Example 20-(1) (326 mg, 800 μmol).

$^1$H-NMR (400 MHZ, CDCl$_3$) δ (ppm): 1.52 (s, 9H), 1.55 (s, 9H), 7.38 (t, J=55.06 Hz, 1H), 8.17 (s, 1H), 8.26 (s, 1H), 10.50 (s, 1H).

(3) Synthesis of 6-(difluoromethyl)-3-hydroxy-1-oxo-1,3-dihydroisobenzofuran-5-carboxylic acid The title compound (88.0 mg, 360 μmol) was produced in the same manner as in Production Example 15-(2) from the compound produced in Production Example 20-(2) (128 mg, 360 μmol).

$^1$H-NMR (400 MHZ, DMSO-d$_6$) δ (ppm): 6.78 (d, J=8.20 Hz, 1H), 7.62 (t, J=54.87 Hz, 1H), 8.07 (s, 1H), 8.17 (s, 1H), 8.43 (d, J=8.20 Hz, 1H).

Production Example 21

Synthesis of 3-hydroxy-6-(methoxymethyl)-1-oxo-1,3-dihydroisobenzofuran-5-carboxylic acid

[Formula 51]

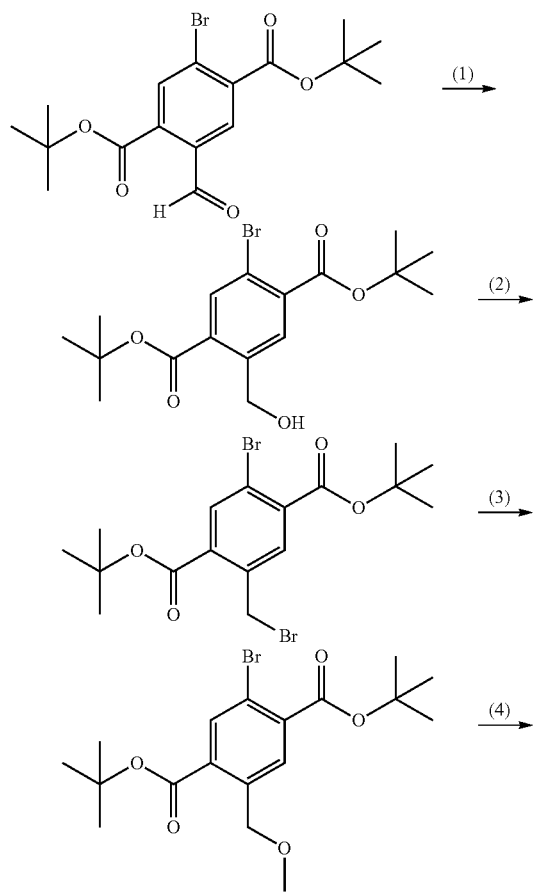

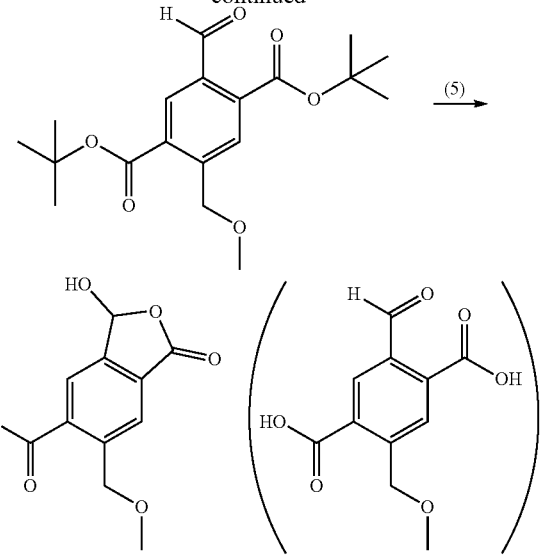

(1) Synthesis of di-tert-butyl 2-bromo-5-(hydroxymethyl)terephthalate

To a solution of di-tert-butyl 2-bromo-5-formylterephthalate (385 mg, 1.00 mmol) produced in Production Example 19-(1) in THF (5.00 mL) was added sodium borohydride (37.8 mg, 1.00 mmol) under an ice bath. The reaction mixture was stirred at the same temperature for 1 hour, then a saturated aqueous ammonium chloride solution and dichloromethane were added to the solution, and then the resultant solution was stirred for 5 minutes. The organic layer was separated with a phase separator, and the solvent was distilled away under a reduced pressure. The residue was purified by silica gel column chromatography (n-heptane/ethyl acetate) to yield the title compound (287 mg, 741 μmol).

$^1$H-NMR (400 MHZ, CDCl$_3$) δ (ppm): 1.61 (s, 9H), 1.61 (s, 9H), 3.62 (t, J=7.22 Hz, 1H), 4.73 (d, J=7.42 Hz, 2H), 7.72 (s, 1H), 8.10 (s, 1H).

(2) Synthesis of di-tert-butyl 2-bromo-5-(bromomethyl)terephthalate

To a solution of the compound produced in Production Example 21-(1) (271 mg, 700 μmol) in DCM (5.00 mL) were added triphenylphosphine (275 mg, 1.05 mmol) and carbon tetrabromide (464 mg, 1.40 mmol) under an ice bath. The resultant solution was stirred at the same temperature for 2 hours, and then the reaction mixture was purified directly by silica gel column chromatography (n-heptane/ethyl acetate) to yield the title compound (230 mg, 511 μmol).

$^1$H-NMR (400 MHZ, CDCl$_3$) δ (ppm): 1.62 (s, 9H), 1.63 (s, 9H), 4.85 (s, 2H), 7.68 (s, 1H), 8.08 (s, 1H).

(3) Synthesis of di-tert-butyl 2-bromo-5-(methoxymethyl)terephthalate

To a solution of the compound produced in Production Example 21-(2) (221 mg, 490 μmol) in dichloromethane (3.00 mL) was added dropwise sodium methoxide (a 28% methanol solution, 177 μL, 735 μmol) under an ice bath. The resultant solution was stirred at the same temperature for 2 hours, then THF (3.00 mL) was added to the reaction mixture, and the resultant solution was further stirred at the same temperature for additional 3 hours. The reaction mixture was purified directly by silica gel column chromatography (n-heptane/ethyl acetate) to yield the title compound (46.0 mg, 115 μmol).

$^1$H-NMR (400 MHZ, CDCl$_3$) δ (ppm): 1.59 (s, 9H), 1.61 (s, 9H), 3.46 (s, 3H), 4.74 (s, 2H), 7.86 (s, 1H), 8.04 (s, 1H).

(4) Synthesis of di-tert-butyl 2-formyl-5-(methoxymethyl)terephthalate

Di-tert-butyl 2-(methoxymethyl)-5-(prop-1-en-1-yl)terephthalate (32.0 mg, 88.0 μmol) was produced as a mixture of geometrical isomers thereof in the same manner as in Production Example 15-(1) from the compound produced in Production Example 21-(3) 45.0 mg, 112 μmol).

The title compound (28.0 mg, 80.0 μmol) was produced in the same manner as in Production Example 15-(1) from di-tert-butyl 2-(methoxymethyl)-5-(prop-1-en-1-yl)terephthalate (30.0 mg, 83.0 μmol).

$^1$H-NMR (400 MHZ, CDCl$_3$) δ (ppm): 1.61 (s, 9H), 1.63 (s, 9H), 3.51 (s, 3H), 4.87 (s, 2H), 8.12 (s, 1H), 8.32 (s, 1H), 10.53 (s, 1H).

(5) Synthesis of 3-hydroxy-6-(methoxymethyl)-1-oxo-1,3-dihydroisobenzofuran-5-carboxylic acid The title compound (18.0 mg, 76.0 μmol) was produced as mixture of tautomers thereof in the same manner as in Production Example 15-(2) from the compound produced in Production Example 21-(4) (27.0 mg, 77.0 μmol).

$^1$H-NMR (400 MHZ, DMSO-d$_6$) δ (ppm): 3.37 (s, 3H), 4.78 (s, 2H), 6.70 (d, J=8.20 Hz, 1H), 7.93 (s, 1H), 7.99 (s, 1H), 8.27 (d, J=8.20 Hz, 1H), 13.59 (br.s., 1H).

$^1$H-NMR (400 MHZ, DMSO-d$_6$) δ (ppm): 3.40 (s, 3H), 4.83 (s, 2H), 8.10 (s, 1H), 8.22 (s, 1H), 10.45 (s, 1H), 13.59 (br.s., 1H).

Production Example 22

Synthesis of 3-hydroxy-1-oxo-6-(trifluoromethyl)-1,3-dihydroisobenzofuran-5-carboxylic acid

[Formula 52]

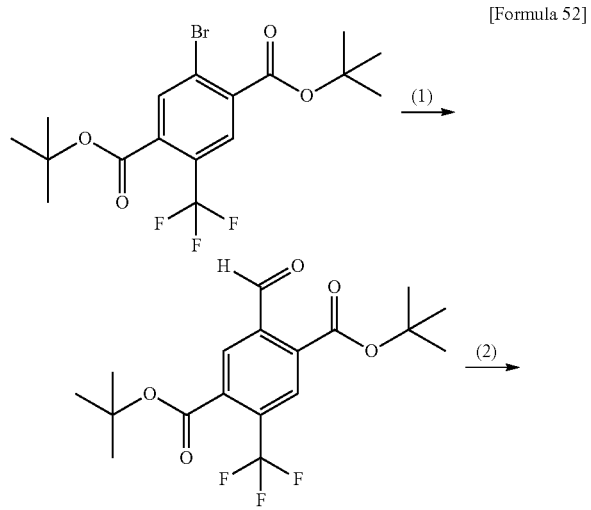

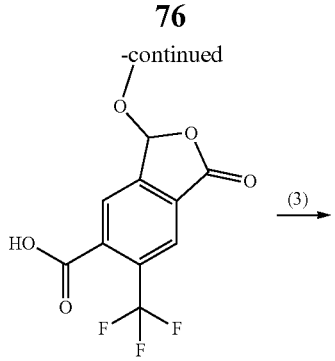

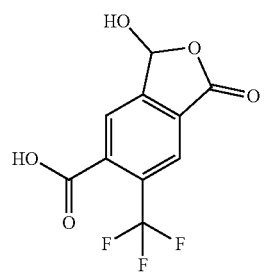

(1) Synthesis of di-tert-butyl 2-formyl-5-(trifluoromethyl)terephthalate

The title compound (165 mg, 441 μmol) was produced in the same manner as in Production Example 15-(1) from di-tert-butyl 2-bromo-5-(trifluoromethyl)terephthalate (205 mg, 482 μmol) produced by the method of Production Example 2-(3).

$^1$H-NMR (400 MHZ, CDCl$_3$) δ (ppm): 1.55 (s, 9H), 1.59 (s, 9H), 8.13 (s, 1H), 8.23 (s, 1H), 10.63 (s, 1H).

(2) Synthesis of 3-methoxy-1-oxo-6-(trifluoromethyl)-1,3-dihydroisobenzofuran-5-carboxylic acid The title compound (125 mg, 453 μmol) was produced in the same manner as in Production Example 15-(2) from the compound produced in Production Example 22-(1) (165 mg, 441 μmol).

$^1$H-NMR (400 MHZ, DMSO-d$_6$) δ (ppm): 3.59 (s, 3H), 6.67 (s, 1H), 8.13 (s, 1H), 8.26 (s, 1H).

ESI-MS m/z 275 [M−H]$^-$ (3) Synthesis of 3-hydroxy-1-oxo-6-(trifluoromethyl)-1,3-dihydroisobenzofuran-5-carboxylic acid To the solution of the compound produced in Production Example 22-(2) (125 mg, 453 μmol) in methanol (1.00 mL) was added 5N hydrochloric acid (10.0 mL, 50.0 mmol). The resultant solution was stirred at 110° C. 2.5 hours. The solution was cooled to room temperature, and then the solvent was distilled away under a reduced pressure to yield the title compound (103 mg, 393 μmol).

$^1$H-NMR (400 MHZ, DMSO-d$_6$) δ (ppm): 6.81 (br.s., 1H), 8.06 (s, 1H), 8.21 (s, 1H).

ESI-MS m/z 261 [M−H]$^-$

Production Example 23

Synthesis of 3-hydroxy-6-methoxy-1-oxo-1,3-dihydroisobenzofuran-5-carboxylic acid

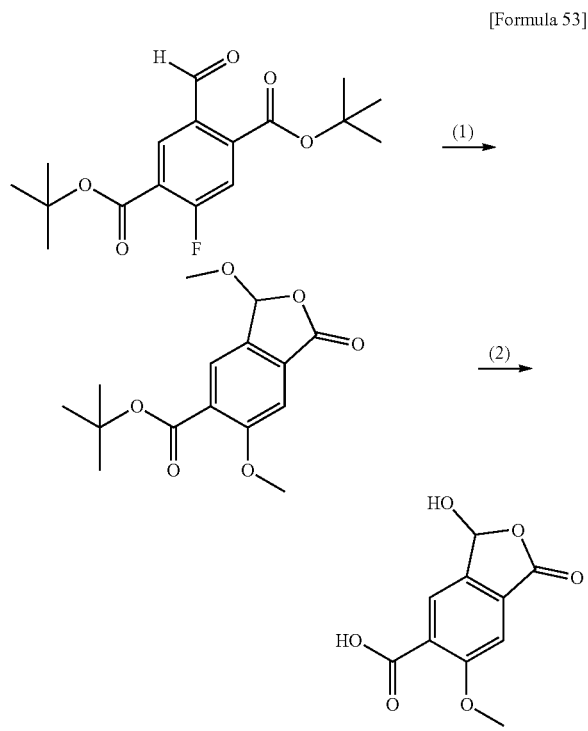

[Formula 53]

(1) Synthesis of tert-butyl 3,6-dimethoxy-1-oxo-1,3-dihydroisobenzofuran-5-carboxylic acid To a solution of di-tert-butyl 2-fluoro-5-formylterephthalate (120 mg, 370 μmol) produced in Production Example 17-(1) in THF (3.00 mL) was added sodium methoxide (a 5.4-M methanol solution, 72.0 μL, 388 μmol) under an ice bath. The resultant solution was stirred at the same temperature for 2 hours, and was then further stirred at room temperature for 1 hour. A small amount of acetic acid was added to terminate the reaction, and the solution was diluted with ethyl acetate. The mixture was washed with water, and the solvent was distilled away under a reduced pressure. The resultant residue was purified by silica gel column chromatography (n-heptane/ethyl acetate) to yield the title compound (27.0 mg, 92.0 μmol).

$^1$H-NMR (400 MHZ, CDCl$_3$) δ (ppm): 1.59 (s, 9H), 3.63 (s, 3H), 3.95 (s, 3H), 6.26 (s, 1H), 7.38 (s, 1H), 7.78 (s, 1H).

(2) Synthesis of 3-hydroxy-6-methoxy-1-oxo-1,3-dihydroisobenzofuran-5-carboxylic acid A mixture (19.0 mg) containing the title compound was produced in the same manner as in Production Example 22-(3) from the compound produced in Production Example 23-(1) (27.0 mg, 92.0 μmol).

ESI-MS m/z 225 [M+H]$^+$

Production Example 24

Synthesis of 3-hydroxy-6-(methylthio)-1-oxo-1,3-dihydroisobenzofuran-5-carboxylic acid

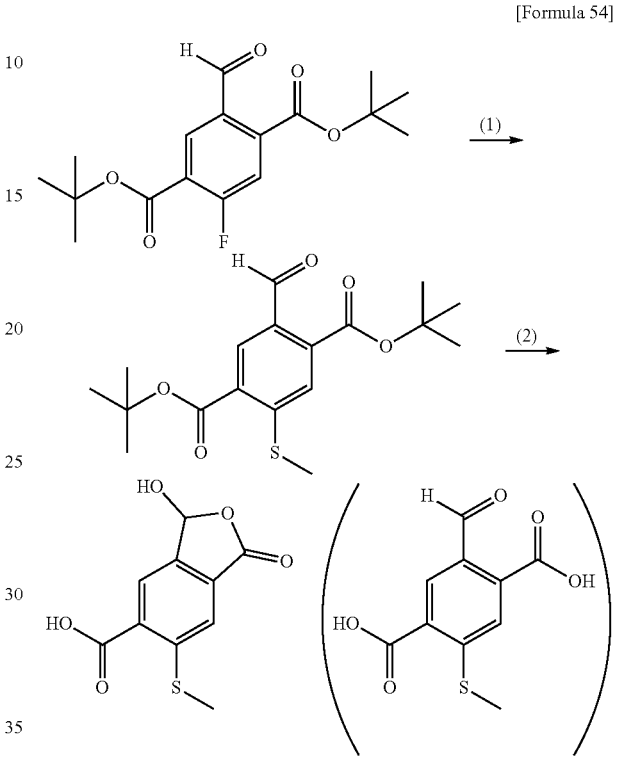

[Formula 54]

(1) Synthesis of di-tert-butyl 2-formyl-5-(methylthio)terephthalate

Sodium methanethiolate (31.3 mg, 444 μmol) was added to a solution of di-tert-butyl 2-fluoro-5-formylterephthalate (120 mg, 370 μmol) produced in Production Example 17-(1) in THF (5.00 mL), and the resultant solution was stirred at room temperature overnight. The reaction mixture was diluted with ethyl acetate, and the organic layer was washed with water and saturated saline. The mixture was dried over anhydrous magnesium sulfate, and the solvent was distilled away under a reduced pressure to yield a crude product (139 mg) of the title compound.

$^1$H-NMR (400 MHZ, CDCl$_3$) δ (ppm): 1.62 (s, 9H), 1.63 (s, 9H), 2.53 (s, 3H), 7.68 (s, 1H), 8.42 (s, 1H), 10.47 (s, 1H).

(2) Synthesis of 3-hydroxy-6-(methylthio)-1-oxo-1,3-dihydroisobenzofuran-5-carboxylic acid A crude product (132 mg) of the title compound was produced as a mixture of tautomers thereof in the same manner as in Production Example 15-(2) from the compound produced in Production Example 24-(1) (137 mg).

$^1$H-NMR (400 MHZ, DMSO-d$_6$) δ (ppm): 2.51 (s, 3H), 6.67 (s, 1H), 7.72 (s, 1H), 8.03 (s, 1H).

$^1$H-NMR (400 MHZ, DMSO-d$_6$) δ (ppm): 2.50 (s, 3H), 7.65 (s, 1H), 8.31 (s, 1H), 10.35 (s, 1H).

ESI-MS m/z 239 [M−H]$^-$

Example 1

Synthesis of 3',7'-di(azetidin-1-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

[Formula 55]

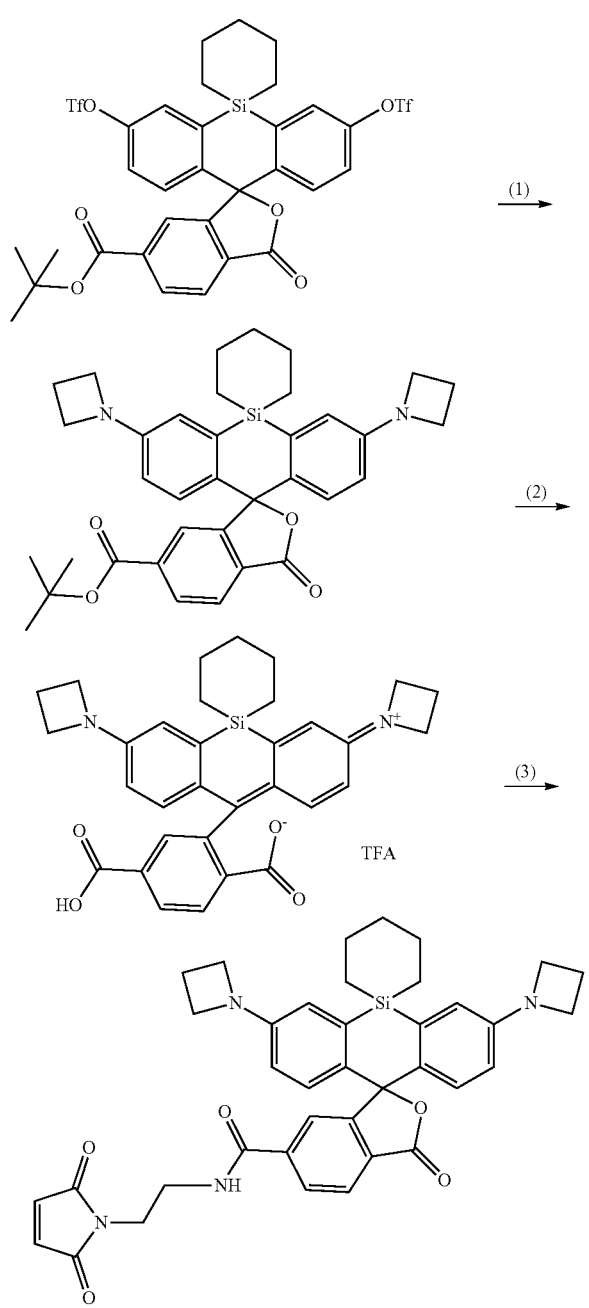

(1) Synthesis of tert-butyl 3',7'-di(azetidin-1-yl)-3-oxo-3H-dispiro[isobenzofuran-1,10'-dibenzo[b,e]siline-5',1''-silinane]-6-carboxylate A mixed solution of tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (100 mg, 128 µmol) produced in Production Example 5-(2), azetidine (20.5 mg, 360 µmol), tris(dibenzylideneacetone)dipalladium (0) (11.8 mg, 13.0 µmol), XPhos (18.4 mg, 39.0 µmol), cesium carbonate (117 mg, 360 µmol) and 1,4-dioxane (5.00 mL) was stirred in a sealed tube at 110° C. for 4.5 hours under a nitrogen atmosphere. Insoluble matters were filtrated out, and the filtrate was concentrated. The residue was purified by silica gel column chromatography (n-heptane/ethyl acetate) to yield the title compound (62.0 mg, 105 µmol).

ESI-MS m/z 593 [M+H]$^+$ (2) Synthesis of 2-(3-(azetidin-1-ium-1-ylidene)-7-(azetidin-1-yl)-3H-spiro[dibenzo[b,e]siline-5,1'-silinan]-10-yl)-4-carboxybenzoate TFA salt TFA (200 µL) was added to a solution of the compound produced in Example 1-(1) (62.0 mg, 105 µmol) in DCM (2.00 mL), and the resultant solution was stirred at room temperature overnight. The solvent was distilled away under a reduced pressure, and remaining TFA was azeotropically removed with methanol to yield a crude product (70.0 mg) of the title compound.

ESI-MS m/z 537 [M+H]$^+$ (3) Synthesis of 3',7'-di(azetidin-1-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide To a solution of the compound produced by the method of Example 1-(2) (15.0 mg) in DMF (1.00 mL) were added TEA (19.0 µL, 138 µmol), N-(2-aminoethyl) maleimide TFA salt (13.5 mg, 53.0 µmol) and PyBOP (18.0 mg, 35.0 µmol). The resultant reaction mixture was stirred at room temperature for 2 hours, and then the mixture was purified directly by reverse-phase silica gel column chromatography (water/acetonitrile, 0.1% formic acid). The fraction containing the desired product was collected, and excess acetonitrile was distilled away under a reduced pressure. The aqueous layer in the residue was neutralized with a saturated aqueous sodium bicarbonate solution, and the aqueous layer was extracted with ethyl acetate. The organic layer was washed with saturated saline, and the resultant product was dried over anhydrous magnesium sulfate. The solvent was distilled away under a reduced pressure, and the resultant residue was purified by silica gel thin-layer chromatography (n-heptane/ethyl acetate) to yield the title compound (10.3 mg, 16.0 µmol).

$^1$H-NMR (400 MHz, CDCl$_3$) δ (ppm): 1.16-1.26 (m, 4H), 1.71 (br.s., 2H), 1.98 (br.s., 2H), 2.10 (br.s., 2H), 2.31-2.44 (m, 4H), 3.61-3.69 (m, 2H), 3.76-3.84 (m, 2H), 3.90 (t, J=7.42 Hz, 8H), 6.25 (dd, J=8.79, 2.54 Hz, 2H), 6.72 (s, 2H), 6.75-6.80 (m, 1H), 6.77 (d, J=8.59 Hz, 2H), 6.84 (d, J=2.73 Hz, 2H), 7.74 (s, 1H), 7.84 (dd, J=8.01, 1.37 Hz, 1H), 7.97-8.02 (m, 1H).

ESI-MS m/z 659 [M+H]$^+$

Example 2

Synthesis of N-(2-(2,5-dioxo-2,5-dihydro-1H-pyrrol-1-yl)ethyl)-3',7'-bis(3-fluoroazetidin-1-yl)-3-oxo-3H-dispiro[isobenzofuran-1,10'-dibenzo[b,e]siline-5',1''-silinane]-6-carboxamide

[Formula 56]

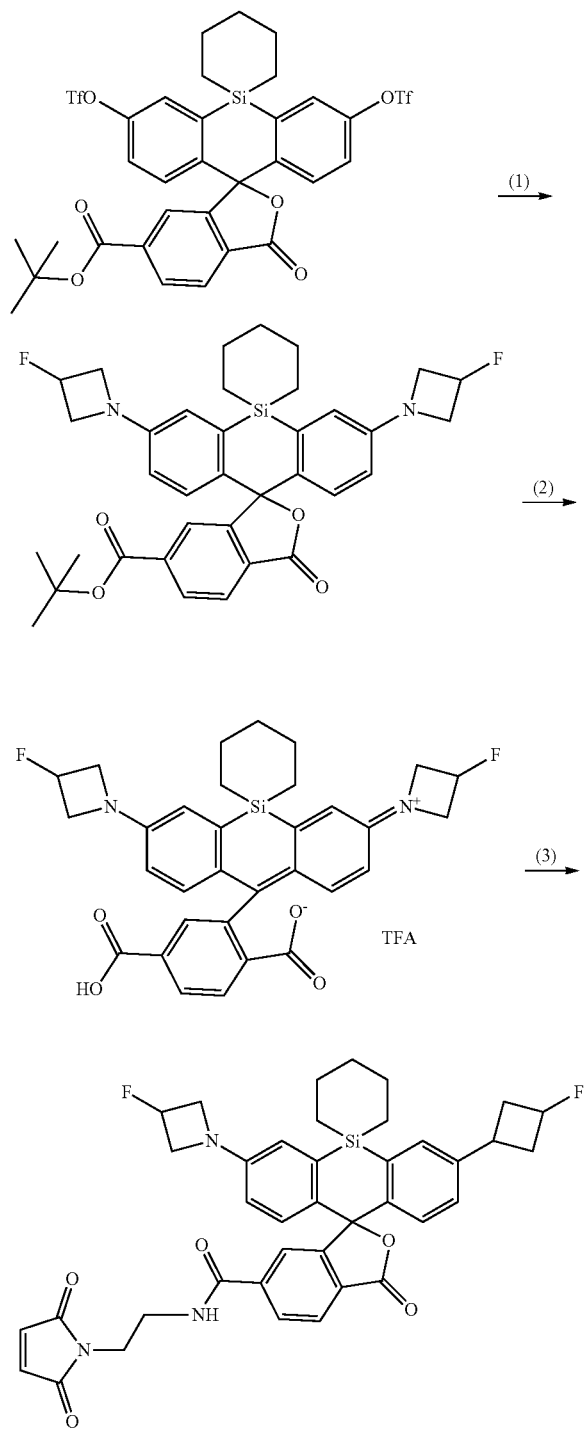

(1) Synthesis of tert-butyl 3',7'-bis(3-fluoroazetidin-1-yl)-3-oxo-3H-dispiro[isobenzofuran-1,10'-dibenzo[b,e]siline-5',1''-silinane]-6-carboxylate A mixture of tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (19.0 mg, 24.0 μmol) produced in Production Example 5-(2), 3-fluoroazetidine hydrochloric acid salt (7.62 mg, 68.0 μmol, CAS No. 617718-46-4), cesium carbonate (47.7 mg, 146 μmol), tris(dibenzylideneacetone)dipalladium (0) (2.23 mg, 2.44 μmol), XPhos (3.49 mg, 7.32 μmol) and 1,4-dioxane (3.00 mL) was stirred in a sealed tube at 100° C. for 4 hours under a nitrogen atmosphere. The resultant solution was cooled to room temperature, and was then diluted with DCM. Insoluble matters were filtrated, and the eluate was concentrated. The residue was purified by silica gel thin-layer chromatography (n-heptane/ethyl acetate) to yield the title compound (7.00 mg, 11.0 μmol).

ESI-MS m/z 629 [M+H]$^+$ (2) Synthesis of 4-carboxy-2-(3-(3-fluoroazetidin-1-ium-1-ylidene)-7-(3-fluoroazetidin-1-yl)-3H-spiro[dibenzo[b,e]siline-5,1'-silinan]-10-yl)benzoate TFA salt A crude product (8.00 mg) of the title compound was produced in the same manner as in Example 1-(2) from the compound produced in Example 2-(1) (7.00 mg, 11.0 μmol).

ESI-MS m/z 573 [M+H]$^+$ (3) Synthesis of N-(2-(2,5-dioxo-2,5-dihydro-1H-pyrrol-1-yl)ethyl)-3',7'-bis(3-fluoroazetidin-1-yl)-3-oxo-3H-dispiro[isobenzofuran-1,10'-dibenzo[b,e]siline-5',1''-silinane]-6-carboxamide To a solution of the compound produced in Example 2-(2) (8.00 mg) in DMF (1.00 mL) were added N-(2-aminoethyl)maleimide TFA salt (6.81 mg, 27.0 μmol), TEA (9.74 μL, 70.0 μmol) and PyBOP (9.09 mg, 17.0 μmol). The reaction mixture was stirred at room temperature overnight, and was then purified directly by reverse-phase silica gel column chromatography (water/acetonitrile, 0.1% formic acid). A crude product produced was purified by silica gel thin-layer chromatography (n-heptane/ethyl acetate) to yield the title compound (2.40 mg, 3.45 μmol).

$^1$H-NMR (400 MHZ, CDCl$_3$) δ (ppm): 1.14-1.24 (m, 4H), 1.73 (br.s., 2H), 1.99 (br.s., 2H), 2.11 (br.s., 2H), 3.60-3.68 (m, 2H), 3.77-3.86 (m, 2H), 3.92-4.06 (m, 4H), 4.15-4.27 (m, 4H), 5.31-5.54 (m, 2H), 6.30 (dd, J=8.79, 2.54 Hz, 2H), 6.72 (s, 2H), 6.81-6.83 (m, 1H), 6.82 (d, J=8.59 Hz, 2H), 6.87 (d, J=2.73 Hz, 2H), 7.75 (d, J=0.78 Hz, 1H), 7.82-7.88 (m, 1H), 8.01 (d, J=8.20 Hz, 1H).

ESI-MS m/z 695 [M+H]$^+$

Example 3

Synthesis of 3',7'-bis(3,3-difluoroazetidin-1-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

[Formula 57]

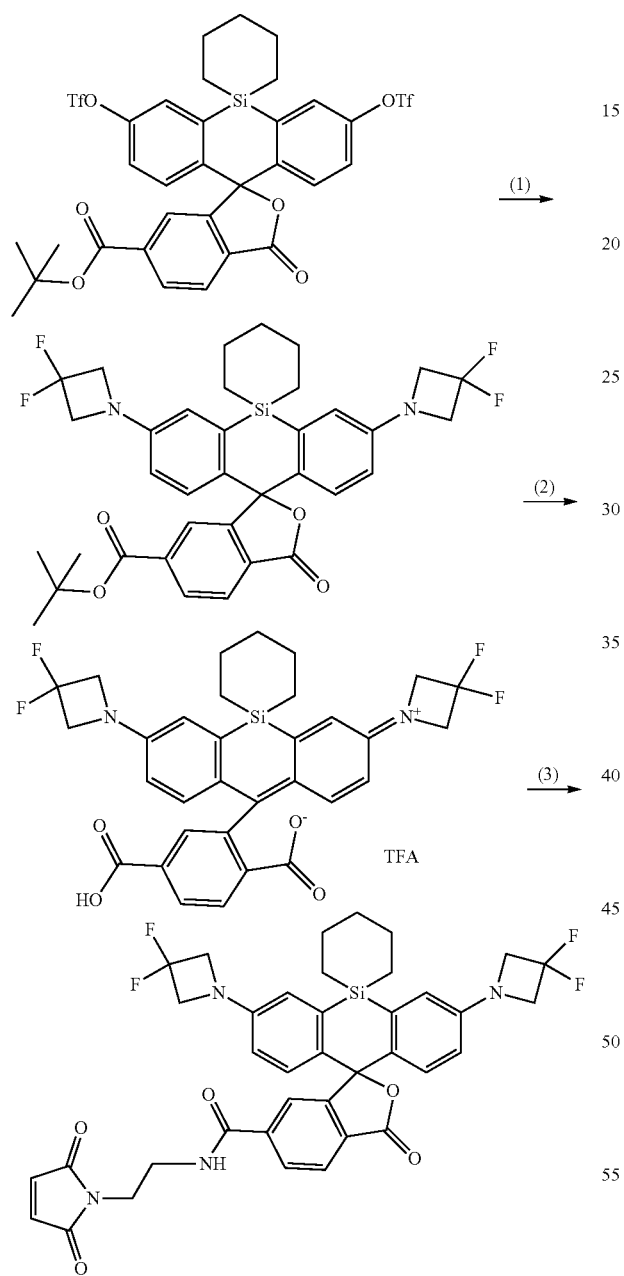

(1) Synthesis of tert-butyl 3',7'-bis(3,3-difluoroazetidin-1-yl)-3-oxo-3H-dispiro[isobenzofuran-1,10'-dibenzo[b,e]siline-5',1''-silinane]-6-carboxylate The title compound (14.0 mg, 21.0 μmol) was produced in the same manner as in Example 1-(1) from tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (19.0 mg, 24.0 μmol) produced in Production Example 5-(2) and 3,3-difluoroazetidine hydrochloric acid salt (8.85 mg, 68.0 μmol, CAS No. 288315-03-7).

ESI-MS m/z 665 [M+H]+

(2) Synthesis of 4-carboxy-2-(3-(3,3-difluoroazetidin-1-ium-1-ylidene)-7-(3,3-difluoroazetidin-1-yl)-3H-spiro[dibenzo[b,e]siline-5,1'-silinan]-10-yl)benzoate TFA salt A crude product (16.0 mg) of the title compound was produced in the same manner as in Example 1-(2) from the compound produced in Example 3-(1) (14.0 mg, 21.0 μmol).

ESI-MS m/z 609 [M+H]+

(3) Synthesis of 3',7'-bis(3,3-difluoroazetidin-1-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide A crude product of the title compound was produced in the same manner as in Example 1-(3) from the compound produced in Example 3-(2) (16.0 mg). The crude produce was further purified by silica gel thin-layer chromatography (DCM/diethyl ether) to yield the title compound (6.20 mg, 8.48 μmol).

$^1$H-NMR (400 MHZ, CDCl$_3$) δ (ppm): 1.17-1.25 (m, 4H), 1.74 (br.s., 2H), 1.99 (br.s., 2H), 2.12 (br.s., 2H), 3.61-3.67 (m, 2H), 3.80-3.85 (m, 2H), 4.25 (t, J=11.7 Hz, 8H), 6.34 (dd, J=8.59, 2.73 Hz, 2H), 6.73 (s, 2H), 6.80-6.86 (m, 1H), 6.87 (d, J=8.59 Hz, 2H), 6.90 (d, J=2.73 Hz, 2H), 7.77 (s, 1H), 7.84 (dd, J=8.01, 1.37 Hz, 1H), 8.00-8.04 (m, 1H).

ESI-MS m/z 731 [M+H]+

Example 4

Synthesis of N-(2-(2,5-dioxo-2,5-dihydro-1H-pyrrol-1-yl)ethyl)-3',7'-bis(3-methoxyazetidin-1-yl)-3-oxo-3H-dispiro[isobenzofuran-1,10'-dibenzo[b,e]siline-5',1''-silinane]-6-carboxamide

[Formula 58]

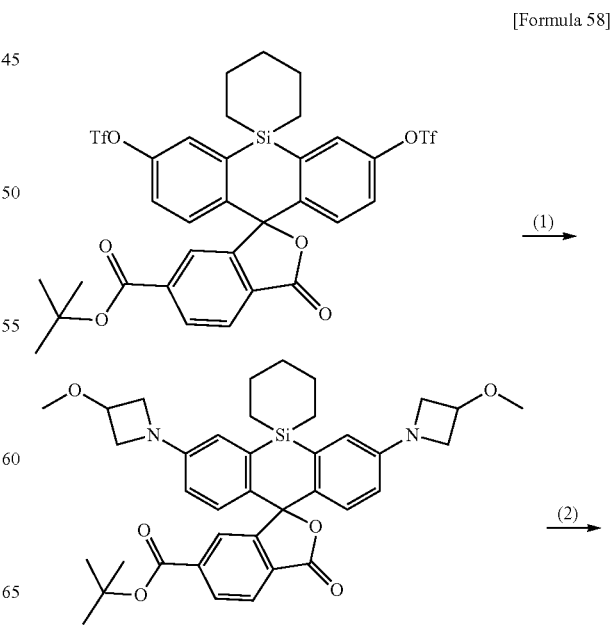

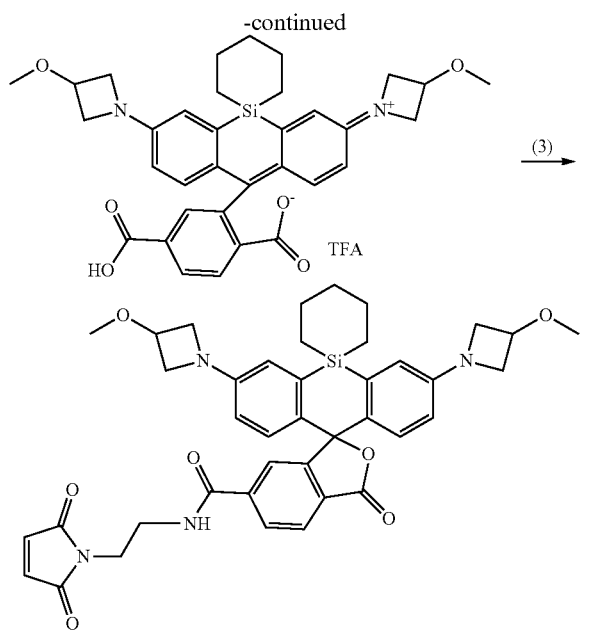

(1) Synthesis of tert-butyl 3',7'-bis(3-methoxyazeti-din-1-yl)-3-oxo-3H-dispiro[isobenzofuran-1,10'-dibenzo[b,e]siline-5',1''-silinane]-6-carboxylate A crude product (18.0 mg) of the title compound was produced in the same manner as in Example 1-(1) from tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (19.0 mg, 24.0 μmol) produced in Production Example 5-(2) and 3-methoxyazetidine hydrochloric acid salt (8.44 mg, 68.0 μmol, CAS No. 148644-09-1).
ESI-MS m/z 653 [M+H]$^+$ (2) Synthesis of 4-carboxy-2-(3-(3-methoxyazeti-din-1-ium-1-ylidene)-7-(3-methoxyazetidin-1-yl)-3H-spiro[dibenzo[b,e]siline-5,1'-silinan]-10-yl)benzoate TFA salt A crude product (20.0 mg) of the title compound was produced in the same manner as in Example 1-(2) from the compound produced in Example 4-(1) (18.0 mg).
ESI-MS m/z 597 [M+H]$^+$ (3) Synthesis of N-(2-(2,5-dioxo-2,5-dihydro-1H-pyrrol-1-yl)ethyl)-3',7'-bis(3-methoxyazetidin-1-yl)-3-oxo-3H-dispiro[isobenzofuran-1,10'-dibenzo[b,e]siline-5',1''-silinane]-6-carboxamide The title compound (8.40 mg, 12.0 μmol) was produced in the same manner as in Example 1-(3) from the compound produced in Example 4-(2) (20.0 mg).
$^1$H-NMR (400 MHZ, CDCl$_3$) δ (ppm): 1.15-1.26 (m, 4H), 1.72 (br.s., 2H), 1.98 (br.s., 2H), 2.12 (br.s., 2H), 3.33 (s, 6H), 3.61-3.67 (m, 2H), 3.69-3.78 (m, 4H), 3.78-3.84 (m, 2H), 4.11 (t, J=7.42 Hz, 4H), 4.30-4.37 (m, 2H), 6.28 (dd, J=8.79, 2.54 Hz, 2H), 6.71 (s, 2H), 6.75-6.81 (m, 1H), 6.78 (d, J=8.59 Hz, 2H), 6.86 (d, J=2.73 Hz, 2H), 7.73 (s, 1H), 7.84 (dd, J=8.01, 1.37 Hz, 1H), 7.99 (d, J=8.59 Hz, 1H).
ESI-MS m/z 719 [M+H]$^+$

Example 5

Synthesis of N-(2-(2,5-dioxo-2,5-dihydro-1H-pyrrol-1-yl)ethyl)-3',7'-bis(3-methylazetidin-1-yl)-3-oxo-3H-dispiro[isobenzofuran-1,10'-dibenzo[b,e]siline-5',1''-silinane]-6-carboxamide

[Formula 59]

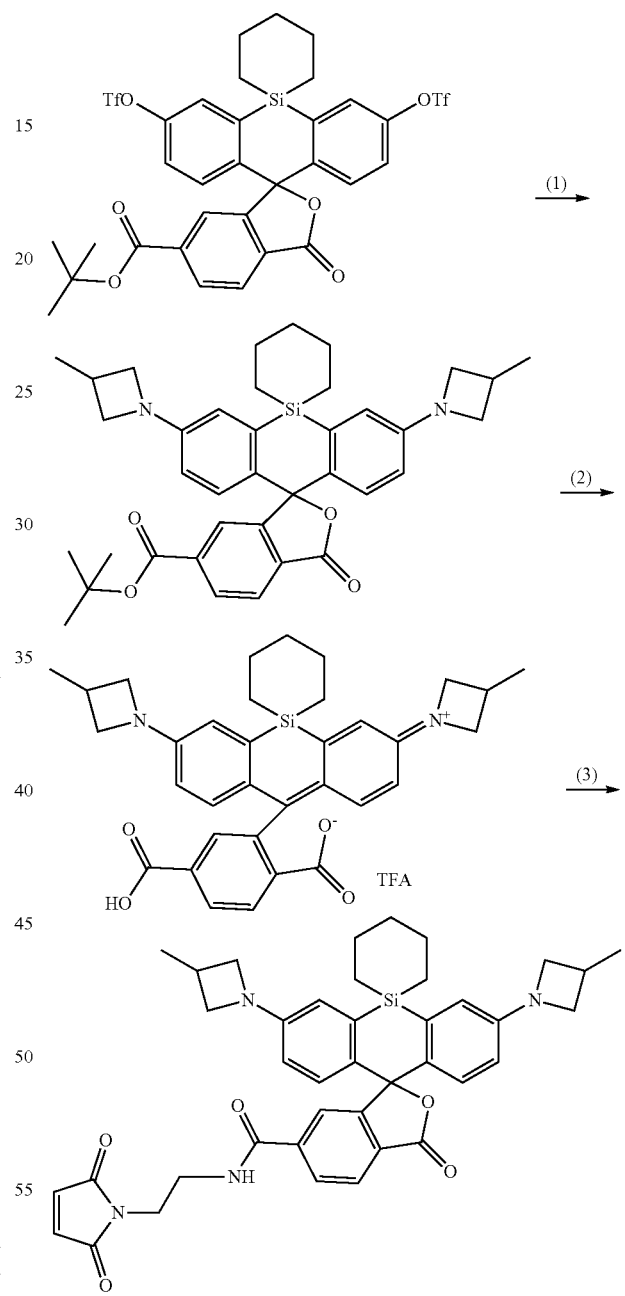

(1) Synthesis of tert-butyl 3',7'-bis(3-methylazeti-din-1-yl)-3-oxo-3H-dispiro[isobenzofuran-1,10'-dibenzo[b,e]siline-5',1''-silinane]-6-carboxylate The title compound (10.0 mg, 16.0 μmol) was produced in the same manner as in Example 1-(1) from tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (19.0 mg, 24.0 μmol) produced in Production Example 5-(2) and 3-methylazetidine hydrochloric acid salt (7.35 mg, 68.0 μmol, CAS No. 935669-28-6).

ESI-MS m/z 621 [M+H]$^+$ (2) Synthesis of 4-carboxy-2-(3-(3-methylazetidin-1-ium-1-ylidene)-7-(3-methylazetidin-1-yl)-3H-spiro[dibenzo[b,e]siline-5,1'-silinan]-10-yl)benzoate TFA salt A crude product (11.0 mg) of the title compound was produced in the same manner as in Example 1-(2) from the compound produced in Example 5-(1) (10.0 mg, 16.0 μmol).

ESI-MS m/z 565 [M+H]$^+$ (3) Synthesis of N-(2-(2,5-dioxo-2,5-dihydro-1H-pyrrol-1-yl)ethyl)-3',7'-bis(3-methylazetidin-1-yl)-3-oxo-3H-dispiro[isobenzofuran-1,10'-dibenzo[b,e]siline-5',1''-silinane]-6-carboxamide A crude product of the title compound was produced in the same manner as in Example 3-(3) from the compound produced in Example 5-(2) (11.0 mg). The crude product produced was purified by silica gel thin-layer chromatography (n-heptane/ethyl acetate) to yield the title compound (2.00 mg, 2.91 μmol).

$^1$H-NMR (400 MHZ, CDCl$_3$) δ (ppm): 1.17-1.23 (m, 4H), 1.26 (s, 3H), 1.28 (s, 3H), 1.71 (br.s., 2H), 1.98 (br.s., 2H), 2.10 (br.s., 2H), 2.76-2.91 (m, 2H), 3.40-3.52 (m, 4H), 3.59-3.69 (m, 2H), 3.76-3.85 (m, 2H), 3.98-4.07 (m, 4H), 6.24 (dd, J=8.59, 2.73 Hz, 2H), 6.72 (s, 2H), 6.72-6.77 (m, 1H), 6.76 (d, J=8.59 Hz, 2H), 6.82 (d, J=2.73 Hz, 2H), 7.73 (s, 1H), 7.83 (dd, J=8.01, 1.37 Hz, 1H), 7.99 (d, J=7.42 Hz, 1H).

ESI-MS m/z 687 [M+H]$^+$

Example 6

Synthesis of 3',7'-bis(3,3-dimethylazetidin-1-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

[Formula 60]

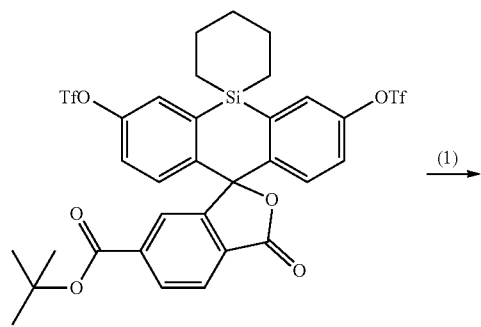

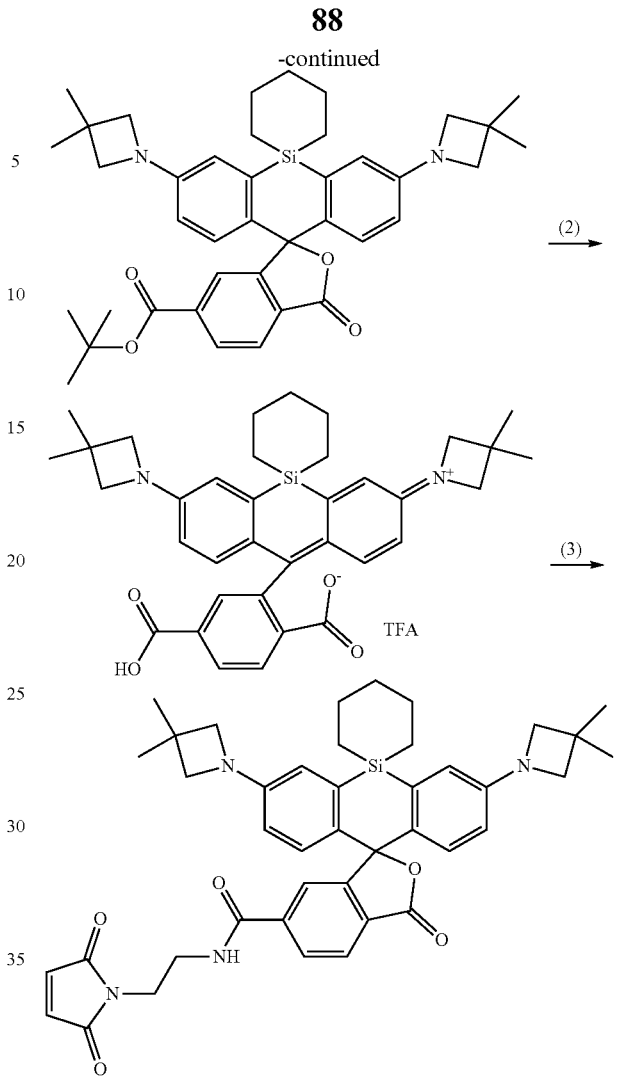

(1) Synthesis of tert-butyl 3',7'-bis(3,3-dimethylazetidin-1-yl)-3-oxo-3H-dispiro[isobenzofuran-1,10'-dibenzo[b,e]siline-5',1''-silinane]-6-carboxylate The title compound (14.0 mg, 22.0 μmol) was produced in the same manner as in Example 1-(1) from tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (20.0 mg, 26.0 μmol) produced in Production Example 5-(2) and 3,3-dimethylazetidine hydrochloric acid salt (8.74 mg, 72.0 μmol, CAS No. 89381-03-3).

$^1$H-NMR (400 MHZ, CDCl$_3$) δ (ppm): 1.17-1.25 (m, 4H), 1.31 (s, 12H), 1.55 (s, 9H), 1.72 (br.s., 2H), 1.97-2.18 (m, 4H), 3.60 (s, 8H), 6.29 (dd, J=8.79, 2.54 Hz, 2H), 6.82 (d, J=2.73 Hz, 2H), 6.86 (d, J=8.59 Hz, 2H), 7.83 (s, 1H), 7.94 (d, J=7.81 Hz, 1H), 8.10 (dd, J=8.20, 1.17 Hz, 1H).

(2) Synthesis of 4-carboxy-2-(3-(3,3-dimethylazetidin-1-ium-1-ylidene)-7-(3,3-dimethylazetidin-1-yl)-3H-spiro[dibenzo[b,e]siline-5,1'-silinan]-10-yl)benzoate TFA salt A crude product (16.0 mg) of the title compound was produced in the same manner as in Example 1-(2) from the compound produced in Example 6-(1) (14.0 mg, 22.0 μmol).

ESI-MS m/z 593 [M+H]$^+$

(3) Synthesis of 3',7'-bis(3,3-dimethylazetidin-1-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide A crude product of the title compound was produced in the same manner as in Example 2-(3) from the compound produced in Example 6-(2) (16.0 mg). The crude product was further purified by silica gel thin-layer chromatography (diethyl ether) to yield the title compound (5.00 mg, 6.99 μmol).

$^1$H-NMR (400 MHZ, CDCl$_3$) δ (ppm): 1.16-1.25 (m, 4H), 1.31 (s, 12H), 1.71 (br.s., 2H), 1.98 (br.s., 2H), 2.10 (br.s., 2H), 3.59 (s, 8H), 3.61-3.67 (m, 2H), 3.78-3.84 (m, 2H), 6.24 (dd, J=8.79, 2.54 Hz, 2H), 6.72 (s, 2H), 6.73-6.78 (m, 3H), 6.82 (d, J=2.73 Hz, 2H), 7.71 (s, 1H), 7.82 (dd, J=8.01, 1.37 Hz, 1H), 7.99 (d, J=7.81 Hz, 1H).

ESI-MS m/z 715 [M+H]$^+$

Example 7

Synthesis of 3',7'-di(7-azabicyclo[2.2.1]heptan-7-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

[Formula 61]

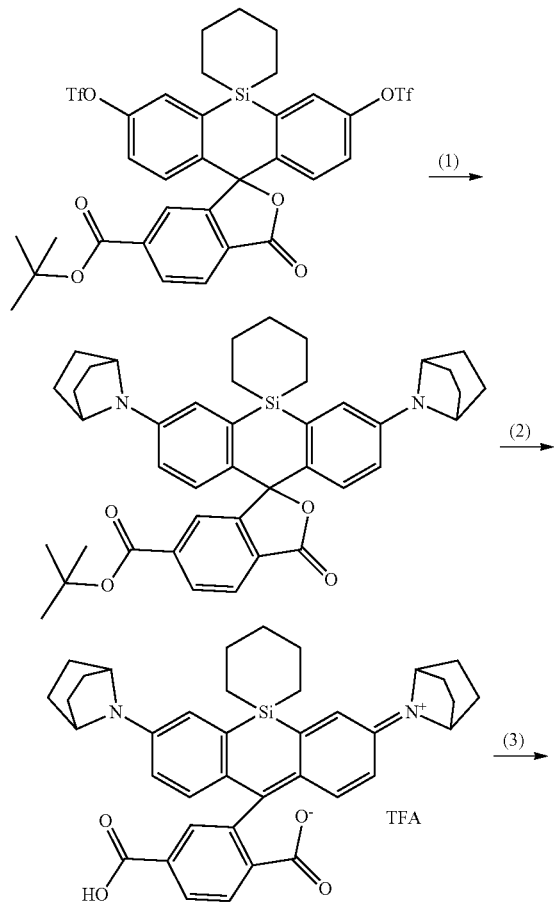

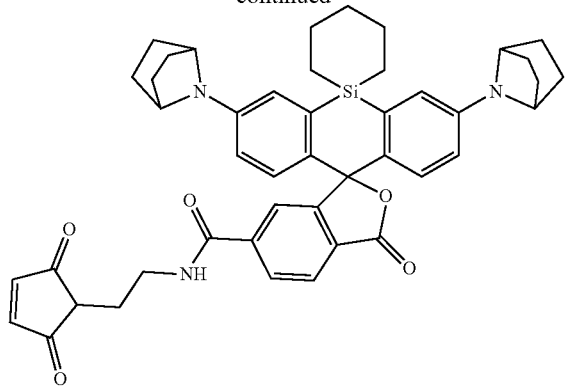

(1) Synthesis of tert-butyl 3',7'-di(7-azabicyclo[2.2.1]heptan-7-yl)-3-oxo-3H-dispiro[isobenzofuran-1,10'-dibenzo[b,e]siline-5',1''-silinane]-6-carboxylate A mixture of tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (12.0 mg, 15.0 μmol) produced in Production Example 5-(2), 7-azabicyclo[2.2.1]heptane (4.19 mg, 43.0 μmol, CAS No. 279-40-3), cesium carbonate (14.1 mg, 43.0 μmol), tris(dibenzylideneacetone)dipalladium (0) (1.41 mg, 1.54 μmol), XPhos (2.20 mg, 4.62 μmol) and 1,4-dioxane (2.00 mL) was stirred in a sealed tube at 100° C. for 2 hours under a nitrogen atmosphere. The resultant solution was cooled to room temperature, and was then diluted with DCM. Insoluble matters were filtrated, and the eluate was concentrated. The residue was purified by NH silica gel thin-layer chromatography (n-heptane/ethyl acetate) to yield a crude product (13.0 mg) of the title compound.

$^1$H-NMR (400 MHZ, CDCl$_3$) δ (ppm): 1.15-1.23 (m, 4H), 1.56 (s, 9H), 1.57-1.63 (m, 8H), 1.74-1.82 (m, 10H), 2.03 (br.s., 2H), 2.12 (br.s., 2H), 4.20 (br.s., 4H), 6.72 (dd, J=8.59, 2.73 Hz, 2H), 6.83 (d, J=8.98 Hz, 2H), 7.31 (d, J=2.73 Hz, 2H), 7.84 (d, J=0.78 Hz, 1H), 7.93-7.97 (m, 1H), 8.12 (dd, J=8.01, 1.37 Hz, 1H).

(2) Synthesis of 2-(3-(7-azabicyclo[2.2.1]heptan-7-ium-7-ylidene)-7-(7-azabicyclo[2.2.1]heptan-7-yl)-3H-spiro[dibenzo[b,e]siline-5,1'-silinan]-10-yl)-4-carboxybenzoate TFA salt A crude product (15.0 mg) of the title compound was produced in the same manner as in Example 1-(2) from the compound produced in Example 7-(1) (13.0 mg).

ESI-MS m/z 617 [M+H]$^+$

(3) Synthesis of 3',7'-di(7-azabicyclo[2.2.1]heptan-7-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide The title compound (2.10 mg, 2.84 μmol) was produced in the same manner as in Example 1-(3) from the compound produced in Example 7-(2) (15.0 mg).

$^1$H-NMR (400 MHZ, CDCl$_3$) δ (ppm): 1.14-1.25 (m, 4H), 1.39-1.47 (m, 8H), 1.73-1.81 (m, 10H), 1.99 (br.s., 2H), 2.14 (br.s., 2H), 3.61-3.67 (m, 2H), 3.78-3.85 (m, 2H), 4.19 (br.s., 4H), 6.64-6.70 (m, 2H), 6.72 (s, 2H), 6.72-6.75 (m, 2H), 6.80 (t, J=5.27 Hz, 1H), 7.31 (d, J=2.73 Hz, 2H), 7.74 (d, J=0.78 Hz, 1H), 7.85 (dd, J=8.20, 1.56 Hz, 1H), 7.98-8.03 (m, 1H).
ESI-MS m/z 739 [M+H]⁺

Example 8

Synthesis of N-(2-(2,5-dioxo-2,5-dihydro-1H-pyrrol-1-yl)ethyl)-3-oxo-3',7'-di(piperidin-1-yl)-3H-dispiro[isobenzofuran-1,10'-dibenzo[b,e]siline-5',1''-silinane]-6-carboxamide

[Formula 62]

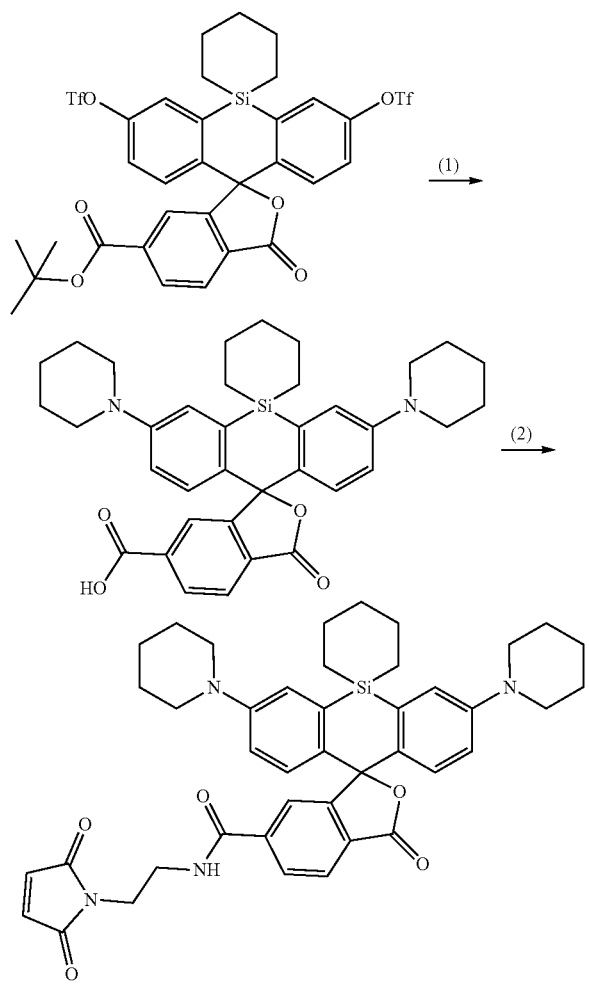

Synthesis of (1)3-oxo-3',7'-di(piperidin-1-yl)-3H-dispiro[isobenzofuran-1,10'-dibenzo[b,e]siline-5',1''-silinane]-6-carboxylic acid A mixture of tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate (25.0 mg, 32.0 μmol) produced in Production Example 5-(2), piperidine (13.7 mg, 161 μmol), tris(dibenzylideneacetone)dipalladium (0) (5.88 mg, 6.42 μmol), XPhos (6.12 mg, 13.0 μmol), cesium carbonate (29.3 mg, 90.0 μmol) and 1,4-dioxane (2.00 mL) was stirred in a sealed tube at 110° C. for 3 hours under a nitrogen atmosphere. The resultant solution was cooled to room temperature, and was then diluted with DCM. Insoluble matters were filtrated out, and the filtrate was concentrated. The residue was purified by silica gel column chromatography (n-heptane/ethyl acetate) to produce an intermediate. The intermediate was dissolved in DCM (4.00 mL), and then TFA (1.00 mL) was added thereto. The reaction mixture was stirred at room temperature overnight, and the solvent was distilled away under a reduced pressure. The residue was neutralized with a saturated aqueous sodium bicarbonate solution, and the aqueous layer was extracted with ethyl acetate. The organic layer was washed with water, and the solvent was distilled away under a reduced pressure. The resultant residue was purified by silica gel column chromatography (n-heptane/ethyl acetate) to yield the title compound (7.20 mg, 12.0 μmol).
ESI-MS m/z 593 [M+H]⁺

(2) Synthesis of N-(2-(2,5-dioxo-2,5-dihydro-1H-pyrrol-1-yl)ethyl)-3-oxo-3',7'-di(piperidin-1-yl)-3H-dispiro[isobenzofuran-1,10'-dibenzo[b,e]siline-5',1''-silinane]-6-carboxamide A mixture of the compound produced in Example 8-(1) (7.00 mg, 12.0 μmol), PyBOP (7.37 mg, 14.0 μmol), N-(2-aminoethyl) maleimide TFA salt (3.60 mg, 14.0 μmol), triethylamine (9.88 μL, 71.0 μmol) and DMF (1.00 mL) was stirred at room temperature for 2 hours. Ice was added to the solution to terminate the reaction, and the aqueous layer was extracted with ethyl acetate. The organic layer was washed with saturated saline three times, and the resultant product was dried over anhydrous magnesium sulfate. The solvent was distilled away under a reduced pressure, and the resultant residue was purified by silica gel thin-layer chromatography (n-heptane/ethyl acetate) to yield a crude product. The crude product was purified by silica gel thin-layer chromatography (DCM/MeOH) to yield the title compound (2.20 mg, 3.08 μmol).
¹H-NMR (400 MHZ, CDCl₃) δ (ppm): 1.23-1.30 (m, 4H), 1.56-1.63 (m, 4H), 1.65-1.78 (m, 10H), 1.95-2.05 (m, 2H), 2.08-2.21 (m, 2H), 3.14-3.24 (m, 8H), 3.59-3.69 (m, 2H), 3.77-3.86 (m, 2H), 6.72 (s, 2H), 6.72-6.77 (m, 3H), 6.80-6.86 (m, 2H), 7.36 (d, J=2.73 Hz, 2H), 7.72 (s, 1H), 7.82 (dd, J=8.01, 1.37 Hz, 1H), 7.97-8.02 (m, 1H).
ESI-MS m/z 715 [M+H]⁺

Example 9

Synthesis of N-(2-(2,5-dioxo-2,5-dihydro-1H-pyrrol-1-yl)ethyl)-3',7'-di(1,4-oxazepan-4-yl)-3-oxo-3H-dispiro[isobenzofuran-1,10'-dibenzo[b,e]siline-5',1''-silinane]-6-carboxamide

[Formula 63]

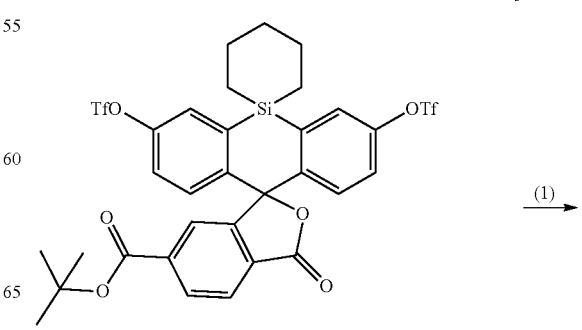

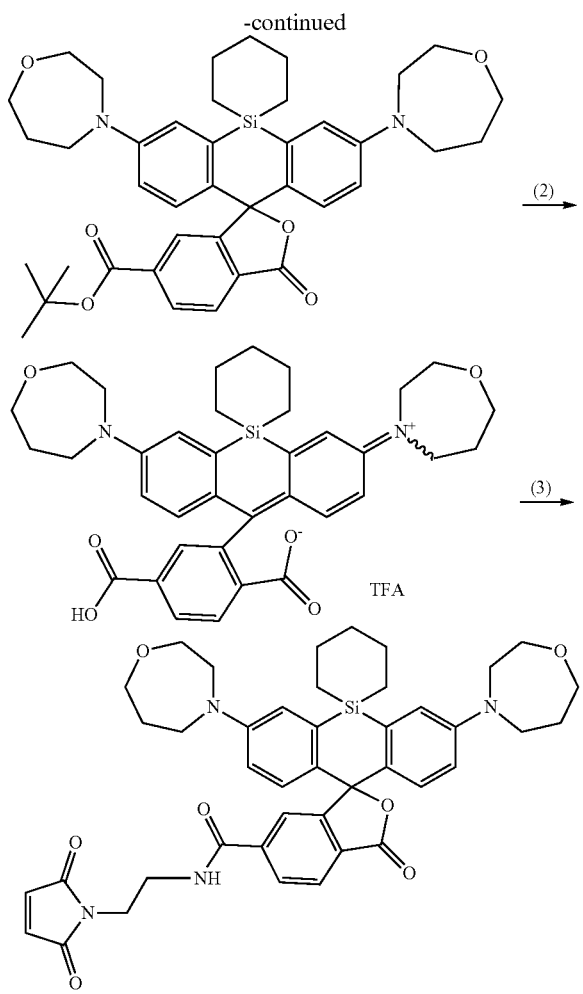

(1) Synthesis of tert-butyl 3',7'-di(1,4-oxazepan-4-yl)-3-oxo-3H-dispiro[isobenzofuran-1,10'-dibenzo[b,e]siline-5',1''-silinane]-6-carboxylate The title compound (9.00 mg, 13.0 μmol) was produced in the same manner as in Example 1-(1) from tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate produced in Production Example 5-(2) (20.0 mg, 26.0 μmol) and 1,4-oxazepane (7.27 mg, 72.0 μmol).

$^1$H-NMR (400 MHZ, CDCl$_3$) δ (ppm): 1.20-1.31 (m, 4H), 1.57 (s, 9H), 1.74 (br.s., 2H), 1.97-2.06 (m, 6H), 2.11 (br.s., 2H), 3.59-3.72 (m, 12H), 3.80-3.86 (m, 4H), 6.57 (dd, J=8.98, 3.12 Hz, 2H), 6.84 (d, J=8.59 Hz, 2H), 7.14 (d, J=2.73 Hz, 2H), 7.90 (d, J=1.17 Hz, 1H), 7.97 (dd, J=7.81, 0.78 Hz, 1H), 8.14 (dd, J=8.01, 1.37 Hz, 1H).

ESI-MS m/z 681 [M+H]$^+$ (2) Synthesis of 2-(3-(1,4-oxazepan-4-ium-4-ylidene)-7-(1,4-oxazepan-4-yl)-3H-spiro[dibenzo[b,e]siline-5,1'-silinan]-10-yl)-4-carboxybenzoate TFA salt A crude product (10.0 mg) of the title compound was produced in the same manner as in Example 1-(2) from the compound produced in Example 9-(1) (9.00 mg, 13.0 μmol).

ESI-MS m/z 625 [M+H]$^+$ (3) Synthesis of N-(2-(2,5-dioxo-2,5-dihydro-1H-pyrrol-1-yl)ethyl)-3',7'-di(1,4-oxazepan-4-yl)-3-oxo-3H-dispiro[isobenzofuran-1,10'-dibenzo[b,e]siline-5',1''-silinane]-6-carboxamide To a solution of the compound produced in Example 9-(2) (10.0 mg) in DMF (2.00 mL) were added TEA (11.0 μL, 81.0 μmol), N-(2-aminoethyl) maleimide TFA salt (4.13 mg, 16.0 μmol) and PyBOP (8.45 mg, 16.0 μmol). The reaction mixture was stirred at room temperature for 3 hours, and then ice was added to the solution to terminate the reaction. The aqueous layer was extracted with ethyl acetate, and an organic layer was washed with saturated saline three times. The organic layer was dried over anhydrous magnesium sulfate, and the solvent was distilled away under a reduced pressure. The resultant residue was purified by silica gel thin-layer chromatography (n-heptane/ethyl acetate) to yield a crude product. The crude product was further purified by silica gel thin-layer chromatography (DCM/MeOH) to yield the title compound (4.05 mg, 5.42 μmol).

$^1$H-NMR (400 MHZ, CDCl$_3$) δ (ppm): 1.15-1.30 (m, 4H), 1.73 (br.s., 2H), 1.91-2.07 (m, 6H), 2.11 (br.s., 2H), 3.56-3.72 (m, 14H), 3.77-3.88 (m, 6H), 6.53 (dd, J=8.79, 2.93 Hz, 2H), 6.72 (s, 2H), 6.76 (d, J=8.98 Hz, 2H), 6.79-6.85 (m, 1H), 7.14 (d, J=3.12 Hz, 2H), 7.77 (s, 1H), 7.85 (dd, J=8.01, 1.37 Hz, 1H), 8.01 (d, J=7.81 Hz, 1H).

ESI-MS m/z 747 [M+H]$^+$

Example 10

Synthesis of N-(2-(2,5-dioxo-2,5-dihydro-1H-pyrrol-1-yl)ethyl)-3',7'-bis(dipropylamino)-3-oxo-3H-dispiro[isobenzofuran-1,10'-dibenzo[b,e]siline-5',1''-silinane]-6-carboxamide

[Formula 64]

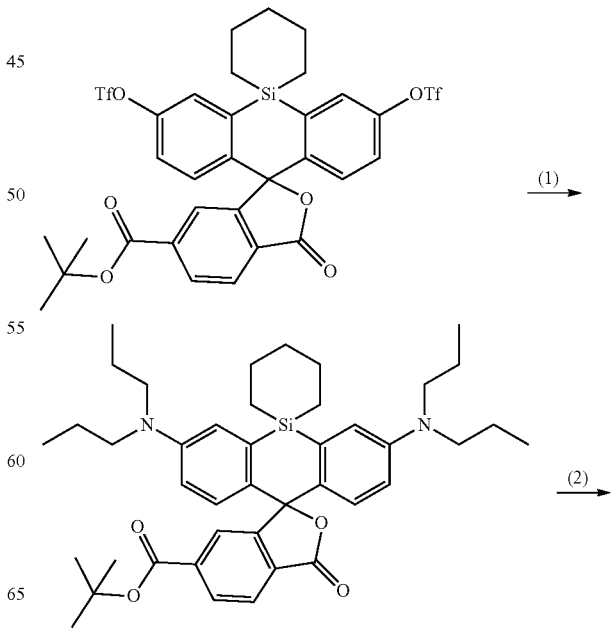

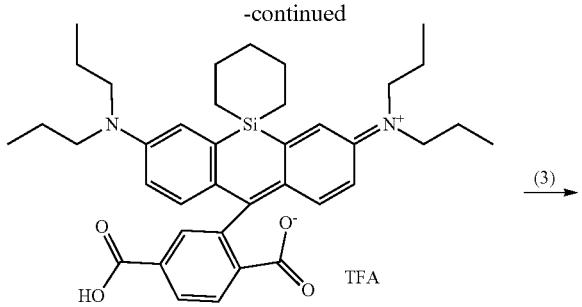

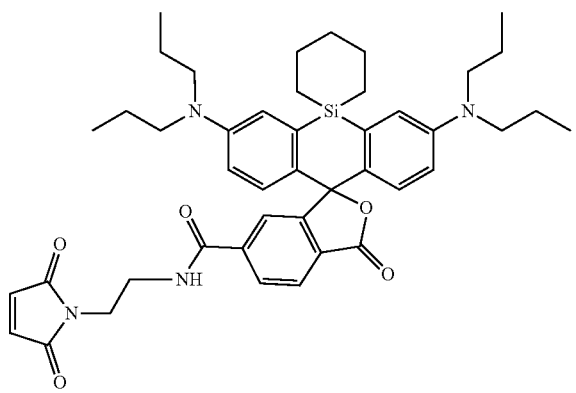

(1) Synthesis of tert-butyl 3',7'-bis(dipropylamino)-3-oxo-3H-dispiro[isobenzofuran-1,10'-dibenzo[b,e]siline-5',1''-silinane]-6-carboxylate The title compound (3.00 mg, 4.41 µmol) was produced in the same manner as in Example 1-(1) from tert-butyl 3-oxo-3',7'-bis(((trifluoromethyl)sulfonyl)oxy)-3H-dispiro[isobenzofuran-1,10'-dibenzo[b,e]siline-5',1''-silinane]-6-carboxylate produced in Production Example 5-(2) (20.0 mg, 26.0 µmol) and dipropylamine (7.28 mg, 72.0 µmol).
ESI-MS m/z 681 [M+H]⁺

(2) Synthesis of 4-carboxy-2-(7-(dipropylamino)-3-(dipropyliminio)-3H-spiro[dibenzo[b,e]siline-5,1'-silinan]-10-yl)benzoate TFA salt A crude product (7.00 mg) of the title compound was produced in the same manner as in Example 1-(2) from the compound produced in Example 10-(1) (3.00 mg, 4.41 µmol).
ESI-MS m/z 625 [M+H]⁺

(3) Synthesis of N-(2-(2,5-dioxo-2,5-dihydro-1H-pyrrol-1-yl)ethyl)-3',7'-bis(dipropylamino)-3-oxo-3H-dispiro[isobenzofuran-1,10'-dibenzo[b,e]siline-5',1''-silinane]-6-carboxamide To a solution of the compound produced in Example 10-(2) (7.00 mg) in DMF (2.00 mL) were added TEA (7.92 µL, 57.0 µmol), N-(2-aminoethyl) maleimide TFA salt (2.89 mg, 11.0 µmol) and PyBOP (5.92 mg, 11.0 µmol). The reaction mixture was stirred at room temperature for 4.5 hours, and then ice was added to the solution to terminate the reaction. The aqueous layer was extracted with ethyl acetate, and then the organic layer was washed with water three times. The solvent was distilled away under a reduced pressure, and the resultant residue was purified by silica gel thin-layer chromatography (diethyl ether) to yield the title compound (2.36 mg, 3.16 µmol).
¹H-NMR (400 MHZ, CDCl₃) δ (ppm): 0.92 (t, J=7.42 Hz, 12H), 1.17-1.24 (m, 4H), 1.56-1.66 (m, 8H), 1.72 (br.s., 2H), 1.99 (br.s., 2H), 2.14 (br.s., 2H), 3.21-3.29 (m, 8H), 3.62-3.69 (m, 2H), 3.79-3.84 (m, 2H), 6.43 (dd, J=8.98, 3.12 Hz, 2H), 6.70 (d, J=8.98 Hz, 2H), 6.71 (s, 2H), 6.73 (br.s., 1H), 7.05 (d, J=2.73 Hz, 2H), 7.75 (s, 1H), 7.84 (dd, J=7.81, 1.56 Hz, 1H), 7.99 (d, J=7.81 Hz, 1H).
ESI-MS m/z 747 [M+H]⁺

Example 11

Synthesis of 3',7'-di(azetidin-1-yl)-N-(2-(2-(2-(2-(2,5-dioxo-2,5-dihydro-1H-pyrrol-1-yl)ethoxy)ethoxy)ethoxy)ethyl)-3-oxo-3H-dispiro[isobenzofuran-1,10'-dibenzo[b,e]siline-5',1''-silinane]-6-carboxamide

[Formula 65]

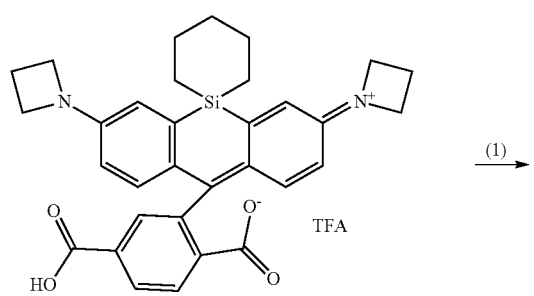

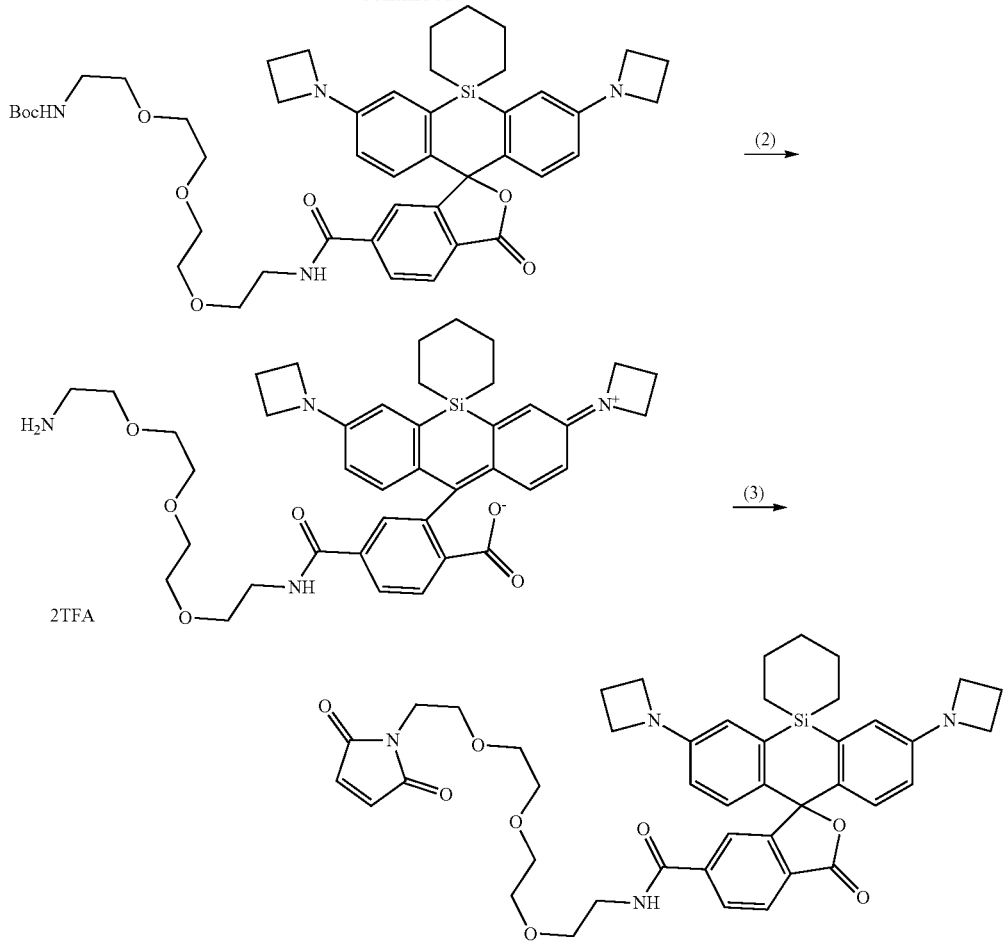

(1) Synthesis of tert-butyl(1-(3',7'-di(azetidin-1-yl)-3-oxo-3H-dispiro[isobenzofuran-1,10'-dibenzo[b,e]siline-5',1''-silinan]-6-yl)-1-oxo-5,8,11-trioxa-2-azatridecan-13-yl) carbamate A mixture of the compound produced in Example 1-(2) (70.0 mg), 13-amino-5,8,11-trioxa-2-azatridecanoic acid 1,1-dimethylethyl ester (37.7 mg, 129 μmol, CAS No. 101187-40-0), PyBop (84.0 mg, 161 μmol), TEA (90.0 μL, 645 μmol) and DMF (2.00 mL) was stirred at room temperature overnight. Ice was added to the reaction mixture to terminate the reaction. The aqueous layer was extracted with ethyl acetate, and the organic layer was washed with saturated saline three times. The mixture was dried over anhydrous magnesium sulfate, and then the solvent was distilled away under a reduced pressure. The residue was purified by silica gel column chromatography (n-heptane/ethyl acetate) to yield the title compound (67.0 mg, 83.0 μmol).

ESI-MS m/z 811 [M+H]$^+$ (2) Synthesis of 4-((2-(2-(2-(2-aminoethoxy)ethoxy)ethoxy)ethyl) carbamoyl)-2-(3-(azetidin-1-ium-1-ylidene)-7-(azetidin-1-yl)-3H-spiro[dibenzo[b,e]siline-5,1'-silinan]-10-yl)benzoate 2TFA salt TFA (800 L) was added to a solution of the compound produced in Example 11-(1) (67.0 mg, 83.0 μmol) in DCM (4.00 mL), and the resultant solution was stirred at room temperature for 1 hour. The solvent was distilled away under a reduced pressure to yield a crude product (80.0 mg) of the title compound.

ESI-MS m/z 711 [M+H]$^+$ (3) Synthesis of 3',7'-di(azetidin-1-yl)-N-(2-(2-(2-(2-(2,5-dioxo-2,5-dihydro-1H-pyrrol-1-yl)ethoxy)ethoxy)ethoxy)ethyl)-3-oxo-3H-dispiro[isobenzofuran-1,10'-dibenzo[b,e]siline-5',1''-silinane]-6-carboxamide To a mixture of the compound produced in Example 11-(2) (80.0 mg), THF (3.03 mL) and a saturated aqueous sodium bicarbonate solution (3.03 mL) was added methyl 2,5-dioxo-2,5-dihydro-1H-pyrrol-1-carboxylate (79.0 mg, 511 μmol, CAS No. 55750-48-6). The reaction mixture was stirred at room temperature overnight, and was then diluted with ethyl acetate. The aqueous layer was extracted with ethyl acetate, and then the organic layer was washed with water and saturated saline. The mixture was dried over anhydrous magnesium sulfate, and then the solvent was distilled away under a reduced pressure. The residue was purified by silica gel thin-layer chromatography (ethyl acetate) to yield the title compound (23.0 mg, 29.0 μmol).

$^1$H-NMR (400 MHZ, CDCl$_3$) δ (ppm): 1.15-1.29 (m, 4H), 1.71 (br.s., 2H), 1.97 (br.s., 2H), 2.11 (br.s., 2H), 2.37 (quin, J=7.22 Hz, 4H), 3.45-3.54 (m, 6H), 3.55-3.63 (m, 6H), 3.63-3.68 (m, 4H), 3.90 (t, J=7.22 Hz, 8H), 6.24 (dd, J=8.59, 2.73 Hz, 2H), 6.60 (s, 2H), 6.75 (d, J=8.59 Hz, 2H), 6.82 (d, J=2.73 Hz, 2H), 7.03-7.09 (m, 1H), 7.75-7.80 (m, 1H), 7.96-8.00 (m, 2H).

ESI-MS m/z 791 [M+H]+

Example 12

Synthesis of 3',7'-di(azetidin-1-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-5-carboxamide

[Formula 66]

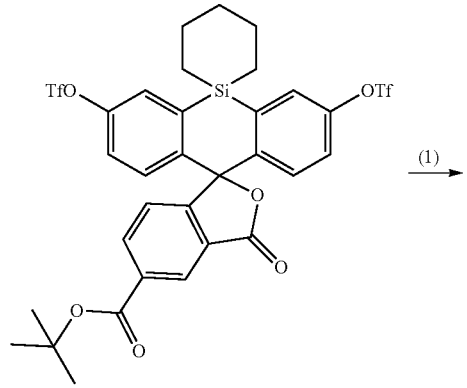

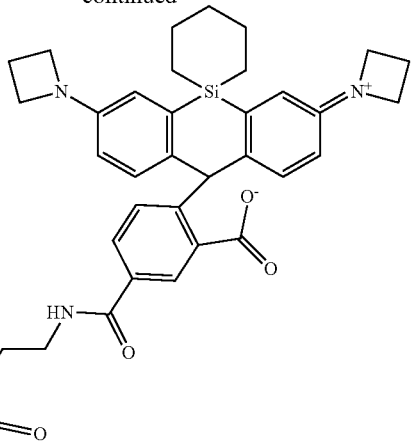

(1) Synthesis of tert-butyl 3',7'-di(azetidin-1-yl)-3-oxo-3H-dispiro[isobenzofuran-1,10'-dibenzo[b,e]siline-5',1''-silinane]-5-carboxylate The title compound (6.00 mg, 10.1 μmol) was produced in the same manner as in Example 2-(1) from tert-butyl 3-oxo-3',7'-bis(((trifluoromethyl)sulfonyl)oxy)-3H-dispiro[isobenzofuran-1,10'-dibenzo[b,e]siline-5',1''-silinane]-5-carboxylate (31.0 mg, 40.0 μmol) produced in Production Example 6-(2).

ESI-MS m/z 593 [M+H]+

(2) Synthesis of 2-(3-(azetidin-1-ium-1-ylidene)-7-(azetidin-1-yl)-3H-spiro[dibenzo[b,e]siline-5,1'-silinan]-10-yl)-5-carboxybenzoate TFA salt A crude product (17.0 mg) of the title compound was produced in the same manner as in Example 1-(2) from the compound produced by the method of Example 12-(1) (15.0 mg, 25.0 μmol).

ESI-MS m/z 537 [M+H]+

(3) Synthesis of 3',7'-di(azetidin-1-yl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-5-carboxamide The title compound (1.50 mg, 2.28 μmol) was produced in the same manner as in Example 3-(3) from the compound produced in Example 12-(2) (17.0 mg).

$^1$H-NMR (400 MHZ, CDCl$_3$) δ (ppm): 1.17-1.26 (m, 4H), 1.72 (br.s., 2H), 1.98 (br.s., 2H), 2.12 (br.s., 2H), 2.32-2.43 (m, 4H), 3.68-3.75 (m, 2H), 3.83-3.88 (m, 2H), 3.90 (t, J=7.22 Hz, 8H), 6.24 (dd, J=8.59, 2.34 Hz, 2H), 6.74 (d, J=8.59 Hz, 2H), 6.76 (s, 2H), 6.78-6.84 (m, 1H), 6.84 (d, J=2.73 Hz, 2H), 7.39 (d, J=8.20 Hz, 1H), 8.11 (dd, J=8.01, 1.76 Hz, 1H), 8.25 (s, 1H).

ESI-MS m/z 659 [M+H]+

Example 13

Synthesis of 3',7'-di(azetidin-1-yl)-5-chloro-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

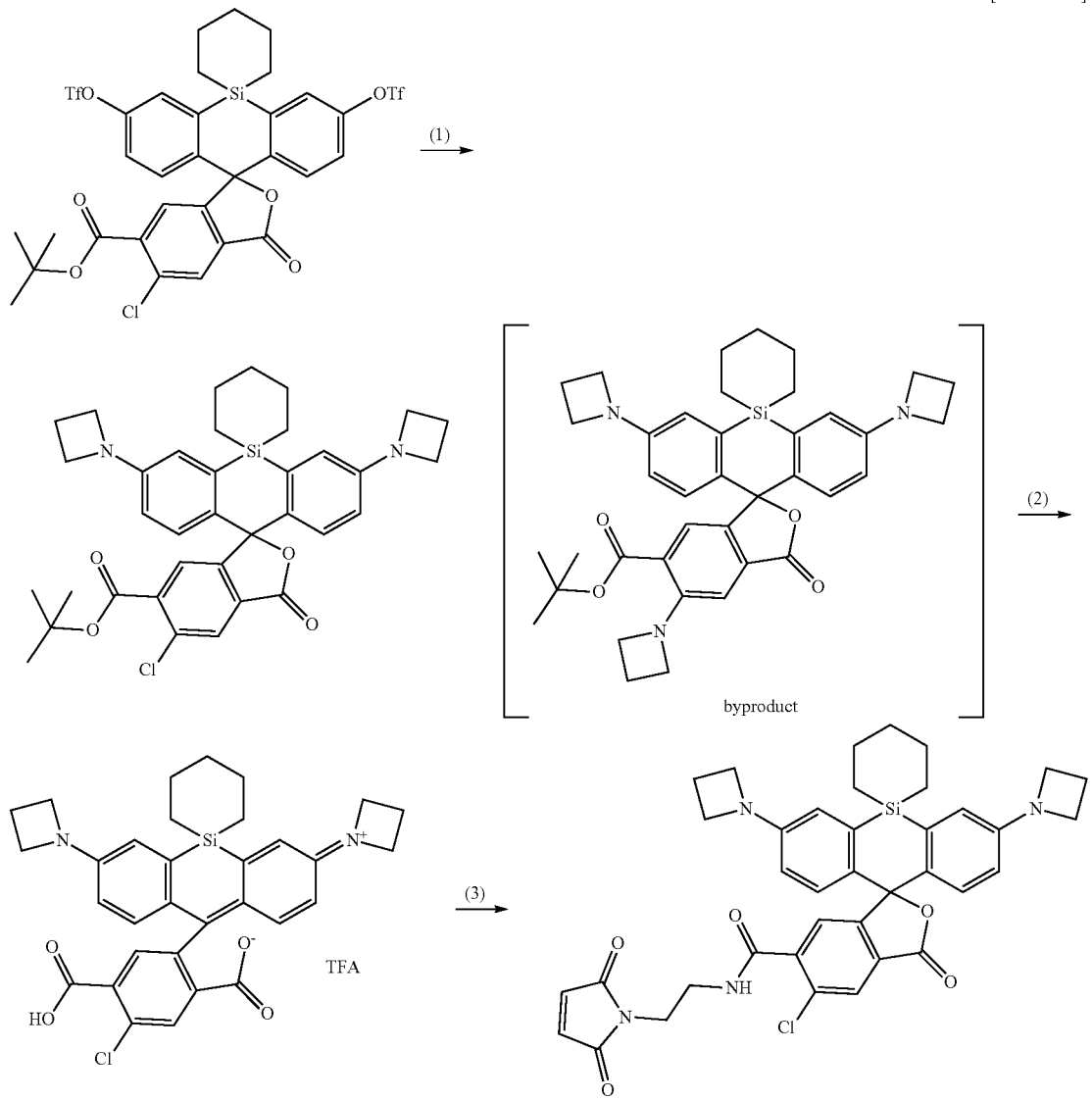

[Formula 67]

(1) Synthesis of tert-butyl 3',7'-di(azetidin-1-yl)-5-chloro-3-oxo-3H-dispiro[isobenzofuran-1,10'-dibenzo[b,e]siline-5',1''-silinane]-6-carboxylate and tert-butyl 3',5,7'-tri(azetidin-1-yl)-3-oxo-3H-dispiro[isobenzofuran-1,10'-dibenzo[b,e]siline-5',1''-silinane]-6-carboxylate A mixture of tert-butyl 5-chloro-3-oxo-3',7'-bis(((trifluoromethyl)sulfonyl)oxy)-3H-dispiro[isobenzofuran-1,10'-dibenzo[b,e]siline-5',1''-silinane]-6-carboxylate produced in Production Example 7-(2) (128 mg, 157 μmol), azetidine (25.2 mg, 441 μmol), cesium carbonate (144 mg, 441 μmol), tris(dibenzylideneacetone)dipalladium (0) (14.4 mg, 16.0 μmol), XPhos (22.5 mg, 47.0 μmol) and toluene (2.00 mL) was stirred in a sealed tube at 110° C. for 4.5 hours under a nitrogen atmosphere. The solution was cooled to room temperature, and then insoluble matters were filtrated out. The eluate was concentrated, and the resultant residue was purified by silica gel column chromatography (n-heptane/ethyl acetate) to yield tert-butyl 3',7'-di(azetidin-1-yl)-5-chloro-3-oxo-3H-dispiro[isobenzofuran-1,10'-dibenzo[b,e]siline-5',1''-silinane]-6-carboxylate.

ESI-MS m/z 627 [M+H]⁺

As a byproduct, tert-butyl 3',5,7'-tri (azetidin-1-yl)-3-oxo-3H-dispiro[isobenzofuran-1,10'-dibenzo[b,e]siline-5',1''-silinane]-6-carboxylate was produced.

ESI-MS m/z 648 [M+H]⁺

(2) Synthesis of 2-(3-(azetidin-1-ium-1-ylidene)-7-(azetidin-1-yl)-3H-spiro[dibenzo[b,e]siline-5,1'-silinan]-10-yl)-4-carboxy-5-chlorobenzoate TFA salt A crude product (15.0 mg) of the title compound was produced in the same manner as in Example 1-(2) from tert-butyl 3',7'-di(azetidin-1-yl)-5-chloro-3-oxo-3H-dispiro[isobenzofuran-1,10'-dibenzo[b,e]siline-5',1''-silinane]-6-carboxylate produced in Example 13-(1).

ESI-MS m/z 571 [M+H]$^+$ (3) Synthesis of 3',7'-di(azetidin-1-yl)-5-chloro-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide A crude product of the title compound was produced in the same manner as in Example 10-(3) from the compound produced in Example 13-(2) (15.0 mg). The crude product was purified by silica gel thin-layer chromatography (DCM/MeOH) to yield the title compound (1.10 mg, 1.59 µmol).

$^1$H-NMR (400 MHZ, CDCl$_3$) δ (ppm): 1.13-1.21 (m, 4H), 1.71 (br.s., 2H), 1.97 (br.s., 2H), 2.10 (br.s., 2H), 2.32-2.43 (m, 4H), 3.64-3.72 (m, 2H), 3.76-3.83 (m, 2H), 3.91 (t, J=7.22 Hz, 8H), 6.28 (dd, J=8.79, 2.54 Hz, 2H), 6.44 (br.s., 1H), 6.68 (s, 2H), 6.76 (d, J=8.59 Hz, 2H), 6.83 (d, J=2.34 Hz, 2H), 7.45 (s, 1H), 7.95 (s, 1H).

ESI-MS m/z 693 [M+H]$^+$

Example 14

Synthesis of 3',7'-di(azetidin-1-yl)-N-(2-(2,5-dioxo-2,5-dihydro-1H-pyrrol-1-yl)ethyl)-5-methyl-3-oxo-3H-dispiro[isobenzofuran-1,10'-dibenzo[b,e]siline-5',1''-silinane]-6-carboxamide

[Formula 68]

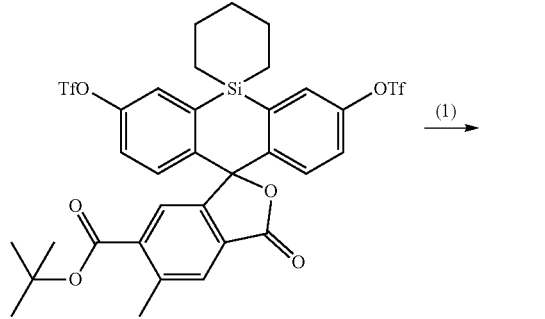

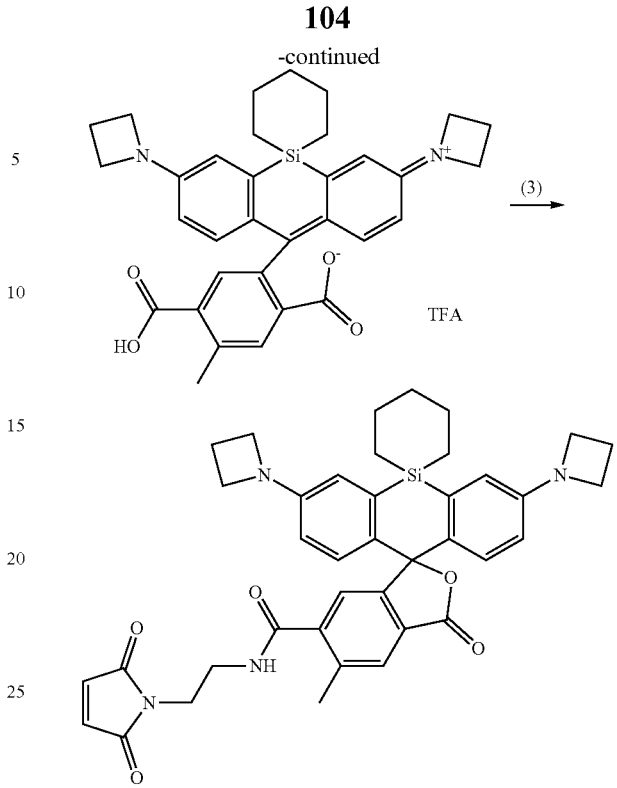

(1) Synthesis of tert-butyl 3',7'-di(azetidin-1-yl)-5-methyl-3-oxo-3H-dispiro[isobenzofuran-1,10'-dibenzo[b,e]siline-5',1''-silinane]-6-carboxylate A crude product (35.0 mg) of the title compound was produced in the same manner as in Example 1-(1) from tert-butyl 5-methyl-3-oxo-3',7'-bis(((trifluoromethyl)sulfonyl)oxy)-3H-dispiro[isobenzofuran-1,10'-dibenzo[b,e]siline-5',1''-silinane]-6-carboxylate (40.0 mg, 50.0 µmol) produced in Production Example 8-(3).

ESI-MS m/z 607 [M+H]$^+$ (2) Synthesis of 2-(3-(azetidin-1-ium-1-ylidene)-7-(azetidin-1-yl)-3H-spiro[dibenzo[b,e]siline-5,1'-silinan]-10-yl)-4-carboxy-5-methylbenzoate TFA salt A crude product (42.0 mg) of the title compound was produced in the same manner as in Example 1-(2) from the compound produced in Example 14-(1) (35.0 mg).
ESI-MS m/z 551 [M+H]$^+$ (3) Synthesis of 3',7'-di(azetidin-1-yl)-N-(2-(2,5-dioxo-2,5-dihydro-1H-pyrrol-1-yl)ethyl)-5-methyl-3-oxo-3H-dispiro[isobenzofuran-1,10'-dibenzo[b,e]siline-5',1''-silinane]-6-carboxamide To a solution of the compound produced in Example 14-(2) (42.0 mg) in DMF (2.00 mL) were added TEA (44.0 µL, 316 µmol), N-(2-aminoethyl) maleimide TFA salt (19.3 mg, 76.0 µmol) and PyBOP (49.3 mg, 95.0 µmol). The reaction mixture was stirred at room temperature for 1.5 hours, and was then diluted with ethyl acetate. The organic layer was washed with water three times, and the solvent was distilled away under a reduced pressure. The resultant residue was purified by silica gel column chromatography (n-heptane/ethyl acetate). A crude product thus produced was purified by silica gel thin-layer chromatography (diethyl ether). The crude product was further purified by silica gel thin-layer chromatography (DCM/MeOH) to yield the title compound (16.0 mg, 24.0 μmol).

$^1$H-NMR (400 MHZ, CDCl$_3$) δ (ppm): 1.18-1.25 (m, 4H), 1.72 (br.s., 2H), 1.98 (br.s., 2H), 2.12 (br.s., 2H), 2.37-2.43 (m, 4H), 2.55 (s, 3H), 3.62-3.67 (m, 2H), 3.77-3.81 (m, 2H), 3.92 (t, J=7.22 Hz, 8H), 6.22 (br.s., 1H), 6.28 (dd, J=8.59, 2.73 Hz, 2H), 6.69 (s, 2H), 6.79 (d, J=8.59 Hz, 2H), 6.85 (d, J=2.34 Hz, 2H), 7.28 (s, 1H), 7.80 (s, 1H).

ESI-MS m/z 673 [M+H]$^+$

Example 15

Synthesis of 3',7'-di(azetidin-1-yl)-N-(2-(2,5-dioxo-2,5-dihydro-1H-pyrrol-1-yl)ethyl)-5-((3-hydroxypropyl)amino)-3-oxo-3H-dispiro[isobenzofuran-1,10'-dibenzo[b,e]siline-5',1''-silinane]-6-carboxamide

[Formula 69]

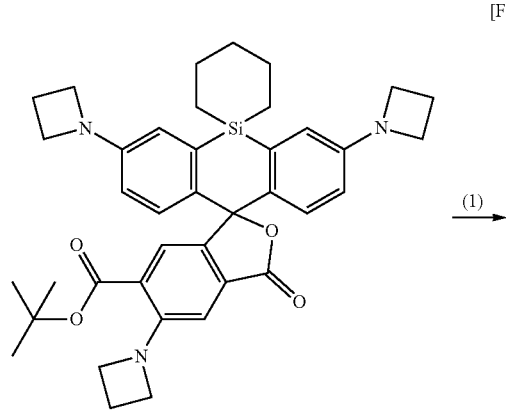

(1)
⟶

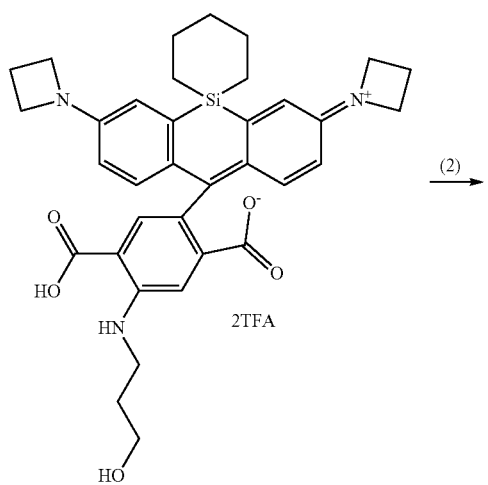

(2)
⟶

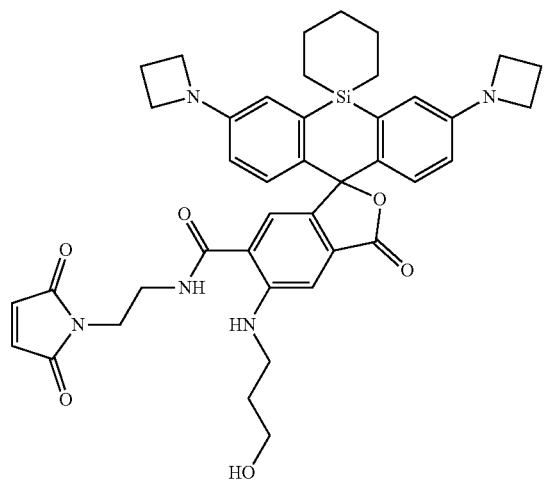

(1) Synthesis of 2-(3-(azetidin-1-ium-1-ylidene)-7-(azetidin-1-yl)-3H-spiro[dibenzo[b,e]siline-5,1'-silinan]-10-yl)-4-carboxy-5-((3-hydroxypropyl)amino) benzoate 2TFA salt A solution of tert-butyl 3',5,7'-tri (azetidin-1-yl)-3-oxo-3H-dispiro[isobenzofuran-1,10'-dibenzo[b,e]siline-5',1''-silinane]-6-carboxylate that had been produced as a byproduct in Example 13-(1) in DCM/TFA (2:1) was stirred at room temperature for 3 hours. The solvent was distilled away under a reduced pressure to yield a mixture (9.00 mg) containing the title compound. The mixture was used in the subsequent reaction without being further purified.

ESI-MS m/z 610 [M+H]$^+$ (2) Synthesis of 3',7'-di(azetidin-1-yl)-N-(2-(2,5-dioxo-2,5-dihydro-1H-pyrrol-1-yl)ethyl)-5-((3-hydroxypropyl)amino)-3-oxo-3H-dispiro[isobenzofuran-1,10'-dibenzo[b,e]siline-5',1''-silinane]-6-carboxamide The title compound (1.22 mg, 1.67 μmol) was produced in the same manner as in Example 10-(3) from the mixture produced in Example 15-(1) (9.00 mg).

$^1$H-NMR (400 MHZ, CDCl$_3$) δ (ppm): 1.17-1.25 (m, 4H), 1.70 (br.s., 2H), 1.86-2.00 (m, 4H), 2.13 (br.s., 2H), 2.32-2.43 (m, 4H), 3.33-3.41 (m, 2H), 3.54-3.60 (m, 2H), 3.77 (dd, J=6.44, 4.49 Hz, 2H), 3.85 (t, J=5.86 Hz, 2H), 3.91 (t, J=7.22 Hz, 8H), 6.23-6.30 (m, 2H), 6.55 (br.s., 1H), 6.67 (s, 2H), 6.84 (d, J=5.47 Hz, 2H), 6.85 (s, 2H), 7.17 (s, 1H), 7.33 (s, 1H)

ESI-MS m/z 732 [M+H]$^+$

Example 16

Synthesis of 3',7'-bis(dimethylamino)-N-(2-(2,5-dioxo-2,5-dihydro-1H-pyrrol-1-yl)ethyl)-5-methyl-3-oxo-3H-dispiro[isobenzofuran-1,10'-dibenzo[b,e]siline-5',1''-silinane]-6-carboxamide

[Formula 70]

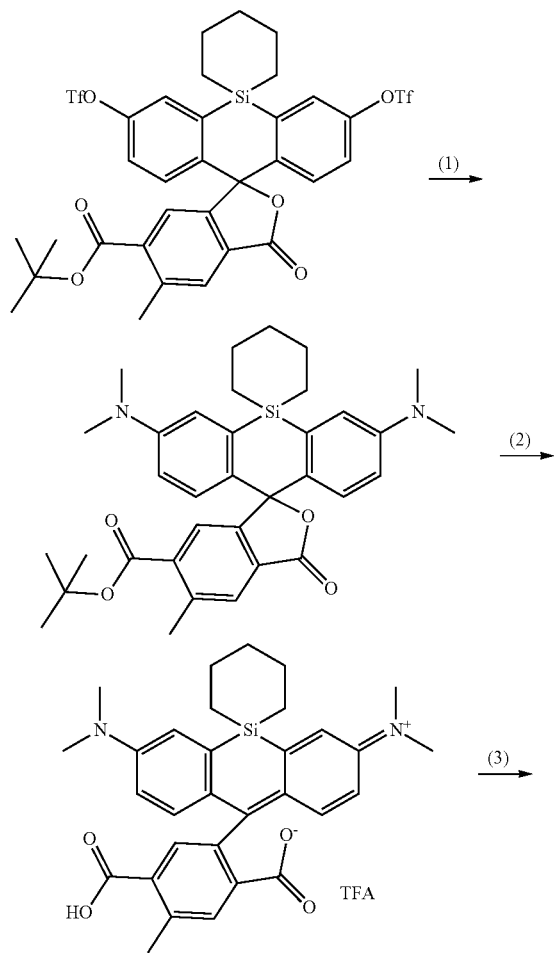

(1) Synthesis of tert-butyl 3',7'-bis(dimethylamino)-5-methyl-3-oxo-3H-dispiro[isobenzofuran-1,10'-dibenzo[b,e]siline-5',1''-silinane]-6-carboxylate The title compound (10.0 mg, 17.0 μmol) was produced in the same manner as in Example 1-(1) from tert-butyl 5-methyl-3-oxo-3',7'-bis(((trifluoromethyl)sulfonyl)oxy)-3H-dispiro[isobenzofuran-1,10'-dibenzo[b,e]siline-5',1''-silinane]-6-carboxylate (40.0 mg, 50.0 μmol) produced in Production Example 8-(3) and dimethylamine (a 2-M THF solution, 71.0 μL, 141 μmol).
ESI-MS m/z 583 [M+H]$^+$ (2) Syn thesis of 4-carboxy-2-(7-(dimethylamino)-3-(dimethyliminio)-3H-spiro[dibenzo[b,e]siline-5,1'-silinan]-10-yl)-5-methylbenzoate TFA salt A crude product (15.0 mg) of the title compound was produced in the same manner as in Example 1-(2) from the compound produced in Example 16-(1) (10.0 mg, 17.0 μmol).
ESI-MS m/z 527 [M+H]$^+$ (3) Synthesis of 3',7'-bis(dimethylamino)-N-(2-(2,5-dioxo-2,5-dihydro-1H-pyrrol-1-yl)ethyl)-5-methyl-3-oxo-3H-dispiro[isobenzofuran-1,10'-dibenzo[b,e]siline-5',1''-silinane]-6-carboxamide To a solution of the compound produced in Example 16-(2) (15.0 mg) in DMF (2.00 mL) were added TEA (16.0 μL, 117 μmol), N-(2-aminoethyl) maleimide TFA salt (7.14 mg, 28.0 μmol) and PyBOP (18.3 mg, 35.0 μmol). The reaction mixture was stirred at room temperature for 1.5 hours, and was then diluted with ethyl acetate. The mixture was washed with water three times, and the solvent was distilled away under a reduced pressure. The resultant residue was purified by silica gel thin-layer chromatography (n-heptane/ethyl acetate) to yield a crude product. The crude product was further purified by silica gel thin-layer chromatography (diethyl ether) to yield the title compound (10.0 mg, 15.0 μmol).
$^1$H-NMR (400 MHZ, CDCl$_3$) δ (ppm): 1.21-1.29 (m, 4H), 1.75 (br.s., 2H), 2.02 (br.s., 2H), 2.17 (br.s., 2H), 2.55 (s, 3H), 3.00 (s, 12H), 3.60-3.68 (m, 2H), 3.75-3.83 (m, 2H), 6.19 (br.s., 1H), 6.58 (dd, J=8.98, 2.73 Hz, 2H), 6.69 (s, 2H), 6.82 (d, J=8.98 Hz, 2H), 7.16 (d, J=2.73 Hz, 2H), 7.27 (s, 1H), 7.81 (s, 1H).
ESI-MS m/z 649 [M+H]$^+$

Example 17

Synthesis of N-(2-(2,5-dioxo-2,5-dihydro-1H-pyrrol-1-yl)ethyl)-3',7'-dimorpholino-3-oxo-3H-dispiro[isobenzofuran-1,10'-dibenzo[b,e]siline-5',1''-silinane]-6-carboxamide

[Formula 71]

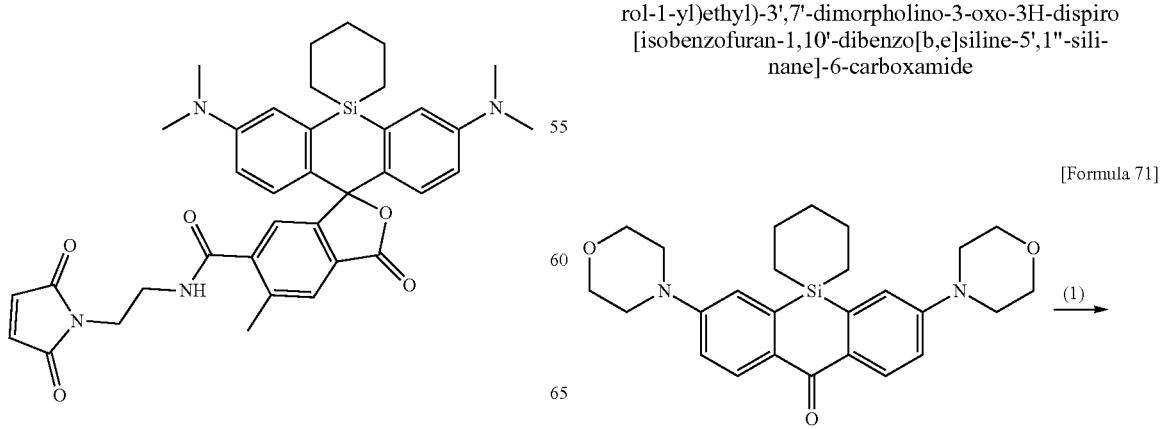

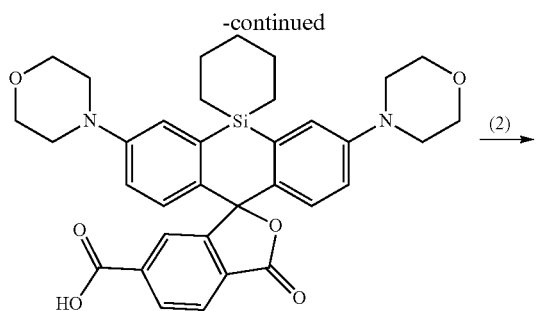

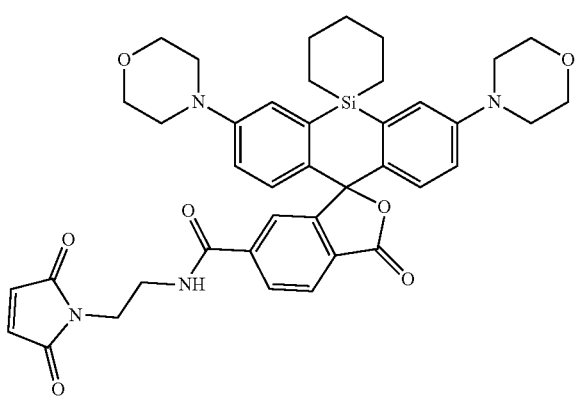

(1) Synthesis of 3',7'-dimorpholino-3-oxo-3H-dispiro[isobenzofuran-1,10'-dibenzo[b,e]siline-5',1"-silinane]-6-carboxylic acid To a solution of 2,2'-(2-bromo-1,4-phenylene)bis(4,4-dimethyl-4,5-dihydrooxazole) (1.56 g, 4.43 mmol, CAS No. 115580-69-3) in THF (20.0 mL) was added dropwise tert-butyllithium (a 1.62-Mn-pentane solution, 2.74 mL, 4.43 mmol) at −78° C. over 20 minutes. The resultant solution was further stirred at the same temperature for 1 hour, and then a solution of 3,7-dimorpholino-10H-spiro[dibenzo[b,e]siline-5,1'-silinan]-10-one (51.0 mg, 114 μmol) produced in Production Example 9 in THF (2.00 mL) was added dropwise to the solution. The reaction mixture was heated to −40° C., and was then stirred at the same temperature for 3 hours. The reaction mixture was heated to room temperature slowly, and was then stirred for 3 days. Acetic acid (5.00 mL) was added to the solution under an ice bath to terminate the reaction. The solvent was distilled away under a reduced pressure, then 5N hydrochloric acid (50.0 mL) was added to the resultant residue, and then the resultant solution was stirred at 80° C. for 4 hours. The mixture was cooled to room temperature, and was then neutralized with a saturated aqueous sodium carbonate solution. The aqueous layer was extracted with ethyl acetate, and the organic layer was dried over anhydrous magnesium sulfate. The solvent was distilled away under a reduced pressure, and the resultant residue was purified by silica gel column chromatography (n-heptane/ethyl acetate (→ethyl acetate/methanol)) to yield a mixture (48.0 mg) containing the title compound.

ESI-MS m/z 597 [M+H]$^+$ (2) Synthesis of N-(2-(2,5-dioxo-2,5-dihydro-1H-pyrrol-1-yl)ethyl)-3',7'-dimorpholino-3-oxo-3H-dispiro[isobenzofuran-1,10'-dibenzo[b,e]siline-5',1"-silinane]-6-carboxamide To a solution of the compound produced in Example 17-(1) (48.0 mg) in DMF (2.00 mL) were added TEA (67.0 μL, 483 μmol), N-(2-aminoethyl) maleimide TFA salt (24.5 mg, 97.0 μmol) and PyBOP (50.2 mg, 97.0 μmol). The reaction mixture was stirred at room temperature for 3.5 hours, and the mixture was purified directly by reverse-phase silica gel column chromatography (water/acetonitrile, 0.1% formic acid) to yield a crude product. The crude product was purified by silica gel thin-layer chromatography (n-heptane/ethyl acetate) to yield the title compound (13.6 mg, 19.0 μmol).

$^1$H-NMR (400 MHZ, CDCl$_3$) δ (ppm): 1.19-1.32 (m, 4H), 1.74 (br.s., 2H), 2.01 (br.s., 2H), 2.14 (br.s., 2H), 3.14-3.22 (m, 8H), 3.61-3.67 (m, 2H), 3.78-3.84 (m, 2H), 3.84-3.89 (m, 8H), 6.73 (s, 2H), 6.73-6.76 (m, 2H), 6.79 (s, 1H), 6.90 (d, J=8.59 Hz, 2H), 7.34 (d, J=2.73 Hz, 2H), 7.74 (s, 1H), 7.82 (dd, J=8.01, 1.37 Hz, 1H), 8.01 (d, J=8.20 Hz, 1H).

ESI-MS m/z 719 [M+H]$^+$

Example 18

Synthesis of N-(2-(2,5-dioxo-2,5-dihydro-1H-pyrrol-1-yl)ethyl)-3',7'-dimorpholino-3-oxo-3H-dispiro[isobenzofuran-1,10'-dibenzo[b,e]siline-5',1"-silinane]-5-carboxamide

[Formula 72]

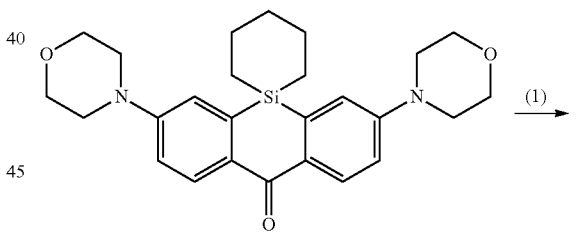

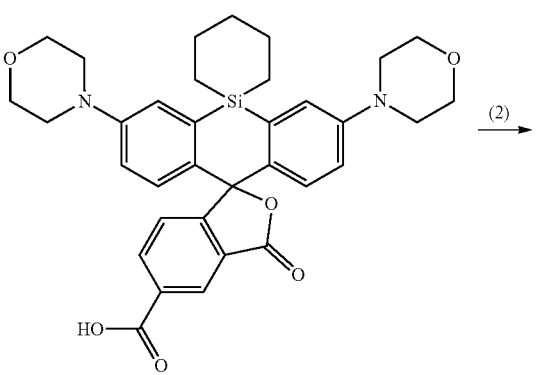

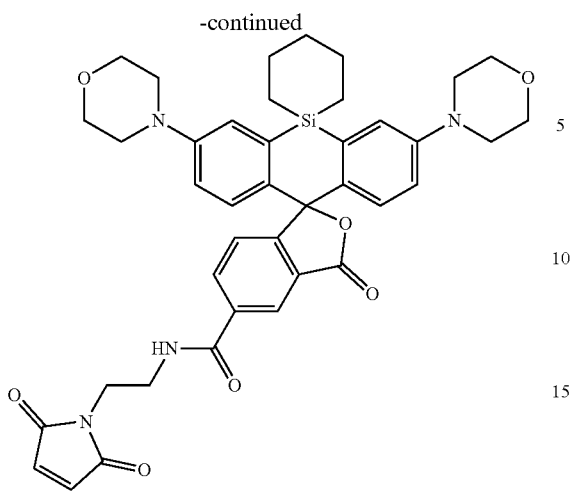

(1) Synthesis of 3',7'-dimorpholino-3-oxo-3H-dispiro[isobenzofuran-1,10'-dibenzo[b,e]siline-5',1''-silinane]-5-carboxylic acid A mixture (44.0 mg) containing the title compound was produced in the same manner as in Example 17-(1) from 3,7-dimorpholino-10H-spiro[dibenzo[b,e]siline-5,1'-silinan]-10-one (51.0 mg, 114 μmol) produced in Production Example 9 and 2,2'-(4-bromo-1,3-phenylene)bis(4,4-dimethyl-4,5-dihydrooxazole) (1.56 g, 4.43 mmol, CAS No. 1426090-01-8).

ESI-MS m/z 597 [M+H]$^+$

(2) Synthesis of N-(2-(2,5-dioxo-2,5-dihydro-1H-pyrrol-1-yl)ethyl)-3',7'-dimorpholino-3-oxo-3H-dispiro[isobenzofuran-1,10'-dibenzo[b,e]siline-5',1''-silinane]-5-carboxamide The title compound (13.7 mg, 19.0 μmol) was produced in the same manner as in Example 17-(2) from the compound produced in 18-(1) (44.0 mg).

$^1$H-NMR (400 MHZ, CDCl$_3$) δ (ppm): 1.19-1.31 (m, 4H), 1.76 (br.s., 2H), 2.02 (br.s., 2H), 2.15 (br.s., 2H), 3.17-3.22 (m, 8H), 3.68-3.74 (m, 2H), 3.84-3.92 (m, 10H), 6.75 (dd, J=8.79, 2.54 Hz, 2H), 6.77 (s, 2H), 6.84 (s, 1H), 6.86-6.90 (m, 2H), 7.35 (d, J=3.12 Hz, 2H), 7.38 (d, J=7.81 Hz, 1H), 8.12 (dd, J=8.01, 1.37 Hz, 1H), 8.28 (s, 1H).

ESI-MS m/z 719 [M+H]$^+$

Example 19

Synthesis of 3',7'-bis(dimethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

[Formula 73]

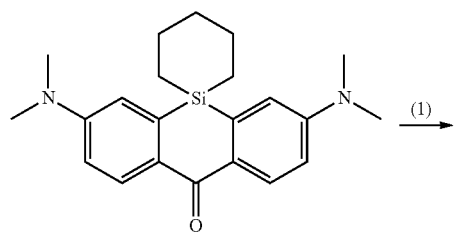

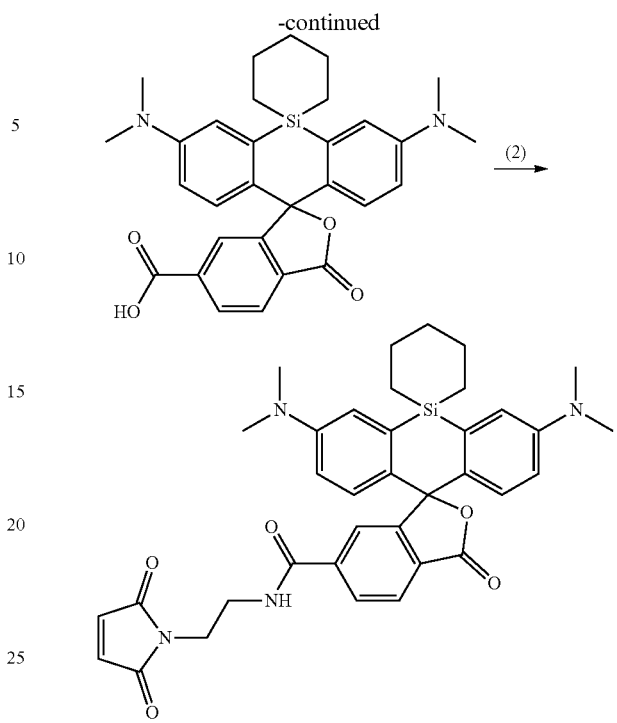

(1) Synthesis of 3',7'-bis(dimethylamino)-3-oxo-3H-dispiro[isobenzofuran-1,10'-dibenzo[b,e]siline-5',1''-silinane]-6-carboxylic acid The title compound (270 mg, 527 μmol) was produced in the same manner as in Example 17-(1) from 3,7-bis(dimethylamino)-10H-spiro[dibenzo[b,e]siline-5,1'-silinan]-10-one (200 mg, 549 μmol) produced in Production Example 10-(2).

ESI-MS m/z 513 [M+H]$^+$

(2) Synthesis of 3',7'-bis(dimethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide To a solution of the compound produced by the method of Example 19-(1) (25.0 mg, 49.0 μmol) in DMF (2.00 mL) were added N-(2-aminoethyl) maleimide TFA salt (28.5 mg, 112 μmol), PyBOP (38.1 mg, 73.0 μmol) and TEA (41.0 μL, 293 μmol). The reaction mixture was stirred at room temperature for 3 days, and was then purified directly by reverse-phase chromatography (water/acetonitrile, 0.1% formic acid). The fraction containing the desired product was collected, then excess acetonitrile was distilled away under a reduced pressure, and then the aqueous layer in the residue was neutralized with a saturated aqueous sodium bicarbonate solution. The aqueous layer was extracted with DCM, and the organic layer was dried over anhydrous magnesium sulfate. The solvent was distilled away under a reduced pressure, and the residue was purified by silica gel thin-layer chromatography (n-heptane/ethyl acetate (→ethyl acetate)) to yield the title compound (2.07 mg, 3.26 μmol).

$^1$H-NMR (400 MHZ, CDCl$_3$) δ (ppm): 1.24-1.33 (m, 4H), 1.73 (br.s., 2H), 2.02 (br.s., 2H), 2.16 (br.s., 2H), 2.97 (s, 12H), 3.61-3.68 (m, 2H), 3.77-3.85 (m, 2H), 6.55 (dd, J=8.79, 2.93 Hz, 2H), 6.72 (s, 2H), 6.74 (s, 1H), 6.80 (d, J=8.98 Hz, 2H), 7.14 (d, J=2.73 Hz, 2H), 7.72 (s, 1H), 7.83 (dd, J=8.01, 1.37 Hz, 1H), 8.00 (d, J=7.81 Hz, 1H).
ESI-MS m/z 635 [M+H]⁺

Example 20

Synthesis of 3',7'-bis(dimethylamino)-N-(2-(2-(2-(2-(2,5-dioxo-2,5-dihydro-1H-pyrrol-1-yl)ethoxy)ethoxy)ethoxy)ethyl)-3-oxo-3H-dispiro[isobenzofuran-1,10'-dibenzo[b,e]siline-5',1''-silinane]-6-carboxamide

[Formula 74]

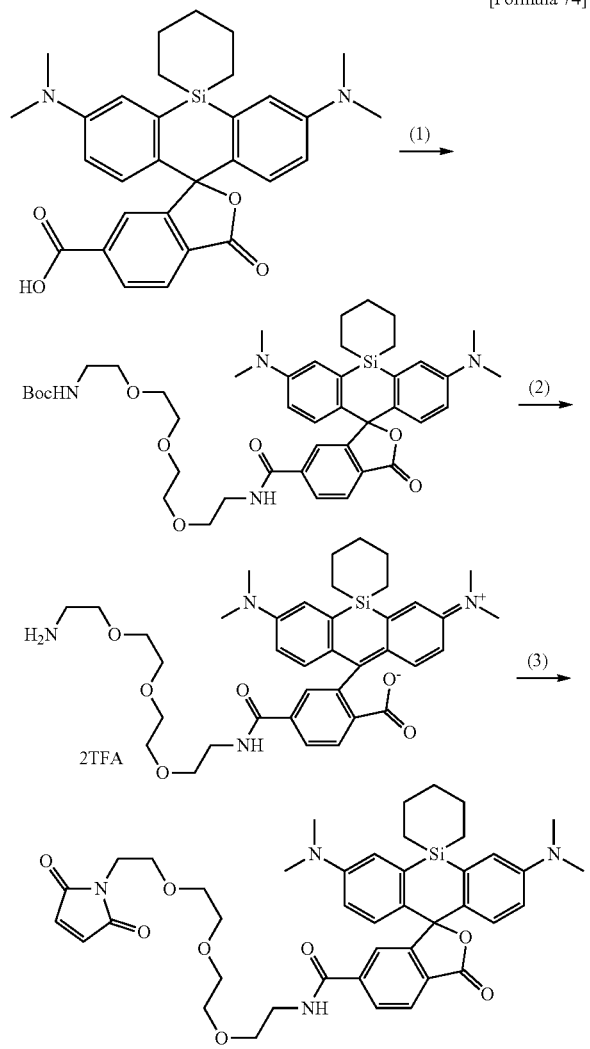

(1) Synthesis of tert-butyl(1-(3',7'-bis(dimethylamino)-3-oxo-3H-dispiro[isobenzofuran-1,10'-dibenzo[b,e]siline-5',1''-silinan]-6-yl)-1-oxo-5,8,11-trioxa-2-aza tridecan-13-yl) carbamate The title compound (178 mg, 226 μmol) was produced in the same manner as in Example 11-(1) from 3',7'-bis(dimethylamino)-3-oxo-3H-dispiro[isobenzofuran-1,10'-dibenzo[b,e]siline-5',1''-silinane]-6-carboxylic acid (270 mg, 527 μmol) produced by the method of Example 19-(1).
ESI-MS m/z 787 [M+H]⁺

(2) Synthesis of 4-((2-(2-(2-(2-aminoethoxy)ethoxy)ethyl) carbamoyl)-2-(7-(dimethylamino)-3-(dimethyliminio)-3H-spiro[dibenzo[b,e]siline-5,1'-silinan]-10-yl)benzoate 2TFA salt A crude product (210 mg) of the title compound was produced in the same manner as in Example 11-(2) from the compound produced in Example 20-(1) (178 mg, 226 μmol).
ESI-MS m/z 687 [M+H]⁺

(3) Synthesis of 3',7'-bis(dimethylamino)-N-(2-(2-(2-(2-(2,5-dioxo-2,5-dihydro-1H-pyrrol-1-yl)ethoxy)ethoxy)ethoxy)ethyl)-3-oxo-3H-dispiro[isobenzofuran-1,10'-dibenzo[b,e]siline-5',1''-silinane]-6-carboxamide A mixture of the compound produced in Example 20-(2) (210 mg), methyl 2,5-dioxo-2,5-dihydro-1H-pyrrole-1-carboxylate (214 mg, 1.38 mmol), THF (8.20 mL) and a saturated aqueous sodium bicarbonate solution (8.20 mL) was stirred at room temperature for 3.5 hours. The resultant solution was diluted with ethyl acetate, and an organic layer was separated. The organic layer was washed with water and saturated saline. The mixture was dried over anhydrous magnesium sulfate, and then the solvent was distilled away under a reduced pressure. The resultant residue was purified by silica gel column chromatography (n-heptane/ethyl acetate) to yield a crude product. The crude product was purified by silica gel thin-layer chromatography (ethyl acetate) to yield a crude product. The crude product was purified by reverse-phase chromatography (water/acetonitrile, 0.1% formic acid). The fraction containing the desired product was collected, then excess acetonitrile was distilled away under a reduced pressure, and then the aqueous layer in the residue was neutralized with a saturated aqueous sodium bicarbonate solution. The aqueous layer was extracted with ethyl acetate, and the organic layer was dried over anhydrous magnesium sulfate. The solvent was distilled away under a reduced pressure to yield the title compound (89.0 mg, 116 μmol).
¹H-NMR (400 MHZ, CDCl₃) δ (ppm): 1.17-1.26 (m, 4H), 1.73 (br.s., 2H), 2.00 (br.s., 2H), 2.16 (br.s., 2H), 2.97 (s, 12H), 3.43-3.53 (m, 6H), 3.54-3.62 (m, 6H), 3.64-3.66 (m, 4H), 6.54 (dd, J=8.79, 2.93 Hz, 2H), 6.60 (s, 2H), 6.78 (d, J=8.59 Hz, 2H), 7.01-7.07 (m, 1H), 7.13 (d, J=2.73 Hz, 2H), 7.76 (s, 1H), 7.95-8.03 (m, 2H).
ESI-MS m/z 767 [M+H]⁺

Example 21

Synthesis of 3',7'-bis(dimethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-5-carboxamide

[Formula 75]

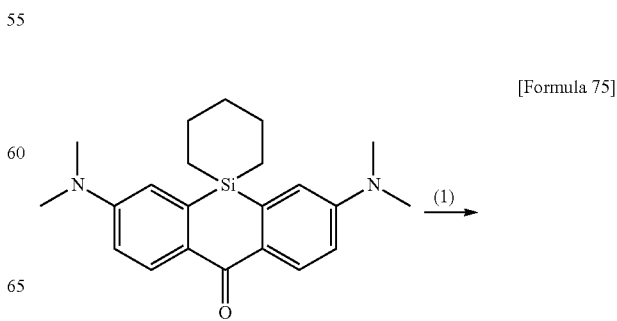

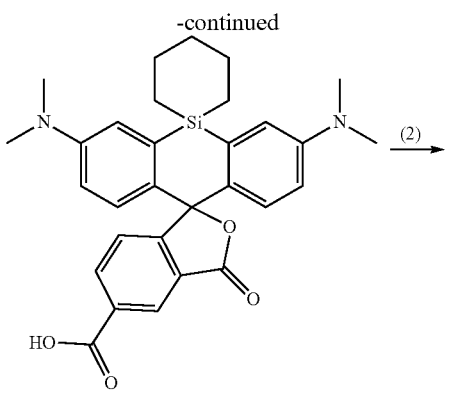

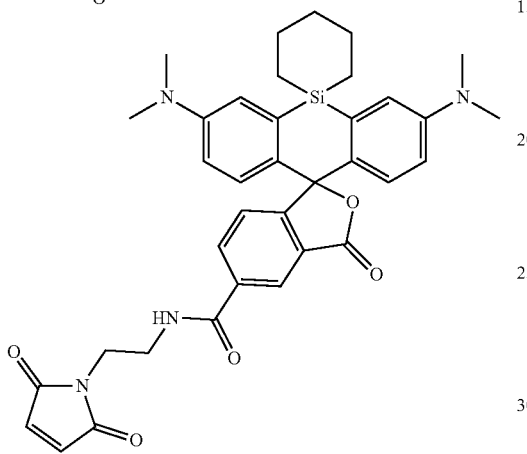

(1) Synthesis of 3',7'-bis(dimethylamino)-3-oxo-3H-dispiro[isobenzofuran-1,10'-dibenzo[b,e]siline-5',1''-silinane]-5-carboxylic acid A mixture (47.7 mg) containing the title compound was produced in the same manner as in Example 18-(1) from 3,7-bis(dimethylamino)-10H-spiro[dibenzo[b,e]siline-5,1'-silinan]-10-one (50.0 mg, 137 μmol) produced in Production Example 10-(2).
ESI-MS m/z 513 [M+H]$^+$ (2) Synthesis of 3',7'-bis(dimethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-5-carboxamide To a solution of the compound produced in Example 21-(1) (47.0 mg, 92.0 μmol) in DMF (1.00 mL) were added diisopropylethylamine (96.0 μL, 550 μmol), N-(2-aminoethyl) maleimide TFA salt (53.6 mg, 211 μmol) and PyBOP (71.6 mg, 138 μmol). The reaction mixture was stirred at room temperature overnight, and then water was added to the reaction mixture to terminate the reaction. The aqueous layer was extracted with ethyl acetate, and then the organic layer was washed with water and saturated saline. The organic layer was dried over magnesium sulfate, and the solvent was distilled away under a reduced pressure. The residue was purified by silica gel thin-layer chromatography (n-heptane/ethyl acetate) to yield a crude product.
The crude product was purified by reverse-phase silica gel column chromatography (water/acetonitrile, 0.1% formic acid). The fraction containing the desired product was collected, and excess acetonitrile was distilled away under a reduced pressure. The aqueous layer was neutralized with an aqueous sodium bicarbonate solution, and was then extracted with ethyl acetate. The organic layer was dried over magnesium sulfate, and the solvent was distilled away under a reduced pressure. The residue was purified by silica gel thin-layer chromatography (diethyl ether) to yield the title compound (5.00 mg, 7.88 μmol).
$^1$H-NMR (400 MHZ, CDCl$_3$) δ (ppm): 1.18-1.30 (m, 4H), 1.74 (br.s., 2H), 2.01 (br.s., 2H), 2.16 (br.s., 2H), 2.98 (s, 12H), 3.67-3.76 (m, 2H), 3.82-3.92 (m, 2H), 6.54 (dd, J=8.98, 2.73 Hz, 2H), 6.73-6.83 (m, 3H), 6.76 (s, 2H), 7.14 (d, J=3.12 Hz, 2H), 7.37 (d, J=8.20 Hz, 1H), 8.10 (dd, J=8.01, 1.76 Hz, 1H), 8.26 (d, J=0.78 Hz, 1H).
ESI-MS m/z 635 [M+H]$^+$ Example 22

Synthesis of 3',7'-bis(dimethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silolane]-6-carboxamide

[Formula 76]

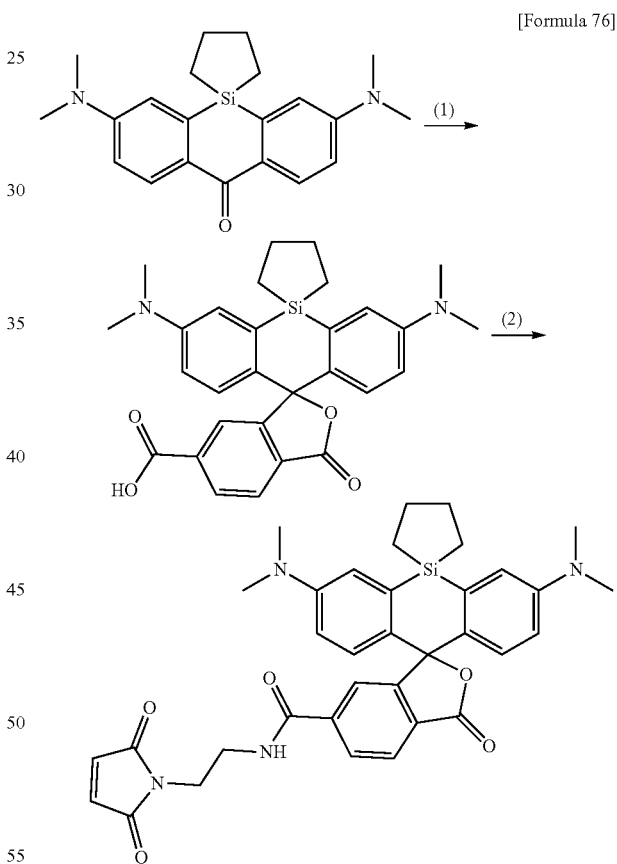

(1) Synthesis of 3',7'-bis(dimethylamino)-3-oxo-3H-dispiro[isobenzofuran-1,10'-dibenzo[b,e]siline-5',1''-silolane]-6-carboxylic acid A mixture (27.0 mg) containing the title compound was produced in the same manner as in Example 17-(1) from 3,7-bis(dimethylamino)-10H-spiro[dibenzo[b,e]siline-5,1'-silolan]-10-one (40.0 mg, 114 μmol) produced in Production Example 11-(2).
ESI-MS m/z 499 [M+H]$^+$ (2) Synthesis of 3',7'-bis(dimethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silolane]-6-carboxamide A mixture of the compound produced in Example 22-(1) (27.0 mg), PyBOP (43.8 mg, 84.0 μmol), N-(2-aminoethyl) maleimide TFA salt (32.8 mg, 129 μmol), TEA (47.0 μL, 337 μmol) and DMF (2.00 mL) was stirred at room temperature overnight. The mixture was purified directly by reverse-phase silica gel column chromatography (water/acetonitrile, 0.1% formic acid). The fraction containing the desired product was collected, excess acetonitrile was distilled away at 0° C. or lower under a reduced pressure. The aqueous layer in the residue was neutralized with a saturated aqueous sodium bicarbonate solution, and the aqueous layer was extracted with ethyl acetate. The solvent was distilled away under a reduced pressure, and the resultant residue was purified by silica gel thin-layer chromatography (diethyl ether) to yield the title compound (3.68 mg, 5.93 μmol).

$^1$H-NMR (400 MHZ, CDCl$_3$) δ (ppm): 1.21 (t, J=7.03 Hz, 2H), 1.25-1.32 (m, 2H), 1.95-2.06 (m, 4H), 2.95 (s, 12H), 3.56-3.64 (m, 2H), 3.76-3.83 (m, 2H), 6.61 (dd, J=8.98, 2.73 Hz, 2H), 6.65 (br.s., 1H), 6.71 (s, 2H), 6.94 (d, J=3.12 Hz, 2H), 7.00 (d, J=8.98 Hz, 2H), 7.67 (d, J=0.78 Hz, 1H), 7.70-7.75 (m, 1H), 7.93-7.97 (m, 1H).

ESI-MS m/z 621 [M+H]$^+$

Example 23

Synthesis of 3',7'-bis(diethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

[Formula 77]

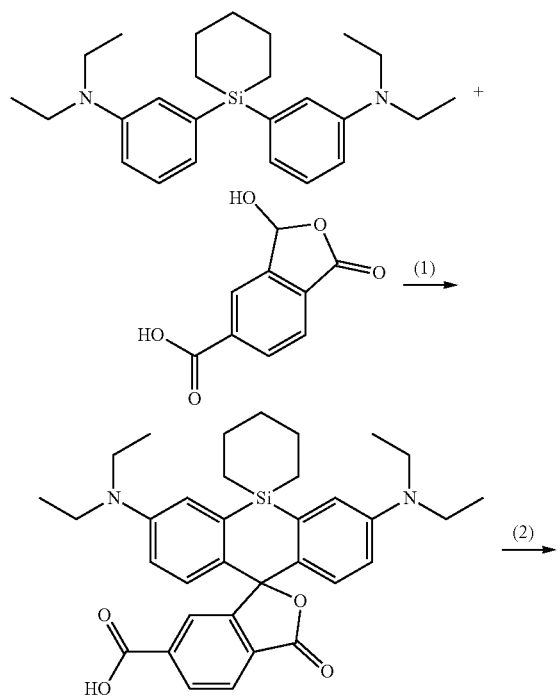

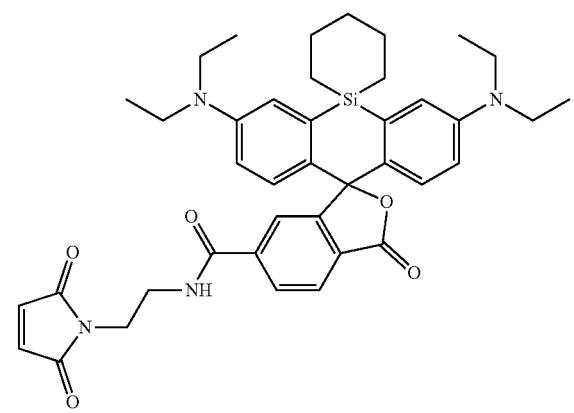

(1) Synthesis of 3',7'-bis(diethylamino)-3-oxo-3H-dispiro[isobenzofuran-1,10'-dibenzo[b,e]siline-5',1''-silinane]-6-carboxylic acid A mixture of 3,3'-(silinane-1,1-diyl)bis(N,N-diethylaniline) (99.0 mg, 250 μmol) produced in Production Example 12, 3-hydroxy-1-oxo-1,3-dihydroisobenzofuran-5-carboxylic acid (146 mg, 750 μmol) produced in Production Example 15-(2), copper (II) bromide (16.8 mg, 75.0 μmol) and acetic acid (215 μL, 3.75 mmol) was stirred at 140° C. for 8 hours. The mixture was cooled to room temperature, and was then purified directly by silica gel column chromatography (n-heptane/ethyl acetate) to yield the title compound (40.0 mg, 70.0 μmol).

$^1$H-NMR (400 MHZ, CDCl$_3$) δ (ppm): 1.04-1.19 (m, 12H), 1.20-1.32 (m, 4H), 1.65-1.85 (m, 2H), 1.95-2.06 (m, 2H), 2.09-2.21 (m, 2H), 3.25-3.42 (m, 8H), 6.49 (dd, J=8.98, 2.73 Hz, 2H), 6.73 (d, J=8.98 Hz, 2H), 7.11 (d, J=3.12 Hz, 2H), 8.00-8.09 (m, 2H), 8.24 (dd, J=8.01, 1.37 Hz, 1H).

ESI-MS m/z 569 [M+H]$^+$ (2) Synthesis of 3',7'-bis(diethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide To a solution of the compound produced in Example 23-(1) (9.67 mg, 17.0 μmol) in DMF (500 μL) were added N-(2-aminoethyl) maleimide TFA salt (9.94 mg, 39.0 μmol), PyBOP (13.3 mg, 26.0 μmol) and TEA (14.0 μL, 102 μmol). The reaction mixture was stirred at room temperature for 18 hours, and then the reaction mixture was purified directly by silica gel column chromatography (n-heptane/ethyl acetate) to yield the title compound (2.00 mg, 2.89 μmol).

$^1$H-NMR (400 MHZ, CDCl$_3$) δ (ppm): 1.14-1.21 (m, 12H), 1.21-1.32 (m, 4H), 1.74 (br.s., 2H), 2.02 (br.s., 2H), 2.11-2.21 (m, 2H), 3.38 (q, J=7.03 Hz, 8H), 3.61-3.71 (m, 2H), 3.78-3.88 (m, 2H), 6.49 (dd, J=8.98, 2.73 Hz, 2H), 6.69-6.80 (m, 3H), 6.73 (s, 2H), 7.11 (d, J=2.73 Hz, 2H), 7.76 (dd, J=1.56, 0.78 Hz, 1H), 7.86 (dd, J=8.01, 1.37 Hz, 1H), 8.01 (dd, J=7.81, 0.78 Hz, 1H).

ESI-MS m/z 691 [M+H]$^+$

Example 24

Synthesis of 3',7'-bis(diethylamino)-N-(2-(2,5-di-oxo-2,5-dihydro-1H-pyrrol-1-yl)ethyl)-3-oxo-3H-dispiro[isobenzofuran-1,10'-dibenzo[b,e]siline-5',1''-silinane]-5-carboxamide

[Formula 78]

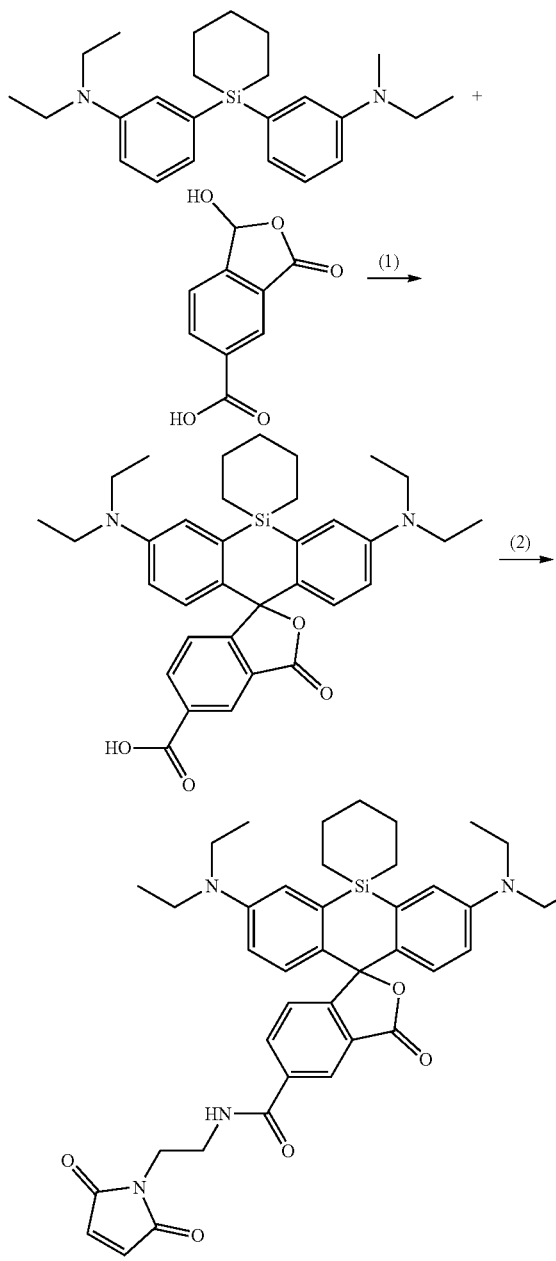

(1) Synthesis of 3',7'-bis(diethylamino)-3-oxo-3H-dispiro[isobenzofuran-1,10'-dibenzo[b,e]siline-5',1''-silinane]-5-carboxylic acid The title compound (49.0 mg, 86.0 μmol) was produced in the same manner as in Example 23-(1) from 3,3'-(silinane-1,1-diyl)bis(N,N-diethylaniline) (99.0 mg, 250 μmol) produced in Production Example 12 and 1-hydroxy-3-oxo-1,3-dihydroisobenzofuran-5-carboxylic acid (146 mg, 750 μmol) produced in Production Example 16-(2).

$^{1}$H-NMR (400 MHZ, CDCl$_3$) δ (ppm): 1.10-1.27 (m, 16H), 1.73 (br.s., 2H), 1.96-2.07 (m, 2H), 2.09-2.22 (m, 2H), 3.37 (q, J=7.03 Hz, 8H), 6.49 (dd, J=8.98, 3.12 Hz, 2H), 6.72 (d, J=8.98 Hz, 2H), 7.10 (d, J=2.73 Hz, 2H), 7.42 (d, J=8.20 Hz, 1H), 8.35 (dd, J=8.01, 1.37 Hz, 1H), 8.69 (d, J=0.78 Hz, 1H).

ESI-MS m/z 569 [M+H]$^+$ (2) Synthesis of 3',7'-bis(diethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-5-carboxamide The title compound (3.00 mg, 4.34 μmol) was produced in the same manner as in Example 23-(2) from the compound produced in Example 24-(1) (10.2 mg, 18.0 μmol).

$^{1}$H-NMR (400 MHZ, CDCl$_3$) δ (ppm): 1.17 (t, J=7.03 Hz, 12H), 1.20-1.30 (m, 4H), 1.74 (br.s., 2H), 1.94-2.05 (m, 2H), 2.11-2.21 (m, 2H), 3.37 (q, J=6.77 Hz, 8H), 3.67-3.77 (m, 2H), 3.82-3.90 (m, 2H), 6.47 (dd, J=8.98, 2.73 Hz, 2H), 6.67-6.77 (m, 4H), 6.91 (t, J=5.27 Hz, 1H), 7.10 (d, J=2.73 Hz, 2H), 7.43 (d, J=8.20 Hz, 1H), 8.14 (dd, J=8.20, 1.56 Hz, 1H), 8.28 (d, J=0.78 Hz, 1H).

ESI-MS m/z 691 [M+H]$^+$

Example 25

Synthesis of 3',7'-bis(diethylamino)-N-(2-(2,5-di-oxo-2,5-dihydro-1H-pyrrol-1-yl)ethyl)-5-fluoro-3-oxo-3H-dispiro[isobenzofuran-1,10'-dibenzo[b,e]siline-5',1''-silinane]-6-carboxamide

[Formula 79]

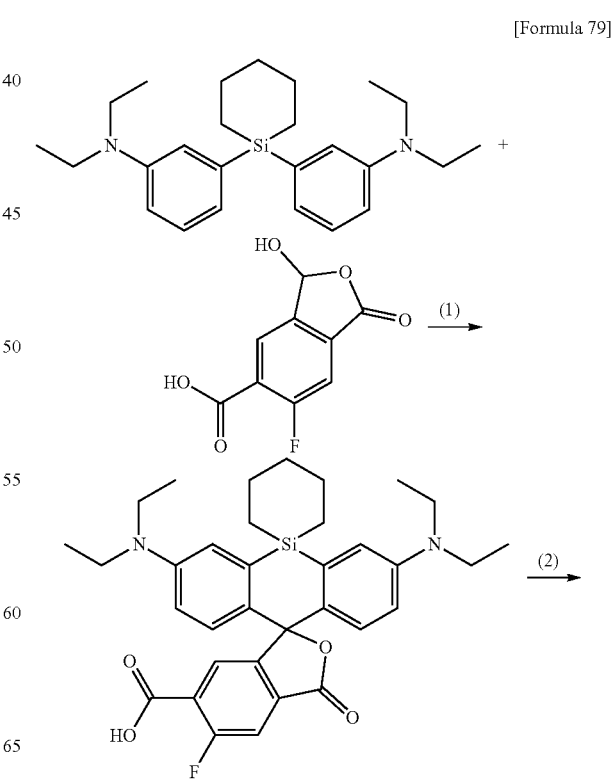

121
-continued

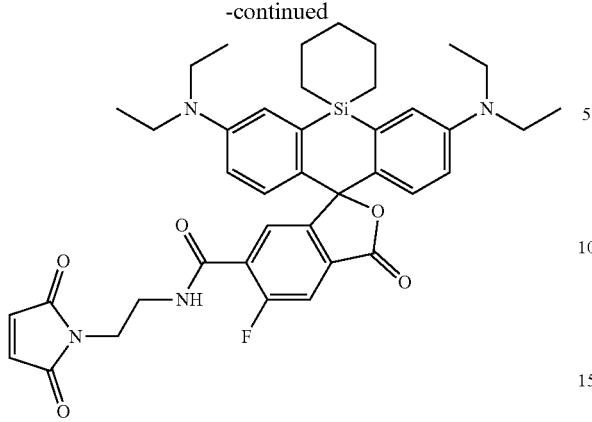

(1) Synthesis of 3',7'-bis(diethylamino)-5-fluoro-3-oxo-3H-dispiro[isobenzofuran-1,10'-dibenzo[b,e]siline-5',1''-silinane]-6-carboxylic acid A mixture of 3,3'-(silinane-1,1-diyl)bis(N,N-diethylaniline) (70.0 mg, 177 μmol) produced in Production Example 12, 6-fluoro-3-hydroxy-1-oxo-1,3-dihydroisobenzofuran-5-carboxylic acid (125 mg) produced in Production Example 17-(2), copper (II) bromide (11.9 mg, 53.0 μmol) and acetic acid (2.00 mL) was stirred at 140° C. for 4 hours. The solvent was distilled away under a reduced pressure, and the residue was neutralized with a saturated aqueous sodium bicarbonate solution. The aqueous layer was extracted with ethyl acetate, and the organic layer was dried over anhydrous magnesium sulfate. The solvent was distilled away under a reduced pressure to yield a crude product (96.0 mg) of the title compound.

ESI-MS m/z 587 [M+H]$^+$

(2) Synthesis of 3',7'-bis(diethylamino)-N-(2-(2,5-dioxo-2,5-dihydro-1H-pyrrol-1-yl)ethyl)-5-fluoro-3-oxo-3H-dispiro[isobenzofuran-1,10'-dibenzo[b,e]siline-5',1''-silinane]-6-carboxamide A mixture of the compound produced in Example 25-(1) (76.0 mg), PyBOP (81.0 mg, 155 μmol), N-(2-aminoethyl)maleimide TFA salt (39.5 mg, 155 μmol), triethylamine (90.0 μL, 648 μmol) and DMF (1.00 mL, 12.9 mmol) was stirred at room temperature 2.5 hours. Ice was added to the solution to terminate the reaction, and the aqueous layer was extracted with ethyl acetate. The organic layer was washed with saturated saline three times, and the resultant product was dried over anhydrous magnesium sulfate. The solvent was distilled away under a reduced pressure, and the resultant residue was purified by silica gel column chromatography (n-heptane/ethyl acetate) to yield the title compound (5.70 mg, 8.04 μmol).

$^1$H-NMR (400 MHZ, CDCl$_3$) δ (ppm): 1.12-1.21 (t, J=7.03 Hz, 12H), 1.21-1.28 (m, 4H), 1.74 (br.s., 2H), 2.02 (br.s., 2H), 2.10-2.22 (m, 2H), 3.38 (q, J=7.03 Hz, 8H), 3.67-3.74 (m, 2H), 3.80-3.88 (m, 2H), 6.49 (dd, J=8.98, 2.73 Hz, 2H), 6.71-6.78 (m, 2H), 6.74 (s, 2H), 7.10 (d, J=2.73 Hz, 2H), 7.13 (br.s., 1H), 7.67 (d, J=9.76 Hz, 1H), 8.02 (d, J=6.25 Hz, 1H).

ESI-MS m/z 709 [M+H]$^+$

122
Example 26

Synthesis of 5-chloro-3',7'-bis(diethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

[Formula 80]

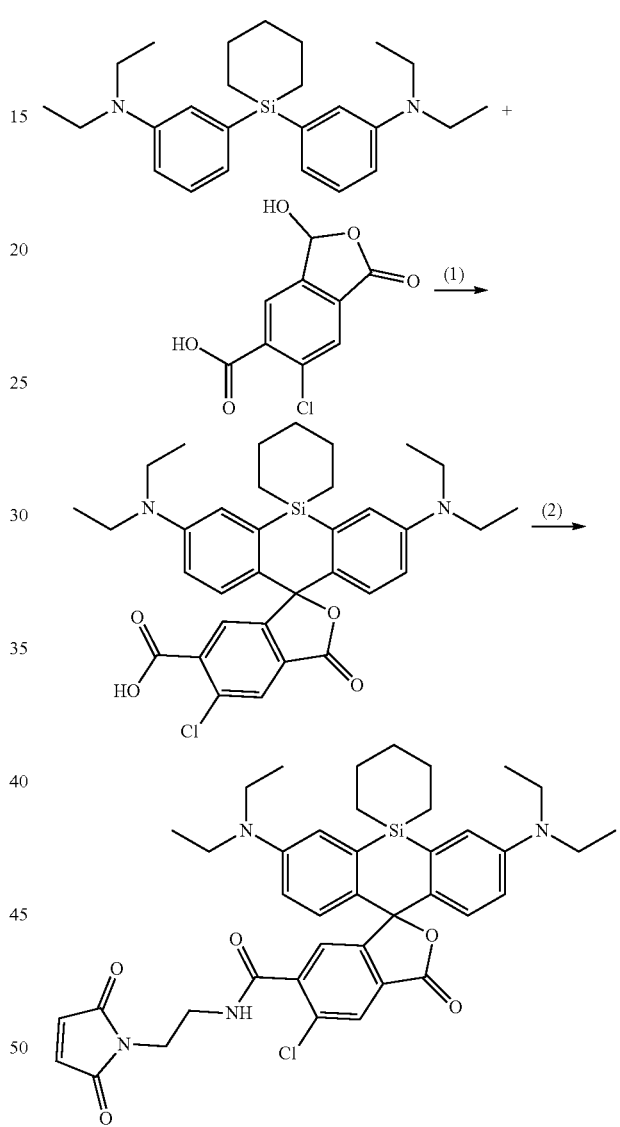

(1) Synthesis of 5-chloro-3',7'-bis(diethylamino)-3-oxo-3H-dispiro[isobenzofuran-1,10'-dibenzo[b,e]siline-5',1''-silinane]-6-carboxylic acid The title compound (8.00 mg, 13.0 μmol) was produced in the same manner as in Example 23-(1) from 3,3'-(silinane-1,1-diyl)bis(N,N-diethylaniline) (39.5 mg, 100 μmol) produced in Production Example 12 and 6-chloro-3-hydroxy-1-oxo-1,3-dihydroisobenzofuran-5-carboxylic acid (68.6 mg, 300 μmol) produced in Production Example 18-(2).

$^1$H-NMR (400 MHZ, CDCl$_3$) δ (ppm): 1.03-1.35 (m, 16H), 1.69 (br.s., 2H), 1.98 (br.s., 2H), 2.02-2.15 (m, 2H), 3.38 (q, J=7.03 Hz, 8H), 6.60 (dd, J=8.59, 2.73 Hz, 2H), 6.83 (d, J=8.98 Hz, 2H), 7.19 (d, J=2.73 Hz, 2H), 7.79 (s, 1H), 7.99 (s, 1H).

ESI-MS m/z 603 [M+H]$^+$ (2) Synthesis of 5-chloro-3',7'-bis(diethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide A crude product of the title compound was produced in the same manner as in Example 23-(2) from the compound produced in Example 26-(1) (7.84 mg, 13.0 µmol). The crude product was purified by reverse-phase silica gel column chromatography (water/acetonitrile, 0.1% formic acid) to yield the title compound (1.60 mg, 2.21 µmol).

$^1$H-NMR (400 MHZ, CDCl$_3$) δ (ppm): 1.18 (t, J=7.03 Hz, 12H), 1.19-1.24 (m, 4H), 1.73 (br.s., 2H), 1.99 (br.s., 2H), 2.14 (br.s., 2H), 3.38 (q, J=7.03 Hz, 8H), 3.63-3.72 (m, 2H), 3.75-3.84 (m, 2H), 6.42 (br.s., 1H), 6.51 (dd, J=8.98, 2.73 Hz, 2H), 6.68 (s, 2H), 6.73 (d, J=8.98 Hz, 2H), 7.08 (d, J=3.12 Hz, 2H), 7.46 (s, 1H), 7.96 (s, 1H).

ESI-MS m/z 725 [M+H]$^+$

Example 27

Synthesis of 5-bromo-3',7'-bis(diethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide

[Formula 81]

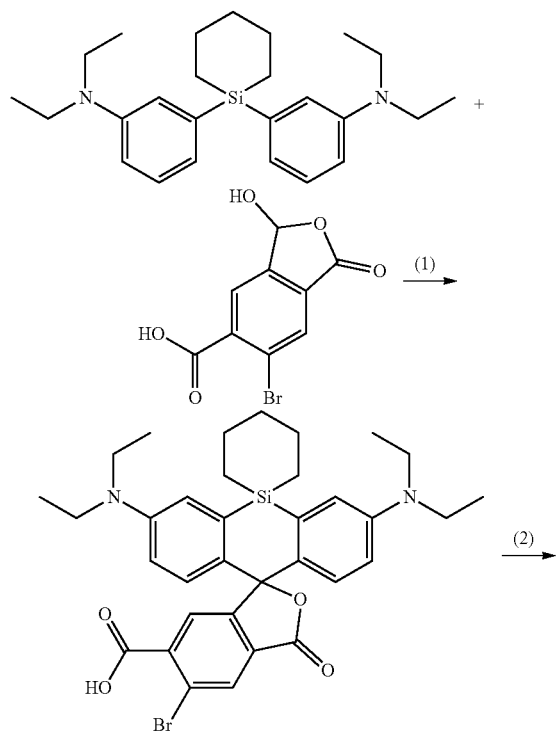

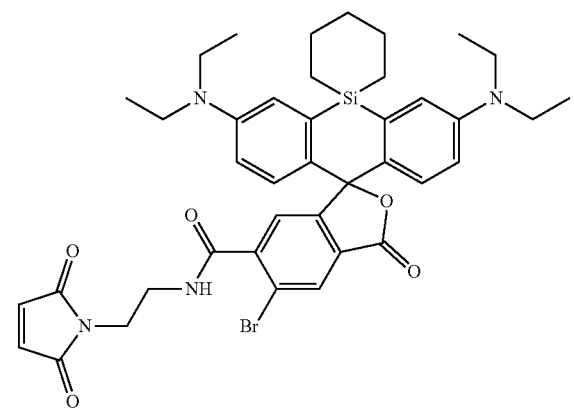

(1) Synthesis of 5-bromo-3',7'-bis(diethylamino)-3-oxo-3H-dispiro[isobenzofuran-1,10'-dibenzo[b,e]siline-5',1''-silinane]-6-carboxylic acid A mixture of 3,3'-(silinane-1,1-diyl)bis(N,N-diethylaniline) (150 mg, 380 µmol) produced in Production Example 12, 6-bromo-3-hydroxy-1-oxo-1,3-dihydroisobenzofuran-5-carboxylic acid (208 mg, 760 µmol) produced in Production Example 19-(2), copper (II) bromide (25.5 mg, 114 µmol) and acetic acid (1.09 mL) was stirred at 140° C. for 6 hours. The reaction mixture was cooled to room temperature, and was then purified directly by reverse-phase chromatography (water/acetonitrile, 0.1% formic acid) to yield the title compound (105 mg, 162 µmol).

$^1$H-NMR (400 MHZ, CDCl$_3$) δ (ppm): 1.10-1.23 (m, 16H), 1.68 (br.s., 2H), 1.91-2.12 (m, 4H), 3.40 (q, J=7.29 Hz, 8H), 6.67 (dd, J=8.98, 2.73 Hz, 2H), 6.88 (d, J=8.98 Hz, 2H), 7.25 (d, J=2.73 Hz, 2H), 7.71 (s, 1H), 8.19 (s, 1H).

ESI-MS m/z 649 [M+H]$^+$ (2) Synthesis of 5-bromo-3',7'-bis(diethylamino)-N-(2-(2,5-dioxo-2,5-dihydro-1H-pyrrol-1-yl)ethyl)-3-oxo-3H-dispiro[isobenzofuran-1,10'-dibenzo[b,e]siline-5',1''-silinane]-6-carboxamide The title compound (4.20 mg, 5.46 µmol) was produced in the same manner as in Example 23-(2) from the compound produced in Example 27-(1) (9.72 mg, 15.0 µmol).

$^1$H-NMR (400 MHZ, CDCl$_3$) δ (ppm): 1.10-1.24 (m, 16H), 1.72 (br.s., 2H), 1.99 (br.s., 2H), 2.12 (br.s., 2H), 3.37 (q, J=7.29 Hz, 8H), 3.62-3.72 (m, 2H), 3.73-3.82 (m, 2H), 6.31 (t, J=5.66 Hz, 1H), 6.51 (dd, J=8.98, 3.12 Hz, 2H), 6.67 (s, 2H), 6.73 (d, J=8.98 Hz, 2H), 7.08 (d, J=2.73 Hz, 2H), 7.35 (s, 1H), 8.14 (s, 1H).

ESI-MS m/z 769, 771 [M+H]$^+$

Example 28

Synthesis of 3',7'-bis(diethylamino)-5-(difluoromethyl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1"-silinane]-6-carboxamide

[Formula 82]

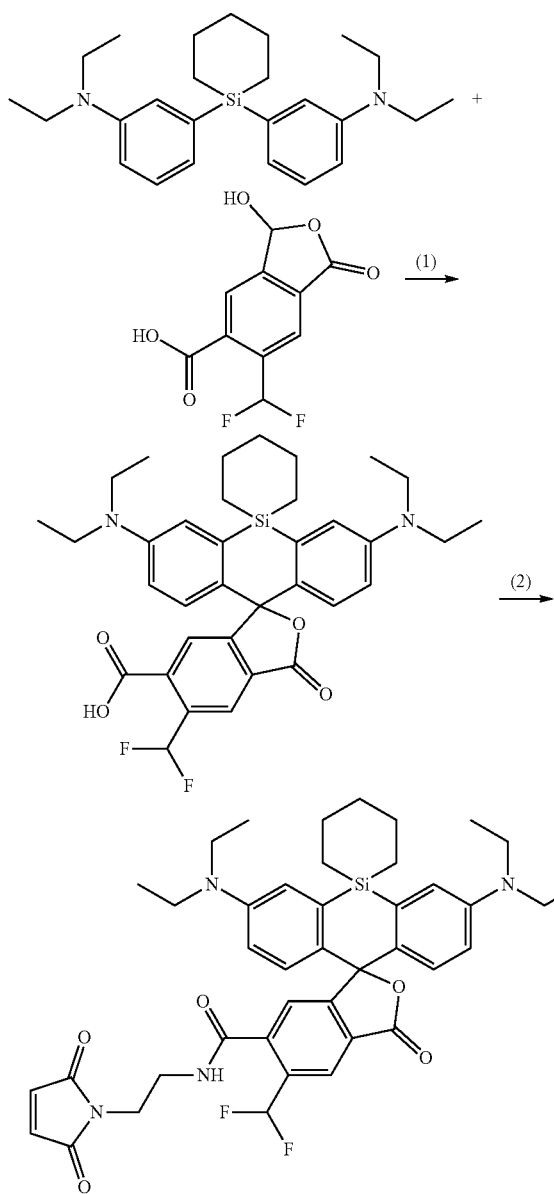

(1) Synthesis of 3',7'-bis(diethylamino)-5-(difluoromethyl)-3-oxo-3H-dispiro[isobenzofuran-1,10'-dibenzo[b,e]siline-5',1"-silinane]-6-carboxylic acid The title compound (22.0 mg, 36.0 μmol) was produced in the same manner as in Example 27-(1) from 3,3'-(silinane-1,1-diyl)bis(N,N-diethylaniline) (70.0 mg, 177 μmol) produced in Production Example 12 and 6-(difluoromethyl)-3-hydroxy-1-oxo-1,3-dihydroisobenzofuran-5-carboxylic acid (87.0 mg, 355 μmol) produced in Production Example 20-(3).

$^1$H-NMR (400 MHZ, MeOH-$d_4$) δ (ppm): 1.11-1.23 (m, 16H), 1.74 (br.s., 2H), 2.00 (br.s., 2H), 2.10 (br.s., 2H), 3.47 (q, J=7.03 Hz, 8H), 6.59 (dd, J=9.18, 2.93 Hz, 2H), 6.78 (d, J=9.37 Hz, 2H), 7.17 (d, J=2.73 Hz, 2H), 7.57 (t, J=55.84 Hz, 1H), 7.80 (s, 1H), 8.32 (s, 1H).

ESI-MS m/z 619 [M+H]$^+$ (2) Synthesis of 3',7'-bis(diethylamino)-5-(difluoromethyl)-N-(2-(2,5-dioxo-2,5-dihydro-1H-pyrrol-1-yl)ethyl)-3-oxo-3H-dispiro[isobenzofuran-1,10'-dibenzo[b,e]siline-5',1"-silinane]-6-carboxamide A mixture of the compound produced in Example 28-(1) (27.8 mg, 45.0 μmol), N-(2-aminoethyl) maleimide TFA salt (26.3 mg, 104 μmol), PyBOP (35.1 mg, 68.0 μmol), triethylamine (38.0 μL, 270 μmol) and DMF (500 μL) was stirred at room temperature for 2 hours. The reaction mixture was purified directly by reverse-phase silica gel column chromatography (water/acetonitrile, 0.1% formic acid) to yield the title compound (11.8 mg, 16.0 μmol).

$^1$H-NMR (400 MHz, MeOH-$d_4$) δ (ppm): 1.16 (t, J=7.03 Hz, 12H), 1.19-1.26 (m, 4H), 1.73 (br.s., 2H), 1.94-2.06 (m, 2H), 2.11-2.17 (m, 2H), 3.38 (q, J=7.03 Hz, 8H), 3.50 (dd, J=6.44, 4.49 Hz, 2H), 3.65-3.73 (m, 2H), 6.52 (dd, J=8.98, 2.73 Hz, 2H), 6.66 (s, 2H), 6.68 (d, J=8.98 Hz, 2H), 7.09 (d, J=3.12 Hz, 2H), 7.12 (t, J=55.26 Hz, 1H), 7.38 (s, 1H), 7.58 (s, 1H), 8.22 (s, 1H).

ESI-MS m/z 741 [M+H]$^+$

Example 29

Synthesis of 3',7'-bis(diethylamino)-N-(2-(2,5-dioxo-2,5-dihydro-1H-pyrrol-1-yl)ethyl)-5-(methoxymethyl)-3-oxo-3H-dispiro[isobenzofuran-1,10'-dibenzo[b,e]siline-5',1"-silinane]-6-carboxamide

[Formula 83]

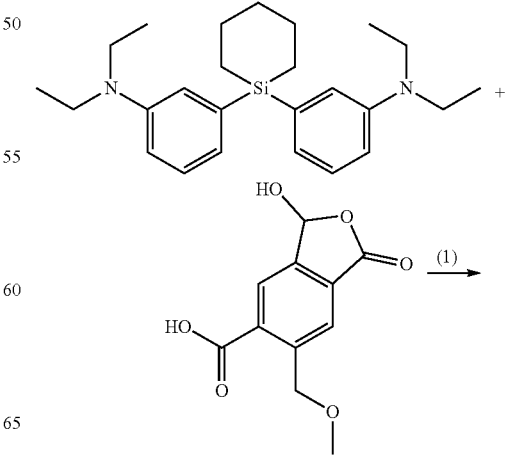

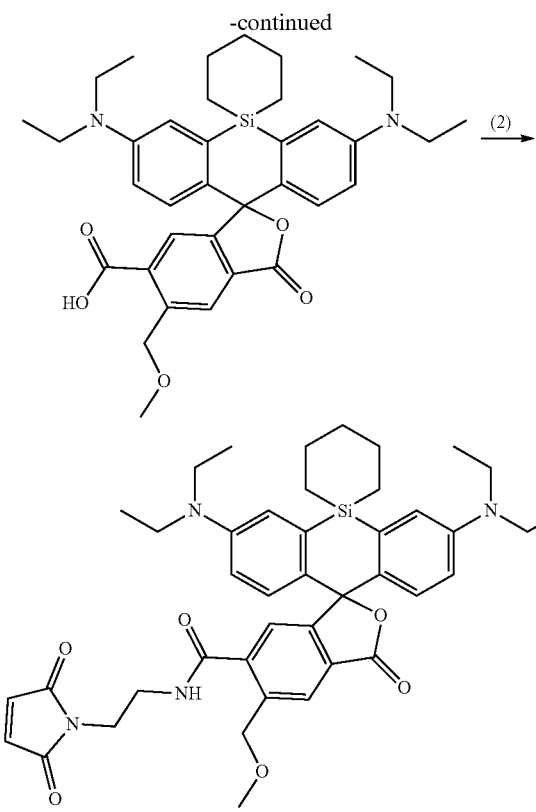

(1) Synthesis of 3',7'-bis(diethylamino)-5-(methoxymethyl)-3-oxo-3H-dispiro[isobenzofuran-1,10'-dibenzo[b,e]siline-5',1''-silinane]-6-carboxylic acid The title compound (7.00 mg, 11.0 μmol) was produced in the same manner as in Example 27-(1) from 3,3'-(silinane-1,1-diyl)bis(N,N-diethylaniline) (14.6 mg, 37.0 μmol) produced in Production Example 12 and 3-hydroxy-6-(methoxymethyl)-1-oxo-1,3-dihydroisobenzofuran-5-carboxylic acid (17.6 mg, 74.0 μmol) produced in Production Example 21-(5).

$^1$H-NMR (400 MHZ, CDCl$_3$) δ (ppm): 1.16 (t, J=7.03 Hz, 12H), 1.20-1.29 (m, 4H), 1.72 (br.s., 2H), 2.00 (br.s., 2H), 2.14 (br.s., 2H), 3.37 (q, J=7.03 Hz, 8H), 3.54 (s, 3H), 4.89 (s, 2H), 6.50 (dd, J=8.98, 2.73 Hz, 2H), 6.75 (d, J=8.98 Hz, 2H), 7.11 (d, J=2.73 Hz, 2H), 8.00 (s, 1H), 8.20 (s, 1H).

ESI-MS m/z 613 [M+H]$^+$

(2) Synthesis of 3',7'-bis(diethylamino)-N-(2-(2,5-dioxo-2,5-dihydro-1H-pyrrol-1-yl)ethyl)-5-(methoxymethyl)-3-oxo-3H-dispiro[isobenzofuran-1,10'-dibenzo[b,e]siline-5',1''-silinane]-6-carboxamide The title compound (1.00 mg, 1.36 μmol) was produced in the same manner as in Example 28-(2) from the compound produced in Example 29-(1) (6.13 mg, 10.0 μmol).

$^1$H-NMR (400 MHZ, CDCl$_3$) δ (ppm): 1.18 (t, J=7.03 Hz, 12H), 1.21-1.26 (m, 4H), 1.74 (br.s., 2H), 2.02 (br.s., 2H), 2.15 (br.s., 2H), 3.38 (q, J=7.03 Hz, 8H), 3.48 (s, 3H), 3.60-3.71 (m, 2H), 3.73-3.84 (m, 2H), 4.64 (s, 2H), 6.50 (dd, J=8.98, 3.12 Hz, 2H), 6.68 (s, 2H), 6.75 (d, J=8.98 Hz, 2H), 7.10 (d, J=2.34 Hz, 2H), 7.38-7.43 (m, 1H), 7.60 (s, 1H), 7.97 (s, 1H).

ESI-MS m/z 735 [M+H]$^+$

Example 30

Synthesis of 3',7'-bis(diethylamino)-N-(2-(2,5-dioxo-2,5-dihydro-1H-pyrrol-1-yl)ethyl)-3-oxo-5-(trifluoromethyl)-3H-dispiro[isobenzofuran-1,10'-dibenzo[b,e]siline-5',1''-silinane]-6-carboxamide

[Formula 84]

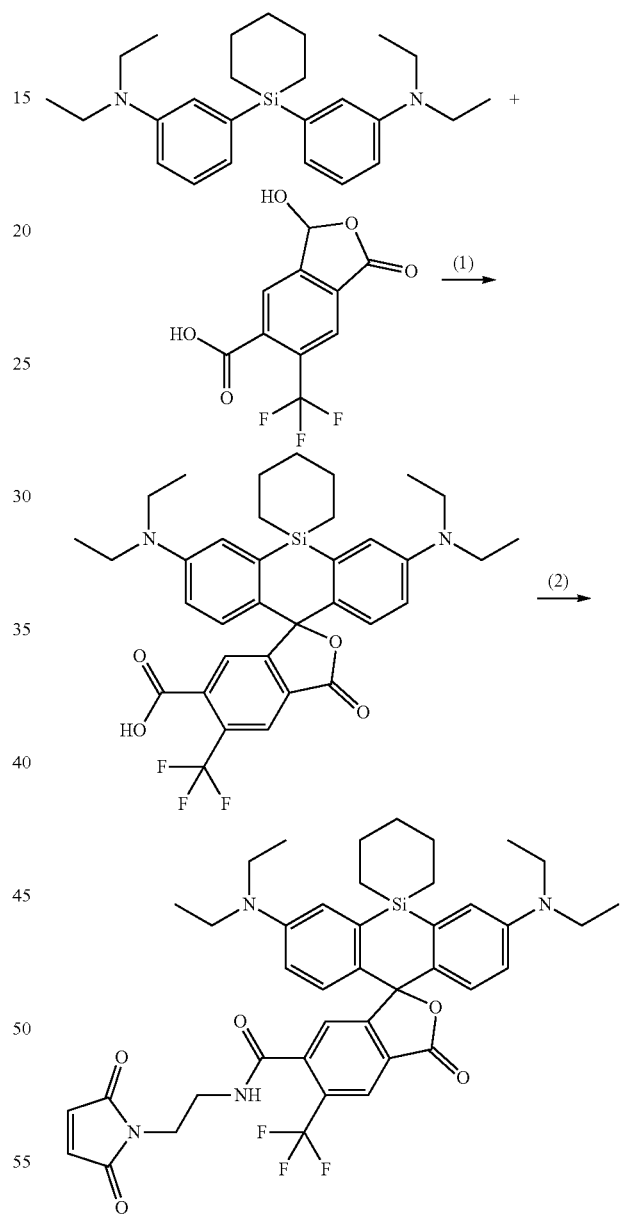

(1) Synthesis of 3',7'-bis(diethylamino)-3-oxo-5-(trifluoromethyl)-3H-dispiro[isobenzofuran-1,10'-dibenzo[b,e]siline-5',1''-silinane]-6-carboxylic acid A crude product (61.0 mg) of the title compound was produced in the same manner as in Example 25-(1) from 3,3'-(silinane-1,1-diyl)bis(N,N-diethylaniline) (50.0 mg, 127 µmol) produced in Production Example 12 and 3-hydroxy-1-oxo-6-(trifluoromethyl)-1,3-dihydroisobenzofuran-5-carboxylic acid (100 mg, 380 µmol) produced in Production Example 22-(3).

ESI-MS m/z 637 [M+H]$^+$ (2) Synthesis of 3',7'-bis(diethylamino)-N-(2-(2,5-dioxo-2,5-dihydro-1H-pyrrol-1-yl)ethyl)-3-oxo-5-(trifluoromethyl)-3H-dispiro[isobenzofuran-1,10'-dibenzo[b,e]siline-5',1''-silinane]-6-carboxamide To a solution of the compound produced in Example 30-(1) (61.0 mg) in DMF (3.00 mL) were added TEA (40.0 µL, 287 µmol), N-(2-aminoethyl) maleimide TFA salt (29.2 mg, 115 µmol) and PyBOP (74.8 mg, 144 µmol). The reaction mixture was stirred at room temperature overnight, and then the mixture was purified directly by reverse-phase chromatography (water/acetonitrile, 0.1% formic acid). The resultant crude product was purified by silica gel column chromatography (n-heptane/ethyl acetate) to yield the title compound (15.0 mg, 20.0 µmol).

$^1$H-NMR (400 MHZ, CDCl$_3$) δ (ppm): 1.18 (t, J=7.03 Hz, 12H), 1.21 (br.s., 2H), 1.26 (br.s., 2H), 1.73 (br.s., 2H), 2.01 (br.s., 2H), 2.09-2.19 (m, 2H), 3.38 (q, J=7.03 Hz, 8H), 3.61-3.69 (m, 2H), 3.73-3.80 (m, 2H), 6.18-6.24 (m, 1H), 6.53 (dd, J=8.98, 3.12 Hz, 2H), 6.65 (s, 2H), 6.69 (d, J=8.98 Hz, 2H), 7.09 (d, J=3.12 Hz, 2H), 7.40 (s, 1H), 8.27 (s, 1H).

ESI-MS m/z 759 [M+H]$^+$

Example 31

Synthesis of 3',7'-bis(diethylamino)-N-(2-(2,5-dioxo-2,5-dihydro-1H-pyrrol-1-yl)ethyl)-5-methoxy-3-oxo-3H-dispiro[isobenzofuran-1,10'-dibenzo[b,e]siline-5',1''-silinane]-6-carboxamide

[Formula 85]

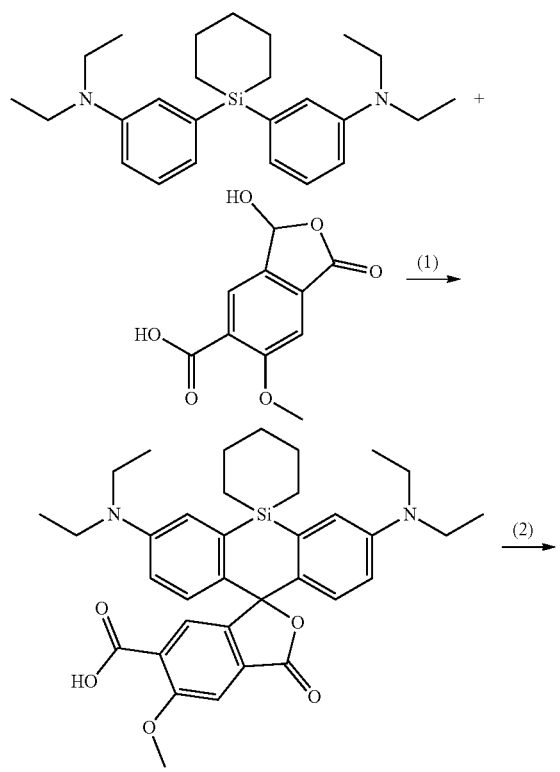

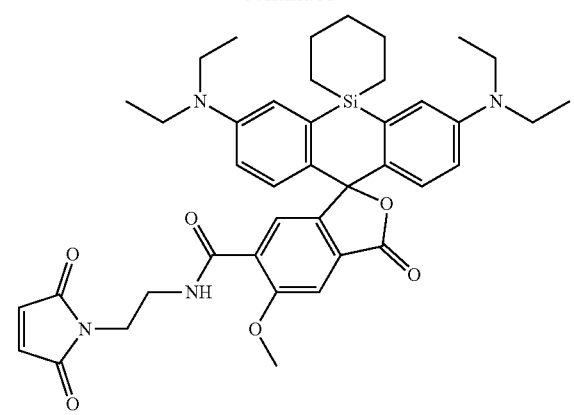

(1) Synthesis of 3',7'-bis(diethylamino)-5-methoxy-3-oxo-3H-dispiro[isobenzofuran-1,10'-dibenzo[b,e]siline-5',1''-silinane]-6-carboxylic acid A mixture of 3,3'-(silinane-1,1-diyl)bis(N,N-diethylaniline) (20.0 mg, 51.0 µmol) produced in Production Example 12, 3-hydroxy-6-methoxy-1-oxo-1,3-dihydroisobenzofuran-5-carboxylic acid (34.1 mg, 152 µmol) produced in Production Example 23-(2), copper (II) bromide (3.40 mg, 15.0 µmol) and acetic acid (2.00 mL) was stirred at 140° C. for 20 hours. The solvent was distilled away under a reduced pressure, and the residue was neutralized with a saturated aqueous sodium bicarbonate solution. The aqueous layer was extracted with ethyl acetate, and then the organic layer was washed with water. The residue was purified by silica gel column chromatography (n-heptane/ethyl acetate (→ethyl acetate/methanol)) to yield a mixture (13.0 mg) containing the title compound.

ESI-MS m/z 599 [M+H]$^+$ (2) Synthesis of 3',7'-bis(diethylamino)-N-(2-(2,5-dioxo-2,5-dihydro-1H-pyrrol-1-yl)ethyl)-5-methoxy-3-oxo-3H-dispiro[isobenzofuran-1,10'-dibenzo[b,e]siline-5',1''-silinane]-6-carboxamide The title compound (1.93 mg, 2.68 µmol) was produced in the same manner as in Example 9-(2) from the compound produced in Example 31-(1) (13.0 mg).

$^1$H-NMR (400 MHZ, CDCl$_3$) δ (ppm): 1.15 (t, J=7.03 Hz, 12H), 1.26 (br.s., 4H), 1.71 (br.s., 2H), 1.98 (br.s., 2H), 2.15 (br.s., 2H), 3.35 (q, J=6.77 Hz, 8H), 3.65-3.73 (m, 2H), 3.80-3.87 (m, 2H), 4.11 (s, 3H), 6.44 (dd, J=8.98, 2.73 Hz, 2H), 6.72 (s, 2H), 6.75 (d, J=8.59 Hz, 2H), 7.09 (d, J=2.73 Hz, 2H), 7.49 (s, 1H), 8.18 (t, J=5.08 Hz, 1H), 8.22 (s, 1H).

ESI-MS m/z 721 [M+H]$^+$

Example 32

Synthesis of 3',7'-bis(diethylamino)-N-(2-(2,5-dioxo-2,5-dihydro-1H-pyrrol-1-yl)ethyl)-5-(methylthio)-3-oxo-3H-dispiro[isobenzofuran-1,10'-dibenzo[b,e]siline-5',1''-silinane]-6-carboxamide

[Formula 86]

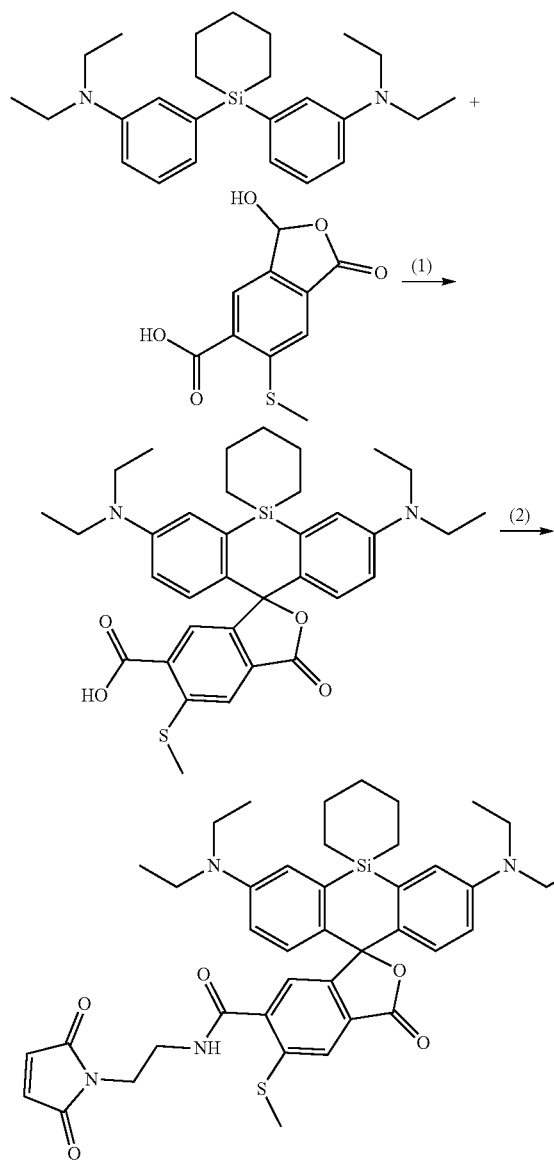

(1) Synthesis of 3',7'-bis(diethylamino)-5-(methylthio)-3-oxo-3H-dispiro[isobenzofuran-1,10'-dibenzo[b,e]siline-5',1''-silinane]-6-carboxylic acid A mixture (38.0 mg) containing the title compound was produced in the same manner as in Example 31-(1) from 3,3'-(silinane-1,1-diyl)bis(N,N-diethylaniline) (70.0 mg, 177 µmol) produced in Production Example 12 and 3-hydroxy-6-(methylthio)-1-oxo-1,3-dihydroisobenzofuran-5-carboxylic acid (128 mg) produced in Production Example 24-(2).

ESI-MS m/z 615 [M+H]$^+$

(2) Synthesis of 3',7'-bis(diethylamino)-N-(2-(2,5-dioxo-2,5-dihydro-1H-pyrrol-1-yl)ethyl)-5-(methylthio)-3-oxo-3H-dispiro[isobenzofuran-1,10'-dibenzo[b,e]siline-5',1''-silinane]-6-carboxamide To a solution of the compound produced in Example 32-(1) (38.0 mg) in DMF (2.00 mL) were added TEA (13.0 µL, 93.0 µmol), N-(2-aminoethyl) maleimide TFA salt (18.9 mg, 74.0 µmol) and PyBOP (38.6 mg, 74.0 µmol). The resultant reaction mixture was stirred at room temperature for 1.5 hours. Ethyl acetate and water were added to the reaction mixture to terminate the reaction. The aqueous layer was extracted with ethyl acetate, and the organic layer was washed with water twice. The solvent was distilled away under a reduced pressure, and the residue was purified by silica gel thin-layer chromatography (n-heptane/ethyl acetate) to yield the title compound (21.5 mg, 29.0 µmol).

$^1$H-NMR (400 MHZ, CDCl$_3$) δ (ppm): 1.07 (t, J=7.03 Hz, 12H), 1.09-1.15 (m, 4H), 1.62 (br.s., 2H), 1.87 (br.s., 2H), 2.05 (br.s., 2H), 2.47 (s, 3H), 3.27 (q, J=7.03 Hz, 8H), 3.54-3.61 (m, 2H), 3.65-3.72 (m, 2H), 6.38-6.41 (m, 1H), 6.40 (dd, J=8.98, 2.73 Hz, 2H), 6.56 (s, 2H), 6.65 (d, J=8.98 Hz, 2H), 7.00 (d, J=3.12 Hz, 2H), 7.31 (s, 1H), 7.68 (s, 1H).

ESI-MS m/z 737 [M+H]$^+$

Example 33

Synthesis of N-(2-(2,5-dioxo-2,5-dihydro-1H-pyrrol-1-yl)ethyl)-3-oxo-3',7'-di(pyrrolidine-1-yl)-3H-dispiro[isobenzofuran-1,10'-dibenzo[b,e]siline-5',1''-silinane]-6-carboxamide

[Formula 87]

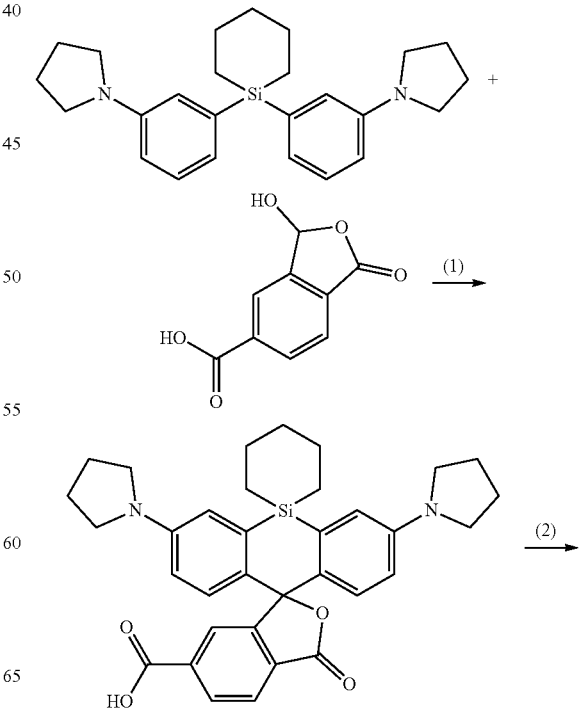

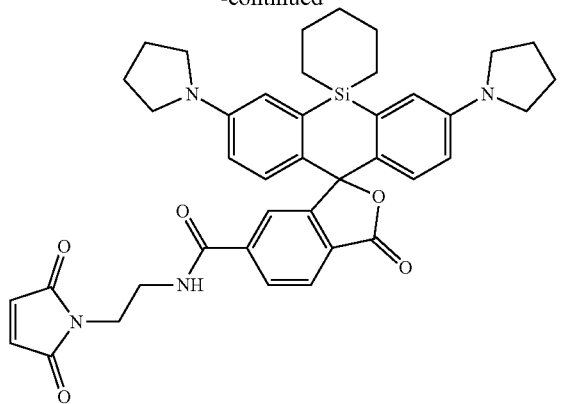

(1) Synthesis of 3-oxo-3',7'-di(pyrrolidine-1-yl)-3H-dispiro[isobenzofuran-1,10'-dibenzo[b,e]siline-5',1''-silinane]-6-carboxylic acid The title compound (28.0 mg, 50.0 μmol) was produced in the same manner as in Example 23-(1) from 1,1'-(silinane-1,1-diylbis(3,1-phenylene))dipyrrolidine (98.0 mg, 250 μmol) produced in Production Example 13 and 3-hydroxy-1-oxo-1,3-dihydroisobenzofuran-5-carboxylic acid (146 mg, 750 μmol) produced in Production Example 15-(2).
$^1$H-NMR (400 MHZ, CDCl$_3$) δ (ppm): 1.15-1.31 (m, 4H), 1.74 (br.s., 4H), 1.93-2.06 (m, 8H), 2.14 (d, J=17.18 Hz, 2H), 3.22-3.36 (m, 8H), 6.41 (dd, J=8.98, 2.73 Hz, 2H), 6.79 (d, J=8.98 Hz, 2H), 6.99 (d, J=2.73 Hz, 2H), 7.97-8.06 (m, 2H), 8.17-8.25 (m, 1H).
ESI-MS m/z 565 [M+H]$^+$ (2) Synthesis of N-(2-(2,5-dioxo-2,5-dihydro-1H-pyrrol-1-yl)ethyl)-3-oxo-3',7'-di(pyrrolidine-1-yl)-3H-dispiro[isobenzofuran-1,10'-dibenzo[b,e]siline-5',1''-silinane]-6-carboxamide The title compound (4.00 mg, 5.82 μmol) was produced in the same manner as in Example 23-(2) from the compound produced in Example 33-(1) (9.60 mg, 17.0 μmol).
$^1$H-NMR (400 MHZ, CDCl$_3$) δ (ppm): 1.16-1.35 (m, 4H), 1.73 (br.s., 2H), 1.89-2.07 (m, 10H), 2.09-2.23 (m, 2H), 3.19-3.38 (m, 8H), 3.57-3.70 (m, 2H), 3.74-3.85 (m, 2H), 6.38 (dd, J=8.59, 2.73 Hz, 2H), 6.66-6.82 (m, 3H), 6.71 (s, 2H), 6.97 (d, J=2.73 Hz, 2H), 7.70 (s, 1H), 7.83 (dd, J=8.01, 1.37 Hz, 1H), 7.99 (d, J=7.81 Hz, 1H).
ESI-MS m/z 687 [M+H]$^+$

Example 34

Synthesis of N-(2-(2,5-dioxo-2,5-dihydro-1H-pyrrol-1-yl)ethyl)-3-oxo-1',2',3',4',8',9',10',11'-octahydro-3H-dispiro[isobenzofuran-1,6'-silino[3,2-g:5,6-g']diquinoline-13',1''-silinane]-6-carboxamide

[Formula 88]

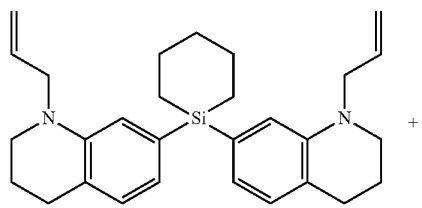

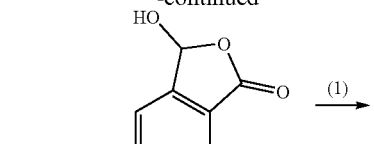

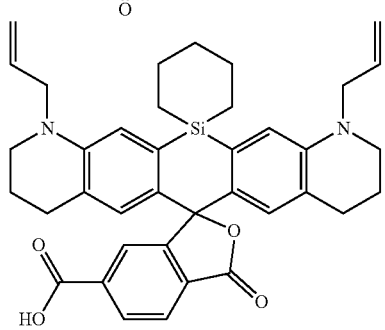

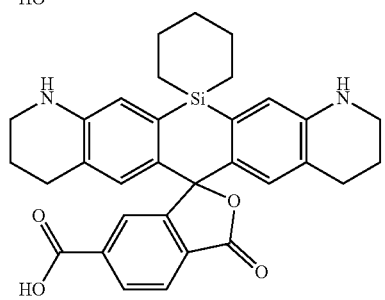

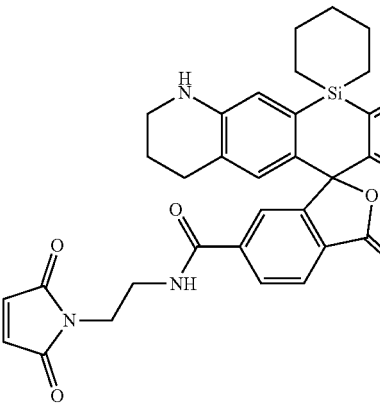

(1) Synthesis of 1',11'-diallyl-3-oxo-1',2',3',4',8',9',10',11'-octahydro-3H-dispiro[isobenzofuran-1,6'-silino[3,2-g:5,6-g']diquinoline-13',1''-silinane]-6-carboxylic acid A crude product was produced in the same manner as in Example 23-(1) from 7,7'-(silinane-1,1-diyl)bis(1-allyl-1,2,3,4-tetrahydroquinoline) (885 mg, 2.00 mmol) produced in Production Example 14-(2) and 3-hydroxy-1-oxo-1,3-dihydroisobenzofuran-5-carboxylic acid (1.17 g, 6.00 mmol) produced in Production Example 15-(2). The crude product was further purified by silica gel column chromatography (n-heptane/ethyl acetate) to yield the title compound (98.0 mg, 159 μmol).
$^1$H-NMR (400 MHZ, CDCl$_3$) δ (ppm): 1.04-1.21 (m, 4H), 1.69 (br.s., 2H), 1.80-1.93 (m, 4H), 1.93-2.13 (m, 4H), 2.43-2.66 (m, 4H), 3.18-3.34 (m, 4H), 3.85-4.02 (m, 4H), 5.14-5.28 (m, 4H), 5.81-5.96 (m, 2H), 6.50 (s, 2H), 6.93 (s, 2H), 7.90 (d, J=0.78 Hz, 1H), 8.00 (dd, J=7.81, 0.78 Hz, 1H), 8.18 (dd, J=8.01, 1.37 Hz, 1H).
ESI-MS m/z 617 [M+H]$^+$ (2) Synthesis of 3-oxo-1',2',3',4',8',9',10',11'-octahydro-3H-dispiro[isobenzofuran-1,6'-silino[3,2-g:5,6-g']diquinoline-13',1''-silinane]-6-carboxylic acid A mixture of the compound produced in Example 34-(1) (30.8 mg, 50.0 μmol), tetrakis(triphenylphosphine)palladium (0) (11.6 mg, 10.0 μmol), 1,3-dimethylbarbituric acid (46.8 mg, 300 μmol) and DCM (5.00 mL) was stirred at room temperature for 10 hours. The reaction mixture was purified directly by reverse-phase chromatography (water/acetonitrile, 0.1% formic acid) to yield the title compound (15.0 mg, 28.0 μmol).
$^1$H-NMR (400 MHZ, MeOH-d$_4$) δ (ppm): 1.03-1.10 (m, 2H), 1.10-1.17 (m, 2H), 1.67 (br.s., 2H), 1.75-1.87 (m, 4H), 1.92-2.01 (m, 2H), 2.07 (br.s., 2H), 2.50 (t, J=6.05 Hz, 4H), 3.22-3.30 (m, 4H), 6.47 (s, 2H), 6.97 (s, 2H), 7.88 (s, 1H), 8.00 (d, J=8.20 Hz, 1H), 8.18 (d, J=8.20 Hz, 1H).
ESI-MS m/z 537 [M+H]$^+$ (3) Synthesis of N-(2-(2,5-dioxo-2,5-dihydro-1H-pyrrol-1-yl)ethyl)-3-oxo-1',2',3',4',8',9',10',11'-octahydro-3H-dispiro[isobenzofuran-1,6'-silino[3,2-g:5,6-g']diquinoline-13',1''-silinane]-6-carboxamide The title compound (2.60 mg, 3.95 μmol) was produced in the same manner as in Example 28-(2) from the compound produced in Example 34-(2) (13.4 mg, 25.0 μmol).
$^1$H-NMR (400 MHZ, MeOH-d$_4$) δ (ppm): 1.11 (dt, J=18.35, 6.83 Hz, 4H), 1.73 (br.s., 2H), 1.79-1.91 (m, 4H), 1.95-2.08 (m, 2H), 2.13 (br.s., 2H), 2.52 (t, J=6.25 Hz, 4H), 3.31-3.37 (m, 4H), 3.51-3.59 (m, 2H), 3.73 (dd, J=6.25, 4.69 Hz, 2H), 6.51 (s, 2H), 6.75 (s, 2H), 7.06 (s, 2H), 7.56 (d, J=1.17 Hz, 1H), 7.93 (dd, J=7.81, 1.56 Hz, 1H), 8.04 (d, J=7.81 Hz, 1H), 8.28 (br.s., 1H).
ESI-MS m/z 659 [M+H]$^+$ Example 35

Synthesis of N-(2-(2,5-dioxo-2,5-dihydro-1H-pyrrol-1-yl)ethyl)-3-oxo-1',2',3',4',8',9',10',11'-octahydro-3H-dispiro[isobenzofuran-1,6'-silino[3,2-g:5,6-g']diquinoline-13',1''-silinane]-5-carboxamide

[Formula 89]

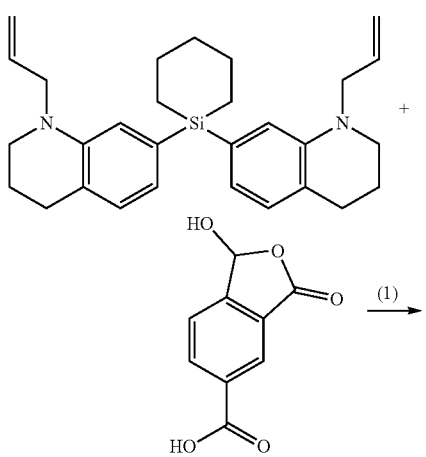

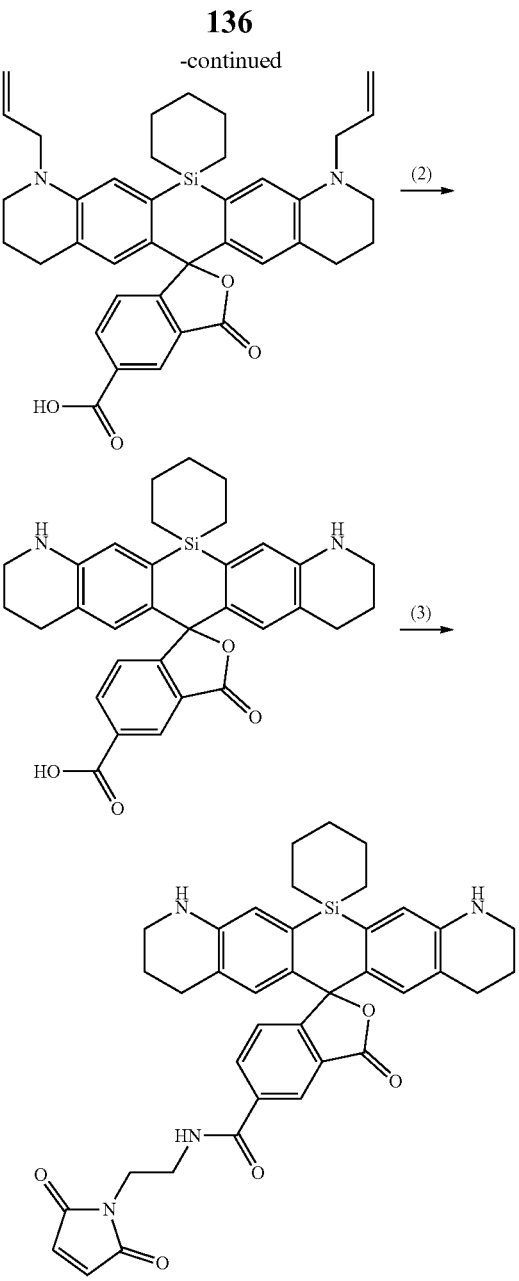

(1) Synthesis of 1',11'-diallyl-3-oxo-1',2',3',4',8',9',10',11'-octahydro-3H-dispiro[isobenzofuran-1,6'-silino[3,2-g:5,6-g']diquinoline-13',1''-silinane]-5-carboxylic acid The title compound (42.0 mg, 68.0 μmol) was produced in the same manner as in Example 27-(1) from 7,7'-(silinane-1,1-diyl)bis(1-allyl-1,2,3,4-tetrahydroquinoline) (102 mg, 230 μmol) produced in Production Example 14-(2) and 1-hydroxy-3-oxo-1,3-dihydroisobenzofuran-5-carboxylic acid (134 mg, 690 μmol) produced in Production Example 16-(2).
$^1$H-NMR (400 MHZ, CDCl$_3$) δ (ppm): 1.05-1.17 (m, 4H), 1.69 (br.s., 2H), 1.79-1.93 (m, 4H), 1.94-2.12 (m, 4H), 2.45-2.67 (m, 4H), 3.18-3.34 (m, 4H), 3.88-3.98 (m, 4H), 5.14-5.30 (m, 4H), 5.88 (ddt, J=16.99, 10.35, 4.88 Hz, 2H), 6.48 (s, 2H), 6.94 (s, 2H), 7.30 (d, J=7.81 Hz, 1H), 8.28 (dd, J=8.01, 1.37 Hz, 1H), 8.68 (d, J=0.78 Hz, 1H).
ESI-MS m/z 617 [M+H]$^+$

(2) Synthesis of 3-oxo-1'2',3',4',8',9',10',11'-octahydro-3H-dispiro[isobenzofuran-1,6'-silino[3,2-g:5,6-g']diquinoline-13',1"-silinane]-5-carboxylic acid The title compound (21.0 mg, 39.0 μmol) was produced in the same manner as in Example 34-(2) from the compound produced in Example 35-(1) (40.1 mg, 65.0 μmol).

$^1$H-NMR (400 MHZ, MeOH-$d_4$) δ (ppm): 1.00-1.15 (m, 4H), 1.66 (br.s., 2H), 1.81 (quin, J=5.86 Hz, 4H), 1.95 (br.s., 2H), 2.07 (br.s., 2H), 2.49 (t, J=6.05 Hz, 4H), 3.22-3.30 (m, 4H), 6.43 (s, 2H), 6.96 (s, 2H), 7.33 (d, J=7.81 Hz, 1H), 8.30 (d, J=7.81 Hz, 1H), 8.62 (s, 1H).

ESI-MS m/z 537 [M+H]$^+$

(3) Synthesis of N-(2-(2,5-dioxo-2,5-dihydro-1H-pyrrol-1-yl)ethyl)-3-oxo-1',2',3',4',8',9',10',11'-octahydro-3H-dispiro[isobenzofuran-1,6'-silino[3,2-g:5,6-g']diquinoline-13',1"-silinane]-5-carboxamide A crude product was produced in the same manner as in Example 28-(2) from the compound produced in Example 35-(2) (19.0 mg, 35.0 μmol). The crude product was further purified by reverse-phase silica gel column chromatography (water/acetonitrile, 0.1% formic acid) to yield the title compound (2.60 mg, 3.95 μmol).

$^1$H-NMR (400 MHZ, CDCl$_3$) δ (ppm): 1.06-1.20 (m, 4H), 1.67 (br.s., 2H), 1.78-1.89 (m, 4H), 1.95 (br.s., 2H), 2.09 (br.s., 2H), 2.48-2.63 (m, 4H), 3.21-3.34 (m, 4H), 3.64-3.76 (m, 2H), 3.81-3.89 (m, 2H), 6.48 (s, 2H), 6.76 (s, 2H), 6.87 (s, 2H), 7.32-7.36 (m, 1H), 8.02 (br.s., 1H), 8.07 (dd, J=8.20, 1.56 Hz, 1H), 8.26 (d, J=1.17 Hz, 1H).

ESI-MS m/z 659 [M+H]$^+$

Example 36

Synthesis of N-(2-(2,5-dioxo-2,5-dihydro-1H-pyrrol-1-yl)ethyl)-3',7'-dihydroxy-3-oxo-3H-dispiro[isobenzofuran-1,10'-dibenzo[b,e]siline-5',1"-silinane]-6-carboxamide

[Formula 90]

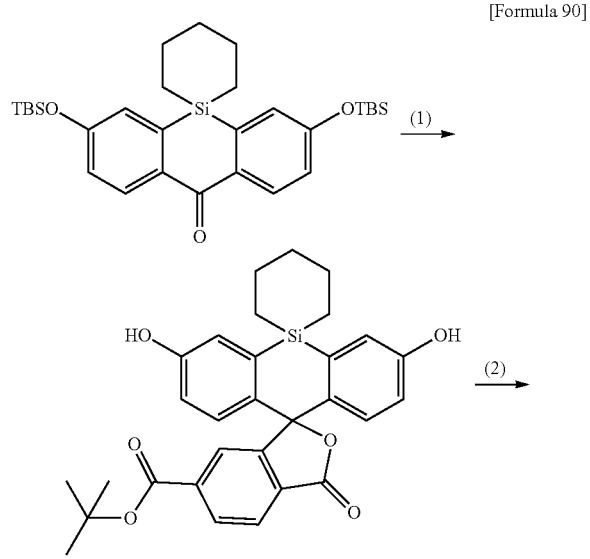

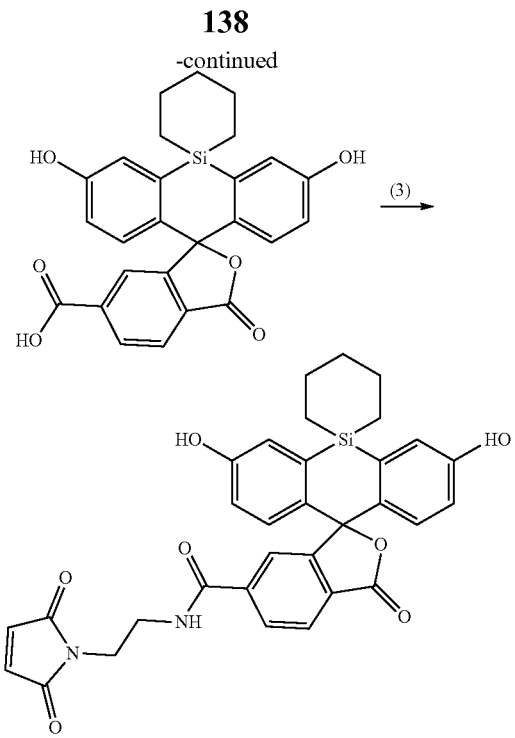

(1) Synthesis of tert-butyl 3',7'-dihydroxy-3-oxo-3H-dispiro[isobenzofuran-1,10'-dibenzo[b,e]siline-5',1"-silinane]-6-carboxylate To a mixed solution of di-tert-butyl 2-bromoterephthalate (1.00 g, 2.80 mmol) in THF (14.0 mL)/n-hexane (7 mL) was added dropwise n-butyllithium (a 2.76-M hexane solution, 1.014 mL, 2.80 mmol) at an inside temperature of −95° C. or lower under a nitrogen atmosphere. The solution was stirred at the same temperature for 10 minutes, and then a solution of 3,7-bis((tert-butyldimethylsily)oxy)-10H-spiro[dibenzo[b,e]siline-5,1'-silinan]-10-one (377 mg, 0.70 mmol) produced in Production Example 4-(3) in THF (7 mL) was added dropwise to the solution at an inside temperature of −95° C. or lower. The solution was stirred at the same temperature for 5 minutes, and then a boron trifluoride diethyl ether complex (178 μL, 1.40 mmol) was added dropwise to the solution. The reaction mixture was heated to room temperature slowly, and was then stirred at room temperature for 12 hours. A saturated aqueous ammonium chloride solution was added to the solution under an ice bath to terminate the reaction. The aqueous layer was extracted with ethyl acetate, and then the organic layer was washed with water and saturated saline. The mixture was dried over anhydrous magnesium sulfate, and the solvent was distilled away to yield a mixture containing an adduct. THF (7.0 mL) and tetrabutylammonium fluoride (a 1.00-M THF solution, 3.5 mL, 3.5 mmol) were added to the mixture, and the resultant solution was stirred at room temperature for 7 hours. A saturated aqueous ammonium chloride solution was added to the solution under an ice bath to terminate the reaction. The aqueous layer was extracted with ethyl acetate, and the organic layer was concentrated under a reduced pressure. The aqueous layer was extracted with ethyl acetate, then the organic layer was concentrated under a reduced pressure, and the resultant residue was purified by silica gel column chromatography (n-heptane/ethyl acetate)

to yield the title compound as a mixture (300 mg) with 3,7-dihydroxy-10H-spiro[dibenzo[b,e]siline-5,1'-silinan]-10-one.

(2) Synthesis of 3',7'-dihydroxy-3-oxo-3H-dispiro [isobenzofuran-1,10'-dibenzo[b,e]siline-5',1''-silinane]-6-carboxylic acid TFA (400 µL) was added to a solution of the compound produced in Example 36-(1) (104.9 mg, 0.20 mmol) in DCM (4.00 mL), and the resultant solution was stirred at room temperature overnight. The solvent was distilled away under a reduced pressure, and remaining TFA was azeotropically removed with methanol to yield a crude product of the title compound.

(3) Synthesis of N-(2-(2,5-dioxo-2,5-dihydro-1H-pyrrol-1-yl)ethyl)-3',7'-dihydroxy-3-oxo-3H-dispiro [isobenzofuran-1,10)'-dibenzo[b,e]siline-5',1''-silinane]-6-carboxamide To a solution of the compound produced by the method of Example 36-(2) in DMF (10.0 mL) were added TEA (170 µL, 1.22 mmol), N-(2-aminoethyl) maleimide TFA salt (118.7 mg, 0.47 mmol) and PyBOP (158.7 mg, 0.30 mmol). The reaction mixture was stirred at room temperature for 2 hours, and the mixture was purified by silica gel column chromatography (hexane/ethyl acetate) to yield the title compound (15.7 mg, 27.0 µmol).

$^1$H-NMR (500 MHZ, MeOH-d$_4$) δ (ppm): 1.16-1.19 (m, 2H), 1.25-1.28 (m, 2H), 1.73-1.78 (m, 2H), 2.00-2.08 (m, 2H), 2.13-2.23 (m, 2H), 3.50-3.58 (m, 2H), 3.68-3.73 (m, 2H), 6.68 (dd, J=8.80, 2.75 Hz, 2H), 6.72 (s, 2H), 6.76-6.79 (m, 2H), 7.32 (d, J=2.70 Hz, 2H), 7.65 (br.s., 1H), 7.93 (dd, J=8.05, 1.35 Hz, 1H), 7.98-8.01 (m, 1H).

ESI-MS m/z 581 [M+H]$^+$

Experiment Example 1

The optimization of the structure of the ring-opened form of each of the compounds produced in Examples was carried out using a quantum chemical calculation software "Gaussian09" (Gaussian), and the atomic charge of a carbon atom located at position-9 (see FIG. 1; in which Example 19 is shown as an example) was calculated by a Mulliken charge method (Calculation conditions: APFD/6-311G+(2d, p), IEFPCM/ethanol).

Comparative Experiment Example 1

As Comparative Examples corresponding to each of the compounds of Examples, the Mulliken charge of a carbon atom located at position-9 was calculated in the same manner as in Experiment Example 1. The calculation was carried out with respect to each of compounds respectively having the same structures as those of the compounds of Examples except that the spiro ring structure had an Si atom having, as substituents, two methyl groups in place of a spiro-ring structure containing an Si atom (wherein the structure is referred to as a "Si spiro-ring moiety", hereinafter) in each of the compounds.

Results of Experiment Example 1 and Comparative Experiment Example 1

Figure 2:
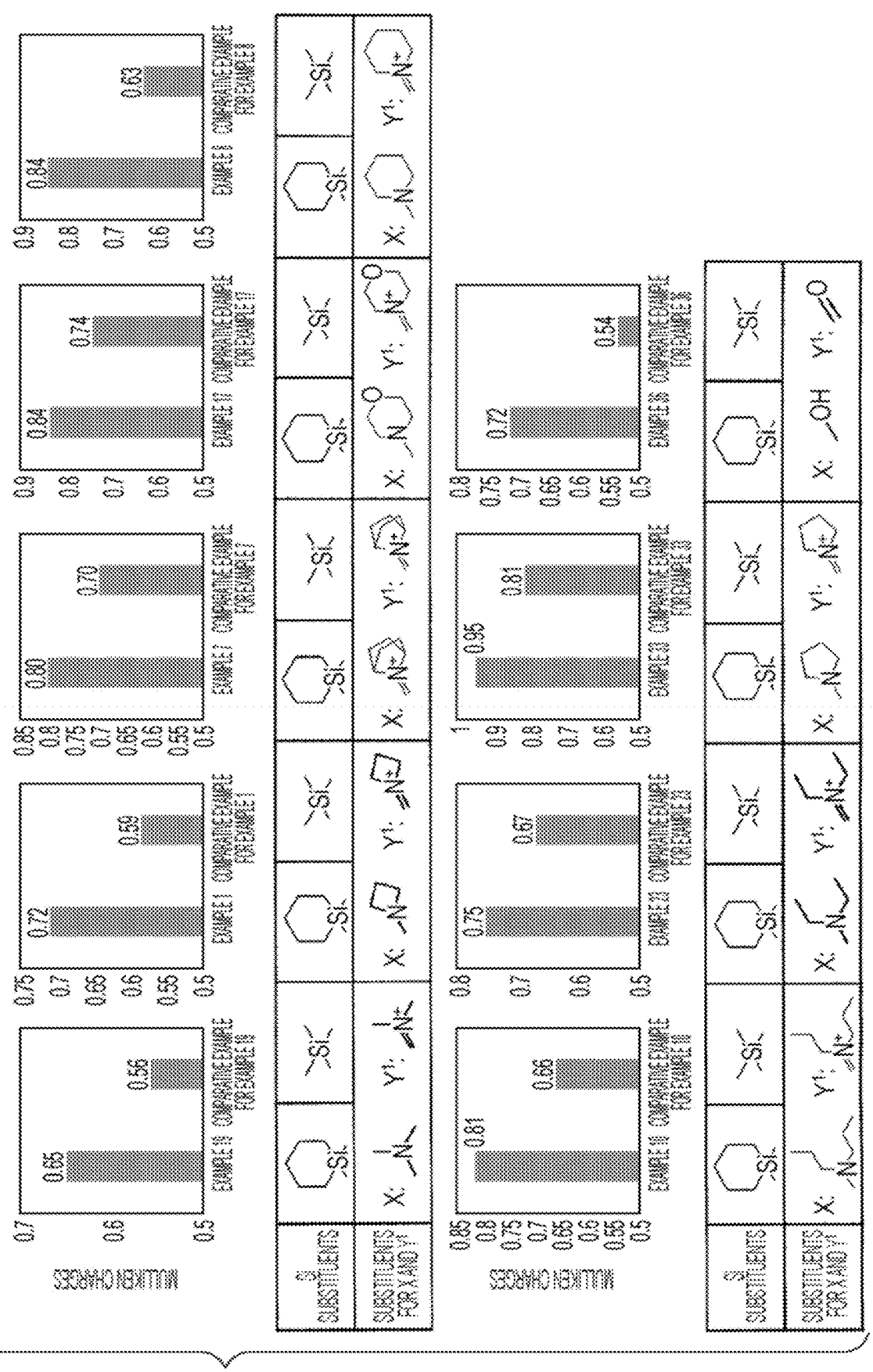
FIG. 2 illustrates graphs showing Mulliken charges of carbon atom located at position-9 in the fluorescent dyes of Examples 1, 7, 8, 10, 17, 19, 23, 33 and 36 and the fluorescent dyes of Comparative Examples for the Examples.

As shown in FIG. 2, the Mulliken charge was increased in each of compounds having the Si spiro-ring moiety. It is considered that the equilibrium can be shifted more easily from a ring-opened form to a ring-closed form and the duty cycle decreases with the increase in the Mulliken charge.

Experiment Example 2

<Labeling of Antibody with Compound>
[Reduction of Antibody with 2-Mercaptoethylamine (MEA)]

First, ethylenediaminetetraacetic acid disodium salt (EDTA·2Na) was mixed with ultrapure water to prepare an ethylenediaminetetraacetic acid (EDTA) solution (0.10 M, pH 6.0) (also referred to as "EDTA solution", hereinafter). Subsequently, NaH$_2$PO$_4$·2H$_2$O and EDTA·2Na were mixed with ultrapure water to prepare a solution of (0.10 M NaH$_2$PO$_4$)/(1.0 mM EDTA) (pH 6.0) (also referred to as a "reaction solution", hereinafter). Subsequently, the reaction solution was mixed with MEA to prepare a 0.35 M MEA solution (also referred to as an "MEA solution", hereinafter). Finally, an anti-amyloid-β antibody 6E10 solution (Biolegend) was mixed with the EDTA solution and the MEA solution in such a manner that the volume ratio of (amyloid-β antibody 6E10 solution):(EDTA solution):(MEA solution) became 100:1:10 by volume, and the resultant solution was warmed to 37° C. for 90 minutes using a heat block (wherein the resultant solution was referred to as an "antibody solution 1", hereinafter).

[Removal of Unreacted MEA]

The resultant solution was centrifuged using Amicon Filters 10 kDa (Merck Millipore) at 14 k×g to produce a solution from which unreacted MEA had been removed (wherein the resultant solution was referred to as an "antibody solution 2", hereinafter).

[Reaction for Labeling of Antibody with Compound]

The antibody concentration in the antibody solution 2 was quantified on the basis of an absorbance of the antibody solution 2. Subsequently, the antibody solution 2 was mixed with each of the compound synthesized in Example 1 and the compound synthesized in Example 19 at an (antibody): (compound) molar ratio of 1:50, and the resultant solution was warmed to 37° C. for 1 hour using a heat block.

[Removal of Unreacted Compound]

The antibody solution after the labeling reaction was added using Amicon Filters 10 kDa (Merck Millipore), phosphate buffered saline (Sigma) (also referred to as "PBS", hereinafter) was added to the antibody solution in such a manner that the total volume became 0.50 mL, and then the resultant solution was centrifuged at 14 k x g to remove the unreacted compound, thereby preparing a solution of the antibody labeled with the compound (also referred to as an "antibody solution 3", hereinafter). Hereinbelow, the antibody labeled with each of the compounds was referred to as a "labeled antibody", hereinafter).

[Evaluation of Number of Labels by MALDI-TOF MS]

First, acetonitrile and trifluoroacetic acid were mixed with ultrapure water to prepare a solution containing 30% of acetonitrile and 0.10% of trifluoroacetic acid (wherein the solution was referred to as a "TA30 solution", hereinafter). 0.10 mL of the TA30 solution was added to 1.0 mg of sinapinic acid, and ultrasonic waves were applied to the resultant solution for 10 minutes. Subsequently, the resultant solution was centrifuged, and a supernatant was used as a matrix. An aliquot (10 µL) of the antibody solution 3 was collected, and was then diluted by two holds with a 0.20% aqueous trifluoroacetic acid solution. ZipTip U-C18 (Merck Millipore) was attached to a micropipetter, the resin at the tip of the micropipetter was washed with 10 µL of the TA30 solution, and then the labeled antibody was adsorbed onto the resin. Subsequently, 3.0 µL of the matrix of sinapinic acid was sucked up to elute the labeled antibody onto a MALDI plate (Bruker). After the sample was dried on the plate, the number of labels was measured using Ultraflex MALDI-TOF MS (Bruker). As a result, it was confirmed that the antibody had been labeled with 1 to 3 molecules of each of the compounds.

<Evaluation of Blinking Time of Single Molecule of Compound>

[Preparation of Glass for Use in Single Molecule Measurement]

A cover glass (Matsunami Glass Ind., Ltd.) was washed using an UV ozone cleaner UV-1 (Samco) for 1 minutes (wherein the cover glass thus prepared was referred to as an "UV ozone-washed glass", hereinafter). In the measurement, the glass which underwent the lapse of 12 hours or more after the washing was used.

[Preparation of Labeled-Antibody-Carried Glass Sample]

The antibody solution 3 was diluted with a PBS solution which had been prepared by mixing PBS with ultrapure water and had a pH value of 7.4 to such a concentration that luminous dots of single-molecule luminescence could be detected without being overlapped with each other. 100 µL of the resultant solution was dropped on the UV ozone-washed glass, and then the UV ozone-washed glass was left stand for 10 minutes under a light-blocked environment at room temperature. The diluted antibody solution 3 was washed with 1.0 mL of ultrapure water three times to prepare a glass sample having the labeled antibody carried on the surface thereof (where in the glass sample was referred to as a "labeled-antibody-carried glass sample", hereinafter).

[Preparation of Observation Solution]

Tris(hydroxymethyl)aminomethane and NaCl were mixed with ultrapure water to prepare tris-buffered saline containing 50 mM of tris(hydroxymethyl)aminomethane and 10 mM of NaCl and having a pH value of 7.4 (wherein the solution was referred to as a "TBS solution", hereinafter). An observation solution was prepared using the TBS solution under the conditions shown in Table 1 (wherein the solution was referred to as an "observation solution", hereinafter).

TABLE 1

|  | Glucose | Glucose oxidase | Catalase | MEA |
|---|---|---|---|---|
| Concentration | 10% (w/v) | 0.50 mg/mL | 40 µg/mL | 50 mM |

[Observation of Luminescence of Single Molecule of Compound Using Microscope]

The observation was carried out using a microscope system composed of a fluorescence microscope IX81 (Olympus), a laser oscillator OBIS (Coherent; laser wavelength: 640 nm) and an EMCCD camera iXon (Andor). The labeled-antibody-carried glass sample was mounted on a stage, and then 50 µL of the observation solution was dropped on the glass sample. The observation was carried out under the image capturing conditions shown in Table 2.

TABLE 2

| Compound | Laser output | Exposure time | EM gain | Objective lens |
|---|---|---|---|---|
| Examples 1 to 35 | 0.30 kW/cm$^2$ | 30 msec | 300 | ×100, NA1.4 |
| Example 36 | 0.41 kW/cm$^2$ | 50 msec | — | ×100, NA1.4 |

[Evaluation of Duty Cycle of Single-Molecule Luminescence]

The time course of the luminance of each of the observed luminous dots was analyzed. A single molecule of each of the compounds which were fluorescent dyes showed such a blinking phenomenon that a light-emitting state and a quenched state were repeated alternately. The time period from the time when the irradiation of excitation light was started to the time when the final change from a light-emitting state to a quenched state was observed was defined as a blinking duration time, and the blinking time of a single molecule of each of the compounds was calculated. An integrated value of emission time (i.e., ON time) was calculated, and then the duty cycle was calculated in accordance with the formula: "(ON time)/(blinking duration time)". Subsequently, an average of duty cycles of single molecules of each of the compounds was determined as a duty cycle of each of the compounds (see Tynan C. J. et. al., PLoS one, 2012, Vol. 7, e36265). In general, the single-molecule luminescence of a fluorescent dye can be detected more easily with the decrease in the duty cycle. Therefore, it is considered that a fluorescent dye having a smaller duty cycle is suitable for super-resolution imaging.

Comparative Experiment Example 2

Figure 3:
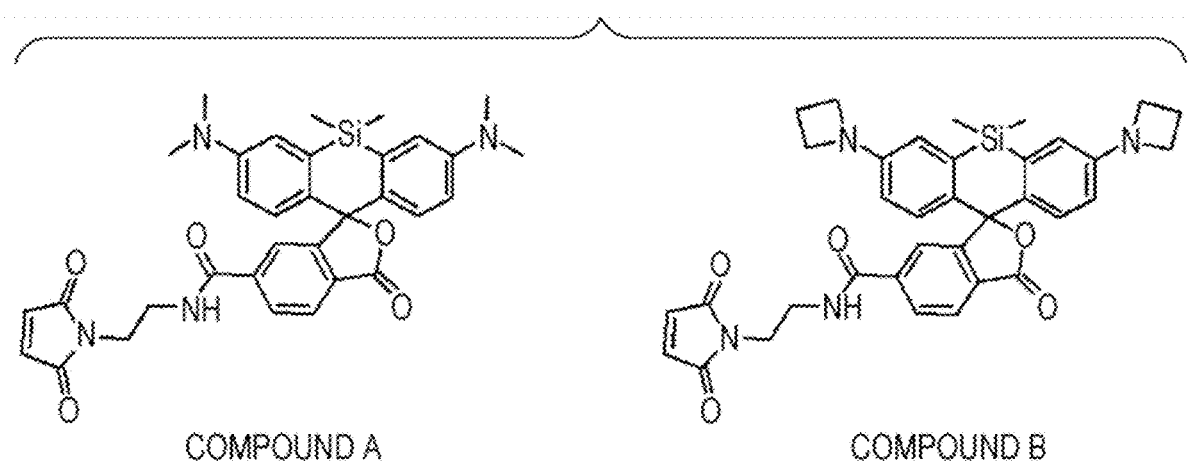
FIG. 3 illustrates the structural formulae of compound A that is Comparative Example of Example 19 and compound B that is Comparative Example for Example 1.
Figure 4:
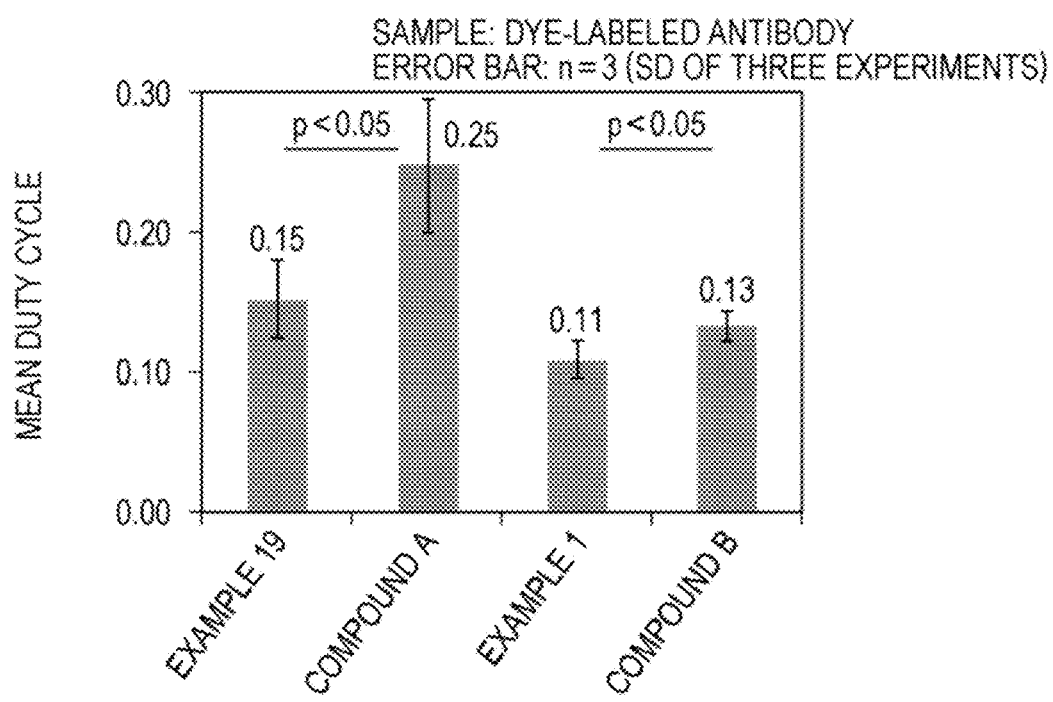
FIG. 4 is a graph showing the duty cycles of the fluorescent dye of Example 19, compound A, the fluorescent dye of Example 1 and compound B.

The duty cycles were measured in the same manner as in Experiment Example 2, except that the compound A (Comparative Example for Example 19) and the compound B (Comparative Example for Example 1) both shown in FIG. 3 were used. As a result, as shown in FIG. 4, it was confirmed that the compounds of Example 19 and Example 1 in each of which an Si spiro-ring moiety had been introduced had smaller duty cycles compared with those of the compound A and the compound B.

Experiment Example 3

The duty cycles of the compounds of Example 1 to Example 36 were measured in the same manner as in Experiment Example 2. The results are shown in FIG. 5. The compound of Example 36 had a hydroxy group or a ketone group at each of position-3 and position-6 in the Si-substituted xanthene backbone, and had a different absorption maximum wavelength from those of the compounds of Example 1 to Example 35. Therefore, the evaluation of the compound of Example 36 was carried out using a research-purpose single-molecule fluorescence microscope HM-1000 (Sysmex Corporation) and also using Prolong (trademark) Live (Thermo Fisher Scientific) as an observation solvent under the conditions shown in Table 2. With respect to the conditions other than the above-mentioned conditions, the duty cycle was measured in the same manner as in Experiment Example 2.

Experiment Example 4

<Super-Resolution Imaging of Microtube in Fixed Cell>

A PBS solution containing 0.5% Triton X-100 was added to Hela cells which had been fixed with a PBS solution containing 4% of paraformaldehyde to perform a permeabilization treatment. Subsequently, a PBS solution containing 3% BSA/0.5% Triton X-100 was added to the solution to block the cells. Two types of cells, i.e., the cells to which an anti-tubulin antibody (T5201, Thermo Fisher Scientific)

(which had been diluted with a PBS solution containing 0.2% BSA/0.1% TritonX-100 to a concentration of 10 μg/mL) was added as a primary antibody and the cells to which the antibody was not added, were prepared. An anti-mouse IgG antibody (ab6708, Abcam), which had been labeled with each of the compound of Example 7 and the compound of Example 36 through a maleimide group, was prepared as a secondary antibody. The antibody was diluted with a PBS solution containing 0.2% BSA/0.1% TritonX-100 to a concentration of 10 μg/mL, and the diluted solution was added. Finally, Prolong (trademark) Live which had been diluted with PBS was added as an observation solvent, and then a light transmission image and a fluorescent image were captured with HM-1000 (Sysmex Corporation). The conditions for the capturing of the fluorescent image are shown in Table 3.

TABLE 3

| Compound | Laser wavelength | Laser output | Exposure time | Number of images picked up | Objective lens |
|---|---|---|---|---|---|
| Example 7 | 637 nm | 1.43 kW/cm² | 30 msec | 50000 | ×100, NA1.4 |
| Example 36 | 561 nm | 0.41 kW/cm² | 50 msec | 20000 | ×100, NA1.4 |

As a result, a microtube structure was not confirmed when a fluorescent image was captured using only the secondary antibody without the addition of the primary antibody, and a fibrous structure characteristic to a microtube was observed visually only when both of the primary antibody and the secondary antibody were added. Consequently, it was confirmed that the antibody staining of a microtube was possible using a secondary antibody labeled with the compound of Example 7 or the compound of Example 36 (see B and C in FIG. 6, and G and H in FIG. 7). Subsequently, the acquired image data were converted to super-resolution images using an image analysis software ImageJ (see Ovesny, M et. al., Bioimage informatics, 2014, 30, 2389-2390) (see D in FIG. 6 and I in FIG. 7). In this experiment, only a single-molecule luminescence was extracted and was used for the conversion to a super-resolution image. With respect to each of the microtube in the image before the conversion to a super-resolution image and the microtube in the converted image, a line profile in the vertical direction and a half width of the line profile were acquired. In the converted image, the half width was smaller than that in the image before the conversion, and the microtube was observed visually with a smaller resolution than the light diffraction limit (about 200 nm). Therefore, it was confirmed that a super-resolution image could be constructed using the compounds of Example 7 and the compound of Example 36 (see E in FIG. 6 and J in FIG. 7).

What is claimed is:

1. A fluorescent dye consisting of a compound represented by formula (I), a tautomer of the compound, or a salt of the compound or the tautomer:

[Formula 1]

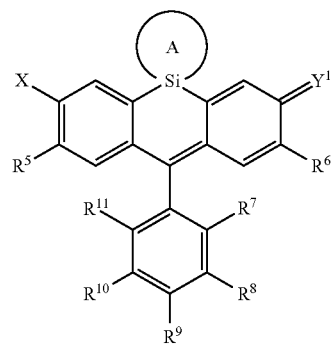

(I)

(wherein:
A represents an optionally substituted C4-C7 heterocyclic ring which contains an Si atom;
X represents —NR$^1$R$^2$;
Y$^1$ represents =N$^+$R$^3$R$^4$;
wherein each of the combination of R$^1$ and R$^2$ and the combination of R$^3$ and R$^4$ together form an optionally substituted N-containing C2-C12 alkyl heterocyclic ring with an N atom to which they bind,
R$^5$ and R$^6$ independently represent an H atom, an optionally substituted C1-C6 alkyl group, or an optionally substituted C1-C6 heteroalkyl group;
R$^7$, R$^8$, R$^9$, R$^{10}$ and R$^{11}$ are independently selected from the group consisting of an H atom, a halogen atom, an optionally substituted C1-C6 alkyl group, an optionally substituted C1-C6 alkoxy group, an optionally substituted C1-C6 alkylthio group, an optionally substituted amino group, an optionally substituted aryl group, an optionally substituted heteroaryl group, —CO$_2$H, —CO$_2$$^-$, —SO$_3$H, —SO$_3$$^-$, and -L-R;
L is 1 to 16 non-hydrogen atoms wherein L optional has a linear structure, a branched structure, and/or a cyclic structure, and wherein, when there are one or more hetero atoms in the non-hydrogen atoms, the hetero atoms are contained as one or more groups independently selected from the group consisting of an ester group, an amine group, an amide group, an ether group, a thioether group and a carbonyl group;
R is selected from a hydroxy group, a carboxyl group, a sulfonate group, an unsaturated imide group, an unsaturated amide group, an unsaturated ester group, an activated carboxylic acid ester group, an amine group, an alcohol group, a nitrile group, a mercaptan group, a boronate group, a phosphoramidite group, a halogenated alkyl group, a halogenated sulfonyl group, an amide or ester group having a halogen atom at alpha-position, an isocyanate group, an isothiocyanate group, an azide group, an aldehyde group, and an acylnitrile group; and
at least one combination of adjacent two substituents among R$^7$, R$^8$, R$^9$, R$^{10}$ and R$^{11}$ may together form a ring.

2. The fluorescent dye according to claim 1, wherein A represents a C4-C7 heterocyclic ring which contains an Si atom and may be substituted by at least one substituent that is independently selected from a halogen atom, a C1-C6 alkyl group, a C1-C6 haloalkyl group, a C1-C6 alkoxy group, a C1-C6 alkylthio group, an amino group, an aryl group, a heteroaryl group, —CO$_2$H and —SO$_3$H.

3. The fluorescent dye according to claim 1, wherein A represents

[Formula 2]

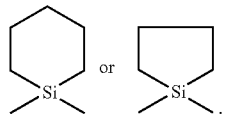

4. The fluorescent dye according to claim 1, wherein, in $R^5$, $R^6$, $R^7$, $R^8$, $R^9$, $R^{10}$ and $R^{11}$,
the substituents in the optionally substituted C1-C6 alkyl group, the optionally substituted C1-C6 heteroalkyl group, the optionally substituted C1-C6 alkoxy group, and the optionally substituted C1-C6 alkylthio group are independently selected from a halogen atom, a C1-C6 alkoxy group, a C1-C6 alkylthio group, an amino group, an aryl group, a heteroaryl group, —$CO_2H$ and —$SO_3H$; and
the substituents in the optionally substituted amino group, the optionally substituted N-containing heterocyclic ring, the optionally substituted aryl group, and the optionally substituted heteroaryl group are independently selected from a halogen atom, a C1-C6 alkyl group, a C1-C6 hydroxyalkyl group, a C1-C6 alkoxy group, a C1-C6 alkylthio group, an amino group, an aryl group, a heteroaryl group, —$CO_2H$ and —$SO_3H$.

5. The fluorescent dye according to claim 1, wherein each of $R^8$ and $R^{11}$ represents an H atom.

6. A fluorescent dye consisting of a compound represented by formula (II), a tautomer of the compound, or a salt of the compound or the tautomer:

[Formula 3]

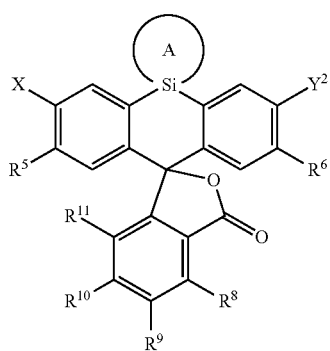

(II)

(wherein:
A represents an optionally substituted C4-C7 heterocyclic ring which contains an Si atom;
X represents a hydroxy group or —$NR^1R^2$;
$Y^2$ represents a hydroxy group or =$N^+R^3R^4$;
$R^1$, $R^2$, $R^3$, $R^4$, $R^5$ and $R^6$ independently represent an H atom, an optionally substituted C1-C6 alkyl group, or an optionally substituted C1-C6 heteroalkyl group;
at least one combination selected from $R^1$ and $R^2$, $R^3$ and $R^4$, $R^1$ and $R^5$, and $R^3$ and $R^6$ may together form an optionally substituted N-containing heterocyclic ring with an N atom to which they bind;
$R^8$, $R^9$, $R^{10}$ and $R^{11}$ are independently selected from the group consisting of an H atom, a halogen atom, an optionally substituted C1-C6 alkyl group, an optionally substituted C1-C6 alkoxy group, an optionally substituted C1-C6 alkylthio group, an optionally substituted amino group, an optionally substituted aryl group, an optionally substituted heteroaryl group, —$CO_2H$, —$CO_2$—$SO_3H$, —$SO_3^-$, and -L-R;

L is 1 to 16 non-hydrogen atoms wherein L optional has a linear structure, a branched structure, and/or a cyclic structure, and wherein, when there are one or more hetero atoms in the non-hydrogen atoms, the hetero atoms are contained as one or more groups independently selected from the group consisting of an ester group, an amine group, an amide group, an ether group, a thioether group and a carbonyl group;

R is selected from a hydroxy group, a carboxyl group, a sulfonate group, an unsaturated imide group, an unsaturated amide group, an unsaturated ester group, an activated carboxylic acid ester group, an amine group, an alcohol group, a nitrile group, a mercaptan group, a boronate group, a phosphoramidite group, a halogenated alkyl group, a halogenated sulfonyl group, an amide or ester group having a halogen atom at alpha-position, an isocyanate group, an isothiocyanate group, an azide group, an aldehyde group, and an acylnitrile group; and at least one combination of adjacent two substituents among $R^8$, $R^9$, $R^{10}$ and $R^{11}$ may together form a ring;

provided that a compound in which at least one of a combination of $R^1$ and $R^5$ and a combination of $R^3$ and $R^6$ together form an optionally substituted N-containing heterocyclic ring with an N atom to which they bind and in which $R^2$ and $R^4$ independently represent an optionally substituted C1-C6 alkyl group, a tautomer of the compound and a salt of the compound or the tautomer are excluded, and provided that the compound represented by formula (III) is not a compound represented by formula (III) wherein A is a C4 heterocyclic ring which contains the Si atom;

X is —$NR^1R^2$;

$Y^2$ is =$N^+R^3R^4$;

$R^1$, $R^2$, $R^3$ and $R^4$ are Me;

$R^5$ and $R^6$ are H;

$R^{11}$ is H;

$R^8$ is either H or $CO_2H$, when $R^8$ is H, $R^{10}$ is $CO_2H$, and when $R^8$ is $CO_2H$, $R^{11}$ is H; and $R^9$ is H.

7. The fluorescent dye according to claim 1, wherein
-L-R represents —CONH-L'-R, L' is 1 to 13 non-hydrogen atoms wherein L' optionally has a linear structure, a branched structure, and/or a cyclic structure, and when there are one or more hetero atoms in the non-hydrogen atoms, the hetero atoms are contained as one or more groups independently selected from the group consisting of an ester group, an amine group, an amide group, an ether group, a thioether group and a carbonyl group.

8. A fluorescent dye consisting of a compound selected from following compounds, a tautomer of the compound, or a salt of the compound or the tautomer:

[Formula 5]
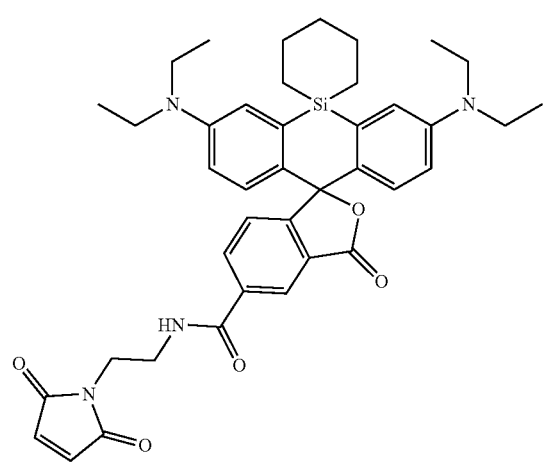
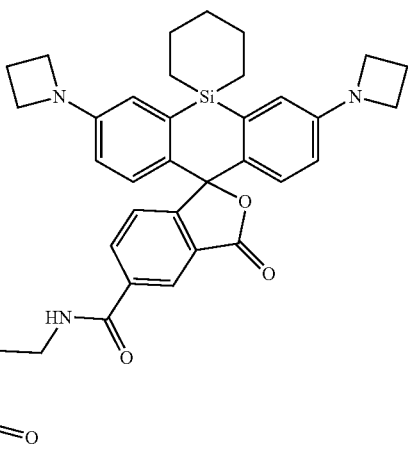
-continued
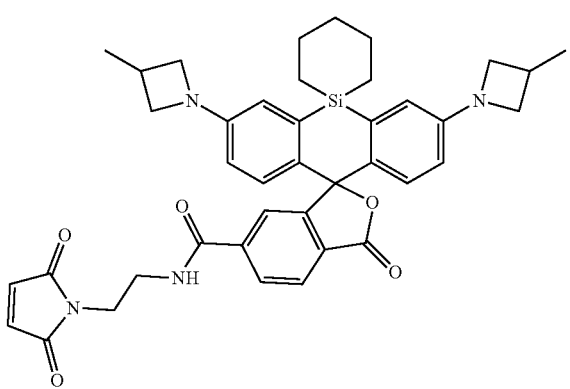

149
-continued
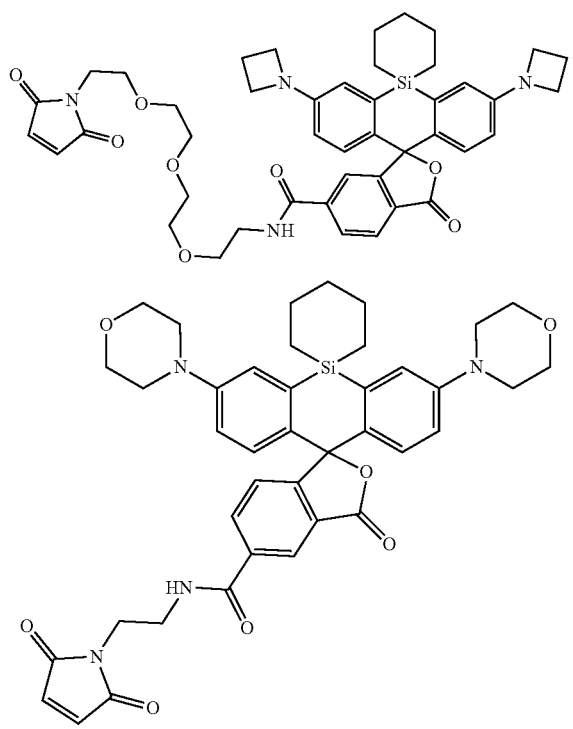
[Formula 6]
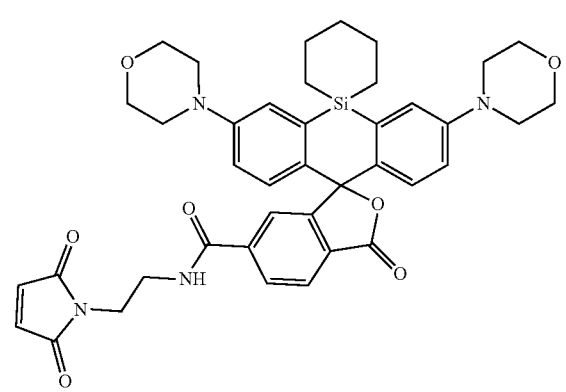
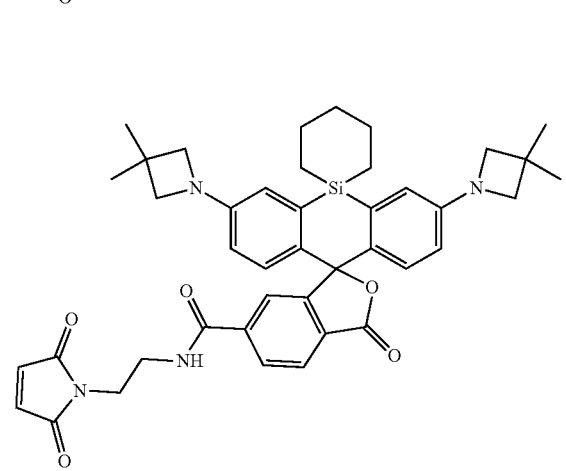
150
-continued
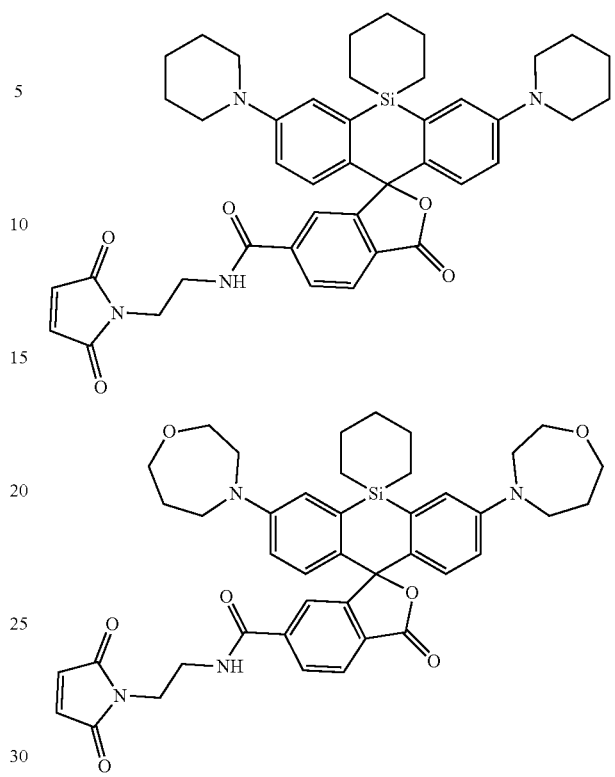
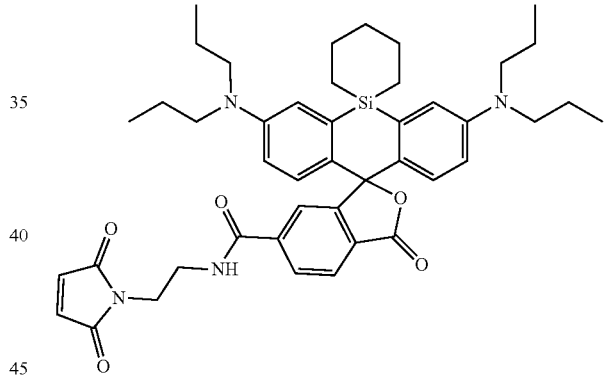
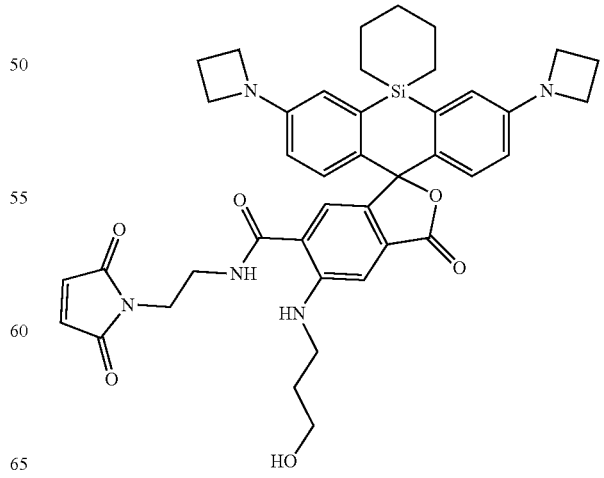

151
-continued

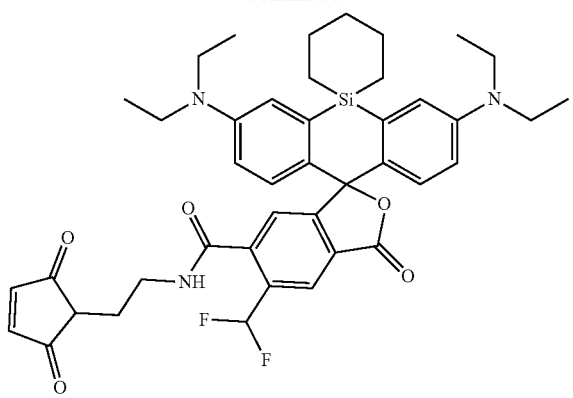

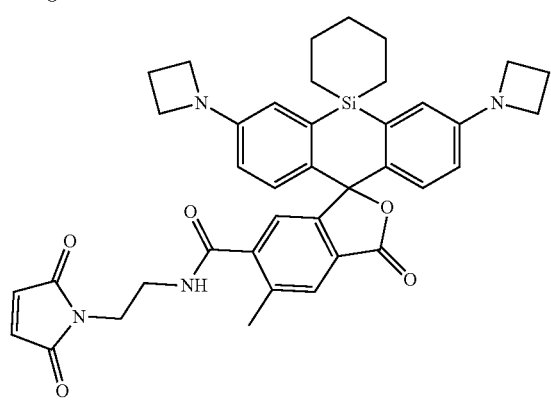

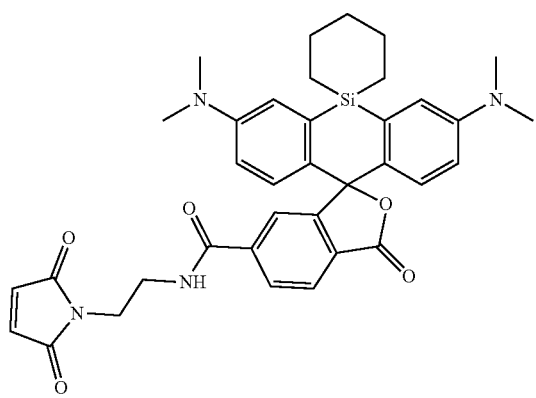

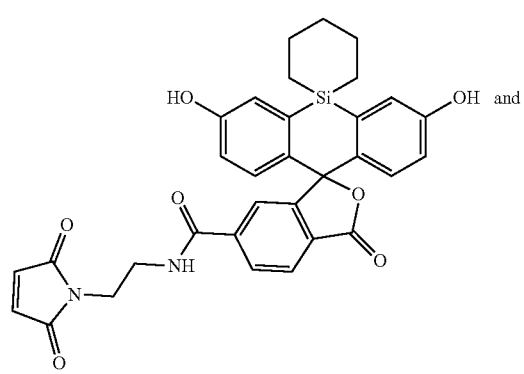

152
-continued

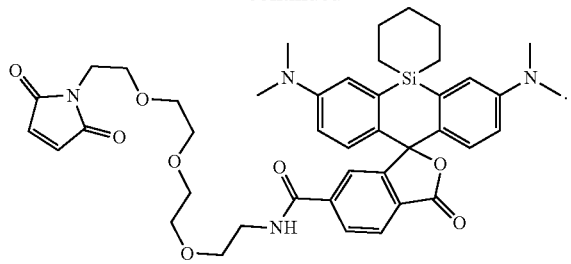 [SMILES: CN(C)c1ccc2c(c1)[Si]1(CCCCC1)c1cc(N(C)C)ccc1C21OC(=O)c2ccc(C(=O)NCCOCCOCCOCCN3C(=O)C=CC3=O)cc21]

9. A labeled composite substance comprising the fluorescent dye according to claim 1 and a composite substance which are bonded to each other.

10. The labeled composite substance according to claim 9, wherein the composite substance is a protein or a nucleic acid.

11. A composition comprising:
   the fluorescent dye according to claim 1 or
   a labeled composite substance comprising the fluorescent dye and a composite substance which are bonded to each other.

12. A method for acquiring information about a substance of interest, comprising:
   binding the the composition according to claim 11 to the substance of interest; and
   acquiring the information about the substance of interest by a super-resolution microscopy.

13. The method according to claim 12, wherein the information about the substance of interest is information about a structure of the substance of interest.

14. The method according to claim 13, wherein the information about the structure of the substance of interest is information about at least one item selected from a size of the substance of interest, a form of the substance of interest and a degree of aggregation of the substance of interest.

15. A fluorescent dye consisting of a compound represented by formula (I), a tautomer of the compound, or a salt of the compound or the tautomer:

[Formula 1]

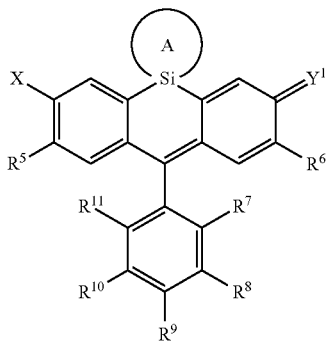

(I)

(wherein:
A represents an optionally substituted C4-C7 heterocyclic ring which contains an Si atom;
X represents a hydroxy group;
$Y^1$ represents =O;
$R^5$ and $R^6$ independently represent an H atom, an optionally substituted C1-C6 alkyl group, or an optionally substituted C1-C6 heteroalkyl group;

R⁷, R⁸, R⁹, R¹⁰ and R¹¹ are independently selected from the group consisting of an H atom, a halogen atom, an optionally substituted C1-C6 alkyl group, an optionally substituted C1-C6 alkoxy group, an optionally substituted C1-C6 alkylthio group, an optionally substituted amino group, an optionally substituted aryl group, an optionally substituted heteroaryl group, —CO₂H, —CO₂⁻, —SO₃H, —SO₃⁻, and -L-R;

L is 1 to 16 non-hydrogen atoms wherein L optional has a linear structure, a branched structure, and/or a cyclic structure, and wherein, when there are one or more hetero atoms in the non-hydrogen atoms, the hetero atoms are contained as one or more groups independently selected from the group consisting of an ester group, an amine group, an amide group, an ether group, a thioether group and a carbonyl group;

R is selected from a hydroxy group, a carboxyl group, a sulfonate group, an unsaturated imide group, an unsaturated amide group, an unsaturated ester group, an activated carboxylic acid ester group, an amine group, an alcohol group, a nitrile group, a mercaptan group, a boronate group, a phosphoramidite group, a halogenated alkyl group, a halogenated sulfonyl group, an amide or ester group having a halogen atom at alpha-position, an isocyanate group, an isothiocyanate group, an azide group, an aldehyde group, and an acylnitrile group; and at least one combination of adjacent two substituents among R⁷, R⁸, R⁹, R¹⁰ and R¹¹ may together form a ring.

16. A fluorescent dye consisting of a compound represented by formula (I), a tautomer of the compound, or a salt of the compound or the tautomer:

[Formula 1]

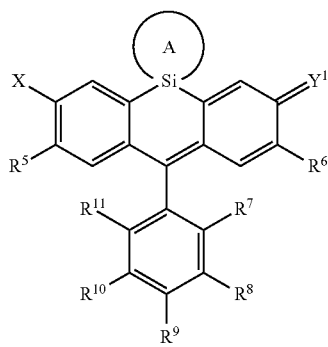

(I)

(wherein:
A represents an optionally substituted C4-C7 heterocyclic ring which contains an Si atom;
X represents a hydroxy group or —NR¹R²,
Y¹ represents =O or =N⁺R³R⁴;
R¹, R², R³, R⁴, R⁵ and R⁶ independently represent an H atom, an optionally substituted C1-C6 alkyl group, or an optionally substituted C1-C6 heteroalkyl group;
at least one combination selected from R¹ and R², R³ and R⁴, R¹ and R⁵, and R³ and R⁶ may together form an optionally substituted N-containing heterocyclic ring with an N atom to which they bind;
R⁷, R⁸, R⁹, R¹⁰ and R¹¹ are independently selected from the group consisting of an H atom, a halogen atom, an optionally substituted C1-C6 alkyl group, an optionally substituted C1-C6 alkoxy group, an optionally substituted C1-C6 alkylthio group, an optionally substituted amino group, an optionally substituted aryl group, an optionally substituted heteroaryl group, —CO₂H, —CO₂⁻, —SO₃H, —SO₃⁻, and -L-R;

-L-R represents —CONH-L'-R,
L' is 1 to 13 non-hydrogen atoms wherein L' optionally has a linear structure, a branched structure, and/or a cyclic structure, and
when there are one or more hetero atoms in the non-hydrogen atoms, the hetero atoms are contained as one or more groups independently selected from the group consisting of an ester group, an amine group, an amide group, an ether group, a thioether group and a carbonyl group;
R is selected from a hydroxy group, a carboxyl group, a sulfonate group, an unsaturated imide group, an unsaturated amide group, an unsaturated ester group, an activated carboxylic acid ester group, an amine group, an alcohol group, a nitrile group, a mercaptan group, a boronate group, a phosphoramidite group, a halogenated alkyl group, a halogenated sulfonyl group, an amide or ester group having a halogen atom at alpha-position, an isocyanate group, an isothiocyanate group, an azide group, an aldehyde group, and an acylnitrile group; and
at least one combination of adjacent two substituents among R⁷, R⁸, R⁹, R¹⁰ and R¹¹ may together form a ring;
either one of R⁹ or R¹⁰ is represented by:

[Formula 4]

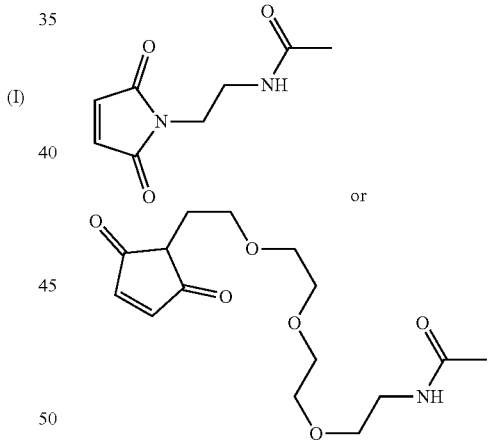

provided that a compound in which at least one of a combination of R¹ and R⁵ and a combination of R³ and R⁶ together form an optionally substituted N-containing heterocyclic ring with an N atom to which they bind and in which R² and R⁴ independently represent an optionally substituted C1-C6 alkyl group, a tautomer of the compound and a salt of the compound or the tautomer are excluded, and
provided that the compound represented by formula (I) is not a compound represented by formula (I) wherein
A is a C4 heterocyclic ring which contains the Si atom;
X is —NR¹R²;
Y¹ is =N⁺R³R⁴;
R¹, R², R³ and R⁴ are Me;
R⁵ and R⁶ are H;

$R^7$ is either $-CO_2^-$ or H, when $R^7$ is $-CO_2^-$, $R^{11}$ is H, and when $R^7$ is H, $R^{11}$ is $-CO_2^-$;

$R^8$ is either H or $CO_2H$, when $R^8$ is H, $R^{10}$ is $CO_2H$, and when $R^8$ is $CO_2H$, $R^{11}$ is H; and $R^9$ is H.

17. A composition comprising:

the fluorescent dye according to claim 6 or a labeled composite substance comprising the fluorescent dye and a composite substance which are bonded to each other.

18. A composition comprising:

the fluorescent dye according to claim 15 or a labeled composite substance comprising the fluorescent dye and a composite substance which are bonded to each other.

19. A composition comprising:

the fluorescent dye according to claim 16 or a labeled composite substance comprising the fluorescent dye and a composite substance which are bonded to each other.

20. The fluorescent dye according to claim 1, wherein the N-containing heterocyclic ring is selected from the group consisting of an azetidine ring, a pyrrolidine ring, a piperidine ring, a morpholine ring and an oxazepane ring.

* * * * *